(12) United States Patent
Gao et al.

(10) Patent No.: US 12,390,539 B2
(45) Date of Patent: Aug. 19, 2025

(54) MINIGENE THERAPY

(71) Applicant: University of Massachusetts, Westborough, MA (US)

(72) Inventors: Guangping Gao, Worcester, MA (US); Hemant Khanna, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 873 days.

(21) Appl. No.: 17/612,653

(22) PCT Filed: May 19, 2020

(86) PCT No.: PCT/US2020/033600
§ 371 (c)(1),
(2) Date: Nov. 19, 2021

(87) PCT Pub. No.: WO2020/236815
PCT Pub. Date: Nov. 26, 2020

(65) Prior Publication Data
US 2022/0233720 A1    Jul. 28, 2022

Related U.S. Application Data

(60) Provisional application No. 62/967,521, filed on Jan. 29, 2020, provisional application No. 62/899,601, (Continued)

(51) Int. Cl.
*A61K 48/00* (2006.01)
*A61K 35/76* (2015.01)
(Continued)

(52) U.S. Cl.
CPC .......... *A61K 48/0058* (2013.01); *A61K 35/76* (2013.01); *A61P 27/02* (2018.01);
(Continued)

(58) Field of Classification Search
None
See application file for complete search history.

(56) References Cited

U.S. PATENT DOCUMENTS 5,478,745 A    12/1995 Samulski et al.
5,552,157 A    9/1996 Yagi
(Continued)

FOREIGN PATENT DOCUMENTS

CN    105408352 A    3/2016
WO    WO 1998/010088 A1    3/1998
(Continued)

OTHER PUBLICATIONS

U.S. Appl. No. 18/345,366, filed Jun. 30, 2023, Gao et al.
(Continued)

*Primary Examiner* — Marcia S Noble
*Assistant Examiner* — Briana N Ebbinghaus
(74) *Attorney, Agent, or Firm* — Wolf, Greenfield & Sacks, P.C.

(57) ABSTRACT

Aspects of the disclosure relate to compositions and methods useful for treating ocular ciliopathies, for example Leber congenital amaurosis (LCA). In some embodiments, the disclosure provides isolated nucleic acids comprising a transgene encoding a CEP290 protein fragment, and methods of treating ocular ciliopathies using the same.

14 Claims, 34 Drawing Sheets

Specification includes a Sequence Listing.

Related U.S. Application Data filed on Sep. 12, 2019, provisional application No. 62/850,405, filed on May 20, 2019.

(51) Int. Cl.

| | |
|---|---|
| *A61P 27/02* | (2006.01) |
| *C07K 14/705* | (2006.01) |
| *C12N 5/079* | (2010.01) |
| *C12N 7/00* | (2006.01) |
| *C12N 15/113* | (2010.01) |
| *C12N 15/86* | (2006.01) |

(52) U.S. Cl.
CPC .......... *C07K 14/705* (2013.01); *C12N 5/0621* (2013.01); *C12N 7/00* (2013.01); *C12N 15/113* (2013.01); *C12N 15/86* (2013.01); *C12N 2310/10* (2013.01); *C12N 2750/14122* (2013.01); *C12N 2750/14142* (2013.01); *C12N 2830/008* (2013.01)

(56) References Cited

U.S. PATENT DOCUMENTS

| | | | |
|---|---|---|---|
| 5,565,213 | A | 10/1996 | Nakamori et al. |
| 5,567,434 | A | 10/1996 | Szoka, Jr. |
| 5,738,868 | A | 4/1998 | Shinkarenko |
| 5,741,516 | A | 4/1998 | Webb et al. |
| 5,795,587 | A | 8/1998 | Gao et al. |
| 6,001,650 | A | 12/1999 | Colosi |
| 6,156,303 | A | 12/2000 | Russell et al. |
| 10,155,794 | B2 | 12/2018 | Drivas et al. |
| 10,253,312 | B2 | 4/2019 | Maeder et al. |
| 10,266,845 | B2 | 4/2019 | Cronin et al. |
| 11,739,346 | B2 | 8/2023 | Gao et al. |
| 2003/0138772 | A1 | 7/2003 | Gao et al. |
| 2011/0117058 | A1 | 5/2011 | Auricchio |
| 2016/0076054 | A1 | 3/2016 | Auricchio et al. |
| 2016/0185832 | A1 | 6/2016 | Drivas et al. |
| 2016/0194374 | A1 | 7/2016 | Wijnholds et al. |
| 2017/0275615 | A1 | 9/2017 | Wu et al. |
| 2017/0348387 | A1 | 12/2017 | Aguirre et al. |
| 2018/0369412 | A1 | 12/2018 | Bennett et al. |
| 2019/0002916 | A1 | 1/2019 | Kalatzis et al. |
| 2019/0062385 | A1 | 2/2019 | Drivas et al. |
| 2020/0056204 | A1 | 2/2020 | Gao et al. |
| 2024/0076692 | A1 | 3/2024 | Gao et al. |

FOREIGN PATENT DOCUMENTS

| | | | |
|---|---|---|---|
| WO | WO 2009/121536 | A1 | 10/2009 |
| WO | WO 2014/170480 | A1 | 10/2014 |
| WO | WO 2015/009575 | A1 | 1/2015 |
| WO | WO 2016/033338 | A1 | 3/2016 |
| WO | WO 2018/026976 | A1 | 2/2018 |
| WO | WO 2018/187552 | A1 | 10/2018 |
| WO | WO 2019/006182 | A1 | 1/2019 |
| WO | WO 2019/077159 | A1 | 4/2019 |

OTHER PUBLICATIONS

EP 20810554.4, Sep. 12, 2023, Partial European Search Report.
EP 20810554.4, Dec. 14, 2023, Extended European Search Report.
Invitation to Pay Additional Fees for Application No. PCT/US2020/033600, mailed Aug. 21, 2020.
International Search Report and Written Opinion for Application No. PCT/US2020/033600, mailed Oct. 26, 2022.
International Preliminary Report on Patentability for Application No. PCT/US2020/033600, mailed Dec. 2, 2021.
Baye et al., The N-terminal region of centrosomal protein 290 (CEP290) restores vision in a zebrafish model of human blindness. Hum Mol Genet. Apr. 15, 2011;20(8):1467-77. doi: 10.1093/hmg/ddr025. Epub Jan. 21, 2011.
Boshart et al., A very strong enhancer is located upstream of an immediate early gene of human cytomegalovirus. Cell. 1985;41(2):521-530. doi:10.1016/s0092-8674(85)80025-8.
Boye et al., Natural history of cone disease in the murine model of Leber congenital amaurosis due to CEP290 mutation: determining the timing and expectation of therapy. PLoS One. Mar. 26, 2014;9(3):e92928. doi: 10.1371/journal.pone.0092928.
Chu et al., SV40 DNA transfection of cells in suspension: analysis of the efficiency of transcription and translation of T-antigen. Gene. 1981;13:197-202.
De Felipe et al., Use of the 2A sequence from foot-and-mouth disease virus in the generation of retroviral vectors for gene therapy. Gene Ther. 1999;6(2):198-208. doi:10.1038/sj.gt.3300811.
Den Hollander et al., Mutations in the CEP290 (NPHP6) gene are a frequent cause of Leber congenital amaurosis. Am J Hum Genet. 2006;79(3):556-561. doi:10.1086/507318.
Fisher et al., Transduction with recombinant adeno-associated virus for gene therapy is limited by leading-strand synthesis. J Virol. Jan. 1996; 70(1): 520-532.
Furler et al., Recombinant AAV vectors containing the foot and mouth disease virus 2A sequence confer efficient bicistronic gene expression in cultured cells and rat substantia nigra neurons. Gene Therapy. Jun. 22, 2001;8:864-873.
Genbank Accession No. NP_079390.3. Jan. 5, 2020. 4 pages.
Gossen et al., Tight control of gene expression in mammalian cells by tetracycline-responsive promoters. Proc Natl Acad Sci U S A. 1992;89(12):5547-5551. doi:10.1073/pnas.89.12.5547.
Graham et al., A new technique for the assay of infectivity of human adenovirus 5 DNA. Virology. 1973;52(2):456-467. doi:10.1016/0042-6822(73)90341-3.
Halpin et al., Self-processing 2A-polyproteins—a system for co-ordinate expression of multiple proteins in transgenic plants. Plant J. 1999;17(4):453-459. doi:10.1046/j.1365-313x.1999.00394.x.
Harvey et al., Inducible control of gene expression: prospects for gene therapy. Curr Opin Chem Biol. 1998;2(4):512-518. doi:10.1016/s1367-5931(98)80128-2.
Klump et al., Retroviral vector-mediated expression of HoxB4 in hematopoietic cells using a novel coexpression strategy. Gene Therapy. Jun. 22, 2001;8:811-817. doi: https://doi.org/10.1038/sj.gt.3301447.
Magari et al., Pharmacologic control of a humanized gene therapy system implanted into nude mice. J Clin Invest. Dec. 1, 1997; 100(11): 2865-2872. doi: 10.1172/JCI119835.
Mattion et al., Foot-and-mouth disease virus 2A protease mediates cleavage in attenuated Sabin 3 poliovirus vectors engineered for delivery of foreign antigens. J Virol. Nov. 1996; 70(11): 8124-8127.
McCarty et al., Self-complementary AAV vectors; advances and applications. Mol Ther. 2008;16(10):1648-1656. doi:10.1038/mt.2008.171.
Mookherjee et al., A CEP290 C-Terminal Domain Complements the Mutant CEP290 of Rd16 Mice in Trans and Rescues Retinal Degernation. Cell Rep. Oct. 16, 2018;25(3):611-623.e6. doi: 10.1016/j.celrep.2018.09.043.
NCBI Reference Sequence No. NM_025114.3. Jul. 5, 2019. 9 pages.
No et al., Ecdysone-inducible gene expression in mammalian cells and transgenic mice. Proc Natl Acad Sci U S A. Apr. 16, 1996; 93(8): 3346-3351. doi: 10.1073/pnas.93.8.3346.
Plantier et al., A factor VIII minigene comprising the truncated intron I of factor IX highly improves the in vitro production of factor VIII. Thromb Haemost. 2001;86(2):596-603.
Ryan et al., Foot-and-mouth disease virus 2A oligopeptide mediated cleavage of an artificial polyprotein. EMBO J. Feb. 15, 1994; 13(4): 928-933.
Tsang et al., CP110 suppresses primary cilia formation through its interaction with CEP290, a protein deficient in human ciliary disease. Dev Cell. Aug. 2008;15(2):187-97. doi: 10.1016/j.devcel.2008.07.004.
Wang et al., Ligand-inducible and liver-specific target gene expression in transgenic mice. Nat Biotechnol. Mar. 1, 1997;15:239-243. doi: https://doi.org/10.1038/nbt0397-239.

(56) References Cited

OTHER PUBLICATIONS

Wang et al., Positive and negative regulation of gene expression in eukaryotic cells with an inducible transcriptional regulator. Gene Therapy. 1997;4:432-441. https://doi.org/10.1038/sj.gt.3300402.

Wright et al., Identification of factors that contribute to recombinant AAV2 particle aggregation and methods to prevent its occurrence during vector purification and formulation. Mol Ther. 2005;12(1):171-178. doi:10.1016/j.ymthe.2005.02.021.

Xiao et al., Rescue of the albino phenotype by introducing a functional tyrosinase minigene into Kunming albino mice. World J Gastroenterol. Jan. 14, 2007; 13(2): 244-249. EPub Jan. 14, 2007. doi: 10.3748/wjg.v13.i2.244.

Zhang et al., Gene therapy using a miniCEP290 fragment delays photoreceptor degeneration in a mouse model of Leber congenital amaurosis (LCA). Human Gene Therapy. Author Manuscript. Submitted Mar. 22, 2017. 26 pages.

Zhang et al., Gene Therapy Using a miniCEP290 Fragment Delays Photoreceptor Degeneration in a Mouse Model of Leber Congenital Amaurosis. Hum Gene Ther. Jan. 2018;29(1):42-50. doi: 10.1089/hum.2017.049. Epub Jul. 5, 2017.

Partial European Search Report for Application No. 20810554.4, mailed Sep. 12, 2023.

Extended European Search Report for Application No. 0810554.4, mailed Dec. 14, 2023.

No Author Listed, Genbank Submission; NCBI, Accession No. NM_025114.2; *Homo sapiens* centrosomal protein 290kDa (CEP290), mRNA; May 24, 2006. 4 pages.

*: p<0.05; : p<0.01; *: p<0.001

US 12,390,539 B2

MINIGENE THERAPY

RELATED APPLICATIONS

This application is a national stage filing under 35 U.S.C. § 371 of international PCT application PCT/US2020/033600, filed May 19, 2020, which claims the benefit under 35 U.S.C. § 119(e) of the filing date of U.S. provisional Application Ser. No. 62/967,521, filed Jan. 29, 2020, U.S. provisional Application Ser. No. 62/850,405, filed May 20, 2019, and U.S. provisional Application Ser. No. 62/899,601, filed Sep. 12, 2019, the entire contents of each application which are incorporated herein by reference.

GOVERNMENT SUPPORT

This invention was made with government support under EY022372, EY029050, NS076991, AI100263, and HL131471, awarded by the National Institutes of Health. The government has certain rights in the invention.

BACKGROUND

Ciliopathies represent a group of diseases and disorders characterized by abnormal cilial formation or function. For example ocular ciliopathies may lead to retinal degeneration, reduced visual acuity, and/or blindness. CEP290-associated Leber congenital amaurosis (LCA) is one of the most common and severe forms of retinal degenerative diseases. However, no treatment or cure currently exists. Generally, the large size of cilia-associated genes, for example the CEP290 gene (~8 kb), has limited the development of successful therapy using conventional Adeno-associated Viral (AAV) vector-mediated gene delivery approaches because the cargo size exceeds the ~4700 bp packaging limit of rAAVs. Use of genome editing (such as CRISPR/Cas9 approach) and antisense oligonucleotides can have off-target effects and are typically applicable to only one type of mutation in a cilia-associated gene. Accordingly, novel compositions and methods for treating ciliopathies are needed.

SUMMARY

Aspects of the disclosure relate to compositions and methods useful for delivering minigenes to a subject. Accordingly, the disclosure is based, in part, on gene therapy vectors, such as viral (e.g., rAAV) vectors, comprising one or more gene fragments encoding a therapeutic gene product, such as a protein or peptide (e.g., a minigene). In some aspects, a gene therapy vector further comprises one or more inhibitory nucleic acids that target an endogenous gene variant (e.g., mutant) that is associated with a disease or disorder (e.g., a gene associated with a ciliopathy). In some embodiments, the one or more inhibitory nucleic acids do not silence gene expression of the gene product encoded by the minigene. In some embodiments, methods are provided for treating ciliopathies (e.g., ocular ciliopathies), for example disorders and diseases characterized by a mutation or deletion of a cilia-associated gene, such as the CEP290 gene which is associated with Leber congenital amaurosis (LCA).

Accordingly, in some aspects, the disclosure relates to an isolated nucleic acid comprising a transgene encoding a CEP290 fragment having the amino acid sequence set forth in any one of SEQ ID NOs: 10-19 or 36.

In some embodiments, a CEP290 fragment is encoded by a nucleic acid having the sequence set forth in any one of SEQ ID NOs: 20-29 and 34-35. In some embodiments, a CEP290 fragment is encoded by a nucleic acid having the sequence set forth in SEQ ID NO: 29 or 34. In some embodiments, a nucleic acid encodes a CEP290 protein fragment comprising amino acids 1-200 and 580-1180 of a human CEP290. In some embodiments, a nucleic acid encodes a CEP290 protein fragment comprising amino acids 1-200 and 580-1180 of SEQ ID NO: 1. In some embodiments, a nucleic acid encodes a CEP290 protein fragment comprising or consisting of the amino acid sequence set forth in SEQ ID NO: 19.

In some embodiments, a CEP290 fragment is encoded by a nucleic acid having the sequence set forth in SEQ ID NO: 35. In some embodiments, a nucleic acid encodes a CEP290 protein fragment comprising amino acids 1-380 and 580-1180 of a human CEP290. In some embodiments, a nucleic acid encodes a CEP290 protein fragment comprising amino acids 1-380 and 580-1180 of SEQ ID NO: 1. In some embodiments, a nucleic acid encodes a CEP290 protein fragment comprising or consisting of the amino acid sequence set forth in SEQ ID NO: 36.

In some embodiments, a transgene further comprises a promoter. In some embodiments, a promoter is a CB6 promoter, a CBA promoter, or a tissue-specific promoter. In some embodiments, a tissue specific promoter is an eye-specific promoter. In some embodiments, an eye-specific promoter is a retinoschisin promoter, K12 promoter, a rhodopsin promoter, a rod-specific promoter, a cone-specific promoter, a rhodopsin kinase promoter (e.g., a GRK1 promoter), or an interphotoreceptor retinoid-binding protein proximal (IRBP) promoter.

In some embodiments, a transgene further comprises an intron (e.g., a chicken-beta actin intron, a synthetic intron, MBL intron, etc.). In some embodiments, the intron is positioned between the promoter and minigene (e.g. Mini-CEP290) coding sequence of the transgene.

In some embodiments, a transgene is flanked by adeno-associated virus (AAV) inverted terminal repeats (ITRs). In some embodiments, AAV ITRs are AAV2 ITRs or a variant thereof, such as ΔITR or mTR ITRs.

In some aspects, the disclosure provides a vector comprising an isolated nucleic acid as described herein. In some embodiments, a vector is a plasmid.

In some aspects, the disclosure relates to a host cell comprising an isolated nucleic acid or a vector as described herein.

In some embodiments, the disclosure provides a recombinant adeno-associated virus (rAAV) comprising: a capsid protein; and, an isolated nucleic acid as described herein.

In some embodiments, a capsid protein is AAV8 capsid protein or AAV5 capsid protein. In some embodiments, a capsid protein is an AAV8 capsid protein or a variant thereof. In some embodiments, a capsid protein is an AAV5 capsid protein or a variant thereof. In some embodiments, a capsid protein comprises the amino acid sequence set forth in SEQ ID NO: 9.

In some embodiments, an rAAV is a self-complementary AAV (scAAV).

In some embodiments, an rAAV is formulated for delivery to the eye. In some embodiments, an rAAV is formulated for subretinal delivery. In some embodiments, an rAAV comprises one or more of the CEP290 fragments described by the disclosure and an AAV8 capsid protein or AAV5 capsid protein. In some embodiments, an rAAV comprises (i) a nucleic acid sequence encoding a CEP290 fragment comprising the amino acid sequence set forth in SEQ ID NO: 19 or 34 operably linked to a rhodopsin kinase (RK) promoter; and (ii) an rAAV8 capsid protein or AAV5 capsid protein. In some embodiments, the rAAV is formulated for subretinal delivery.

In some aspects, the disclosure provides a composition comprising an rAAV as described herein, and a pharmaceutically acceptable excipient. In some embodiments, a composition comprises a plurality of the rAAVs. In some embodiments, each rAAV of a plurality encodes a different CEP290 fragment.

In some aspects, the disclosure provides a method for treating an ocular ciliopathy in a subject in need thereof, the method comprising administering to a subject having an ocular ciliopathy a therapeutically effective amount of an isolated nucleic acid, rAAV, or composition as described herein.

In some embodiments, an ocular ciliopathy is associated with a mutation of the CEP290 gene in the subject or a deletion of a CEP290 gene in a subject. In some embodiments, a mutation in a CEP290 gene is an intronic mutation, a nonsense mutation, a frameshift mutation, a missense mutation, or any combination thereof. In some embodiments, the mutation or deletion of CEP290 results in retinal degeneration, photoreceptor degeneration, retinal dysfunction, and/or loss of vision.

In some embodiments, an ocular ciliopathy is Leber congenital amaurosis (LCA), Joubert syndrome, Bardet-Biedl syndrome, Meckel syndrome, Usher syndrome, Nephronophthisis, or Senior-Løken syndrome. In some embodiments, the ocular ciliopathy is Leber congenital amaurosis (LCA). In some embodiments such as Retinitis Pigmentosa (RP), the severity of an ocular ciliopathy is modified by CEP290.

In some embodiments, a subject is a human characterized by one or more CEP290 mutations (e.g., one or more mutations in a CEP290 gene) that occurs at position c.2991+ 1655. In some embodiments, at least one mutation is A1655G.

In some embodiments, administration of an isolated nucleic acid, rAAV, or composition results in delivery of a CEP290 fragment (e.g., a transgene encoding a CEP290 fragment) to the eye of a subject. In some embodiments, administration is via injection. In some embodiments, injection comprises subretinal injection or intravitreal injection. In some embodiments, administration is topical administration to the eye of the subject. In some embodiments, administration is by subretinal administration.

In some embodiments, an effective amount (e.g., administration of an effective amount of an isolated nucleic acid (messenger RNA), isolated CEP290 fragment protein, rAAV, or composition) results in photoreceptor (PR) function (e.g., increased PR function as measured by ERG). In some embodiments, an effective amount (e.g., administration of an effective amount of an isolated nucleic acid (messenger RNA), isolated CEP290 fragment protein, rAAV, or composition) results in photoreceptor (PR) function (e.g., increased PR function as measured by ERG), for up to fourteen weeks.

BRIEF DESCRIPTION OF DRAWINGS

FIG. 7A shows Cep290$^{rd16}$ mice subretinally injected at P0/P1 stage with indicated miniCEP290s or GFP, and analyzed by ERG at 3 weeks post injection. Age-matched uninjected WT or Cep290$^{rd16}$ (littermates) mice were used as controls for ERG. The ERG a-wave is represented by arrows while b-wave vis depicted using arrowheads. Data represent analysis of at least 6 mice. ***: p<0.0001; ns: not significant. FIG. 7B shows scotopic a-wave and b-wave amplitude for mice subretinally injected at P0/P1 stage with indicated miniCEP290s or GFP, and analyzed by ERG at 3 weeks post injection.

FIG. 8A shows Cep290$^{rd16}$ retinas injected with indicated miniCEP290$^{580-1180}$ or GFP stained with DAPI. FIG. 8B shows Cep290$^{rd16}$ retinas injected with indicated miniCEP290$^{580-1180}$ or GFP assessed by ultrathin sectioning. ONL (outer nuclear layer) is marked with vertical lines. WT retinal section is shown for comparison. INL: inner nuclear layer. FIG. 8C shows improved expression of RDS detected in the miniCEP290$^{580-1180}$ injected Cep290$^{rd16}$ mice. GFP staining marks the injected regions. FIG. 8D shows retinal cryosections of Cep290$^{rd16}$ mice injected with the indicated miniCEP290s were stained with GFP (injected regions), rhodopsin (RHO; rod-specific; or M-opsin (MOP; cone-specific) antibodies and DAPI (nuclei). Outer segment (OS)- enriched opsin staining is detected in the miniCEP290$^{580-1180}$-injected retinas. Dramatically reduced expression of opsins is detected in the miniCEP290$^{2037-2479}$-injected retinas. ONL: outer nuclear layer; INL: inner nuclear layer; GCL: ganglion cell layer.

Figure 9:
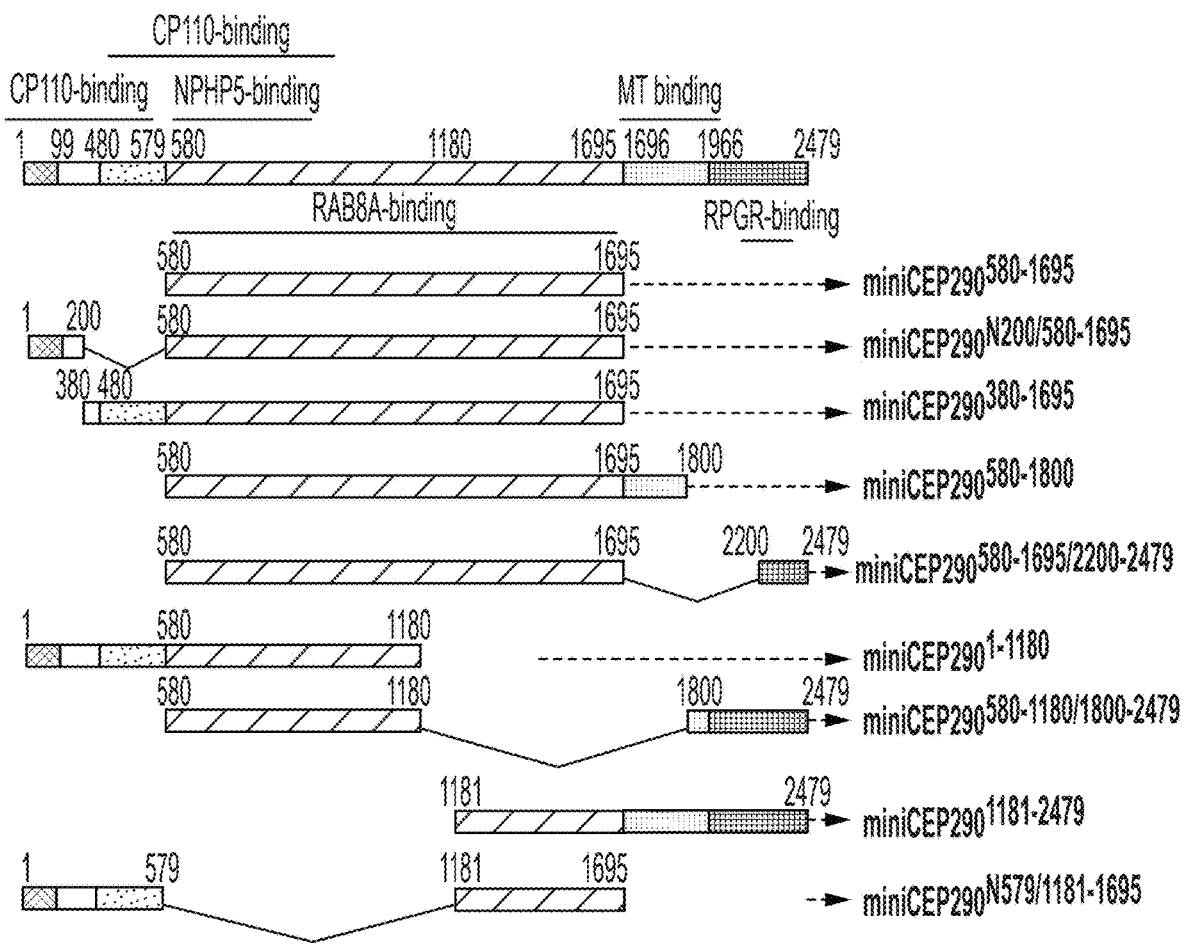

FIG. 9 shows additional embodiments of CEP290 minigenes.

Figure 10:
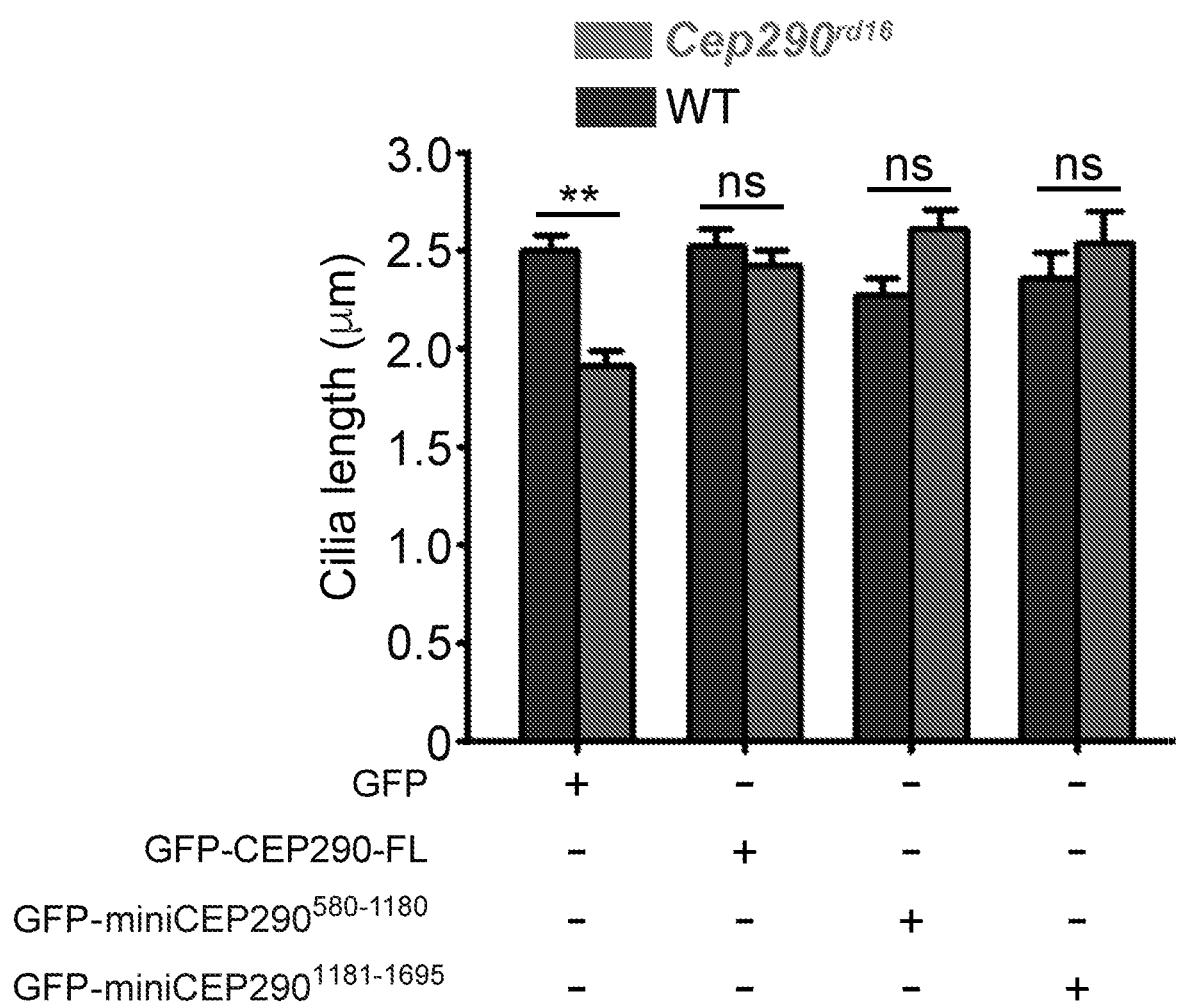

FIG. 10 shows the cilia length of Cep290$^{rd16}$ fibroblasts transiently transfected with plasmid encoding GFP alone or GFP-fused indicated variants, using anti-GFP antibody (n>200) quantified using ImageJ.

Figure 11:
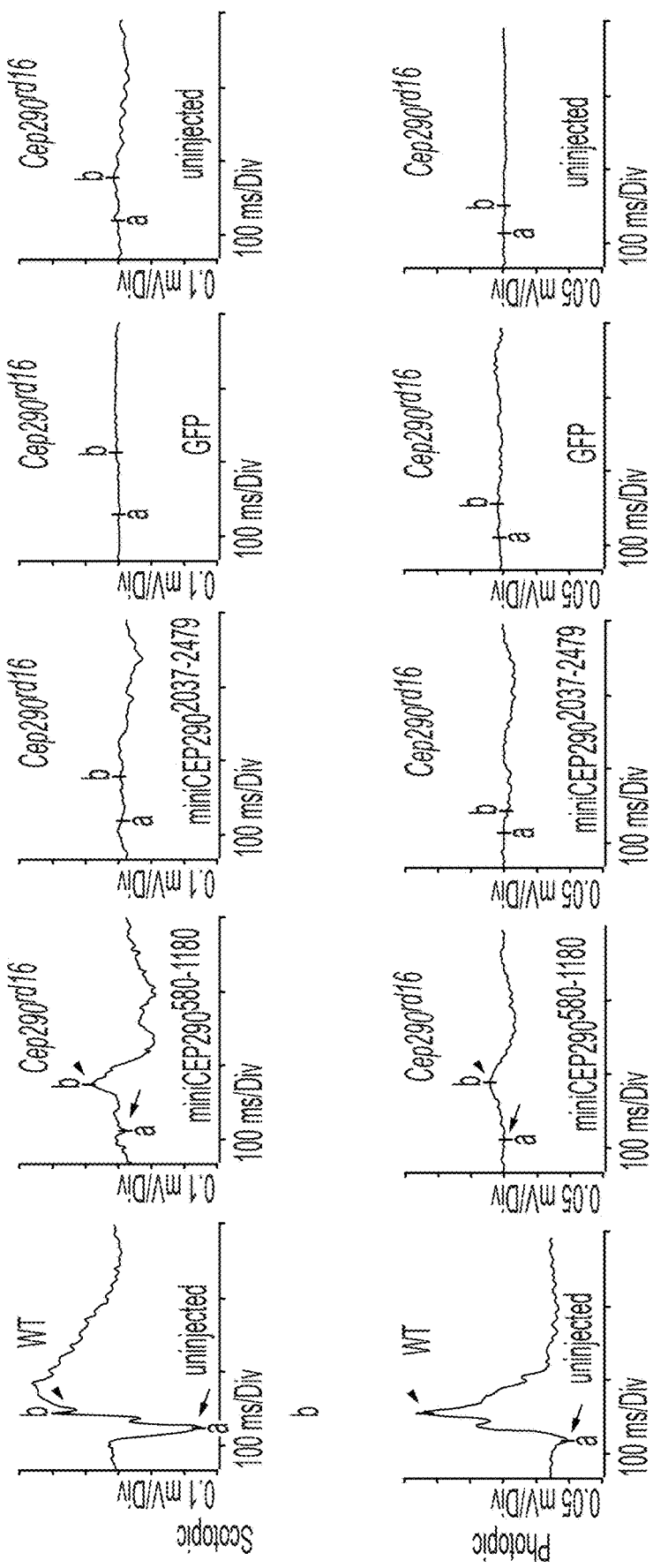

FIG. 11 shows Cep290$^{rd16}$ mice subretinally injected at P0/P1 stage with indicated miniCEP290s or GFP, and analyzed by ERG at 3 weeks post injection. Age-matched uninjected WT or Cep290$^{rd16}$ (littermates) mice were used as controls for ERG. The ERG a-wave is represented by arrows while b-wave vis depicted using arrowheads. Data represent analysis of at least 6 mice. ***: p<0.0001; ns: not significant.

Figure 12:
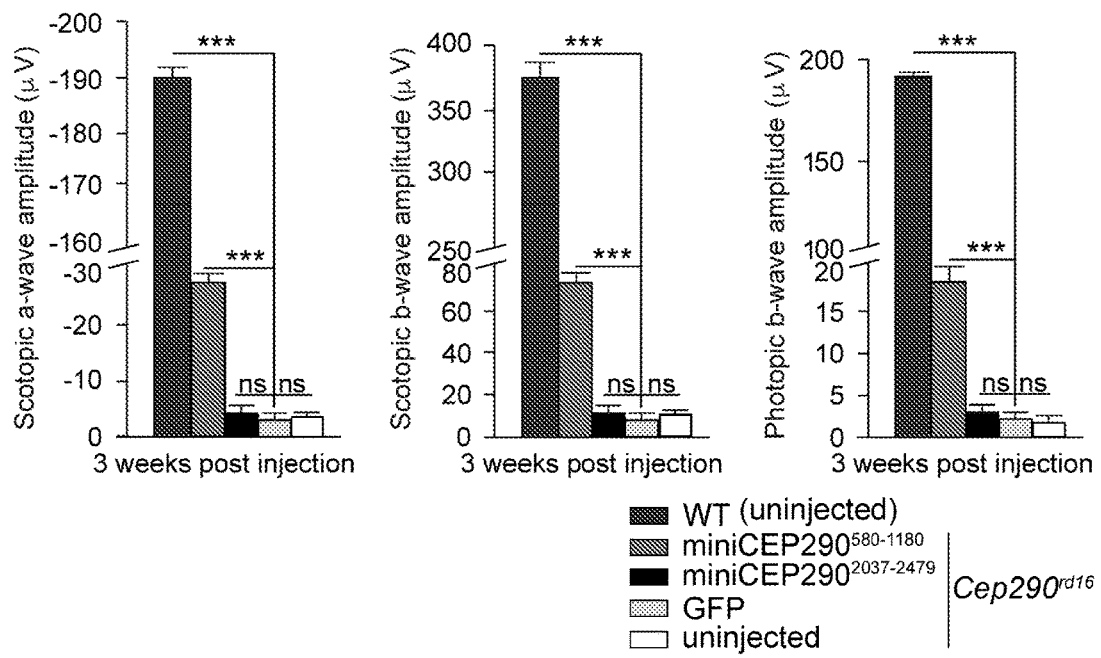
Figure 12:
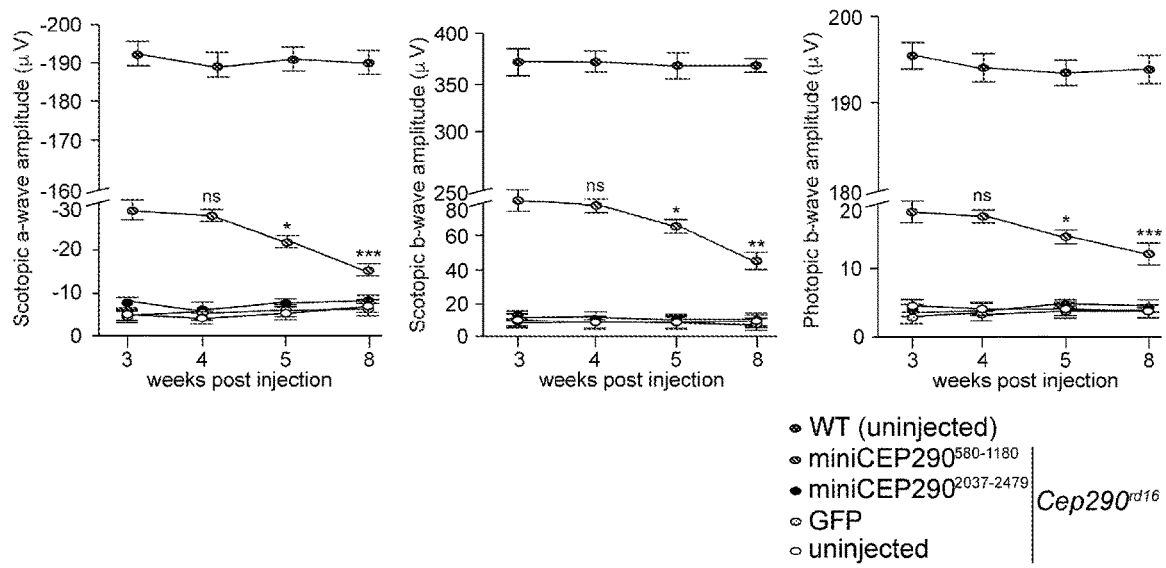

FIG. 12 shows scotopic a-wave and b-wave amplitude for mice subretinally injected at P0/P1 stage with indicated miniCEP290s or GFP, and analyzed by ERG at 3 weeks post injection Scotopic (a- and b-waves) and photopic b-wave analysis of the injected mice performed at 4 and 5 weeks post injection and compared to the ERG at 3 weeks are shown. Age-matched uninjected WT and GFP-injected Cep290$^{rd16}$ mice were used as controls.

Figure 13:
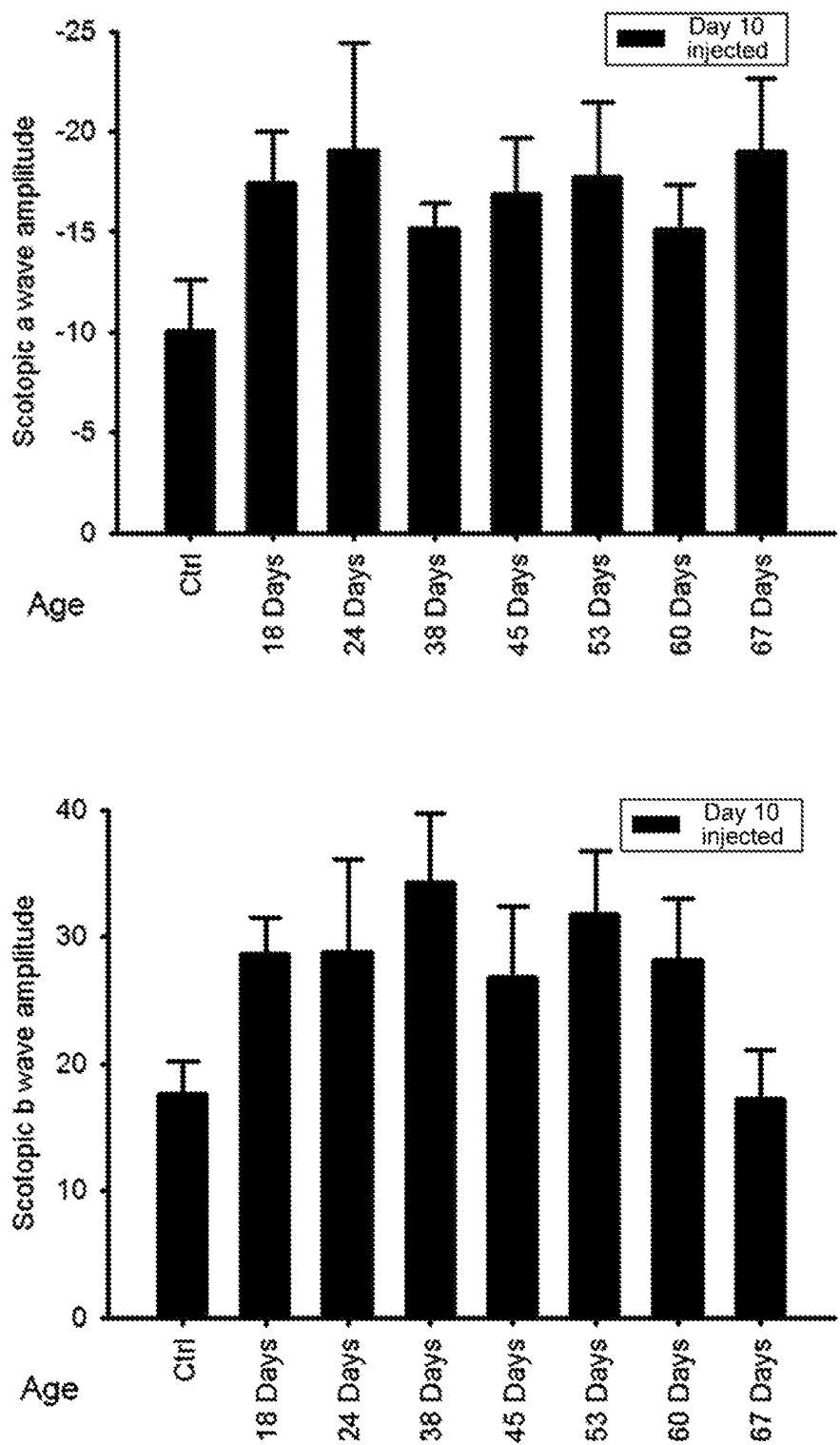

FIG. 13 shows scotopic a-wave and b-wave amplitude for 10-day old mice subretinally injected with the indicated miniCEP290 construct (GRK-580-1180). ERG were recorded at the indicated days after injection.

Figure 14:
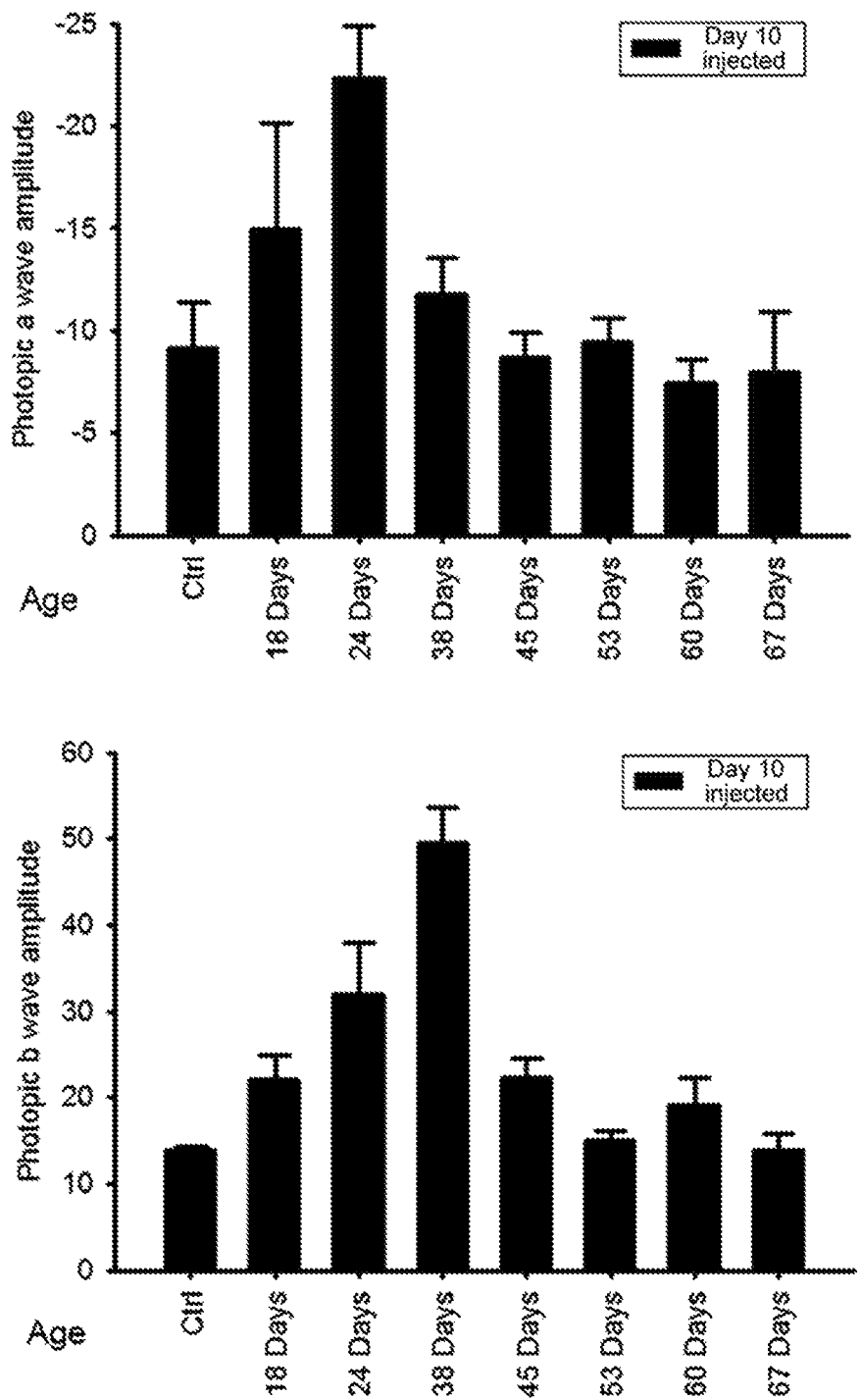

FIG. 14 shows photopic a-wave and b-wave amplitude for 10-day old mice subretinally injected with the indicated miniCEP290 construct (GRK-580-1180). ERG were recorded at the indicated days after injection.

Figure 15:
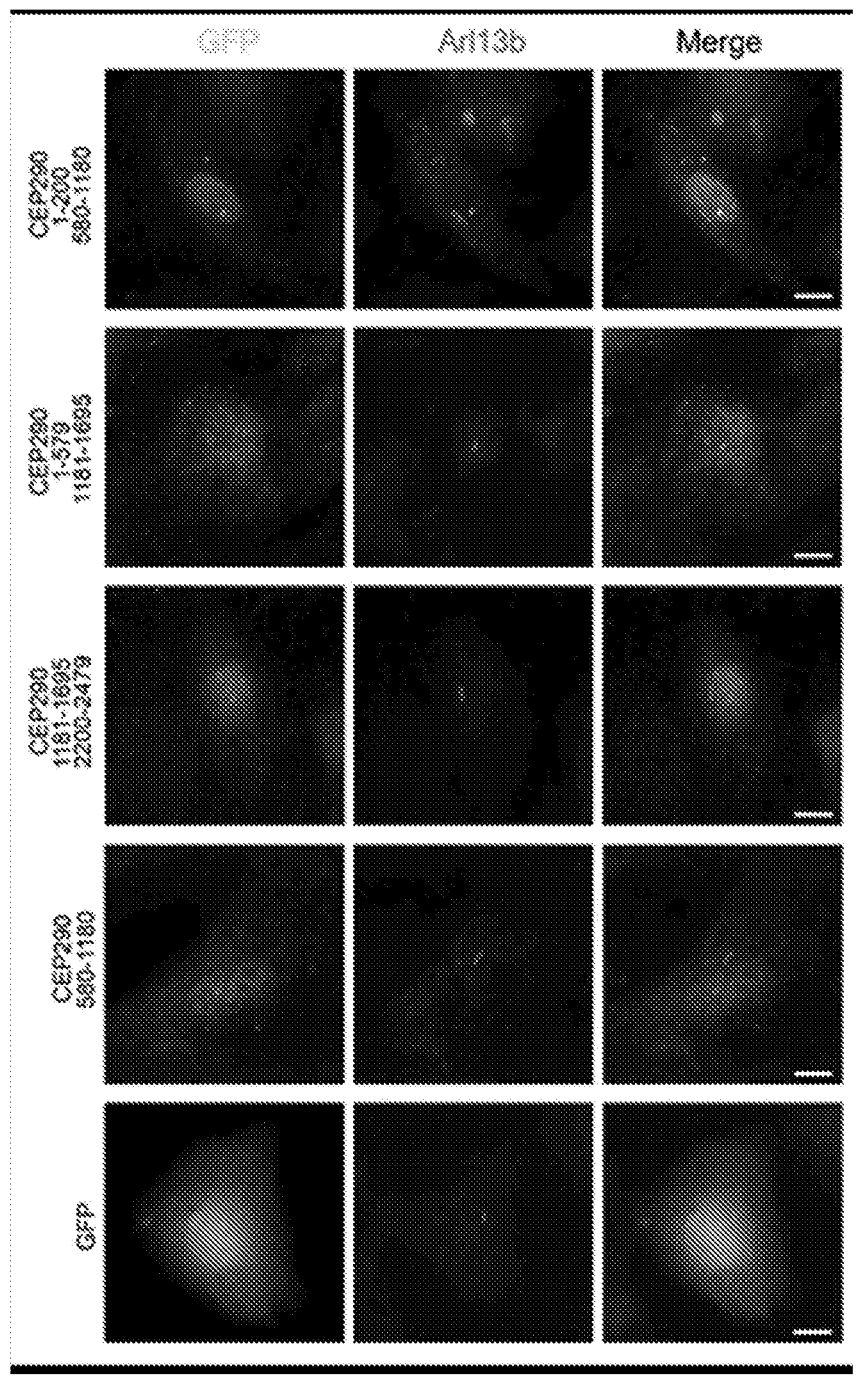

FIG. 15 shows micrographs of rd16 mouse embryonic fibroblasts transiently transfected with cDNA encoding the indicated minigenes and GFP.

Figure 16:
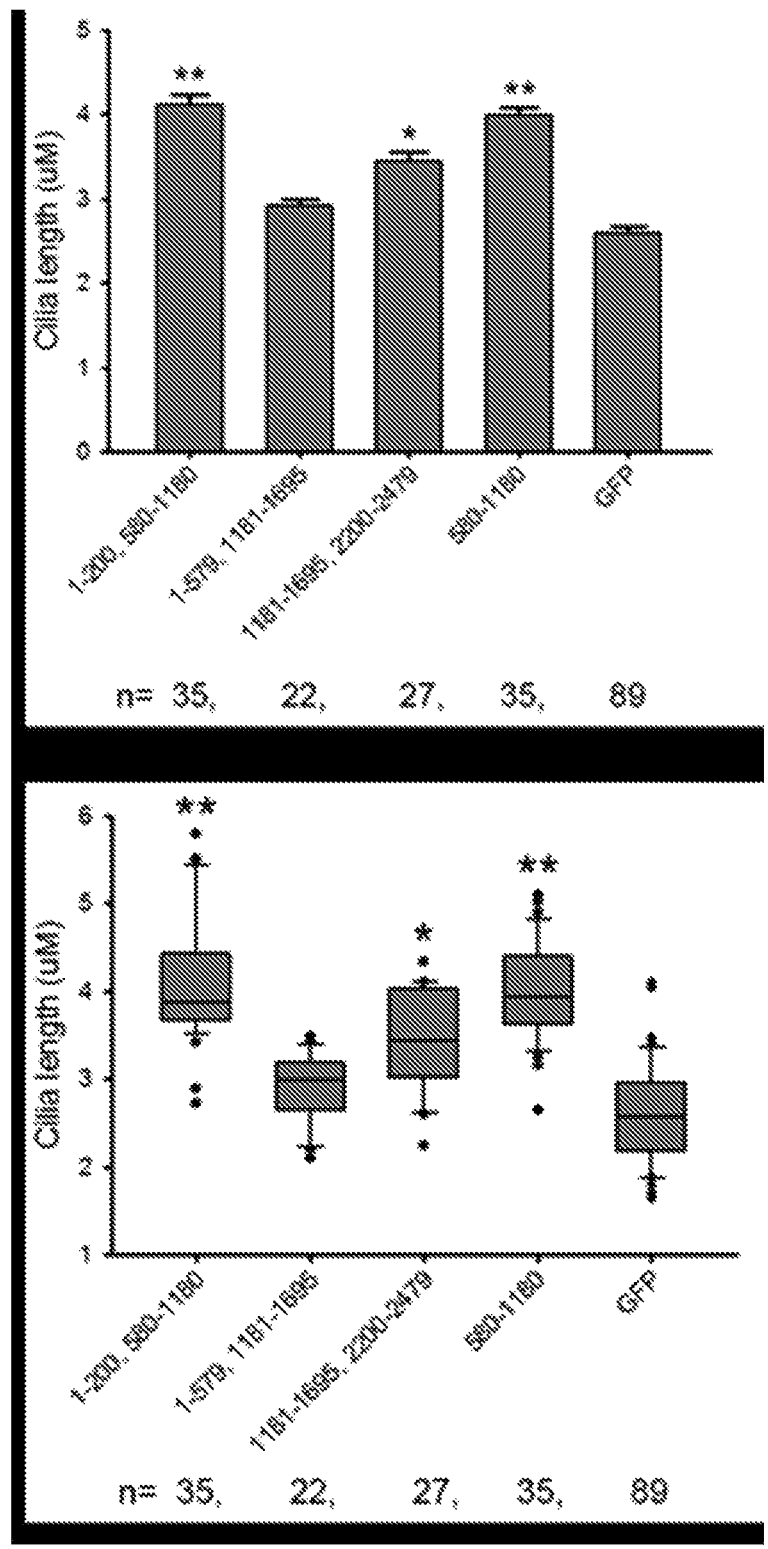

FIG. 16 shows data for cilia length measurement of rd16 mouse embryonic fibroblasts transiently transfected with cDNA encoding the indicated minigenes encoding the protein and GFP.

Figure 17B:
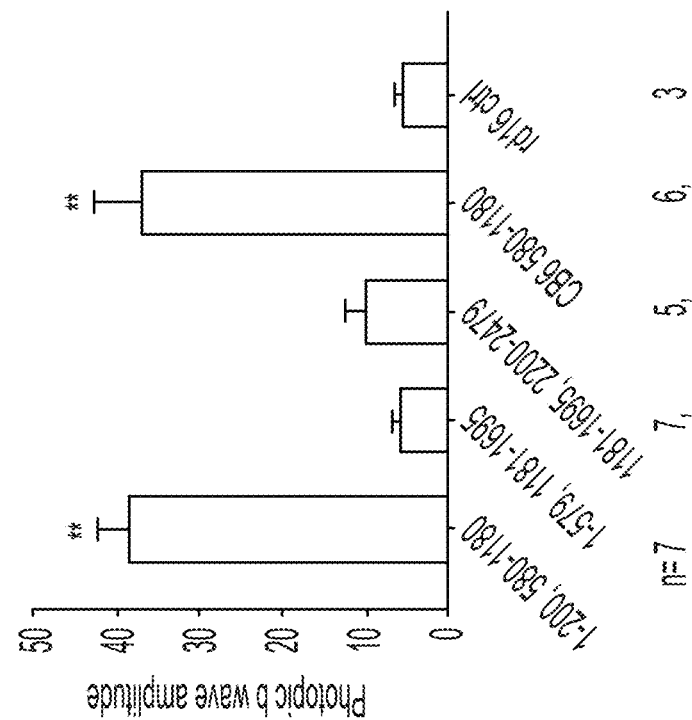
Figure 17A:
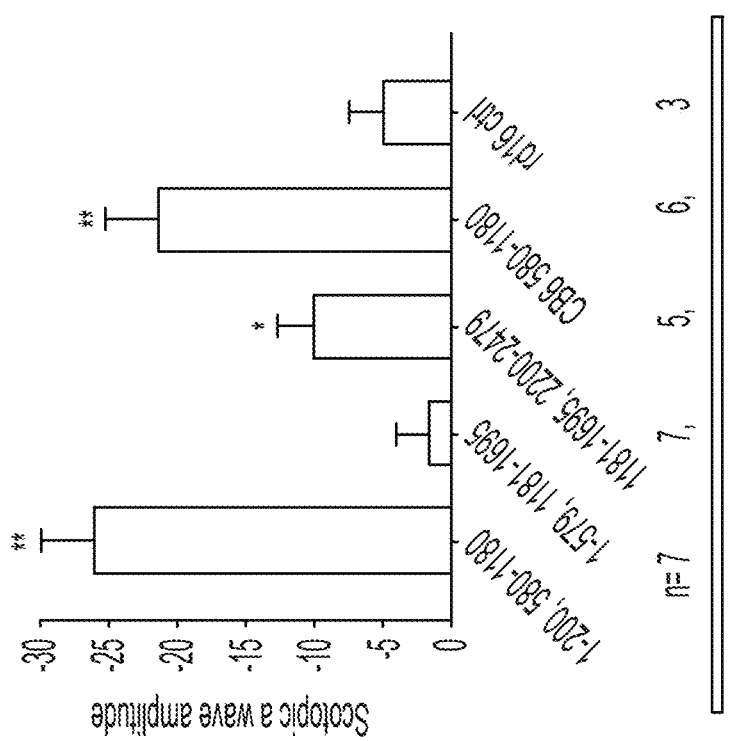
Figure 17C:
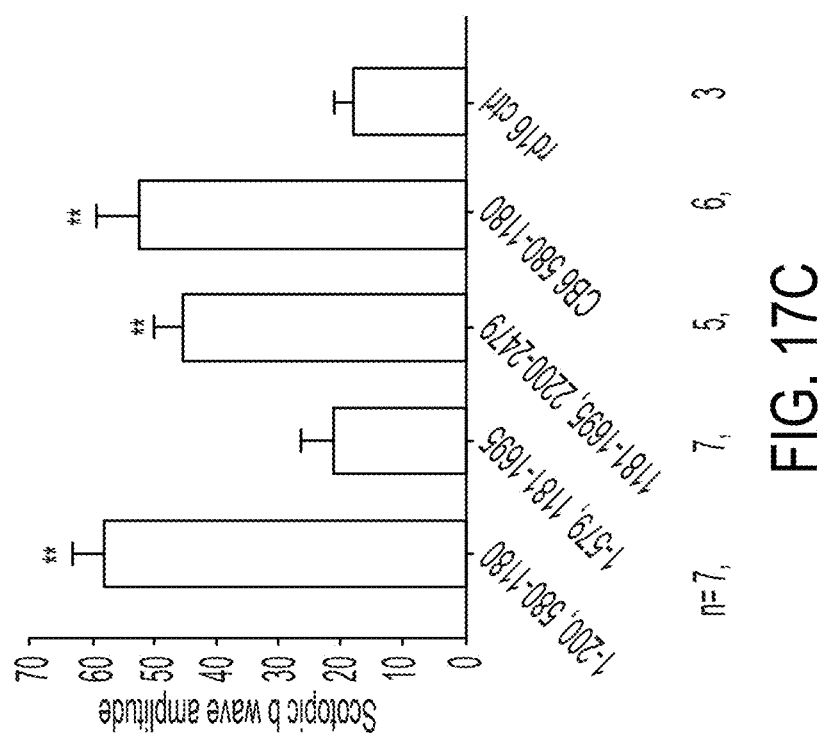
Figure 17D:
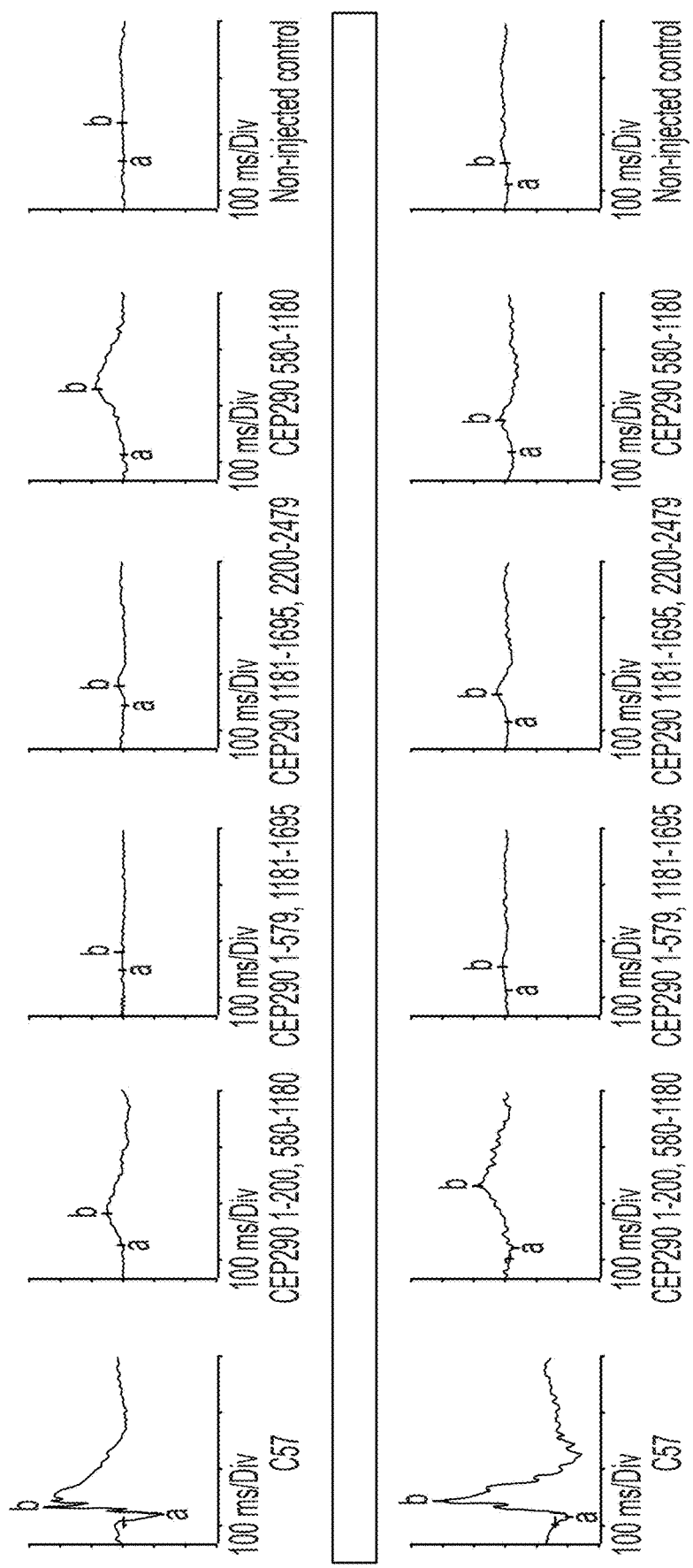

FIGS. 17A-17D show scotopic and photopic wave amplitudes of CB6-promoter driving the indicated minigenes were subretinally injected into 10 day old rd16 mice. FIG. 17A shows scotopic a-wave amplitude. FIG. 17B shows photopic b-wave amplitude. FIG. 17C shows scotopic b-wave amplitude. FIG. 17D shows ERG of rd16 mice injected with CB6-1-200-580-1180 miniCEP290. ERG were recorded at indicated days after injection and compared to others.

Figure 18:
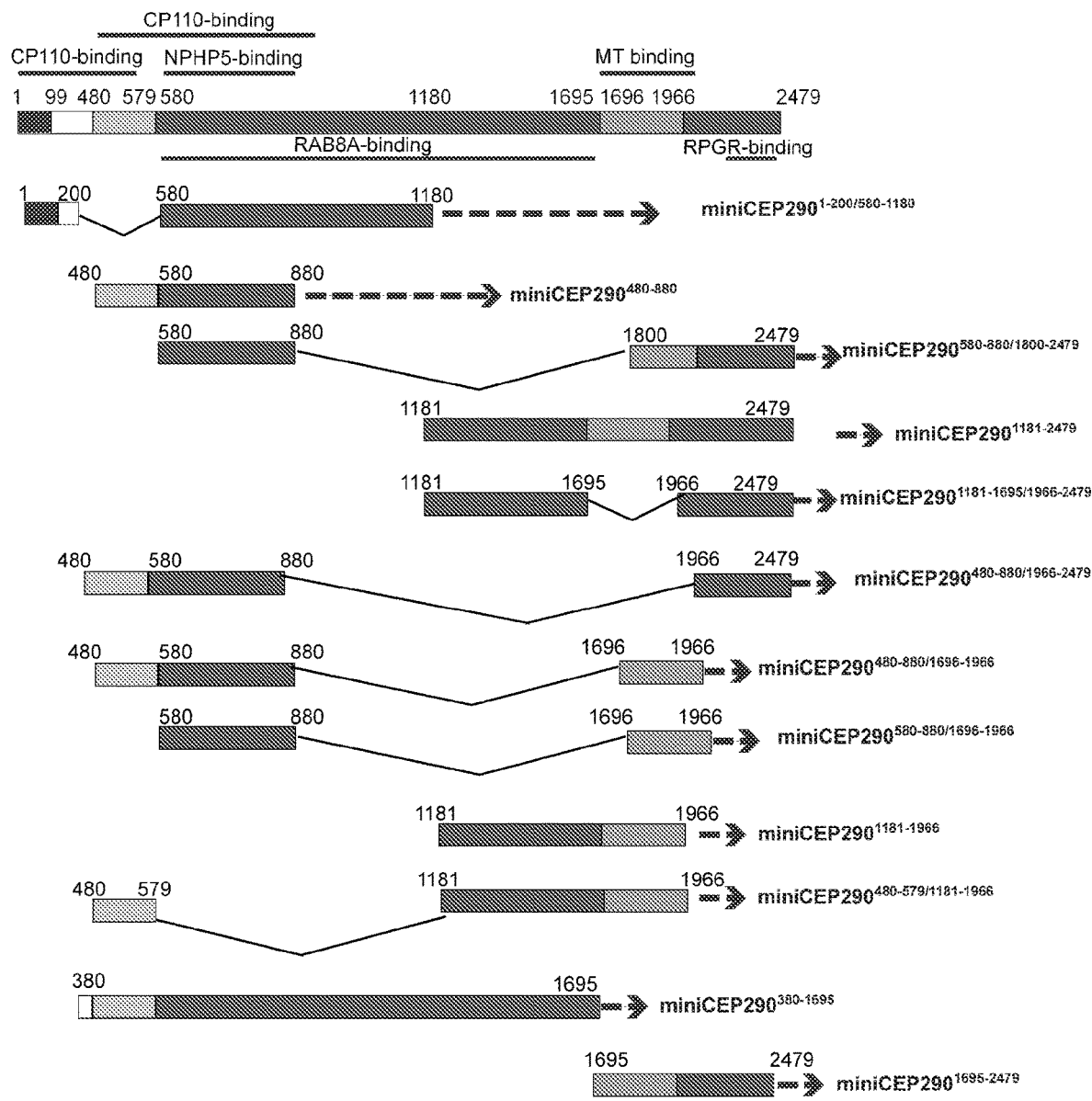

FIG. 18 is a schematic depicting additional CEP290 minigenes.

Figure 19:
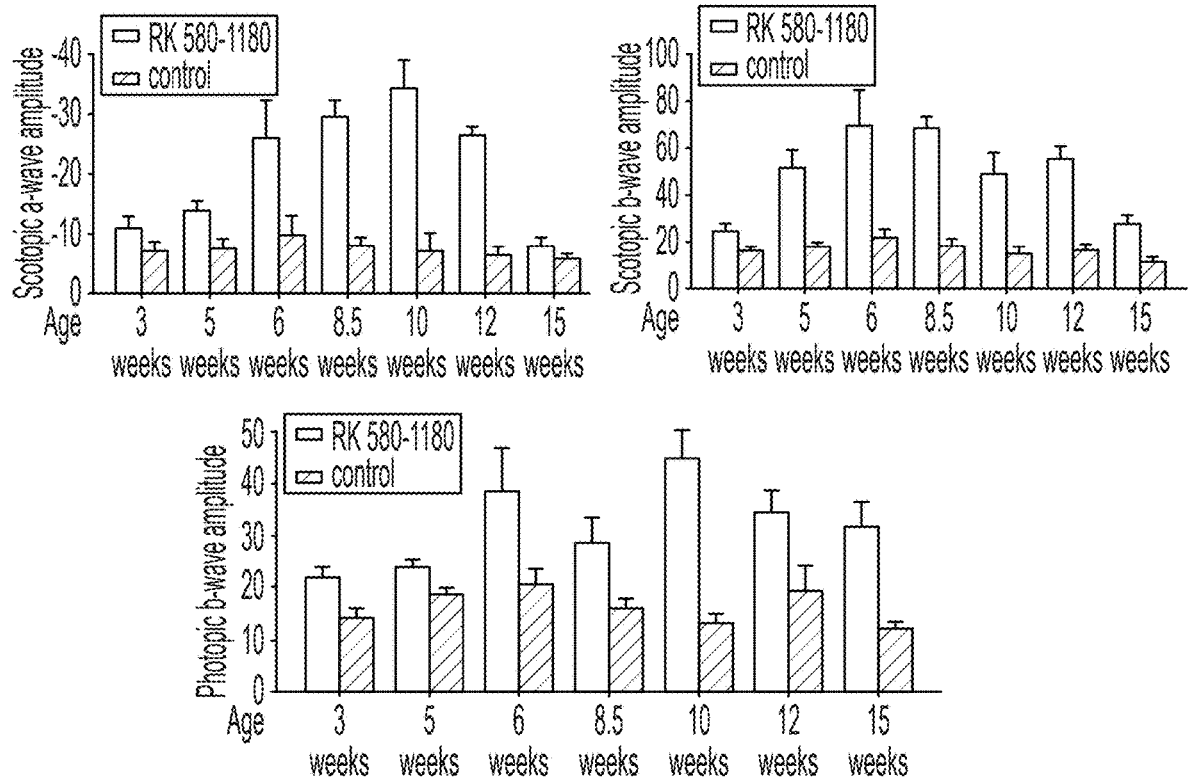

FIG. 19 shows representative data for ERG analysis of Rhodopsin Kinase (RK) promoter-driven expression of miniCEP290-580-1180 in subretinally-injected mice. Rescue effect lasted more than 10 weeks post-injection.

Figure 20:
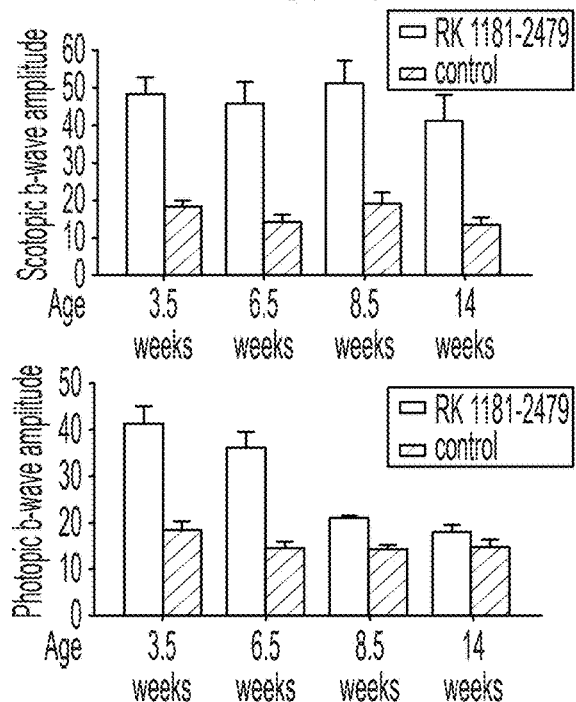

FIG. 20 shows representative data for ERG analysis of Rhodopsin Kinase (RK) promoter-driven expression of miniCEP290-1181-2479 in subretinally-injected mice. Rescue effect lasted up to 8.5 weeks post-injection.

Figure 21:
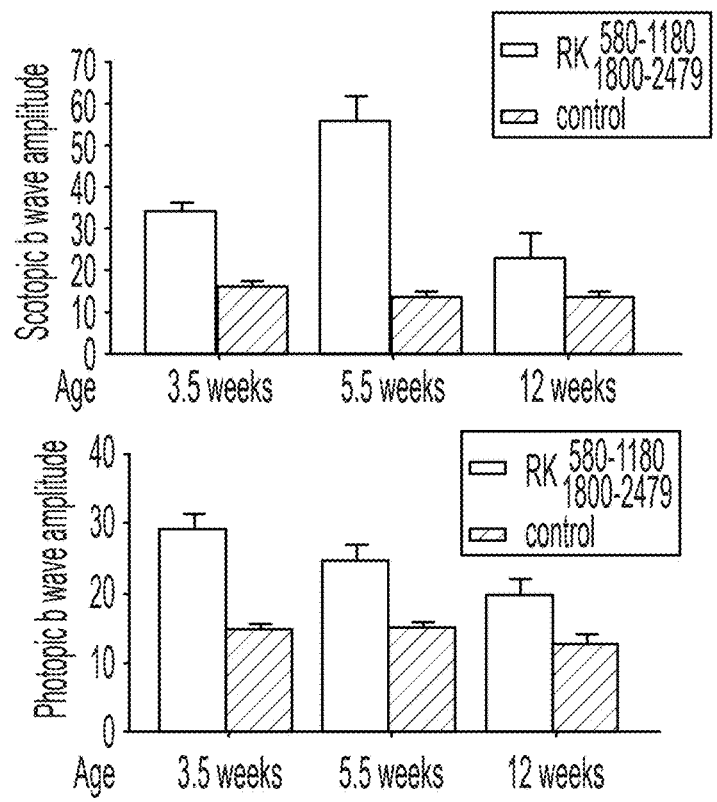

FIG. 21 shows representative data for ERG analysis of Rhodopsin Kinase (RK) promoter-driven expression of miniCEP290-580-1180/1800-2479 in subretinally-injected mice. Rescue effect lasted up to 5.5 weeks post-injection.

Figure 22:
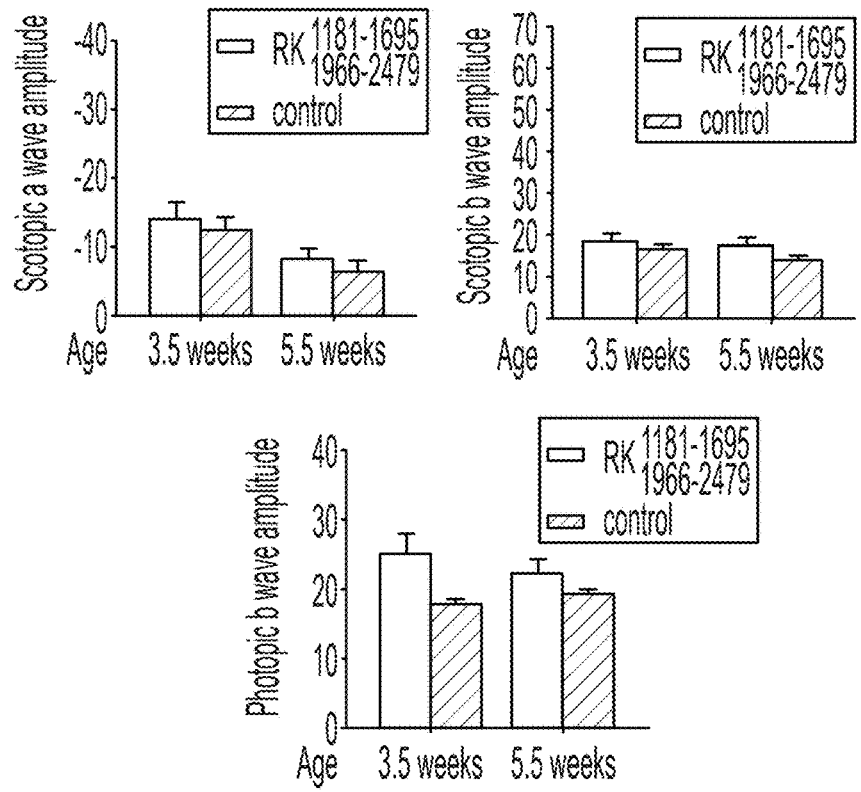

FIG. 22 shows representative data for ERG analysis of Rhodopsin Kinase (RK) promoter-driven expression of miniCEP290-1181-1695/1966-2479 in subretinally-injected mice.

Figure 23:
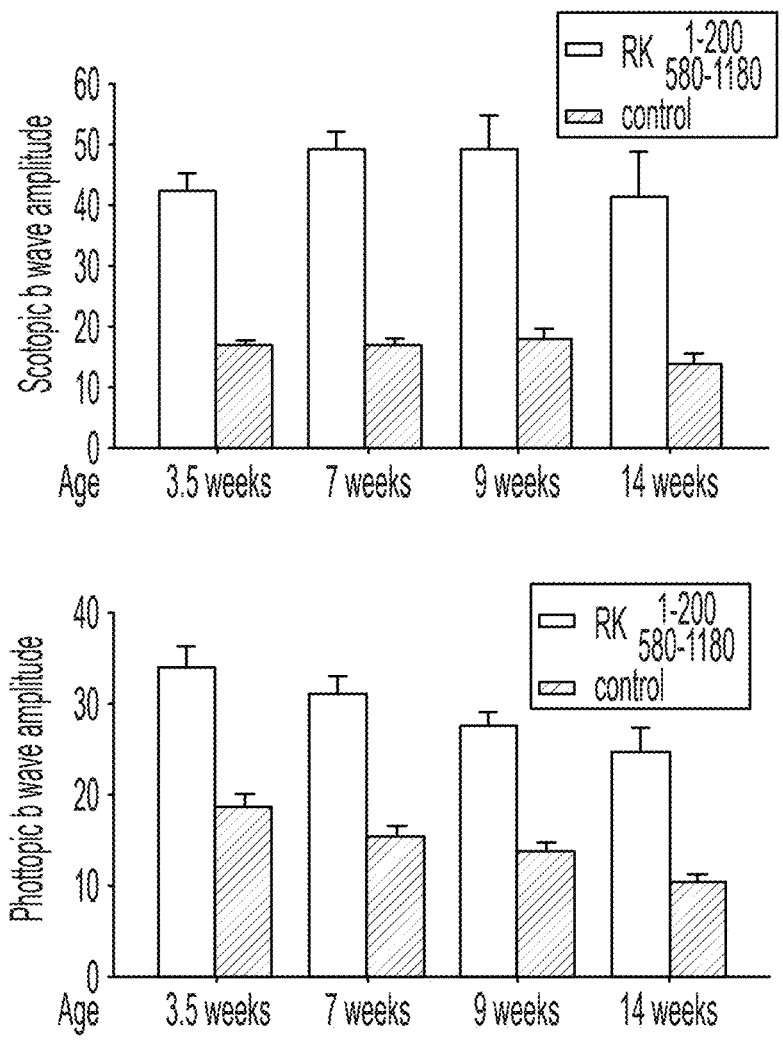

FIG. 23 shows representative data for ERG analysis of Rhodopsin Kinase (RK) promoter-driven expression of miniCEP290-1-200/580-1180 in subretinally-injected mice. Rescue effect lasted more than 14 weeks post-injection.

Figure 24A:
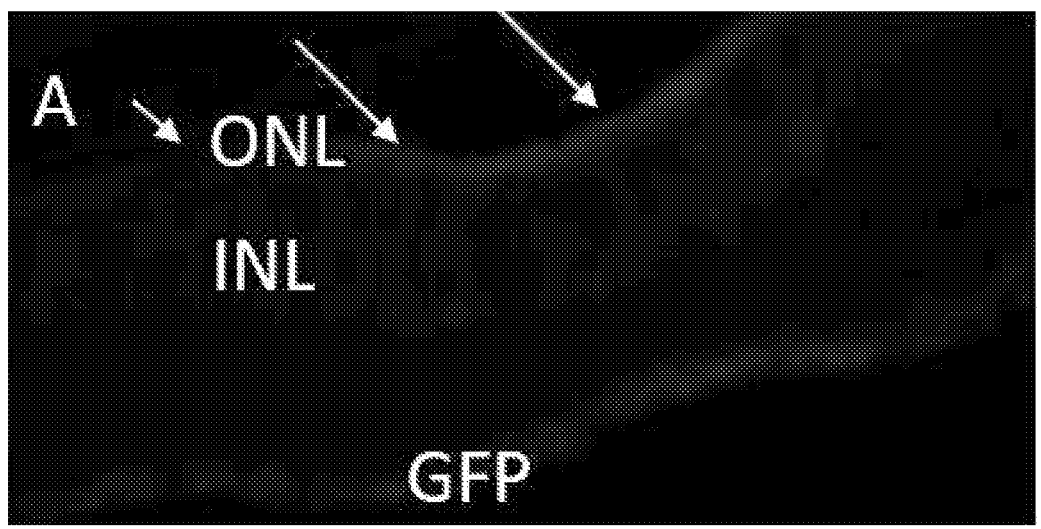
Figure 24B:
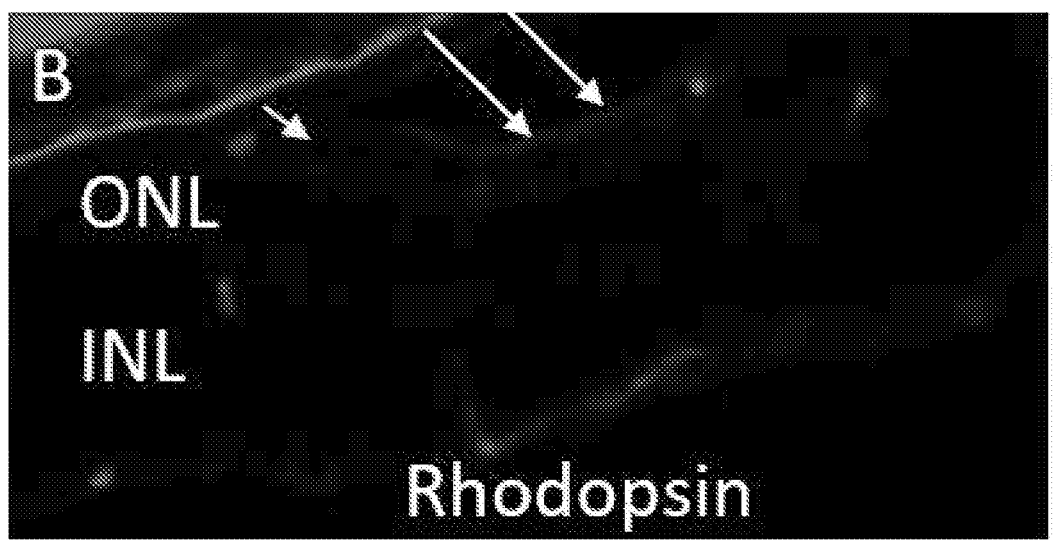
Figure 24C:
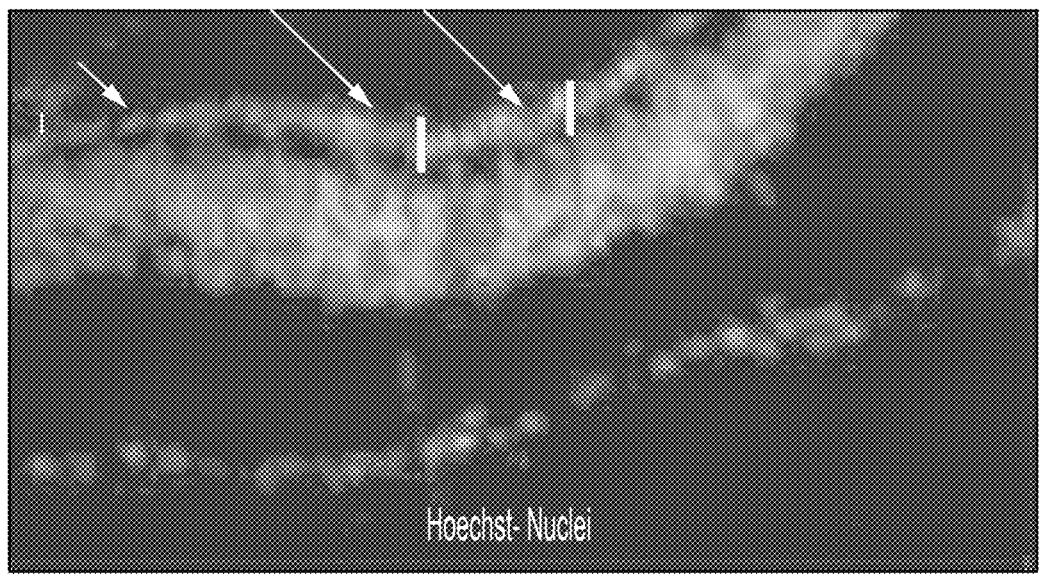

FIGS. 24A-24C show data from a morphological analysis of Rhodopsin Kinase (RK) promoter driving miniCEP290-1-200/580-1180: the minigene was subretinally delivered with AAV8 at P10 stage to Cep290$^{rd16}$ mice. The analysis was performed at 9 weeks of age. FIG. 24A shows miniCEP290-1-200/580-1180 immunofluorescence analysis of the injected retinal region (GFP; longer arrows). FIG. 24B shows data indicating improvement in rhodopsin (longer arrows) after delivery of miniCEP290-1-200/580-1180. Shorter arrows do not show GFP expression (non-transduced) and consequently exhibit undetectable rhodopsin expression. FIG. 24C shows nuclear staining data indicating more nuclear layers in the outer nuclear layer (ONL) region in the miniCEP290-1-200/580-1180-transduced area (longer arrows and longer vertical bars) as compared to the untransduced region (shorter arrow and shorter vertical bar).

Figure 25A:
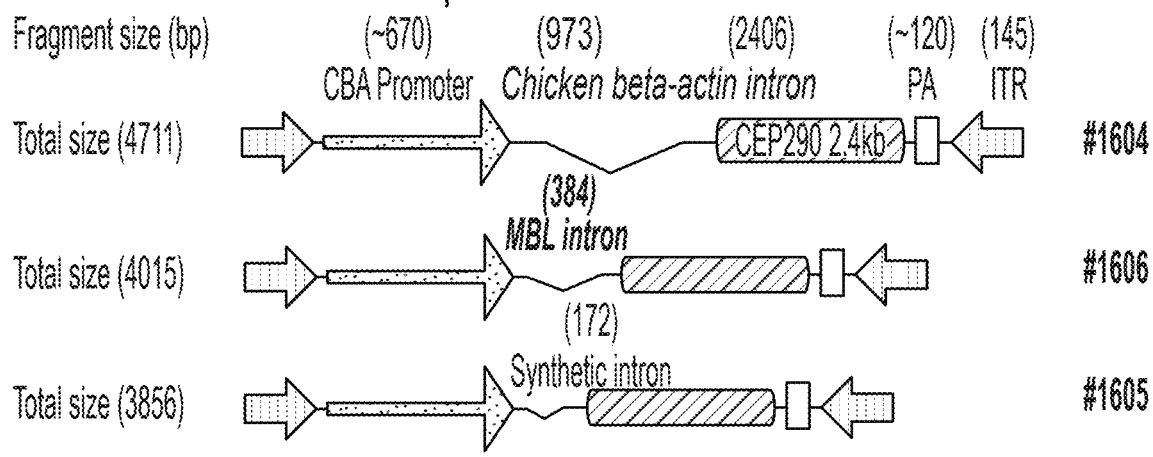
Figure 25B:
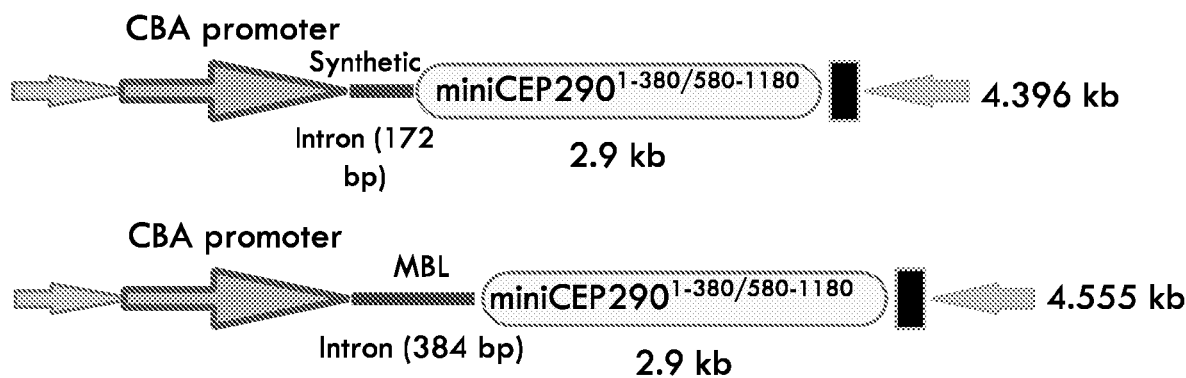
Figure 25C:
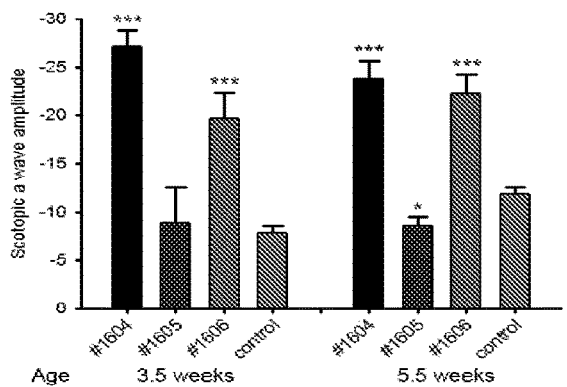
Figure 25C:
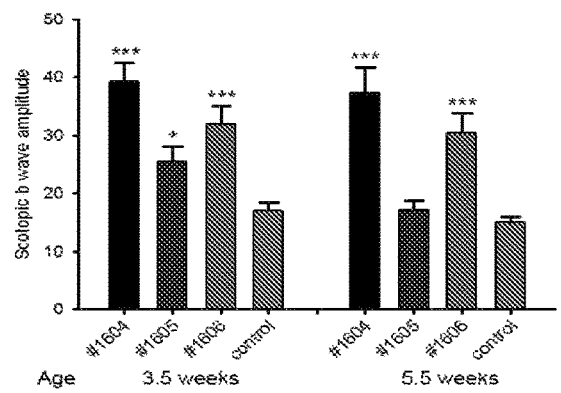
Figure 25C:
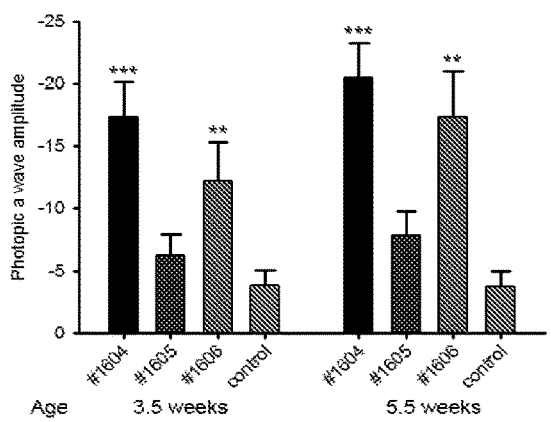
Figure 25C:
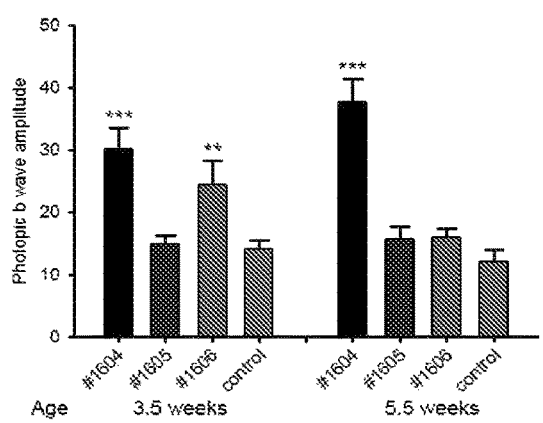

FIGS. 25A-25C show codon optimized miniCEP290 constructs. FIG. 25A shows codon optimized miniCEP290 (1-200/580-1180) constructs with different promoters and introns. FIG. 25B shows codon optimized miniCEP290 (1-380/580-1180) constructs with different promoters and introns. FIG. 25C shows representative data for codon optimized miniCEP290 (1-200/580-1180) constructs packaged into AAV5 capsid and injected subretinally into mice at P10 stage. The mice were then analyzed by ERG (both scotopic and photopic) at the ages indicated.

DETAILED DESCRIPTION

In some aspects, the disclosure relates to compositions and methods useful for treating certain genetic diseases, for example monogenic diseases, ciliopathies, etc. Monogenic diseases are diseases that are diseases that result from abnormal expression or function of a single allele of a gene. Examples of monogenic diseases include but are not limited to thalassemia, sickle cell anemia, hemophilia, cystic fibrosis, Tay Sachs disease, Fragile X syndrome, Huntington's disease, etc. Ciliopathies are genetic disorders that affect the expression or function of cellular cilia, for example ocular ciliopahies. Examples of ciliopathies include but are not limited to Alstrom syndrome, Bardet-Biedl syndrome, Joubert syndrome, Merckel syndrome, nephronophthisis, orofaciodigital syndrome, Senior-Locken syndrome, polycystic kidney disease, primary ciliary dyskinesia, and situs inversus.

The disclosure is based, in part, on isolated nucleic acids, vectors (e.g., plasmids, bacmids, etc.), and gene therapy vectors, such as viral (e.g., rAAV) vectors, comprising one or more gene fragments encoding a therapeutic gene product, such as a protein or peptide (e.g., a minigene), and optionally one or more inhibitory nucleic acids that target an endogenous gene variant (e.g., mutant) that is associated with a disease or disorder (e.g., a gene associated with a ciliopathy).

A gene therapy vector may be a viral vector (e.g., a lentiviral vector, an adeno-associated virus vector, etc.), a plasmid, a closed-ended DNA (e.g., ceDNA), etc. In some embodiments, a gene therapy vector is a viral vector. In some embodiments, an expression cassette encoding a minigene is flanked by one or more viral replication sequences, for example lentiviral long terminal repeats (LTRs) or adeno-associated virus (AAV) inverted terminal repeats (ITRS).

As used herein, "minigene" refers to an isolated nucleic acid sequence encoding a recombinant peptide or protein where one or more non-essential elements of the corresponding gene encoding the naturally-occurring peptide or protein have been removed and where the peptide or protein encoded by the minigene retains function of the corresponding naturally-occurring peptide or protein. A "therapeutic minigene" refers to a minigene encoding a peptide or protein useful for treatment of a genetic disease, for example, human centrosomal protein 290 (CEP290), dystrophin, dysferlin, Factor VIII, Amyloid precursor protein (APP), Tyrosinase (Tyr), etc. Minigenes are known in the art and are described, for example by Karpati and Acsadi (1994) *Clin Invest Med* 17(5):499-509; Plantier et al. (2001) *Thromb Haemost.* 86(2):596-603; and Xiao et al. (2007) *World J. Gastroenterol.* 13(2):244-9.

Generally, an isolated nucleic acid encoding a minigene (e.g., a therapeutic minigene) is between about 10% and about 99% (e.g., about 10%, about 15%, about 20%, about 25%, about 30%, about 40% about 50%, about 60%, about 70%, about 75%, about 80%, about 90%, about 99%, etc.) truncated with respect to a nucleic acid sequence encoding the corresponding naturally-occurring wild-type protein. For example, in some embodiments, a minigene encoding a CEP290 protein fragment is about 76% truncated (e.g., comprises about 24% of the nucleic acid sequence) compared to a wild-type CEP290 gene.

Aspects of the disclosure relate to isolated nucleic acids comprising a transgene encoding one or more CEP290 fragments. A "fragment" refers to a protein encoded by at least two discontinuous nucleotide sequence portions that are in frame with each other and encode a functional protein. A CEP290 fragment may comprise an amino acid sequence corresponding to one or more domains of a CEP290 protein (e.g., SEQ ID NO: 1) or portions thereof, for example one or more of a CP110-binding domain (or a portion thereof), NPHP5-binding domain (or a portion thereof), RAB8A-binding domain (or a portion thereof), a microtubule (MT) binding domain (or a portion thereof), and a RPGR binding domain (or a portion thereof). In some embodiments, a CP110-binding domain corresponds to amino acid positions 1-579 of a wild-type CEP290 protein (e.g., SEQ ID NO: 1). In some embodiments, a NPHP5-binding domain corresponds to amino acid positions 580-880 of a wild-type CEP290 protein (e.g., SEQ ID NO: 1). In some embodiments, a RAB8A-binding domain corresponds to amino acid positions 580-1695 of a wild-type CEP290 protein (e.g., SEQ ID NO: 1). In some embodiments, a MT-binding domain corresponds to amino acid positions 1696-1966 of a wild-type CEP290 protein (e.g., SEQ ID NO: 1). In some embodiments, a RPGR-binding domain corresponds to amino acid positions 1966 to 2479 of a wild-type CEP290 protein (e.g., SEQ ID NO: 1).

In some embodiments, an isolated nucleic acid encodes a CEP290 fragment comprising the amino acid sequence set forth in any one of SEQ ID NOs: 10-19 and 36. In some embodiments, an isolated nucleic acid comprises the nucleic acid sequence set forth in any one of SEQ ID NOs: 20-29 and 34-35. In some embodiments, an isolated nucleic acid comprises a nucleic acid sequence that is at least 70%, 80%, 90%, 95%, or 99% identical to the nucleic acid sequence set forth in any one of SEQ ID NOs: 20-29 and 34-35.

In some embodiments, the nucleic acid encodes a CEP290 protein fragment corresponding to amino acids 1-200 and 580-1180 of human CEP290. In some embodiments, the nucleic acid encodes a CEP290 fragment comprising amino acids 1-200 and 580-1180 of SEQ ID NO: 1. In some embodiments, an isolated nucleic acid comprises the nucleic acid sequence set forth in SEQ ID NO: 29 or 34. In some embodiments, the nucleic acid encodes a CEP290 fragment corresponding to the amino acid sequence as set forth in SEQ ID NO: 19.

In some embodiments, the nucleic acid encodes a CEP290 protein fragment corresponding to amino acids 1-380 and 580-1180 of human CEP290. In some embodiments, the nucleic acid encodes a CEP290 fragment comprising amino acids 1-380 and 580-1180 of SEQ ID NO: 1. In some embodiments, an isolated nucleic acid comprises the nucleic acid sequence set forth in SEQ ID NO: 35. In some embodiments, the nucleic acid encodes a CEP290 fragment corresponding to the amino acid sequence as set forth in SEQ ID NO: 36.

In some embodiments, a nucleic acid sequence encoding a CEP290 fragment is codon-optimized. In some embodiments a codon-optimized CEP290 fragment is encoded by the nucleic acid sequence set forth in SEQ ID NO: 34 or 35. In some embodiments, a codon-optimized nucleic acid sequence encodes a CEP290 minigene comprising the amino acid sequence set forth in SEQ ID NO: 19 or 36.

In some embodiments, a nucleic acid comprises an expression cassette comprising the sequence set forth in SEQ ID NO: 29 or 34 (e.g., a nucleic acid sequence encoding the amino acid sequence set forth in SEQ ID NO: 19) operably linked to a promoter (e.g., a rhodopsin kinase (RK) promoter). In some embodiments, the expression cassette is flanked by adeno-associated virus (AAV) inverted terminal repeats (ITRs). In some embodiments, the ITRs are AAV2 ITRs. In some embodiments, the nucleic acid is encapsidated by one or more AAV capsid proteins. In some embodiments, the one or more AAV capsid proteins are AAV8 or AAV5 capsid proteins.

In some aspects, the disclosure relates to an isolated nucleic acids (e.g., vectors, such as viral vectors) comprising an expression cassette comprising a first isolated nucleic acid sequence encoding a therapeutic minigene and a second isolated nucleic acid sequence encoding one or more inhibitory nucleic acids, wherein the expression cassette is flanked by viral replication sequences, and wherein the one or more inhibitory nucleic acids do not bind to the isolated nucleic acid encoding the therapeutic minigene.

In some aspects, the disclosure relates to AAV-mediated delivery of CEP290 gene fragments (e.g. encoding CEP290 protein fragments) lacking the "M region" to cells (e.g., ocular cells) of a subject having a disease or disorder characterized by a mutation or deletion of the CEP290 gene, which restores or improves cilial length and rescues or improves photoreceptor function. This discovery is surprising in view of previous disclosures, for example US 2016/0185832, which describes that the "M region" of the CEP290 gene is necessary to mediate microtubule localization and cilium formation. In some embodiments, the Examples section of this disclosure describes domains (e.g., fragments) of CEP290 protein that retain function in photoreceptors and can be delivered using the conventional AAV vectors.

Accordingly, in some aspects, the disclosure provides an isolated nucleic acid comprising: a first region comprising a first adeno-associated virus (AAV) inverted terminal repeat (ITR), or a variant thereof; and, a second region comprising a transgene encoding a CEP290 protein fragment, wherein the CEP290 protein fragment does not comprise amino acid positions 1695 to 1966 of SEQ ID NO: 1.

In some aspects, the disclosure provides an isolated nucleic acid comprising: a first region comprising a first adeno-associated virus (AAV) inverted terminal repeat (ITR), or a variant thereof; and, a second region comprising a transgene encoding a CEP290 protein fragment, wherein the CEP290 protein fragment comprises at least 500 contiguous amino acids of SEQ ID NO: 1. In some embodiments, the at least 500 contiguous amino acids comprises or consists of a sequence selected from SEQ ID NOs: 2, 3 and 4.

In some embodiments, the second region does not comprise amino acid positions 1695 to 1966 of SEQ ID NO: 1. In some embodiments, the transgene comprises no more than 1120 contiguous amino acids of SEQ ID NO: 1.

In some embodiments, the transgene comprises amino acid positions 580 to 1695 of SEQ ID NO: 1. In some embodiments, the CEP290 protein fragment encoded by the transgene comprises a sequence set forth in SEQ ID NO: 2. In some embodiments, the CEP290 protein fragment encoded by the transgene comprises amino acid positions 580 to 1180 of SEQ ID NO: 1, or amino acid positions 1181 to 1695 of SEQ ID NO: 1. In some embodiments, the CEP290 protein fragment encoded by the transgene comprises or consists of a sequence set forth in SEQ ID NO: 3 or 4. In some embodiments, the CEP290 protein fragment encoded by the transgene comprises (or consists of) amino acid positions 1 to 200 of SEQ ID NO: 1 and amino acid positions 580 to 1180 of SEQ ID NO: 1. In some embodiments, the CEP290 protein fragment encoded by the transgene comprises or consists of a sequence set forth in SEQ ID NO: 29 or 34. It should be appreciated that CEP290 protein fragments delivered by the transgene may be translated as a single fusion protein comprising two or more fragments, or as separate polypeptides.

In some embodiments, the transgene comprises or consists of a nucleic acid sequence selected from SEQ ID NO: 5, 6 and 7.

In some embodiments, a gene therapy vector further comprises one or more inhibitory nucleic acids that do not silence gene expression of the gene product encoded by the minigene but do silence gene expression of an endogenous protein corresponding to a wild-type or disease-associated variant of the protein encoded by the minigene. For example, in some embodiments, a gene therapy vector comprises a minigene encoding a CEP290 protein fragment and one or more inhibitory nucleic acids (e.g., dsRNA, siRNA, shRNA, miRNA, amiRNA, etc.) that inhibit expression of endogenously expressed CEP290 (e.g., a CEP290 mutant selected from c.2991+1655A>G, c.2249T>G, c.7341dupA, c.2118_2122dupTCAGG, c.3814C>T, c.679_680delGA, c.265dupA, c.180+1G?T, c.1550delT, c.4115_4116delTA, c.4966G>T, and c.5813_5817delCTTTA) but do not inhibit expression of the CEP290 fragment encoded by the minigene. The skilled artisan will also appreciate that, in some embodiments, one or more inhibitory nucleic acids that that inhibit expression of endogenously expressed CEP290 but do not inhibit expression of the CEP290 fragment encoded by the minigene may be administered to a subject in a manner that is separate from the gene therapy construct.

In some aspects, the CEP290 fragment is encoded by the messenger RNA. In other aspects, the CEP290 fragment is the protein delivered to the affected cells. In some embodiments one or more CEP290 fragments is delivered to affected cells by a nanoparticle or microsphere-based delivery system. In some embodiments, a nanoparticle or microsphere-based delivery system is formulated to penetrate the affected cell, for example via inclusion of a cell permeable peptide (cpp) sequence to the CEP290 fragment(s) or delivery system (e.g., nanoparticle).

Methods for Treating Ocular Ciliopathies

Aspects of the invention relate to certain protein-encoding transgenes (e.g., fragments of human CEP290) that when delivered to a subject are effective for promoting growth of ocular cilia (e.g., cilia of photoreceptors) and rescue of photoreceptor structure and function in the subject. Accordingly, methods and compositions described by the disclosure are useful, in some embodiments, for the treatment of ocular ciliopathies associated with mutations or deletions of CEP290 gene, such as Leber congenital amaurosis (LCA), Joubert syndrome, Bardet-Biedl syndrome, Meckel syndrome, Usher syndrome, and Senior-Løken syndrome.

As used herein "treat" or "treating" refers to (a) preventing or delaying onset of ocular ciliopathies associated with mutations or deletions of CEP290 gene (such as Leber congenital amaurosis (LCA), Joubert syndrome, Bardet-Biedl syndrome, Meckel syndrome, Usher syndrome, or Senior-Løken syndrome); (b) reducing severity of ocular ciliopathies associated with mutations or deletions of CEP290 gene; (c) reducing or preventing development of symptoms characteristic of ocular ciliopathies associated with mutations or deletions of CEP290 gene; (d) and/or preventing worsening of symptoms characteristic of ocular ciliopathies associated with mutations or deletions of CEP290 gene. Signs and symptoms of ocular ciliopathies associated with mutations or deletions of CEP290 gene include, for example, photoreceptor degeneration, impairment of photoreceptor function, cell death, etc.

Methods for delivering a transgene (e.g., a gene encoding a CEP290 protein or a fragment thereof) to a subject are provided by the disclosure. The methods typically involve administering to a subject an effective amount of an isolated nucleic acid encoding a CEP290 protein fragment, or a rAAV comprising a nucleic acid for expressing a CEP290 protein fragment.

The human CEP290 gene consists of 52 exons, which encode for a protein of ~290 kDa (2479 amino acids). In some embodiments, the human CEP290 gene encodes a protein comprising the amino acid sequence set forth in SEQ ID NO: 1, and as described as GenBank Accession Number (NP_079390.3). In some embodiments, the human CEP290 gene (e.g., NCBI Reference Sequence: NM_025114.3) comprises a sequence set forth in SEQ ID NO: 8.

CEP290 is a multidomain protein and contains numerous coiled-coil domains distributed over the entire length of the protein. In addition, the CEP290 protein contains membrane and microtubule-binding domains and myosin-tail homology domain. Typically, CEP290 predominantly localizes to the centrosomes and transition zone of primary cilia and to the CC of photoreceptors. Previous publications have observed that the domain of CEP290 that localizes the protein to centrosomes (e.g., the "M region" of the CEP290 gene, as described in US 2016/0185832) is necessary to mediate microtubule localization and cilium formation. In some embodiments, the "M region" refers to amino acid residues 1695 to 1966 of human CEP290, as described in US 2016/0185832.

Aspects of the instant disclosure are based, in part, on the surprising discovery that certain CEP290 fragments lacking the "M" region mediate effective rescue of cilial formation and photoreceptor rescue when expressed in a subject in need thereof, for example via administration of a viral vector (e.g., rAAV).

Accordingly in some aspects, the disclosure provides a transgene encoding a CEP290 protein fragment, wherein the CEP290 protein fragment does not comprise amino acid positions 1695 to 1966 (e.g., a region encompassing the "M" region) of SEQ ID NO: 1. A "CEP protein fragment" refers to a 2 to 2479 (e.g., any integer between 2 and 2479) amino acid portion of a CEP290 protein. In some embodiments, the CEP protein fragment comprises a contiguous amino acid portion (e.g., amino acids 580 to 1180) of CEP290 (e.g., SEQ ID NO: 1). In some embodiments, the CEP protein fragment comprises one or more (e.g., 2, 3, 4, 5, 6, 7, 8, 9, 10, or more) interrupted amino acid portions (e.g., amino acids 1 to 10, 580 to 1180 and 1967 to 2470) of CEP290 (e.g., SEQ ID NO: 1). In some embodiments, a CEP protein fragment comprises a methionine (M) amino acid residue at its N-terminus.

In some embodiments, the CEP290 protein fragment comprises at least 500 contiguous amino acids of SEQ ID NO: 1. For example, in some embodiments, the CEP290 protein fragment comprises (or consists of) amino acids 580 to 1695, or amino acids 580 to 1180, or amino acids 1181 to 1695, of CEP290 (e.g., SEQ ID NO: 1). In some embodiments, the at least 500 contiguous amino acids comprises or consists of a sequence selected from SEQ ID NOs: 2, 3 and 4.

In some embodiments, a CEP290 protein comprises amino acids 480 to 579 of CEP290 (e.g., SEQ ID NO: 1). In some embodiments, a CEP290 protein fragment comprises amino acids 480 to 580 of CEP290 (e.g., SEQ ID NO: 1). In some embodiments, a CEP290 protein comprises amino acids 480 to 880 of CEP290 (e.g., SEQ ID NO: 1). In some embodiments, a CEP290 protein comprises amino acids 580 to 880 of CEP290 (e.g., SEQ ID NO: 1). In some embodiments, a CEP290 protein comprises amino acids 580 to 1180 of CEP290 (e.g., SEQ ID NO: 1). In some embodiments, a CEP290 protein comprises amino acids 1181 to 1695 of CEP290 (e.g., SEQ ID NO: 1). In some embodiments, a CEP290 protein comprises amino acids 1181 to 1966 of CEP290 (e.g., SEQ ID NO: 1). In some embodiments, a CEP290 protein comprises amino acids 1181 to 2479 of CEP290 (e.g., SEQ ID NO: 1). In some embodiments, a CEP290 protein comprises amino acids 1696 to 1966 of CEP290 (e.g., SEQ ID NO: 1). In some embodiments, a CEP290 protein comprises amino acids 1966 to 2479 of CEP290 (e.g., SEQ ID NO: 1). In some embodiments, a CEP290 protein comprises amino acids 1800 to 2479 of CEP290 (e.g., SEQ ID NO: 1). In some embodiments, a CEP290 fragment comprises two or more (e.g., 2, 3, 4, 5, 6, or more) of the foregoing fragments. In some embodiments, a CEP290 fragment comprises two or more (e.g., 2, 3, 4, 5, 6, or more) of the foregoing fragments that are not contiguous in SEQ ID NO: 1. In some embodiments, a CEP290 protein fragment comprises or consists of the amino acid sequence set forth in any one of SEQ ID NOs: 10-19. In some embodiments, a CEP290 protein comprises amino acids 1-200 and 580-1180 of human CEP290. In some embodiments, a CEP290 protein comprises amino acids 1-200 and 580-1180 of SEQ ID NO: 1. In some embodiments, a CEP290 protein comprises the amino acid sequence set forth in SEQ ID NO: 19. In some embodiments, a CEP290 protein is encoded by the nucleic acid sequence set forth in SEQ ID NO: 29 or 34. In some embodiments, a CEP290 protein comprises amino acids 1-380 and 580-1180 of human CEP290. In some embodiments, a CEP290 protein comprises amino acids 1-380 and 580-1180 of SEQ ID NO: 1. In some embodiments, a CEP290 protein comprises the amino acid sequence set forth in SEQ ID NO: 36. In some embodiments, a CEP290 protein is encoded by the nucleic acid sequence set forth in SEQ ID NO: 35.

In some embodiments, the disclosure provides a transgene comprising a nucleic acid (e.g., isolated nucleic acid) encoding a CEP290 protein fragment. In some embodiments, the transgene comprises or consists of a nucleic acid sequence selected from SEQ ID NO: 5, 6 and 7. In some embodiments, the transgene comprises or consists of a nucleic acid sequence selected from any one of SEQ ID NOs: 20-29.

In some embodiments, the transgenes encoding a CEP290 fragment described by the disclosure mediate cilial growth and photoreceptor rescue, and are therefore useful for treating ciliopathies, for example ocular ciliopathies. Generally, a "ciliopathy" refers to a disease or disorder characterized by defective (or lack of) protein function resulting in abnormal formation or function of cilia in a cell of a subject. An "ocular ciliopathy" is a ciliopathy where abnormal formation or function of cilia occurs in ocular cells (e.g., rods, cones, photoreceptor cells, etc.) of a subject, typically resulting in retinal degeneration, loss of vision and blindness. Examples of ciliopathies include but are not limited to earlier onset developmental anomalies such as Meckel Gruber Syndrome and Joubert Syndrome, to relatively later onset diseases, such as Bardet-Biedl Syndrome, Senior-Loken Syndrome, and Usher Syndrome. In some embodiments, retinal dystrophies (e.g., due to an ocular ciliopathy) are more commonly presented in a non-syndromic manner.

In some embodiments, the ocular ciliopathy is Leber congenital amaurosis (LCA). Generally, LCA is a clinically and genetically heterogeneous disease with early onset severe retinal degeneration starting either at birth or by 5-7 years of age. In some embodiments, the LCA is LCA1, LCA2, LCA3, LCA4, LCA5, LCA6, LCA7, LCA8, LCA9, LCA10, LCA11, LCA12, LCA13, LCA14, LCA15, LCA16, or LCA17. In some embodiments, the LCA is LCA10 (e.g., LCA associated with one or more muations in a CEP290 gene). Generally, a mutation or mutations in CEP290 account for >26% of LCA (LCA10; OMIM 611755). In some embodiments, LCA is characterized by a deletion of the CEP290 gene in a subject. Generally, a mutation in CEP290 that results in LCA may be an intronic mutation, a nonsense mutation, a frameshift mutation, a missense mutation, or any combination thereof. Examples of CEP290 gene mutations associated with LCA include but are not limited to c.2991+1655A>G, c.2249T>G, c.7341dupA, c.2118_2122dupTCAGG, c.3814C>T, c.679_680delGA, c.265dupA, c.180+1G?T, c.1550delT, c.4115_4116delTA, c.4966G>T, and c.5813_5817delCTTTA, for example as described by den Hollander et al. (2006) Am J Hum Genet. 79(3):556-561. In some embodiments, the mutation in CEP290 is a deep intronic mutation, for example at position c.2991+1655A. In some embodiments, the deep intronic mutation is c.2991+1655A>G. In some embodiments, the severity of an ocular ciliopathy is modified by CEP290 mutations. For example, as described in Rao et al. (2016). Hum Mol Genet, 25(10):2005-2012. Deletions and or mutations in a CEP290 gene of a subject (e.g., a subject having or suspected of having a ciliopathy associated with a deletion or mutation of CEP290 gene) may be identified from a sample obtained from the subject (e.g., a DNA sample, RNA sample, blood sample, or other biological sample) by any method known in the art. For example, in some embodiments, a nucleic acid (e.g., DNA, RNA, or a combination thereof) is extracted from a biological samples obtained from a subject and nucleic acid sequencing is performed in order to identify a mutation in the CEP290 gene. Examples of nucleic acids sequencing techniques include but are not limited to Maxam-Gilbert sequencing, pyrosequencing, chain-termination sequencing, massively parallel signature sequencing, single-molecule sequencing, nanopore sequencing, Illumina sequencing, etc. In some embodiments, a mutation or deletion in CEP290 gene is detected indirectly, for example by quantifying CEP290 protein expression (e.g., by Western blot) or function (e.g., by analyzing cilial growth, structure, function, etc.), or by direct sequencing of the DNA and comparing the sequence obtained to a control DNA sequence (e.g., a wild-type CEP290 DNA sequence).

In some aspects, the disclosure provides a method for treating an ocular ciliopathy in a subject in need thereof, the method comprising administering to a subject having an ocular ciliopathy a therapeutically effective amount of an isolated nucleic acid, or a rAAV, as described by the disclosure. In some embodiments, the administration is subretinal administration.

An "effective amount" of a substance is an amount sufficient to produce a desired effect. In some embodiments, an effective amount of an isolated nucleic acid (e.g., an isolated nucleic acid comprising a transgene encoding a CEP290 protein fragment as described herein) is an amount sufficient to transfect (or infect in the context of rAAV mediated delivery) a sufficient number of target cells of a target tissue of a subject. In some embodiments, a target tissue is ocular tissue (e.g., photoreceptor cells, rod cells, cone cells, retinal ganglion cells, retinal cells, retinal pigmented epithelial cells, etc.). In some embodiments, an effective amount of an isolated nucleic acid (e.g., which may be delivered via an rAAV) may be an amount sufficient to have a therapeutic benefit in a subject, e.g., to increase or supplement the expression of a gene or protein of interest (e.g., CEP290), to improve in the subject one or more symptoms of disease (e.g., a symptom of an ocular ciliopathy, such as LCA), etc., such as light perception, photoreceptor function (electroretinography) and structure of the retina. The effective amount will depend on a variety of factors such as, for example, the species, age, weight, health of the subject, and the tissue to be targeted, and may thus vary among subject and tissue as described elsewhere in the disclosure.

Isolated Nucleic Acids

In some aspects, the disclosure provides isolated nucleic acids that are useful for expressing human CEP290, or a fragment thereof. A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

The isolated nucleic acids of the invention may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more proteins (e.g., human CEP290, or a fragment thereof). The transgene may also comprise a region encoding, for example, a miRNA binding site, and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. In some embodiments, one or more additional nucleotide sequences are found between the transgene and the 5' and/or 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV5, AAV6, AAV6.2, AAV7, AAV8, AAV9, AAV10, AAV11, and variants thereof. In some embodiments, the isolated nucleic acid comprises a region (e.g., a first region) encoding an AAV2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV5, AAV6, AAV6.2, AAV7, AAV8, AAV9, AAV10, AAV11, and variants thereof. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example as described by McCarthy (2008) *Molecular Therapy* 16(10): 1648-1656.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences (e.g., Nrl-response element, CRX-response element, RET-1, etc.); efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., miRNA).

A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, Petal., Human Gene Therapy, 2000; 11: 1921-1931.; and Klump, H et al., Gene Therapy, 2001; 8: 811-817).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is a CB6 promoter. In some embodiments, a transgene comprises a CB6 promoter operably linked to the nucleic acid sequence set forth in any one of SEQ ID NOs: 5-7, 20-29, and 34-35. In some embodiments, a promoter is an enhanced chicken β-actin promoter. In some embodiments, a promoter is a U6 promoter. In some embodiments, a promoter is a chicken beta-actin (CBA) promoter. In some embodiments, a transgene comprises a CBA promoter operably linked to the nucleic acid sequence set forth in any one of SEQ ID NOs: 5-7, 20-29, and 34-35. In some embodiments, a longer version of a CB promoter is used. In some embodiments, longer versions of the CB promoter enhance expression of a transgene.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the tissue-specific promoter is an eye-specific promoter. Examples of eye-specific promoters include but are not limited to a retinoschisin promoter, K12 promoter, a rhodopsin promoter, a rod-specific promoter, a cone-specific promoter, a rhodopsin kinase promoter, a GRK1 promoter, an interphotoreceptor retinoid-binding protein proximal (IRBP) promoter, retinal pigmented epithelium-specific promoter (e.g., RPE65, Best1, etc.) and an opsin promoter (e.g., a red opsin promoter, a blue opsin promoter, etc.). In some embodiments, a transgene comprises an IRBP promoter operably linked to the nucleic acid sequence set forth in any one of SEQ ID NOs: 5-7, 20-29, and 34-35.

In some embodiments, a transgene comprises a rhodopsin kinase promoter operably linked to the nucleic acid sequence set forth in SEQ ID NO: 29 or 34. In some embodiments, a transgene comprises a rhodopsin kinase promoter operably linked to the nucleic acid sequence encoding the amino acids 1-200 and 580-1180 of human CEP290. In some embodiments, a transgene comprises a rhodopsin kinase promoter operably linked to the nucleic acid sequence encoding the amino acids 1-200 and 580-1180 of SEQ ID NO: 1. In some embodiments, a transgene comprises a rhodopsin kinase promoter operably linked to the nucleic acid sequence encoding the amino acid sequence set forth in SEQ ID NO: 19.

In some embodiments, a transgene comprises a rhodopsin kinase promoter operably linked to the nucleic acid sequence set forth in SEQ ID NO: 35. In some embodiments, a transgene comprises a rhodopsin kinase promoter operably linked to the nucleic acid sequence encoding the amino acids 1-380 and 580-1180 of human CEP290. In some embodiments, a transgene comprises a rhodopsin kinase promoter operably linked to the nucleic acid sequence encoding the amino acids 1-380 and 580-1180 of SEQ ID NO: 1. In some embodiments, a transgene comprises a rhodopsin kinase promoter operably linked to the nucleic acid sequence encoding the amino acid sequence set forth in SEQ ID NO: 36.

Aspects of the disclosure relate to isolated nucleic acids comprising a transgene encoding one or more CEP290 fragments and a photoreceptor-specific promoter. A photoreceptor-specific promoter may target rod photoreceptor cells, cone photoreceptor cells, or rod and cone photoreceptor cells. In some embodiments, the photoreceptor-specific promoter is a GRK promoter (e.g., a GRK promoter). In some embodiments, a transgene comprises a GRK promoter operably linked to the nucleic acid sequence set forth in any one of SEQ ID NOs: 5-7, 20-29, and 34-35.

In some embodiments, a transgene further comprises one or more (e.g., 1, 2, 3, 4, 5, or more) introns. The length of an intron may vary. In some embodiments, an intron ranges from between about 100 nucleotides in length to about 1000 nucleotides in length (e.g., between 100 and 500, 250 and 700, 500 and 1000, etc.). In some embodiments, an intron comprises a chicken beta-actin (CBA) intron, for example as set forth in SEQ ID NO: 37. In some embodiments, an intron comprises a synthetic intron, for example an intron comprising the sequence set forth in SEQ ID NO: 38. In some embodiments, an intron comprises a MBL intron, for example as set forth in SEQ ID NO: 39. In some embodiments, an intron is positioned between a promoter (e.g., a CBA promoter, etc.) and a miniCEP290 protein coding sequence (e.g., a sequence set forth in any one of SEQ ID NOs: 5-7, 20-29, and 34-35).

In some aspects, the disclosure relates to an rAAV vector comprising an expression cassette comprising a nucleic acid encoding the sequence set forth in SEQ ID NO: 29 or 34 (e.g., a nucleic acid sequence encoding the amino acid sequence set forth in SEQ ID NO: 19) operably linked to a rhodopsin kinase (RK) promoter, wherein the expression cassette is flanked by AAV2 ITRs. In some embodiments, the rAAV vector is encapsidated by one or more AAV capsid proteins. In some embodiments, the one or more AAV capsid proteins are AAV8 capsid proteins or AAV5 capsid proteins.

In some embodiments, a promoter is a RNA polymerase III (pol III) promoter. Non-limiting examples of pol III promoters include U6 and H1 promoter sequences. In some embodiments, a promoter is a RNA polymerase II (pol II) promoter. Non-limiting examples of pol II promoters include T7, T3, SP6, RSV, and cytomegalovirus promoter sequences. In some embodiments, a pol III promoter sequence drives expression of one or more inhibitory nucleic acids and a pol II promoter sequence drives expression of a minigene.

Recombinant Adeno-Associated Viruses (rAAVs)

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

In some aspects, the disclosure relates to an rAAV comprising (i) a nucleic acid (e.g., rAAV vector) comprising an expression cassette comprising a nucleic acid encoding the sequence set forth in SEQ ID NO: 29 or 34 (e.g., a nucleic acid sequence encoding the amino acid sequence set forth in SEQ ID NO: 19) operably linked to a rhodopsin kinase (RK) promoter, wherein the expression cassette is flanked by AAV2 ITRs, and (ii) one or more AAV capsid proteins. In some embodiments, the one or more capsid proteins are AAV5 or AAV8 capsid proteins.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV2, AAV3, AAV4, AAV5, AAV6, AAV7, AAV8, AAVrh8, AAV9, and AAV10. In some embodiments, an AAV capsid protein is of a serotype derived from a non-human primate, for example AAVrh8 serotype. In some embodiments, the AAV capsid protein is of a serotype that has tropism for the eye of a subject, for example an AAV (e.g., AAV5, AAV6, AAV6.2, AAV7, AAV8, AAV9, AAVrh.8, AAVrh.10, AAVrh.39 and AAVrh.43) that transduces ocular cells of a subject more efficiently than other vectors. In some embodiments, an AAV capsid protein is of an AAV8 serotype or an AAV5 serotype. In some embodiments, the AAV capsid protein comprises the sequence set forth in SEQ ID NO: 9.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a protein (e.g., a CEP290 protein fragment). In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene.

The foregoing methods for packaging recombinant vectors in desired AAV capsids to produce the rAAVs of the disclosure are not meant to be limiting and other suitable methods will be apparent to the skilled artisan.

Delivery of CEP290 Transgenes to the Eye

Methods for delivering a transgene to ocular (e.g., photoreceptors, such as rod cells or cone cells, retinal cells, retinal pigmented epithelial cells, etc.) tissue in a subject are provided herein. The methods typically involve administering to a subject an effective amount of an isolated nucleic acid, rAAV, or composition comprising a nucleic acid for expressing a transgene (e.g., a CEP290 protein fragment) in the subject. A subject may be any suitable mammalian organism. In some embodiments, a subject is a human. Additional examples of subjects include mouse, rat, non-human primate, pig, dog, cat, or horse subjects.

An "effective amount" of a rAAV is an amount sufficient to infect a sufficient number of cells of a target tissue in a subject. In some embodiments, a target tissue is ocular (e.g., photoreceptor, retinal, retinal pigmented epithelium, etc.) tissue. An effective amount may be an amount sufficient to have a therapeutic benefit in a subject, e.g., to improve in the subject one or more symptoms of disease, e.g., a symptom of an ocular ciliopathy (e.g., an ocular ciliopathy associated with a deletion or mutation of CEP290 gene, such as LCA). In some cases, an effective amount may be an amount sufficient to produce a stable somatic transgenic animal model. The effective amount will depend on a variety of factors such as, for example, the species, age, weight, health of the subject, and the ocular tissue to be targeted, and may thus vary among subject and tissue.

An effective amount may also depend on the rAAV used. The invention is based, in part on the recognition that rAAV comprising capsid proteins having a particular serotype (e.g., AAV5, AAV6, AAV6.2, AAV7, AAV8, AAV9, AAVrh.8, AAVrh.10, AAVrh.39, and AAVrh.43) mediate more efficient transduction of ocular (e.g., photoreceptor, retinal, etc.) tissue that rAAV comprising capsid proteins having a different serotype. Thus in some embodiments, the rAAV comprises a capsid protein of an AAV serotype selected from the group consisting of: AAV5, AAV6, AAV6.2, AAV7, AAV8, AAV9, AAVrh.8, AAVrh.10, AAVrh.39, and AAVrh.43. In some embodiments, the rAAV comprises a capsid protein of AAV8 serotype (SEQ ID NO: 9). In some embodiments, the capsid protein comprises an amino acid sequence that is at least 70%, at least 80%, at least 90%, at least 95%, or at least 99% identical to SEQ ID NO: 9. In some embodiments, the capsid protein is AAV5 capsid protein.

In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

An effective amount may also depend on the mode of administration. For example, targeting an ocular (e.g., photoreceptor, retinal, etc.) tissue by intrastromal administration or subcutaneous injection may require different (e.g., higher or lower) doses, in some cases, than targeting an ocular (e.g., photoreceptor, retinal, etc.) tissue by another method (e.g., systemic administration, topical administration, subretinal administration, etc.). In some embodiments, intrastromal injection (IS) of rAAV having certain serotypes (e.g., AAV5, AAV6, AAV6.2, AAV7, AAV8, AAV9, AAVrh.8, AAVrh.10, AAVrh.39, and AAVrh.43) mediates efficient transduction of ocular (e.g., corneal, photoreceptor, retinal, etc.) cells. Thus, in some embodiments, the injection is intrastromal injection (IS). In some embodiments, the administration is via injection, optionally subretinal injection or intravitreal injection. In some embodiments, the injection is subretinal injection. In some embodiments, the injection is superchoroidal injection. In some embodiments, the injection is topical administration (e.g., topical administration to an eye). In some cases, multiple doses of a rAAV are administered.

Without wishing to be bound by any particular theory, efficient transduction of ocular (e.g., photoreceptor, retinal, retinal pigmented epithelial, etc.) cells by rAAV described herein may be useful for the treatment of a subject having an ocular disease (e.g., an ocular ciliopathy). Accordingly, methods and compositions for treating ocular disease are also provided herein. In some aspects, the disclosure provides a method for treating an ocular ciliopathy (e.g., an ocular ciliopathy associated with a deletion or mutation of CEP290 gene), the method comprising: administering to a subject having or suspected of having an ocular ciliopathy an effective amount of rAAV, wherein the rAAV comprises (i) a capsid protein having a serotype selected from the group consisting of AAV5, AAV6, AAV6.2, AAV7, AAV8, AAV9, AAVrh.8, AAVrh.10, AAVrh.39, and AAVrh.43, and (ii) a nucleic acid comprising a promoter operably linked to a transgene (e.g., a transgene encoding a CEP290 protein fragment as described by the disclosure).

In some embodiments, administration of a rAAV (or isolated nucleic acid) as described by the disclosure results in transduction of a cell or cells comprising a cilium, optionally a photoreceptor sensory cilium. The photoreceptor (PR) sensory cilium is nucleated from the basal body at the apical surface of the inner segment. As the microtubules extend, they form a doublet microtubule structure, called the connecting cilium (CC). The CC is analogous to the transition zone of a prototypic cilium and extends into the outer segment (OS) of the photoreceptor cell. The CC is acts as a conduit for unidirectional or bidirectional transport of cargo moieties between the inner and the outer segments. The CC also acts as a 'gatekeeper' to regulate the entry or exit of the cargo, which aids in the maintenance of its unique composition. In some embodiments, administration of a rAAV (or isolated nucleic acid) as described by the disclosure results in growth or formation of a photoreceptor sensory cilium, a connecting cilium, or a combination thereof.

In some embodiments, delivery of a rAAV (or isolated nucleic acid) as described by the disclosure, for example miniCEP290-1-200/580-1180, results in improved structural and/or functional rescue (e.g., as measured by ERG, immunofluorescence analysis, etc.) relative to previously described miniCEP290 vectors (e.g., miniCEP290-580-1180). In some embodiments, delivery of the rAAV improves structural and/or functional rescue by between 2-fold and 100-fold (e.g., 2, 3, 4, 5, 10, 20, 25, 50, 75, 100-fold). In some embodiments, delivery of the rAAV improves structural and/or functional rescue of more than 100-fold (e.g., 100-fold, 200-fold, 300-fold, 400-fold, 500-fold, etc.).

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human.

Delivery of the rAAVs to a mammalian subject may be by, for example, intraocular injection, subretinal injection, superchoroidal injection, or topical administration (e.g., eye drops). In some embodiments, the intraocular injection is intrastromal injection, subconjunctival injection, or intravitreal injection. In some embodiments, the injection is not topical administration. Combinations of administration methods (e.g., topical administration and intrastromal injection) can also be used.

The compositions of the disclosure may comprise an rAAV alone, or in combination with one or more other viruses (e.g., a second rAAV encoding having one or more different transgenes, such as a plurality of rAAVs where each rAAV encodes a different CEP290 fragment). In some embodiments, a composition comprises 1, 2, 3, 4, 5, 6, 7, 8, 9, 10, or more different rAAVs each having one or more different transgenes. The skilled artisan recognizes that in some embodiments, a subject is administered a plurality of isolated nucleic acids (or vectors, such as plasmids, lentiviral vectors, etc.), where each nucleic acid of the plurality encodes a different CEP290 fragment.

In some embodiments, a composition further comprises a pharmaceutically acceptable carrier. Suitable carriers may be readily selected by one of skill in the art in view of the indication for which the rAAV or composition is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions (e.g., compositions comprising one or more rAAVs) are administered in sufficient amounts to transfect the cells of a desired tissue (e.g., ocular tissue, such as photoreceptor, retinal, etc., tissue) and to provide sufficient levels of gene transfer and expression without undue adverse effects. Examples of pharmaceutically acceptable routes of administration include, but are not limited to, direct delivery to the selected organ (e.g., subretinal delivery to the eye), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of an rAAV is an amount sufficient to target infect an animal, target a desired tissue. The effective amount will depend primarily on factors such as the species, age, weight, health of the subject, and the tissue to be targeted, and may thus vary among animal and tissue. In some embodiments, the volume of an rAAV (e.g., a composition comprising an rAAV) administered ranges from about 10 µl to about 1000 µl per eye. In some embodiments, an rAAV is administered at a dosage between about $10^{11}$ to about $10^{13}$ genome copies per eye, or from about $10^{11}$ to about $10^{14}$ rAAV genome copies/ml. In some embodiments, an effective amount is produced by multiple doses of an rAAV.

In some embodiments, a dose of rAAV is administered to a subject no more than once per calendar day (e.g., a 24-hour period). In some embodiments, the dose is administered to a subject only once in the lifetime of the subject. In some embodiments, a single dose is administered in each eye of the subject only once in the lifetime of the subject. In some embodiments, administration is bilateral administration, and the doses may be administered about 1 week, about 2 weeks, about 3 weeks, about 4 weeks, about 1 month, or about 2 months apart. In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year). In some embodiments, a dose of rAAV is administered postnatally. In some embodiments, a dose of rAAV is administered postnatally between day 7 and day 13. In some embodiments, a dose of rAAV is administered postnatal day 10.

In some embodiments, rAAV compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, rAAVs in suitably formulated pharmaceutical compositions disclosed herein are delivered directly to target tissue, e.g., direct to ocular tissue (e.g., photoreceptor, retinal, etc., tissue) However, in certain circumstances it may be desirable to separately or in addition deliver the rAAV-based therapeutic constructs via another route, e.g., subcutaneously, intrapancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by intravitreal injection or subretinal injection.

The pharmaceutical forms suitable for injectable use include suspension-based formulations, sterile aqueous solutions or dispersions, and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing a rAAV, the kit comprising a container housing an isolated nucleic acid comprising a transgene encoding a CEP290 protein fragment having the amino acid sequence set forth in any one of SEQ ID NOs: 2-4 and 10-19. In some embodiments, the kit further comprises a container housing an isolated nucleic acid encoding an AAV capsid protein, for example an AAV8 capsid protein (e.g., SEQ ID NO: 9) or an AAV5 capsid protein.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

Exemplary embodiments of the invention will be described in more detail by the following examples. These embodiments are exemplary of the invention, which one skilled in the art will recognize is not limited to the exemplary embodiments.

EXAMPLES

Example 1

Therapeutic Strategies for CEP290-LCA

The relative sparing of the central region of the CEP290-LCA patient retinas indicates that gene therapy may be a viable option for visual restoration in patients. However, progress in the development of mutation-independent gene replacement strategies for CEP290-LCA has been delayed largely because of unsuitability of the long CEP290 gene to be packaged into conventional AAV vector system for gene therapy. This example describes delivery of CEP290 fragments via AAV to treat CEP290-LCA. In some embodiments, the described CEP290 fragments restore cilial growth and photoreceptor function in a mutation-independent manner, and are thus useful for treatment of nonsyndromic LCA and retinal degeneration in systemic ciliopathies due to CEP290 mutations.

Figure 1:
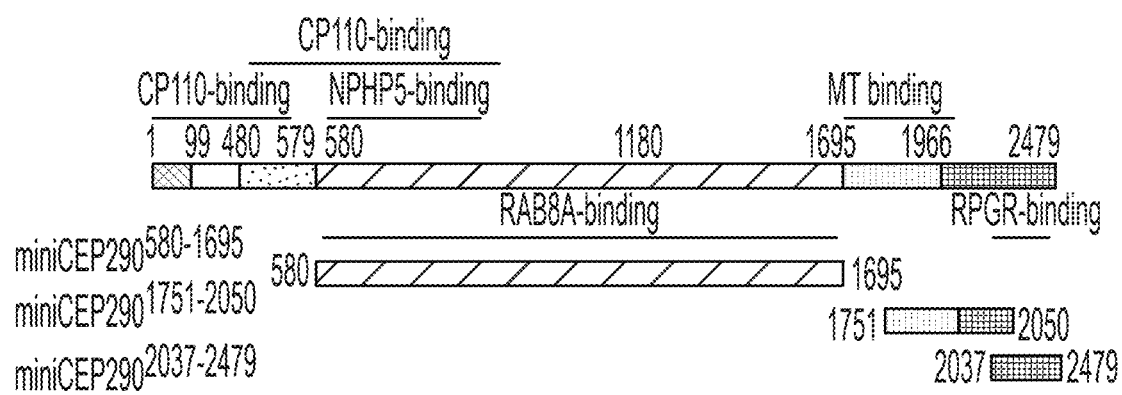
FIG. 1 shows schematic depiction of the full-length CEP290 gene representing the locations of distinct protein interaction domains.

The full-length CEP290 cDNA is ~8 kb long, which generally exceeds the packaging limit of conventional AAV vectors. A schematic depiction of the full-length CEP290 gene representing the locations of distinct protein interaction domains is shown in FIG. 1. Here, CEP290 fragments that retain function in photoreceptors (PR) and can be delivered using the conventional AAV vectors were identified. As CEP290 is a ciliary protein and regulates cilia growth, an in vitro assay of cilia growth was developed in order to use as a surrogate marker to test the function of shorter CEP290 regions. It was observed that mouse embryonic fibroblasts (MEFs) derived from a Cep290-mutant (Cep290$^{rd16}$) mouse, which recapitulates the early onset severe PR degeneration phenotype, have fewer ciliated cells and the cells that formed cilia were shorter compared to controls. This observation is consistent with previous studies that revealed fewer and shorter cilia in fibroblasts derived from CEP290-LCA patient samples.

Figure 2A:
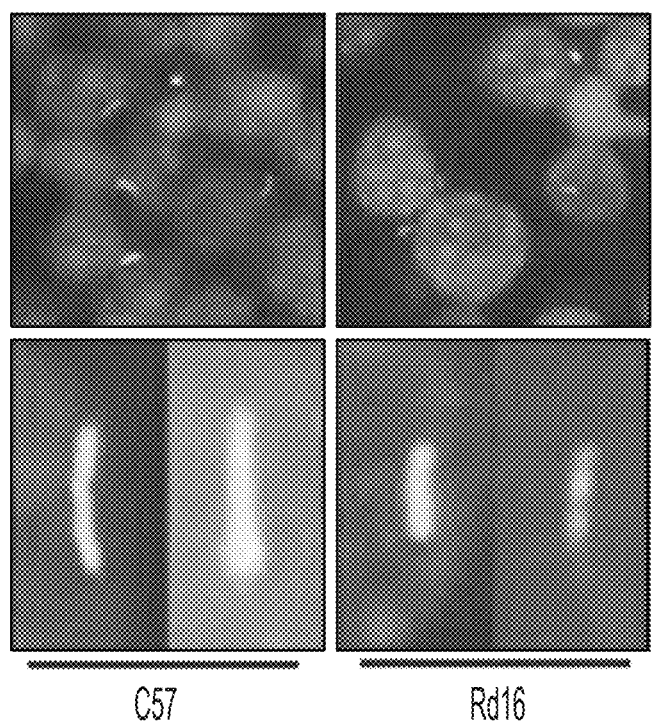
FIG. 2A shows microscopy data relating to cilial number and length in mouse embryonic fibroblasts (MEFs) from wild-type (WT) and Cep290$^{rd16}$ mice that were serum-starved for 24 h (for cilia growth) and then stained with anti-acetylated α-tubulin antibody (cilia marker). The lower images depict higher magnification of cilia.
Figure 2B:
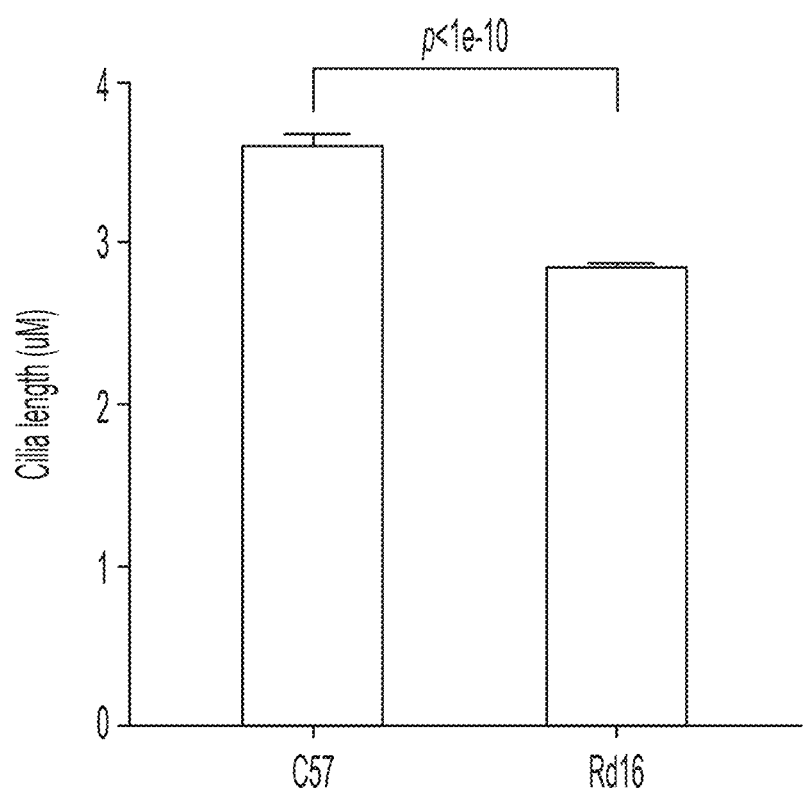
FIG. 2B shows a statistically significant decrease in the length of cilia in mutant MEFs.

As shown in FIGS. 2A-2B, cilia of Cep290$^{rd16}$ MEFs are ~2.7 μm in length as compared to controls, which have ~3.8 μm long cilia. In addition, fewer cells with cilia were detected among Cep290$^{rd16}$ MEFs as compared to controls.

Figure 3:
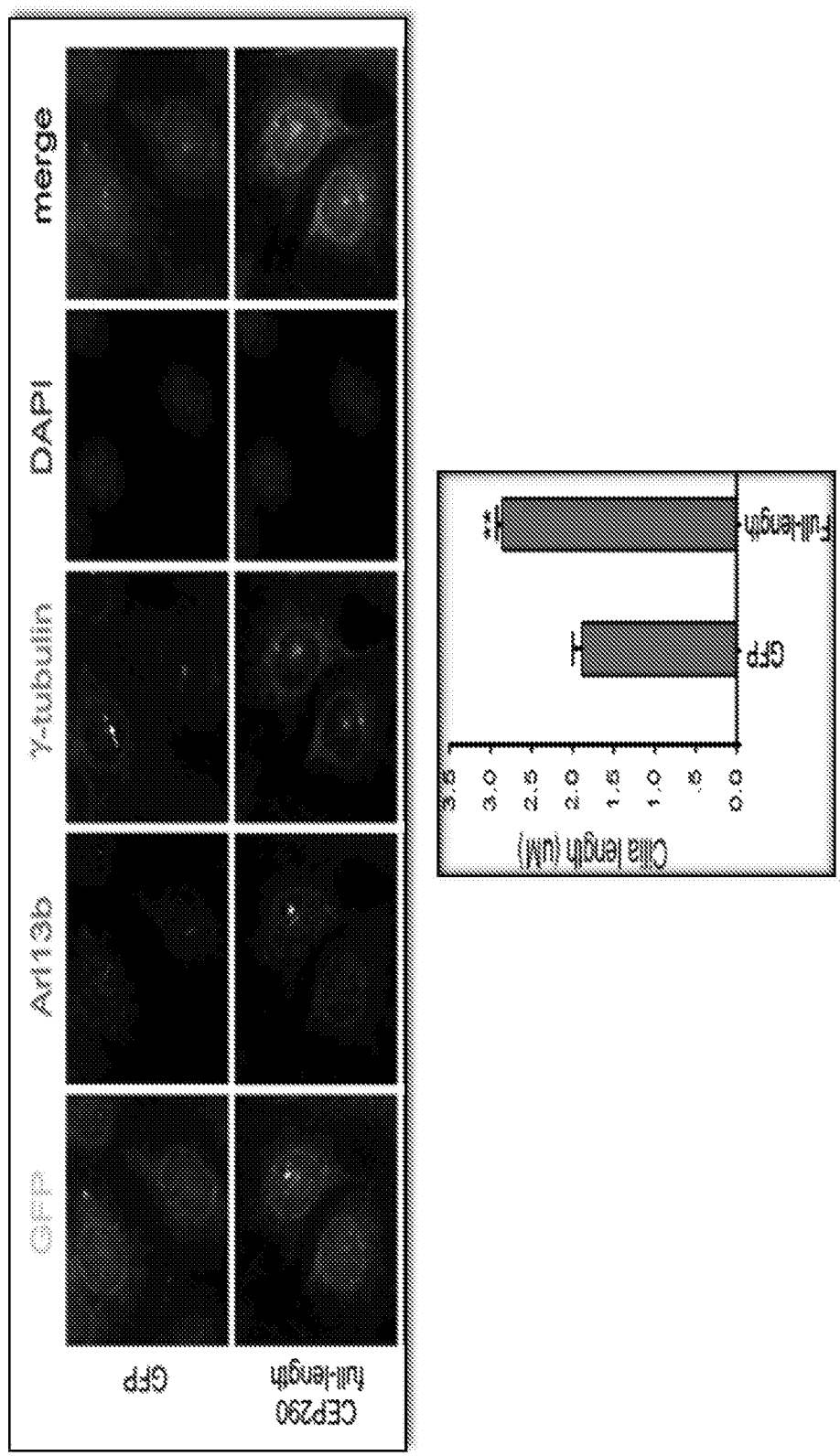
FIG. 3 shows Cep290$^{rd16}$ MEFs transfected with constructs encoding GFP or GFP-CEP290, followed by staining with ARL13b (cilia marker) and γ-tubulin. A significant increase in cilia length of cells expressing full-length CEP290 was observed. GFP-encoding construct was used as negative control. **: p<0.001.

Next, the effect of expressing full-length human CEP290 protein on cilia length in Cep290$^{rd16}$ MEFs was investigated. It was observed that the full-length human CEP290 protein correctly localizes to cilia, as determined by co-staining with ARL13b, which is a cilia marker (FIG. 3). Expressing GFP protein did not result in its localization to cilia. Additionally, measurement of cilia length showed that expression of CEP290 protein significantly rescued the cilia length of Cep290$^{rd16}$ MEFs as compared to expression of GFP.

Construction of vCEP290

Figure 4A:
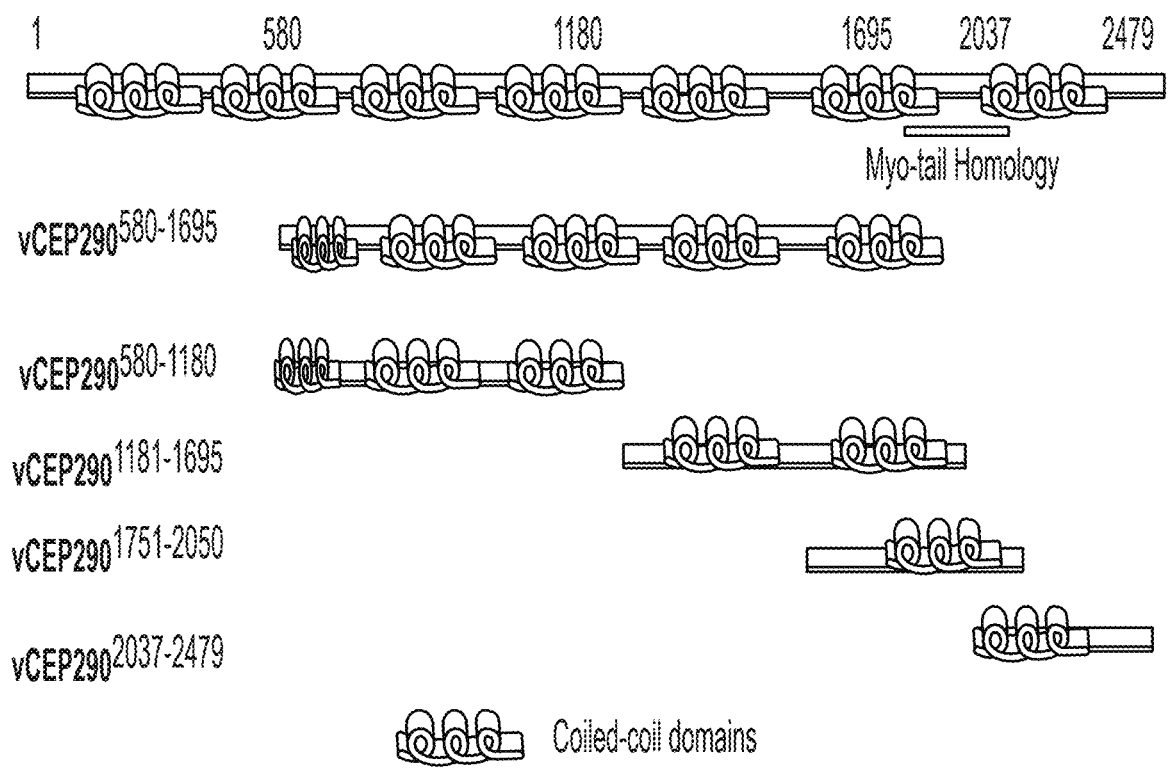
FIG. 4A shows a schematic representation of the human CEP290 protein and deleted variants. Myo-tail: Myosin tail homology domain. Additional protein-interaction domains are also not shown.
Figure 4B:
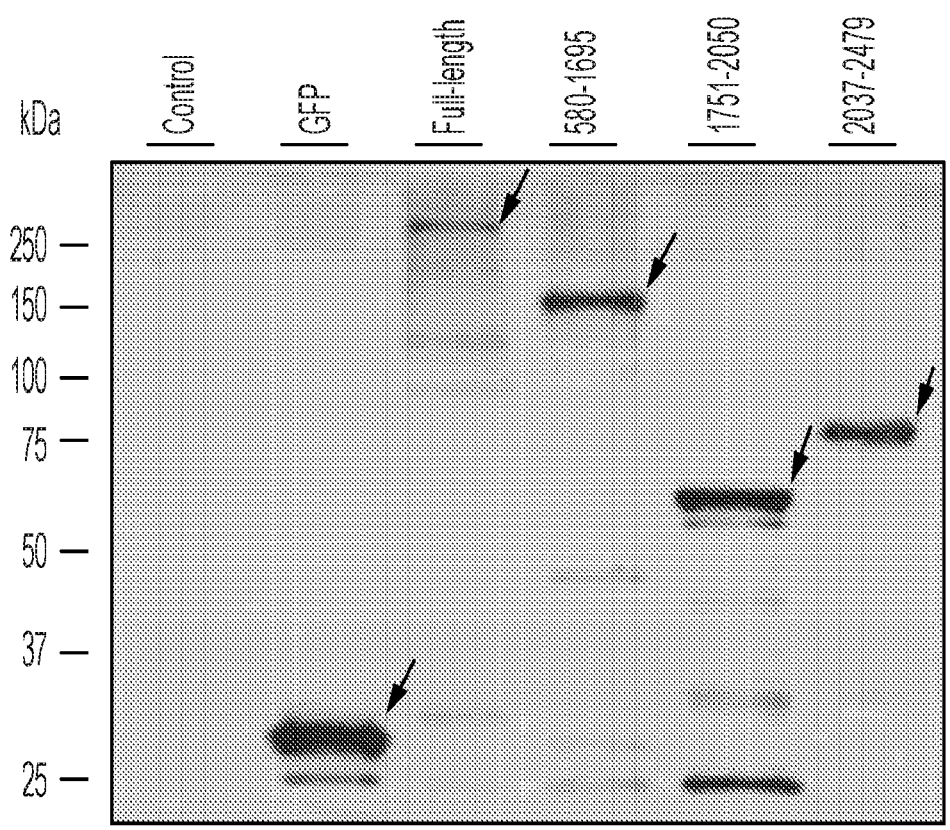
FIG. 4B shows immunoblot analysis using anti-GFP antibody of mouse fibroblasts transiently transfected with the constructs described in FIG. 4A. Specific protein bands (depicted by arrows) were detected indicating that the deleted variants are stably expressed in cells.

The CEP290 gene encodes a predominantly coiled-coil protein. Constructs that removed repetitive domains of human CEP290, such as plasmids encoding GFP-fused miniCEP290$^{580-1695}$, miniCEP290$^{1751-2050}$ and miniCEP290$^{2037-2479}$ (FIG. 4A), were produced. Variants were cloned into pEGFP-C1 vector expressing the gene under the control of CMV promoter. The constructs express stable CEP290 protein fragments as determined by immunoblot analysis of protein extracts from transiently transfected mouse embryonic fibroblasts (FIG. 4B; see arrows). To test the functional potential of the miniCEP290s, a surrogate assay system using Cep290$^{rd16}$ MEFs (mouse embryonic fibroblasts) was used. FIG. 9 shows additional examples of CEP290 variants.

Effect of vCEP290 on Cilia Length

Figure 5A:
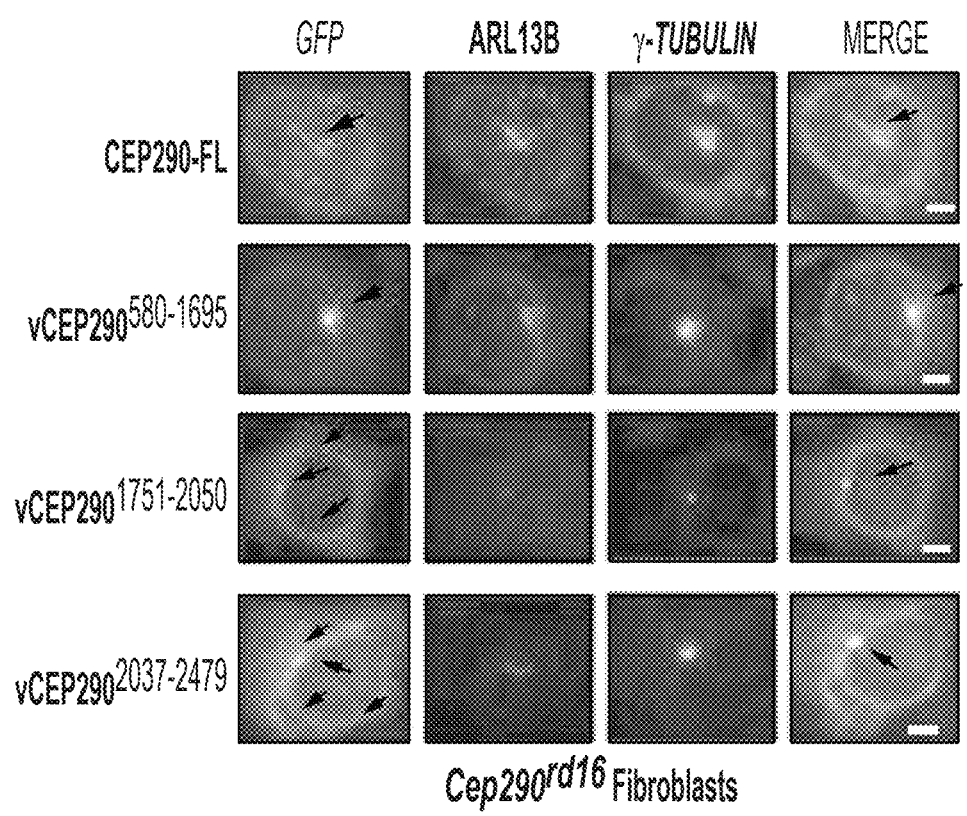
FIG. 5A shows immunostaining of Cep290$^{rd16}$ fibroblasts transiently transfected with plasmid encoding GFP-fused full-length (FL) CEP290 and indicated variants with GFP, γ-tubulin, ARL13B antibodies. Nuclei were stained with DAPI. Longer arrows indicate basal body/ciliary localization of the proteins whereas shorter arrows mark the diffuse staining.
Figure 5B:
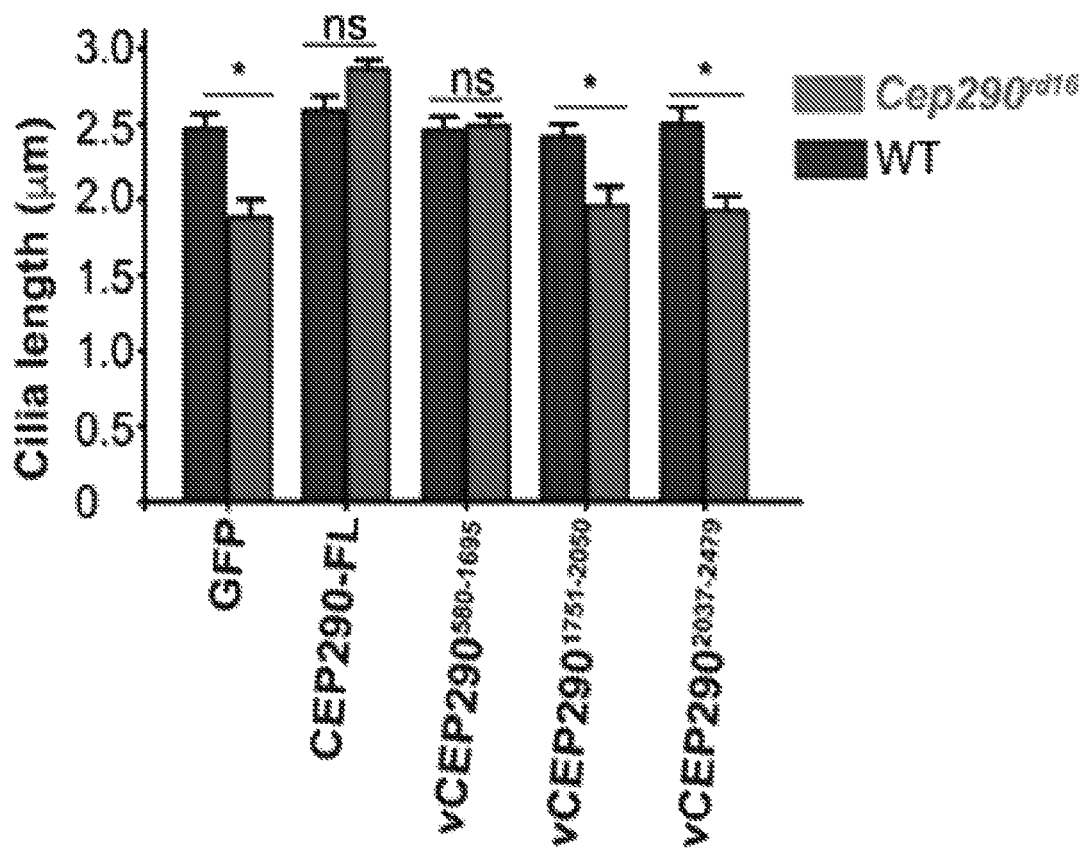
FIG. 5B shows cilia length of cells (n>200) described in FIG. 5A quantified using ImageJ. *: p<0.001. ns: not significant.

As shown in FIG. 5A, expression of different GFP-vCEP290-encoding plasmids into Cep290$^{rd16}$ or wild type mouse embryonic fibroblasts indicates that vCEP290$^{580-1695}$ localizes predominantly to the basal bodies (co-localization with γ-tubulin) and proximal cilia (co-localization with ADP-Ribosylation Factor-Like 13B; ARL13B; ciliary marker). Expression of other variants indicated a relatively diffuse pattern of localization. The ability of the vCEP290 to modulate cilia length in Cep290$^{rd16}$ fibroblasts was then assessed. As shown in FIG. 5B, cilia length of the mutant fibroblasts was significantly increased when vCEP290$^{580-1695}$ was expressed. Other variants, and the negative control expressing only GFP, did not reveal a change in the cilia length of the fibroblasts. No effect on cilia length of the wild type fibroblasts was observed.

Figure 6A:
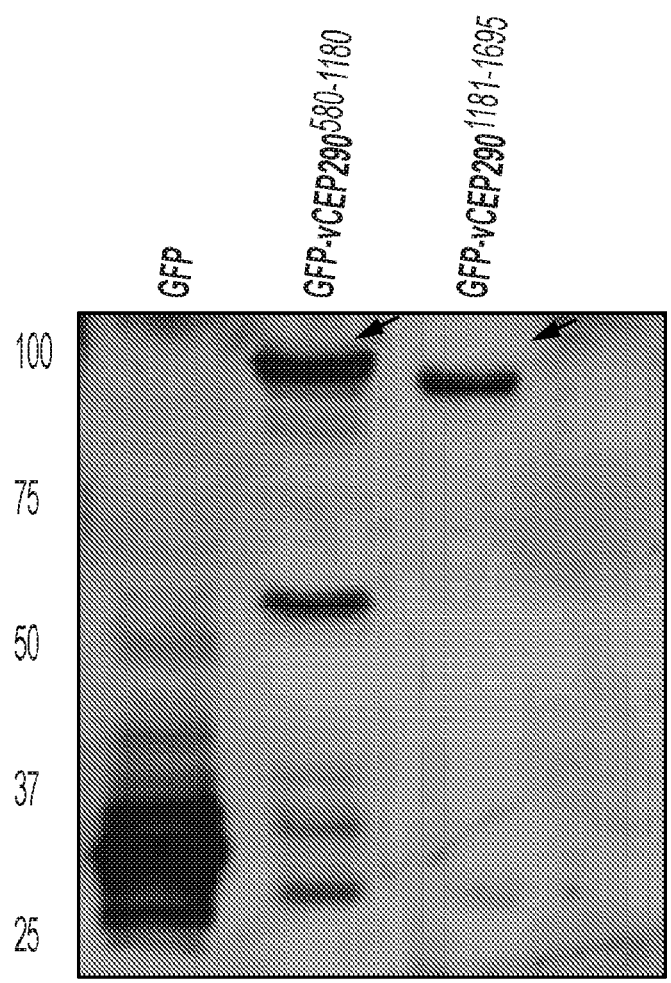
FIG. 6A shows immunoblot analysis of Cep290$^{rd16}$ fibroblasts transiently transfected with plasmid encoding GFP alone or GFP-fused indicated variants, using anti-GFP antibody. Arrows point to the expected size protein product. Molecular mass marker is shown in kDa.
Figure 6B:
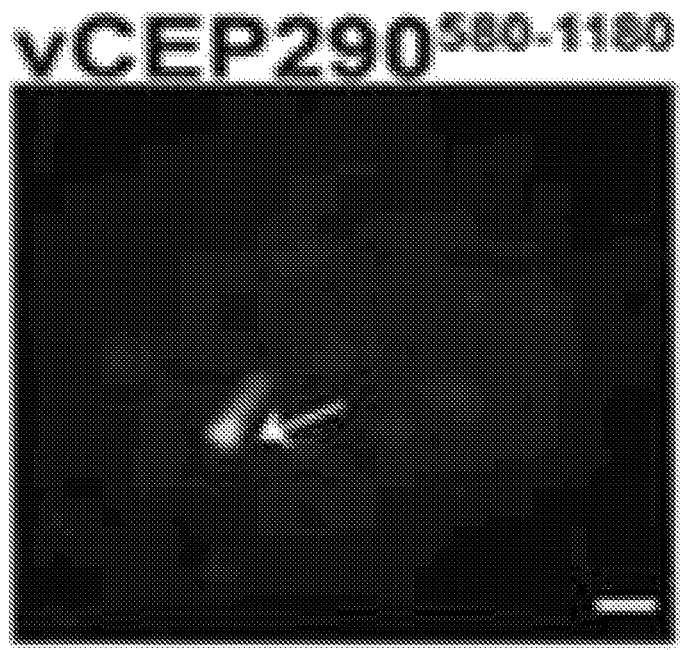
FIG. 6B shows immunostaining of the cells using GFP and ARL13B (cilia marker) antibodies. Nuclei were stained with DAPI. Arrows indicate basal body/ciliary localization of the proteins.
Figure 6B:
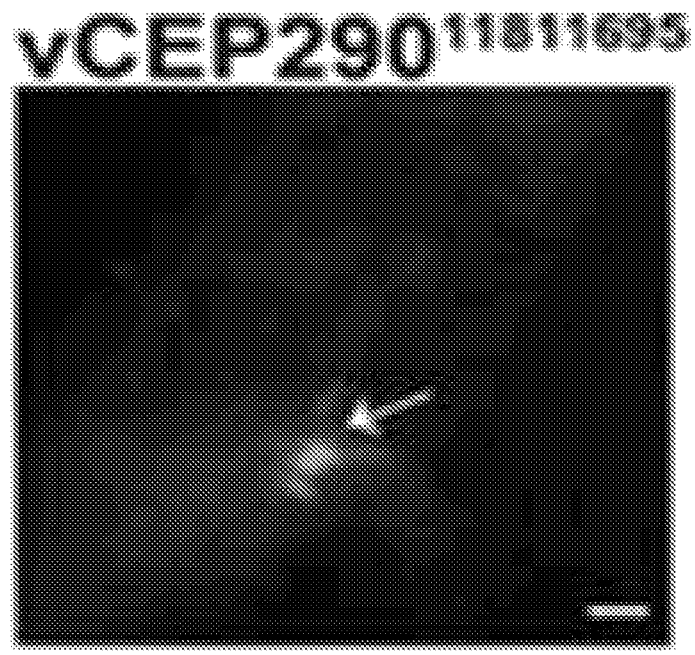
Figure 6C:
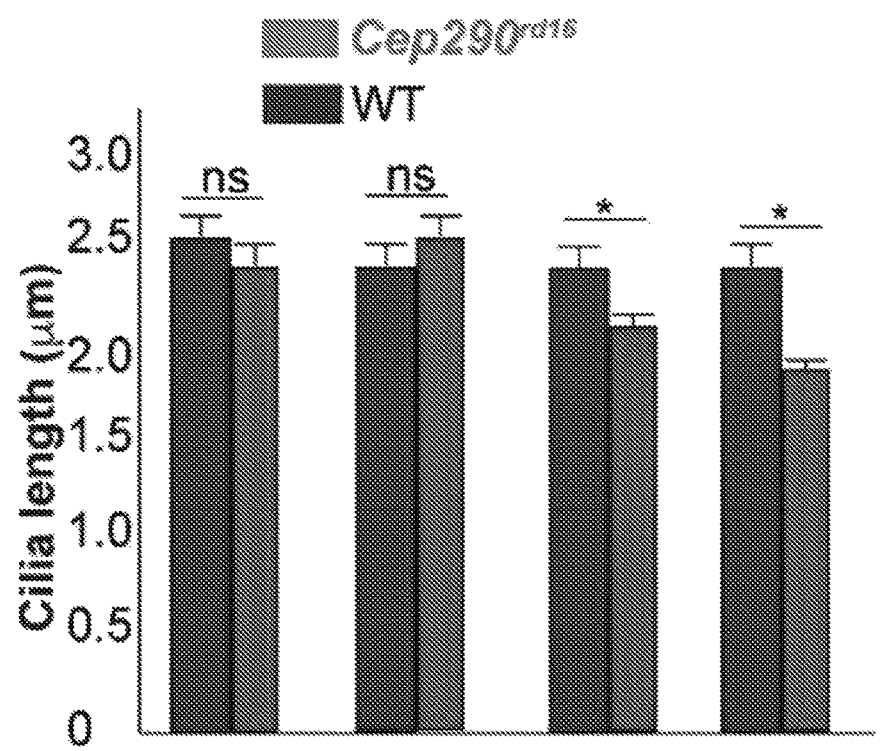
FIG. 6C shows the cilia length of the cells (n>200) quantified using ImageJ. *: p<0.001.
Figure 7A:
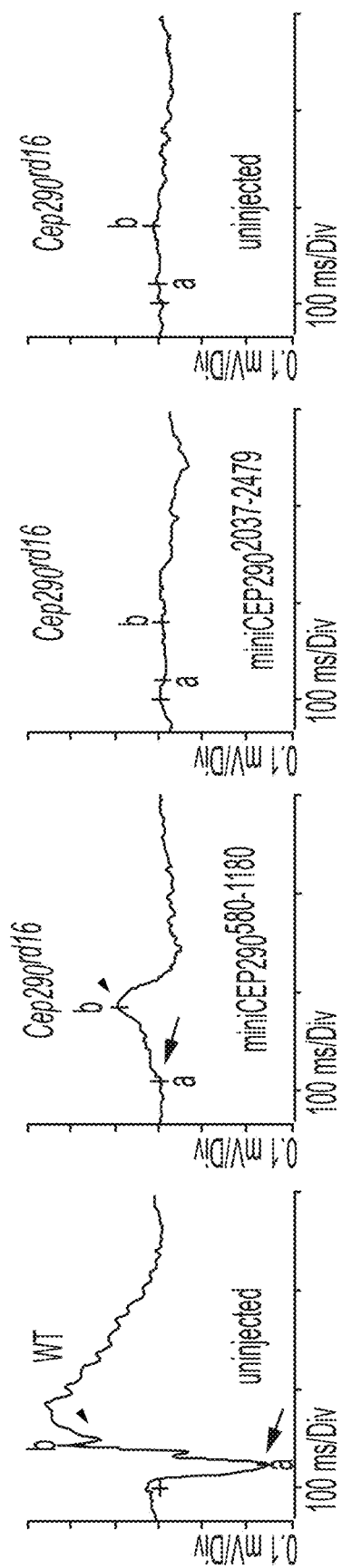
FIGS. 7A-7B show in vivo physiological rescue potential of miniCEP290$^{580-1180}$.
Figure 7B:
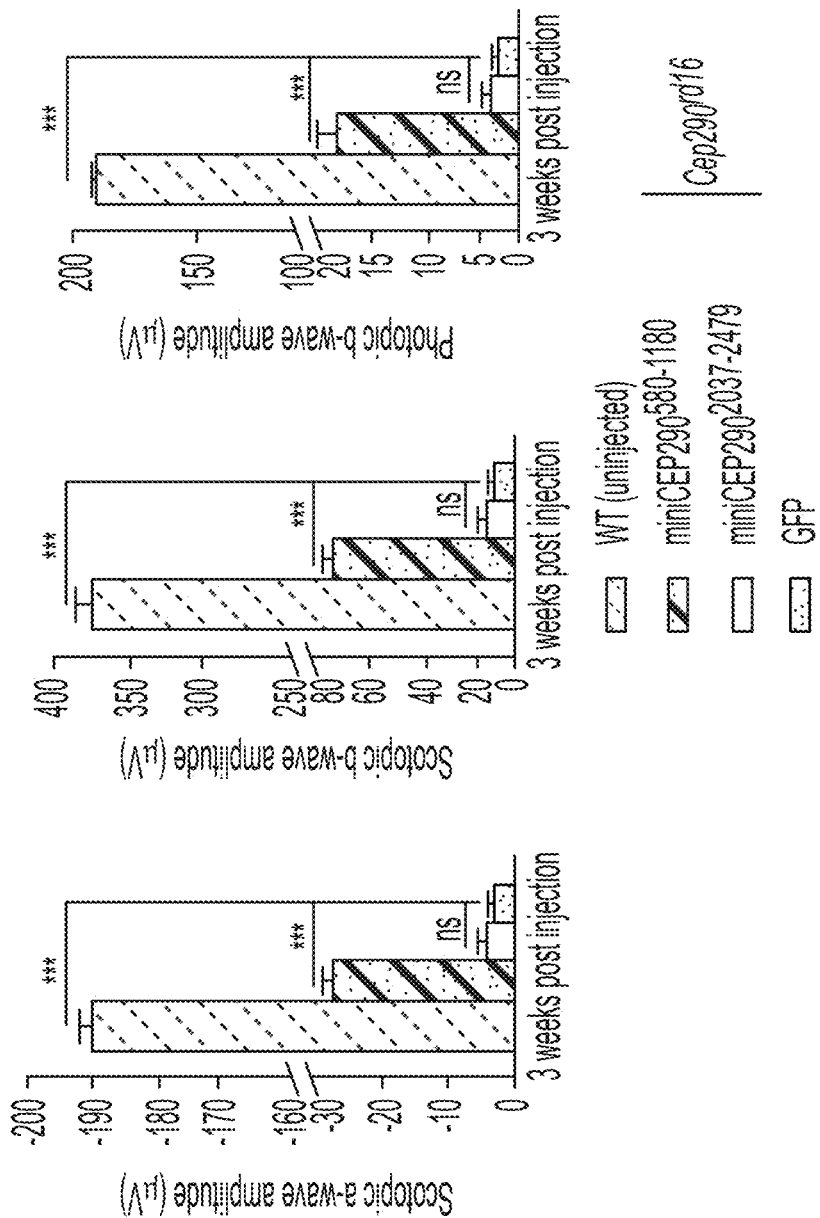

Whether further shortening vCEP290$^{580-1695}$ will result in a cilia length rescue was then investigated. Plasmids encoding GFP-fused vCEP290$^{580-1180}$ and vCEP290$^{1181-1695}$ were produced and their expression, localization and potential to rescue cilia length in Cep290$^{rd16}$ fibroblasts were tested. Both variants exhibited optimal expression as determined by immunoblotting using anti-GFP antibody, and localization to cilia (FIGS. 6A-6B). Data for vCEP290$^{1181-1695}$ indicate predominant localization to the base of cilia and diffuse staining around the basal body. Cilia rescue assay data indicate that expression of either variant results in a significant increase in the cilia length of Cep290$^{rd16}$ fibroblasts (FIG. 6C and FIG. 10).

Potential of vCEP290 In Vivo

Functionality of vCEP290 constructs in vivo was investigated. vCEP290$^{580-1180}$, vCEP290$^{1181-1695}$ and vCEP290$^{2037-2479}$ (as negative control since it did not rescue the cilia length defect in the fibroblasts) were cloned into an AAV2 vector having a CBA promoter and containing an IRES (internal ribosome entry site) between the gene of interest (e.g., vCEP290) and GFP. This permits both CEP290 and GFP to be translated from a single bicistronic mRNA and assists in identifying transduced photoreceptors using an anti-GFP antibody. Each rAAV (e.g., AAV2/8-CBA-vCep290$^{580-1180}$_IRES-GFP, AAV2/8-CBA-vCep290$^{1181-1695}$IRES-GFP, AAV2/8-CBA-vCep290$^{2037-2472}$-IRES-GFP, and negative control AAV2/8-CBA-GFP) were injected at 8×10$^9$ vg/eye in 1 μl volume into the subretinal space of Cep290$^{rd16}$ pups at P0 stage. The mice were assessed for PR function and retinal morphology up to 5 weeks after injection.

Analysis of PR function by electroretinography (ERG) at 3 weeks post-injection revealed improvement (25-30%) in both scotopic (rod PR-mediated) and photopic (cone PR-mediated) (FIGS. 7A-7B, and FIGS. 11-12) responses of the miniCEP290$^{580-1180}$-injected mice. No improvement was detected using miniCEP290$^{2037-2479}$ or GFP. Further analysis revealed that the improvement in the ERG was stable up to 4 weeks post injection.

Figure 8A:
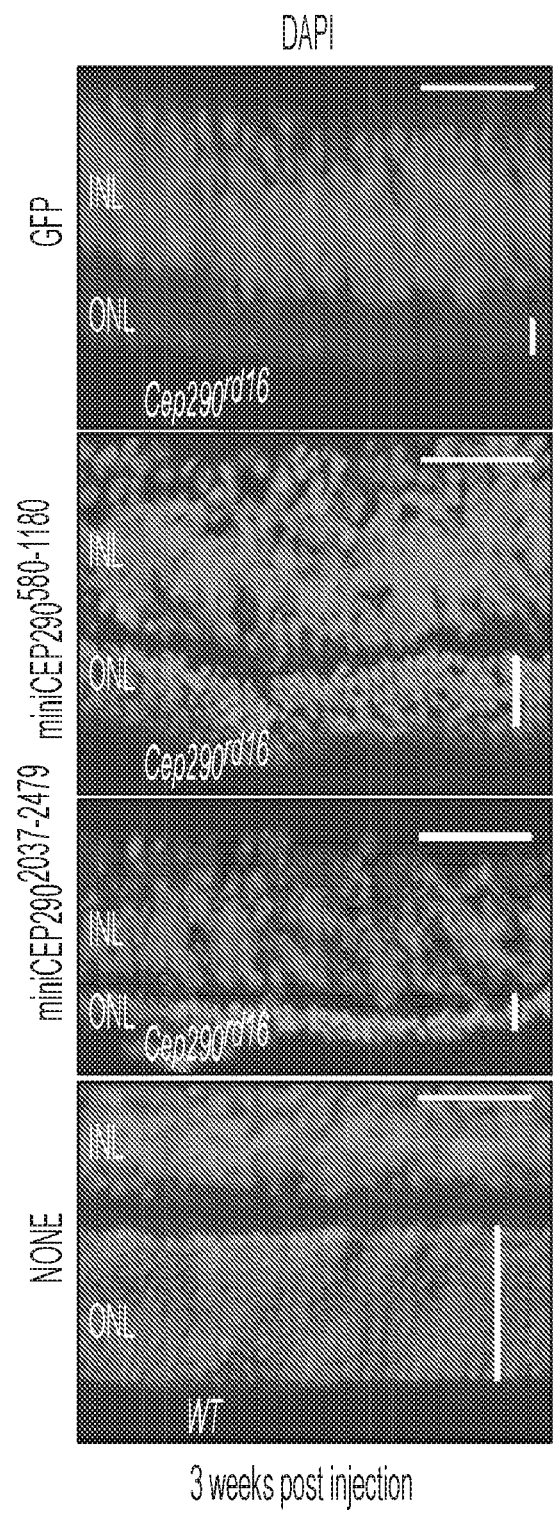
FIGS. 8A-8D show in vivo morphological rescue of photoreceptors by miniCEP290$^{580-1180}$.
Figure 8B:
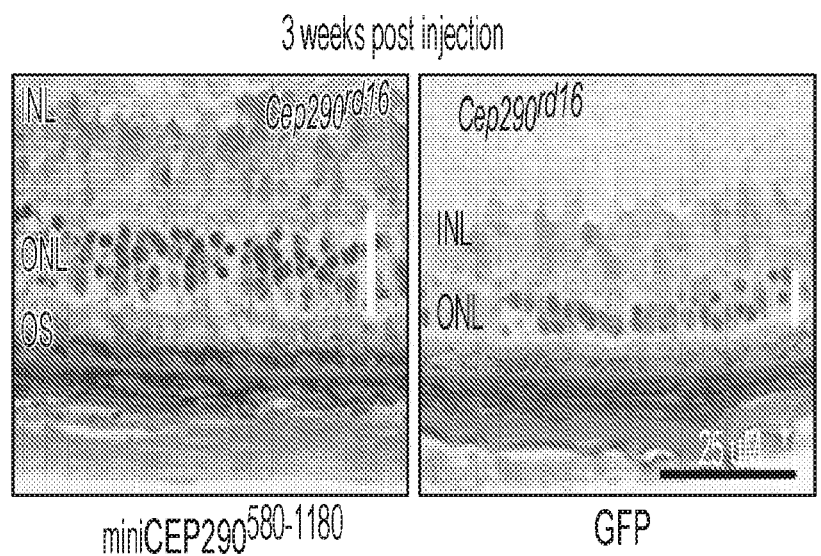

The number of layers of the ONL, which correlates with PR survival, were also counted in retinal cryosections: ~6-7 layers were observed in Cep290$^{rd16}$ retinas injected with miniCep290$^{580-1180}$; 4-5 layers were observed in Cep290$^{rd16}$ retinas injected with miniCep290$^{1181-1695}$ and; 2-3 layers were observed in retinas injected with miniCep290$^{2037-2472}$ or GFP (equivalent to uninjected Cep290$^{rd16}$ at 3 weeks of age), as shown in FIG. 8A. It was also observed that ultrathin sections of the CEP290$^{rd16}$ retinas injected with mini-CEP290$^{580-1180}$ exhibited significant preservation of the outer nuclear layer (ONL) (FIG. 8B).

Figure 8C:
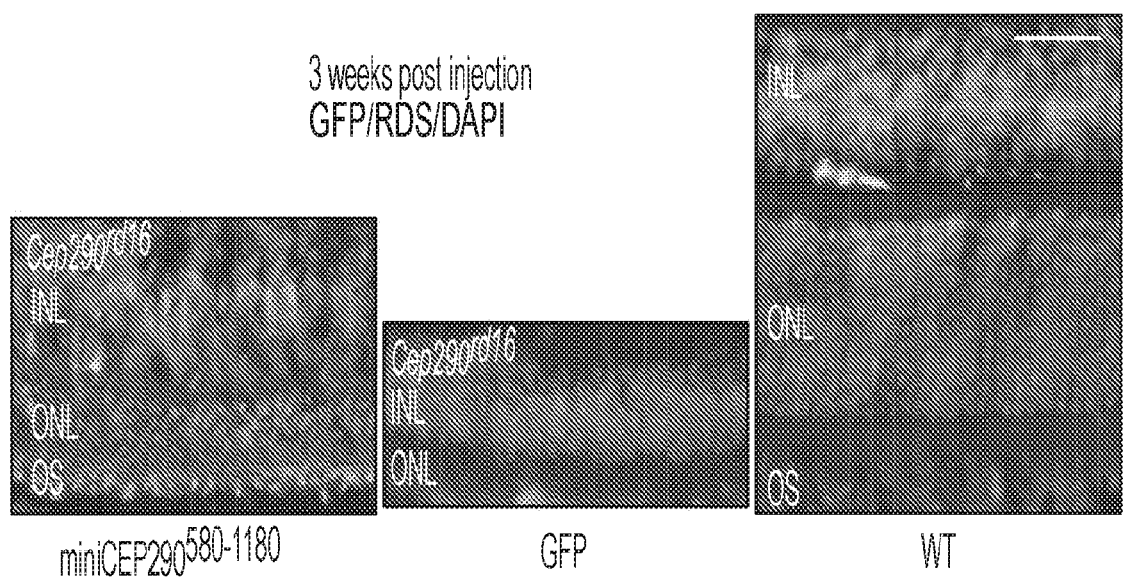
Figure 8D:
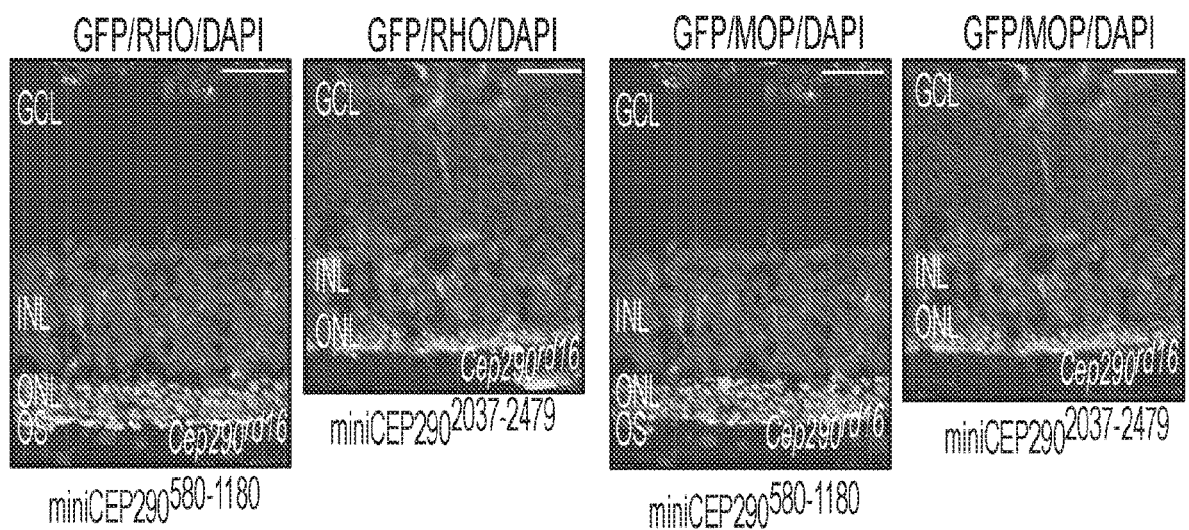

The structural preservation of photoreceptor (PR) outer segment in the miniCEP290$^{580-1180}$-injected mice was examined by staining with peripherin-RDS (retinal degeneration slow, PR outer segment marker 45). RDS is a structural protein that specifically localizes to the outer segment (OS) discs and maintains the OS structure. The miniCEP290$^{580-1180}$-injected Cep290rd16 mice exhibited improved RDS localization to the outer segment as compared to undetectable RDS expression in the GFP-injected mice (FIG. 8C). The expression of rhodopsin and cone opsins, two of the key phototransduction proteins, was also examined. Undetectable opsin expression was detected in the miniCEP290$^{2037-2479}$-injected retinas. However, the miniCEP290$^{580-1180}$-injected retinas revealed detectable expression of rhodopsin and cone opsins in the outer segments (FIG. 8D). Some staining of cone opsins in the inner segment and outer nuclear layer was also observed. Overall, the data indicate that the expression of miniCEP290$^{580-1180}$ can improve the function, morphology and opsin trafficking of CEP290$^{rd16}$ retinas.

Materials and Methods

Cell Culture, Transient Transfection and Immunostaining

MEFs derived from the WT and Cep290$^{rd16}$ mice were maintained in DMEM with 10% FBS. Transient transfection with GFP-CEP290-FL or GFP-miniCEP290s was performed using Lipofectamine 2000 (Thermo Fisher). The transfected cells were either harvested for immunoblotting or were serum-starved to induce cilia growth. The ciliated cells were then immunostained, imaged under Leica microscope (DM5500). Images were then processed for cilia length evaluation using Image J.

Constructs and AAV Production

For in vitro experiments, full-length or miniCEP290-expressing cDNAs were cloned into pEGFP-C1 plasmid expressing GFP-tagged proteins under the control of CMV promoter. For AAV production, the miniCEP290-encoding cDNAs were cloned into a pAAV2 vector plasmid between a CMVenhancer/CBA (chicken β-actin) promoter upstream of IRES (internal ribosome entry site) GFP and β-globin intron. This expression cassette was flanked with AAV2 inverted terminal repeats (ITRs). The recombinant AAV2 genomes were packaged with AAV8 capsid by HEK293-triple transfection method and purified by CsCl gradient centrifugation method.

Subretinal Injection

Wild type C57BL6/J mice were obtained from a commercial source. The Cep290$^{rd16}$ mice were also obtained. The Cep290$^{rd16}$ mouse pups (P0/P1) were subretinally injected unilaterally with 8×10$^9$ vg/µl (total volume 1 µl) of the virus.

ERG and Immunofluorescence Microscopy of the Retina

Scotopic and photopic ERGs were performed. For scotopic response, mice were dark adapted overnight and all procedures were performed under dim red light. Light adapted (photopic) ERGs were recorded after light adaptation with a background illumination of 30 cd/m$^2$ (white 6500 K) for 8 min.

Immunofluorescence microscopy was performed by staining retinal cryosection sections with primary antibodies: rhodopsin, M-opsin, and peripherin-RDS, ARL13B, GFP (Abcam), and γ-tubulin. After washing with PBS (phosphate buffered saline), Alexa-488 or Alexa-546-conjugated secondary antibodies were added and the sections were further incubated for 1 h. After washing, nuclei were stained with DAPI and cells were imaged using a Leica microscope (DM5500).

Example 2

This example describes in vivo experiments to investigate CEP290 minigene expression. Briefly, 10-day old rd16 mice were subretinally injected with a CEP290 minigene construct. Expression of the CEP290 minigene was driven by a GRK promoter. Post-injection, rod (scotopic) and cone (photopic) photoreceptor response was assessed. FIG. 13 shows scotopic a-wave and b-wave amplitude for 10-day old mice subretinally injected with the indicated miniCEP290 construct (GRK-580-1180). ERG were recorded at the indicated days after injection. FIG. 14 shows photopic a-wave and b-wave amplitude for 10-day old mice subretinally injected with the indicated miniCEP290 construct (GRK-580-1180). ERG were recorded at the indicated days after injection. Data indicate a sustained response in rod cells of up to 67 days, and an increase in cone cell activity, relative to miniCEP290 constructs driven by a CB6 promoter.

In vitro experiments were also performed. FIG. 15 shows micrographs of rd16 mouse embryonic fibroblasts transiently transfected with cDNA encoding the indicated minigenes encoding the protein and GFP. Expression of the minigenes was driven by a CB6 promoter. FIG. 16 shows data for cilia length measurement of rd16 mouse embryonic fibroblasts transiently transfected with cDNA encoding the indicated minigenes encoding the protein and GFP. Data indicate an increase in cilia length in miniCEP290 transfected cells relative to control (GFP) transfected cells.

FIGS. 17A-17D show scotopic and photopic wave amplitudes of CB6-promoter driving the indicated minigenes were subretinally injected into 10 day old rd16 mice. FIG. 17A shows scotopic a-wave amplitude. FIG. 17B shows photopic b-wave amplitude. FIG. 17C shows scotopic b-wave amplitude. FIG. 17D shows ERG of rd16 mice injected with CB6-1-200-580-1180 miniCEP290. ERG were recorded at indicated days after injection and compared to others.

Example 3

FIG. 18 is a schematic depicting additional embodiments of CEP290 minigenes. In some embodiments, expression of the minigenes is driven by a CB6 promoter. In some embodiments, expression of the minigenes is driven by an eye-specific promoter, for example a Rhodopsin Kinase (RK) promoter such as a GRK promoter.

Mice at P10 stage were subretinally injected with the AAV-vectors encoding the minigene constructs. The minigene was encapsulated in an AAV8 capsid protein. The ERG was performed at the indicated ages after injection, as described in the Figures.

FIG. 19 shows representative data for ERG analysis of Rhodopsin Kinase (RK) promoter-driven expression of miniCEP290-580-1180 in subretinally-injected mice. Rescue effect lasted more than 10 weeks post-injection.

FIG. 20 shows representative data for ERG analysis of Rhodopsin Kinase (RK) promoter-driven expression of miniCEP290-1181-2479 in subretinally-injected mice. Rescue effect lasted up to 8.5 weeks post-injection.

FIG. 21 shows representative data for ERG analysis of Rhodopsin Kinase (RK) promoter-driven expression of miniCEP290-580-1180/1800-2479 in subretinally-injected mice. Rescue effect lasted up to 5.5 weeks post-injection.

FIG. 22 shows representative data for ERG analysis of Rhodopsin Kinase (RK) promoter-driven expression of miniCEP290-1181-1695/1966-2479 in subretinally-injected mice.

FIG. 23 shows representative data for ERG analysis of Rhodopsin Kinase (RK) promoter-driven expression of miniCEP290-1-200/580-1180 in subretinally-injected mice. Rescue effect lasted more than 14 weeks post-injection.

Example 4

Leber congenital amaurosis (LCA) is a debilitating eye disorder and is considered one of the most severe forms of retinal degeneration. Mutations in CEP290 (LCA10) account for >26% of all LCA cases and are the most frequent cause of LCA. Adeno-associated viral (AAV) vectors are currently the most efficient vectors for gene delivery to the retina. However, the development of a gene therapy for LCA10 has been challenging because the size of the CEP290 gene is too large to be packaged into conventional AAV vectors. Mutation specific anti-sense oligo and gene editing therapies have been previously reported.

This example describes a mutation-independent gene therapy delivered with an AAV vector to treat LCA10, that results in severe vision loss at infancy. Versions of CEP290 minigene constructs (miniCEP290) that are functional and can be delivered into the subretinal space using AAV vectors were produced.

CEP290 minigene [e.g., CEP290 amino acid 580-1180 domain] under the control of a ubiquitous promoter was observed to improve the function and survival of photoreceptors in neonatal Cep290-mutant mice ($Cep290^{rd16}$). However, the effect was short-lived with degeneration ensuing after 5 weeks of age. Data indicate that the expression of CEP290-580-1180 under the control of the photoreceptor-specific rhodopsin kinase promoter improved the electroretinogram (ERG) response for both rod and cone photoreceptors by ~1.5 folds. This example describes a miniCEP290 gene construct that encodes amino acids 1-200 and 580-1180 (miniCEP290-1-200/580-1180) which improved photoreceptor structural and functional rescue by ~500% when delivered at postnatal day 10 in $Cep290^{rd16}$ mice. Data also indicate that the expression of the new miniCEP290 prolonged the survival and improved the protein trafficking defects in the photoreceptors in the Cep290rd16 mice.

FIGS. 24A-24C show a morphological analysis of Rhodopsin Kinase (RK) promoter driving miniCEP290-580-1180: the minigene was subretinally delivered with AAV8 at P10 stage. The analysis was performed at 9 weeks of age. FIG. 24A shows miniCEP290-580-1180 immunofluorescence analysis of the injected retinal region (GFP; longer arrows). FIG. 24B shows improvement in rhodopsin (longer arrows). Shorter arrows do not show GFP expression (non-transduced) and consequently exhibit undetectable rhodopsin expression. FIG. 24C shows nuclear staining also shows more nuclear layers in the outer nuclear layer (ONL) region in the transduced area (longer arrows and longer vertical bars) as compared to the untransduced region (shorter arrow and shorter vertical bar). Rescue effect lasted more than 14 weeks post-injection.

Example 5

Codon-optimized MiniCEP290 constructs were produced and packaged into rAAVs using AAV5 capsid proteins. The sequences were codon-optmized to increase protein production, reduce tandem rare codons (which can reduce the efficiency of translation or even disengage the translational machinery), prolong the half-life of the mRNA, and to break stem-loop structures. FIGS. 25A-25C show codon optimized miniCEP290 constructs. FIG. 25A shows codon optimized miniCEP290 1-200/580-1180 constructs with promoters (e.g., chicken beta-actin promoter) and different introns (chicken beta-actin intron, synthetic intron, MBL intron, etc.). FIG. 25B shows codon optimized miniCEP290 1-380/580-1180 constructs with different promoters and introns. FIG. 25C shows representative data for codon optimized miniCEP290 1-200/580-1180 constructs packaged into AAV5 capsid and injected subretinally into mice at P10 stage. The mice were then analyzed by ERG (both scotopic and photopic) at the ages indicated.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. An isolated nucleic acid comprising a transgene encoding a CEP290 fragment having the amino acid sequence set forth in SEQ ID NO: 19 operably linked to a promoter, wherein the promoter is a retinoschisin promoter, K12 promoter, a rhodopsin promoter, a rhodopsin kinase promoter, or an interphotoreceptor retinoid-binding protein proximal (IRBP) promoter, optionally wherein the rhodopsin kinase promoter is a GRK1 promoter.

2. The isolated nucleic acid of claim 1, wherein the CEP290 fragment is encoded by a nucleic acid having the sequence set forth in SEQ ID NO: 19.

3. The isolated nucleic acid of claim 1, wherein the transgene is flanked by adeno-associated virus (AAV) inverted terminal repeats (ITRs).

4. A recombinant adeno-associated virus (rAAV) comprising:
   (i) a capsid protein; and,
   (ii) the isolated nucleic acid of claim 1.

5. The rAAV of claim 4, wherein the capsid protein is AAV2, AAV3, AAV4, AAV5, AAV6, AAV7, AAV8, AAVrh8, AAV9, or AAV10 capsid protein, optionally wherein the capsid protein comprises the sequence set forth in SEQ ID NO: 9.

6. A composition comprising the rAAV of claim 4, and a pharmaceutically acceptable excipient.

7. A recombinant adeno-associated virus (rAAV) vector comprising an expression cassette comprising a nucleic acid encoding the amino acid sequence set forth in SEQ ID NO: 19 operably linked to a promoter, wherein the expression cassette is flanked by adeno-associated virus 2 (AAV2) inverted terminal repeats (ITRs).

8. The rAAV vector of claim 7, wherein the nucleic acid comprises the sequence set forth in SEQ ID NO: 29 or 34.

9. The rAAV vector of claim 7, wherein the expression cassette comprises an intron positioned between the promoter and the nucleic acid sequence encoding the amino acid sequence set forth in SEQ ID NO: 19, optionally wherein the intron comprises a chicken beta-actin intron, a synthetic intron, or a MBL intron.

10. A recombinant adeno-associated virus (rAAV) comprising:
   (i) a nucleic acid encoding the amino acid sequence set forth in SEQ ID NO: 19 operably linked to a promoter, wherein the expression cassette is flanked by adeno-associated virus 2 (AAV2) inverted terminal repeats (ITRs); and
   (ii) one or more AAV capsid proteins.

11. The rAAV of claim 10, wherein the one or more AAV capsid proteins are AAV8 capsid proteins or AAV5 capsid proteins.

12. The rAAV of claim 10, wherein the promoter is a rhodopsin kinase (RK) promoter or a chicken beta-actin promoter.

13. The rAAV of claim 10 further comprising an intron positioned between the promoter and the nucleic acid sequence encoding the amino acid sequence set forth in SEQ ID NO: 19.

14. The rAAV of claim 13, wherein the intron comprises a chicken beta-actin intron, a synthetic intron, or a MBL intron.

* * * * *

SEQUENCE LISTING

```
<160> NUMBER OF SEQ ID NOS: 39

<210> SEQ ID NO 1
<211> LENGTH: 2479
<212> TYPE: PRT
<213> ORGANISM: Homo sapiens

<400> SEQUENCE: 1

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Asn Glu Gln Leu
        165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220
```

```
Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
            245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
                340                 345                 350

Leu Gln Gln Gly Ile Gln Glu Arg Asp Ser Gln Ile Lys Met Leu Thr
            355                 360                 365

Glu Gln Val Glu Gln Tyr Thr Lys Glu Met Glu Lys Asn Thr Cys Ile
370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415

Lys Glu Lys Thr Lys Glu Ala Glu Arg Thr Ala Glu Leu Ala Glu Ala
            420                 425                 430

Asp Ala Arg Glu Lys Asp Lys Glu Leu Val Glu Ala Leu Lys Arg Leu
        435                 440                 445

Lys Asp Tyr Glu Ser Gly Val Tyr Gly Leu Glu Asp Ala Val Val Glu
450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
        515                 520                 525

Gln Gln Tyr Arg Ala Glu Asn Gln Ile Leu Leu Lys Glu Ile Glu Ser
530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
        595                 600                 605

Asn Glu Phe Leu Ser Arg Glu Leu Ile Glu Lys Glu Arg Asp Leu Glu
        610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
```

```
                645               650               655
Ala Ile Lys Glu Met Gln Lys Asp Pro Asp Val Lys Gly Gly Glu Thr
            660               665               670

Ser Leu Ile Ile Pro Ser Leu Glu Arg Leu Val Asn Ala Ile Glu Ser
            675               680               685

Lys Asn Ala Glu Gly Ile Phe Asp Ala Ser Leu His Leu Lys Ala Gln
            690               695               700

Val Asp Gln Leu Thr Gly Arg Asn Glu Glu Leu Arg Gln Glu Leu Arg
705               710               715               720

Glu Ser Arg Lys Glu Ala Ile Asn Tyr Ser Gln Gln Leu Ala Lys Ala
                725               730               735

Asn Leu Lys Ile Asp His Leu Glu Lys Glu Thr Ser Leu Leu Arg Gln
            740               745               750

Ser Glu Gly Ser Asn Val Val Phe Lys Gly Ile Asp Leu Pro Asp Gly
            755               760               765

Ile Ala Pro Ser Ser Ala Ser Ile Ile Asn Ser Gln Asn Glu Tyr Leu
            770               775               780

Ile His Leu Leu Gln Glu Leu Glu Asn Lys Glu Lys Lys Leu Lys Asn
785               790               795               800

Leu Glu Asp Ser Leu Glu Asp Tyr Asn Arg Lys Phe Ala Val Ile Arg
                805               810               815

His Gln Gln Ser Leu Leu Tyr Lys Glu Tyr Leu Ser Glu Lys Glu Thr
            820               825               830

Trp Lys Thr Glu Ser Lys Thr Ile Lys Glu Glu Lys Arg Lys Leu Glu
            835               840               845

Asp Gln Val Gln Gln Asp Ala Ile Lys Val Lys Glu Tyr Asn Asn Leu
850               855               860

Leu Asn Ala Leu Gln Met Asp Ser Asp Glu Met Lys Lys Ile Leu Ala
865               870               875               880

Glu Asn Ser Arg Lys Ile Thr Val Leu Gln Val Asn Glu Lys Ser Leu
                885               890               895

Ile Arg Gln Tyr Thr Thr Leu Val Glu Leu Glu Arg Gln Leu Arg Lys
            900               905               910

Glu Asn Glu Lys Gln Lys Asn Glu Leu Leu Ser Met Glu Ala Glu Val
            915               920               925

Cys Glu Lys Ile Gly Cys Leu Gln Arg Phe Lys Glu Met Ala Ile Phe
930               935               940

Lys Ile Ala Ala Leu Gln Lys Val Val Asp Asn Ser Val Ser Leu Ser
945               950               955               960

Glu Leu Glu Leu Ala Asn Lys Gln Tyr Asn Glu Leu Thr Ala Lys Tyr
                965               970               975

Arg Asp Ile Leu Gln Lys Asp Asn Met Leu Val Gln Arg Thr Ser Asn
            980               985               990

Leu Glu His Leu Glu Cys Glu Asn Ile Ser Leu Lys Glu Gln Val Glu
            995               1000              1005

Ser Ile Asn Lys Glu Leu Glu Ile Thr Lys Glu Lys Leu His Thr
            1010              1015              1020

Ile Glu Gln Ala Trp Glu Gln Glu Thr Lys Leu Gly Asn Glu Ser
            1025              1030              1035

Ser Met Asp Lys Ala Lys Lys Ser Ile Thr Asn Ser Asp Ile Val
            1040              1045              1050

Ser Ile Ser Lys Lys Ile Thr Met Leu Glu Met Lys Glu Leu Asn
            1055              1060              1065
```

-continued

Glu Arg Gln Arg Ala Glu His Cys Gln Lys Met Tyr Glu His Leu
1070                1075                1080

Arg Thr Ser Leu Lys Gln Met Glu Glu Arg Asn Phe Glu Leu Glu
1085                1090                1095

Thr Lys Phe Ala Glu Leu Thr Lys Ile Asn Leu Asp Ala Gln Lys
1100                1105                1110

Val Glu Gln Met Leu Arg Asp Glu Leu Ala Asp Ser Val Ser Lys
1115                1120                1125

Ala Val Ser Asp Ala Asp Arg Gln Arg Ile Leu Glu Leu Glu Lys
1130                1135                1140

Asn Glu Met Glu Leu Lys Val Glu Val Ser Lys Leu Arg Glu Ile
1145                1150                1155

Ser Asp Ile Ala Arg Arg Gln Val Glu Ile Leu Asn Ala Gln Gln
1160                1165                1170

Gln Ser Arg Asp Lys Glu Val Glu Ser Leu Arg Met Gln Leu Leu
1175                1180                1185

Asp Tyr Gln Ala Gln Ser Asp Glu Lys Ser Leu Ile Ala Lys Leu
1190                1195                1200

His Gln His Asn Val Ser Leu Gln Leu Ser Glu Ala Thr Ala Leu
1205                1210                1215

Gly Lys Leu Glu Ser Ile Thr Ser Lys Leu Gln Lys Met Glu Ala
1220                1225                1230

Tyr Asn Leu Arg Leu Glu Gln Lys Leu Asp Glu Lys Glu Gln Ala
1235                1240                1245

Leu Tyr Tyr Ala Arg Leu Glu Gly Arg Asn Arg Ala Lys His Leu
1250                1255                1260

Arg Gln Thr Ile Gln Ser Leu Arg Arg Gln Phe Ser Gly Ala Leu
1265                1270                1275

Pro Leu Ala Gln Gln Glu Lys Phe Ser Lys Thr Met Ile Gln Leu
1280                1285                1290

Gln Asn Asp Lys Leu Lys Ile Met Gln Glu Met Lys Asn Ser Gln
1295                1300                1305

Gln Glu His Arg Asn Met Glu Asn Lys Thr Leu Glu Met Glu Leu
1310                1315                1320

Lys Leu Lys Gly Leu Glu Glu Leu Ile Ser Thr Leu Lys Asp Thr
1325                1330                1335

Lys Gly Ala Gln Lys Val Ile Asn Trp His Met Lys Ile Glu Glu
1340                1345                1350

Leu Arg Leu Gln Glu Leu Lys Leu Asn Arg Glu Leu Val Lys Asp
1355                1360                1365

Lys Glu Glu Ile Lys Tyr Leu Asn Asn Ile Ile Ser Glu Tyr Glu
1370                1375                1380

Arg Thr Ile Ser Ser Leu Glu Glu Ile Val Gln Gln Asn Lys
1385                1390                1395

Phe His Glu Glu Arg Gln Met Ala Trp Asp Gln Arg Glu Val Asp
1400                1405                1410

Leu Glu Arg Gln Leu Asp Ile Phe Asp Arg Gln Gln Asn Glu Ile
1415                1420                1425

Leu Asn Ala Ala Gln Lys Phe Glu Glu Ala Thr Gly Ser Ile Pro
1430                1435                1440

Asp Pro Ser Leu Pro Leu Pro Asn Gln Leu Glu Ile Ala Leu Arg
1445                1450                1455

-continued

```
Lys Ile Lys Glu Asn Ile Arg Ile Ile Leu Glu Thr Arg Ala Thr
1460                1465                1470

Cys Lys Ser Leu Glu Glu Lys Leu Lys Glu Lys Glu Ser Ala Leu
1475                1480                1485

Arg Leu Ala Glu Gln Asn Ile Leu Ser Arg Asp Lys Val Ile Asn
1490                1495                1500

Glu Leu Arg Leu Arg Leu Pro Ala Thr Ala Glu Arg Glu Lys Leu
1505                1510                1515

Ile Ala Glu Leu Gly Arg Lys Glu Met Glu Pro Lys Ser His His
1520                1525                1530

Thr Leu Lys Ile Ala His Gln Thr Ile Ala Asn Met Gln Ala Arg
1535                1540                1545

Leu Asn Gln Lys Glu Glu Val Leu Lys Lys Tyr Gln Arg Leu Leu
1550                1555                1560

Glu Lys Ala Arg Glu Glu Gln Arg Glu Ile Val Lys Lys His Glu
1565                1570                1575

Glu Asp Leu His Ile Leu His His Arg Leu Glu Leu Gln Ala Asp
1580                1585                1590

Ser Ser Leu Asn Lys Phe Lys Gln Thr Ala Trp Asp Leu Met Lys
1595                1600                1605

Gln Ser Pro Thr Pro Val Pro Thr Asn Lys His Phe Ile Arg Leu
1610                1615                1620

Ala Glu Met Glu Gln Thr Val Ala Glu Gln Asp Asp Ser Leu Ser
1625                1630                1635

Ser Leu Leu Val Lys Leu Lys Lys Val Ser Gln Asp Leu Glu Arg
1640                1645                1650

Gln Arg Glu Ile Thr Glu Leu Lys Val Lys Glu Phe Glu Asn Ile
1655                1660                1665

Lys Leu Gln Leu Gln Glu Asn His Glu Asp Glu Val Lys Lys Val
1670                1675                1680

Lys Ala Glu Val Glu Asp Leu Lys Tyr Leu Leu Asp Gln Ser Gln
1685                1690                1695

Lys Glu Ser Gln Cys Leu Lys Ser Glu Leu Gln Ala Gln Lys Glu
1700                1705                1710

Ala Asn Ser Arg Ala Pro Thr Thr Thr Met Arg Asn Leu Val Glu
1715                1720                1725

Arg Leu Lys Ser Gln Leu Ala Leu Lys Glu Lys Gln Gln Lys Ala
1730                1735                1740

Leu Ser Arg Ala Leu Leu Glu Leu Arg Ala Glu Met Thr Ala Ala
1745                1750                1755

Ala Glu Glu Arg Ile Ile Ser Ala Thr Ser Gln Lys Glu Ala His
1760                1765                1770

Leu Asn Val Gln Gln Ile Val Asp Arg His Thr Arg Glu Leu Lys
1775                1780                1785

Thr Gln Val Glu Asp Leu Asn Glu Asn Leu Leu Lys Leu Lys Glu
1790                1795                1800

Ala Leu Lys Thr Ser Lys Asn Arg Glu Asn Ser Leu Thr Asp Asn
1805                1810                1815

Leu Asn Asp Leu Asn Asn Glu Leu Gln Lys Lys Gln Lys Ala Tyr
1820                1825                1830

Asn Lys Ile Leu Arg Glu Lys Glu Glu Ile Asp Gln Glu Asn Asp
1835                1840                1845

Glu Leu Lys Arg Gln Ile Lys Arg Leu Thr Ser Gly Leu Gln Gly
```

1850                1855                1860

Lys Pro Leu Thr Asp Asn Lys Gln Ser Leu Ile Glu Glu Leu Gln
    1865                1870                1875

Arg Lys Val Lys Lys Leu Glu Asn Gln Leu Glu Gly Lys Val Glu
    1880                1885                1890

Glu Val Asp Leu Lys Pro Met Lys Glu Lys Asn Ala Lys Glu Glu
    1895                1900                1905

Leu Ile Arg Trp Glu Glu Gly Lys Lys Trp Gln Ala Lys Ile Glu
    1910                1915                1920

Gly Ile Arg Asn Lys Leu Lys Glu Lys Glu Gly Glu Val Phe Thr
    1925                1930                1935

Leu Thr Lys Gln Leu Asn Thr Leu Lys Asp Leu Phe Ala Lys Ala
    1940                1945                1950

Asp Lys Glu Lys Leu Thr Leu Gln Arg Lys Leu Lys Thr Thr Gly
    1955                1960                1965

Met Thr Val Asp Gln Val Leu Gly Ile Arg Ala Leu Glu Ser Glu
    1970                1975                1980

Lys Glu Leu Glu Glu Leu Lys Lys Arg Asn Leu Asp Leu Glu Asn
    1985                1990                1995

Asp Ile Leu Tyr Met Arg Ala His Gln Ala Leu Pro Arg Asp Ser
    2000                2005                2010

Val Val Glu Asp Leu His Leu Gln Asn Arg Tyr Leu Gln Glu Lys
    2015                2020                2025

Leu His Ala Leu Glu Lys Gln Phe Ser Lys Asp Thr Tyr Ser Lys
    2030                2035                2040

Pro Ser Ile Ser Gly Ile Glu Ser Asp Asp His Cys Gln Arg Glu
    2045                2050                2055

Gln Glu Leu Gln Lys Glu Asn Leu Lys Leu Ser Ser Glu Asn Ile
    2060                2065                2070

Glu Leu Lys Phe Gln Leu Glu Gln Ala Asn Lys Asp Leu Pro Arg
    2075                2080                2085

Leu Lys Asn Gln Val Arg Asp Leu Lys Glu Met Cys Glu Phe Leu
    2090                2095                2100

Lys Lys Glu Lys Ala Glu Val Gln Arg Lys Leu Gly His Val Arg
    2105                2110                2115

Gly Ser Gly Arg Ser Gly Lys Thr Ile Pro Glu Leu Glu Lys Thr
    2120                2125                2130

Ile Gly Leu Met Lys Lys Val Val Glu Lys Val Gln Arg Glu Asn
    2135                2140                2145

Glu Gln Leu Lys Lys Ala Ser Gly Ile Leu Thr Ser Glu Lys Met
    2150                2155                2160

Ala Asn Ile Glu Gln Glu Asn Glu Lys Leu Lys Ala Glu Leu Glu
    2165                2170                2175

Lys Leu Lys Ala His Leu Gly His Gln Leu Ser Met His Tyr Glu
    2180                2185                2190

Ser Lys Thr Lys Gly Thr Glu Lys Ile Ile Ala Glu Asn Glu Arg
    2195                2200                2205

Leu Arg Lys Glu Leu Lys Lys Glu Thr Asp Ala Ala Glu Lys Leu
    2210                2215                2220

Arg Ile Ala Lys Asn Asn Leu Glu Ile Leu Asn Glu Lys Met Thr
    2225                2230                2235

Val Gln Leu Glu Glu Thr Gly Lys Arg Leu Gln Phe Ala Glu Ser
    2240                2245                2250

-continued

Arg Gly Pro Gln Leu Glu Gly Ala Asp Ser Lys Ser Trp Lys Ser
    2255            2260            2265

Ile Val Val Thr Arg Met Tyr Glu Thr Lys Leu Lys Glu Leu Glu
    2270            2275            2280

Thr Asp Ile Ala Lys Lys Asn Gln Ser Ile Thr Asp Leu Lys Gln
    2285            2290            2295

Leu Val Lys Glu Ala Thr Glu Arg Glu Gln Lys Val Asn Lys Tyr
    2300            2305            2310

Asn Glu Asp Leu Glu Gln Gln Ile Lys Ile Leu Lys His Val Pro
    2315            2320            2325

Glu Gly Ala Glu Thr Glu Gln Gly Leu Lys Arg Glu Leu Gln Val
    2330            2335            2340

Leu Arg Leu Ala Asn His Gln Leu Asp Lys Glu Lys Ala Glu Leu
    2345            2350            2355

Ile His Gln Ile Glu Ala Asn Lys Asp Gln Ser Gly Ala Glu Ser
    2360            2365            2370

Thr Ile Pro Asp Ala Asp Gln Leu Lys Glu Lys Ile Lys Asp Leu
    2375            2380            2385

Glu Thr Gln Leu Lys Met Ser Asp Leu Glu Lys Gln His Leu Lys
    2390            2395            2400

Glu Glu Ile Lys Lys Leu Lys Lys Glu Leu Glu Asn Phe Asp Pro
    2405            2410            2415

Ser Phe Phe Glu Glu Ile Glu Asp Leu Lys Tyr Asn Tyr Lys Glu
    2420            2425            2430

Glu Val Lys Lys Asn Ile Leu Leu Glu Glu Lys Val Lys Lys Leu
    2435            2440            2445

Ser Glu Gln Leu Gly Val Glu Leu Thr Ser Pro Val Ala Ala Ser
    2450            2455            2460

Glu Glu Phe Glu Asp Glu Glu Glu Ser Pro Val Asn Phe Pro Ile
    2465            2470            2475

Tyr

<210> SEQ ID NO 2
<211> LENGTH: 1116
<212> TYPE: PRT
<213> ORGANISM: Homo sapiens

<400> SEQUENCE: 2

Thr Glu Asn Ile Ser Gln Gly Asp Arg Ile Ser Glu Arg Lys Leu Asp
1               5                   10                  15

Leu Leu Ser Leu Lys Asn Met Ser Glu Ala Gln Ser Lys Asn Glu Phe
            20                  25                  30

Leu Ser Arg Glu Leu Ile Glu Lys Glu Arg Asp Leu Gly Arg Ser Arg
        35                  40                  45

Thr Val Ile Ala Lys Phe Gln Asn Lys Leu Lys Glu Leu Val Glu Glu
    50                  55                  60

Asn Lys Gln Leu Glu Glu Gly Met Lys Glu Ile Leu Gln Ala Ile Lys
65                  70                  75                  80

Glu Met Gln Lys Asp Pro Asp Val Lys Gly Gly Glu Thr Ser Leu Ile
                85                  90                  95

Ile Pro Ser Leu Glu Arg Leu Val Asn Ala Ile Glu Ser Lys Asn Ala
            100                 105                 110

Glu Gly Ile Phe Asp Ala Ser Leu His Leu Lys Ala Gln Val Asp Gln
        115                 120                 125

Leu Thr Gly Arg Asn Glu Glu Leu Arg Gln Glu Leu Arg Glu Ser Arg
    130                 135                 140

Lys Glu Ala Ile Asn Tyr Ser Gln Gln Leu Ala Lys Ala Asn Leu Lys
145                 150                 155                 160

Ile Asp His Leu Glu Lys Glu Thr Ser Leu Leu Arg Gln Ser Glu Gly
                165                 170                 175

Ser Asn Val Val Phe Lys Gly Ile Asp Leu Pro Asp Gly Ile Ala Pro
            180                 185                 190

Ser Ser Ala Ser Ile Ile Asn Ser Gln Asn Glu Tyr Leu Ile His Leu
        195                 200                 205

Leu Gln Glu Leu Glu Asn Lys Glu Lys Lys Leu Lys Asn Leu Glu Asp
    210                 215                 220

Ser Leu Glu Asp Tyr Asn Arg Lys Phe Ala Val Ile Arg His Gln Gln
225                 230                 235                 240

Ser Leu Leu Tyr Lys Glu Tyr Leu Ser Glu Lys Glu Thr Trp Lys Thr
                245                 250                 255

Glu Ser Lys Thr Ile Lys Glu Glu Lys Arg Lys Leu Glu Asp Gln Val
            260                 265                 270

Gln Gln Asp Ala Ile Lys Val Lys Glu Tyr Asn Asn Leu Leu Asn Ala
        275                 280                 285

Leu Gln Met Asp Ser Asp Glu Met Lys Lys Ile Leu Ala Glu Asn Ser
    290                 295                 300

Arg Lys Ile Thr Val Leu Gln Val Asn Glu Lys Ser Leu Ile Arg Gln
305                 310                 315                 320

Tyr Thr Thr Leu Val Glu Leu Glu Arg Gln Leu Arg Lys Glu Asn Glu
                325                 330                 335

Lys Gln Lys Asn Glu Leu Leu Ser Met Glu Ala Glu Val Cys Glu Lys
            340                 345                 350

Ile Gly Cys Leu Gln Arg Phe Lys Glu Met Ala Ile Phe Lys Ile Ala
        355                 360                 365

Ala Leu Gln Lys Val Val Asp Asn Ser Val Ser Leu Ser Glu Leu Glu
    370                 375                 380

Leu Ala Asn Lys Gln Tyr Asn Glu Leu Thr Ala Lys Tyr Arg Asp Ile
385                 390                 395                 400

Leu Gln Lys Asp Asn Met Leu Val Gln Arg Thr Ser Asn Leu Glu His
                405                 410                 415

Leu Glu Cys Glu Asn Ile Ser Leu Lys Glu Gln Val Glu Ser Ile Asn
            420                 425                 430

Lys Glu Leu Glu Ile Thr Lys Glu Lys Leu His Thr Ile Glu Gln Ala
        435                 440                 445

Trp Glu Gln Glu Thr Lys Leu Gly Asn Glu Ser Ser Met Asp Lys Ala
    450                 455                 460

Lys Lys Ser Ile Thr Asn Ser Asp Ile Val Ser Ile Ser Lys Lys Ile
465                 470                 475                 480

Thr Met Leu Glu Met Lys Glu Leu Asn Glu Arg Gln Arg Ala Glu His
                485                 490                 495

Cys Gln Lys Met Tyr Glu His Leu Arg Thr Ser Leu Lys Gln Met Glu
            500                 505                 510

Glu Arg Asn Phe Glu Leu Glu Thr Lys Phe Ala Glu Leu Thr Lys Ile
        515                 520                 525

Asn Leu Asp Ala Gln Lys Val Glu Gln Met Leu Arg Asp Glu Leu Ala
    530                 535                 540

-continued

Asp Ser Val Ser Lys Ala Val Ser Asp Ala Asp Arg Gln Arg Ile Leu
545                 550                 555                 560

Glu Leu Glu Lys Asn Glu Met Glu Leu Lys Val Glu Val Ser Lys Leu
            565                 570                 575

Arg Glu Ile Ser Asp Ile Ala Arg Arg Gln Val Glu Ile Leu Asn Ala
            580                 585                 590

Gln Gln Gln Ser Arg Asp Lys Glu Val Glu Ser Leu Arg Met Gln Leu
        595                 600                 605

Leu Asp Tyr Gln Ala Gln Ser Asp Glu Lys Ser Leu Ile Ala Lys Leu
    610                 615                 620

His Gln His Asn Val Ser Leu Gln Leu Ser Glu Ala Thr Ala Leu Gly
625                 630                 635                 640

Lys Leu Glu Ser Ile Thr Ser Lys Leu Gln Lys Met Glu Ala Tyr Asn
            645                 650                 655

Leu Arg Leu Glu Gln Lys Leu Asp Glu Lys Glu Gln Ala Leu Tyr Tyr
            660                 665                 670

Ala Arg Leu Glu Gly Arg Asn Arg Ala Lys His Leu Arg Gln Thr Ile
        675                 680                 685

Gln Ser Leu Arg Arg Gln Phe Ser Gly Ala Leu Pro Leu Ala Gln Gln
    690                 695                 700

Glu Lys Phe Ser Lys Thr Met Ile Gln Leu Gln Asn Asp Lys Leu Lys
705                 710                 715                 720

Ile Met Gln Glu Met Lys Asn Ser Gln Gln Glu His Arg Asn Met Glu
            725                 730                 735

Asn Lys Thr Leu Glu Met Glu Leu Lys Leu Lys Gly Leu Glu Glu Leu
            740                 745                 750

Ile Ser Thr Leu Lys Asp Thr Lys Gly Ala Gln Lys Val Ile Asn Trp
        755                 760                 765

His Met Lys Ile Glu Glu Leu Arg Leu Gln Glu Leu Lys Leu Asn Arg
    770                 775                 780

Glu Leu Val Lys Asp Lys Glu Ile Lys Tyr Leu Asn Asn Ile Ile
785                 790                 795                 800

Ser Glu Tyr Glu Arg Thr Ile Ser Ser Leu Glu Glu Glu Ile Val Gln
            805                 810                 815

Gln Asn Lys Phe His Glu Glu Arg Gln Met Ala Trp Asp Gln Arg Glu
            820                 825                 830

Val Asp Leu Glu Arg Gln Leu Asp Ile Phe Asp Arg Gln Gln Asn Glu
        835                 840                 845

Ile Leu Asn Ala Ala Gln Lys Phe Glu Glu Ala Thr Gly Ser Ile Pro
850                 855                 860

Asp Pro Ser Leu Pro Leu Pro Asn Gln Leu Glu Ile Ala Leu Arg Lys
865                 870                 875                 880

Ile Lys Glu Asn Ile Arg Ile Leu Glu Thr Arg Ala Thr Cys Lys
            885                 890                 895

Ser Leu Glu Glu Lys Leu Lys Glu Lys Glu Ser Ala Leu Arg Leu Ala
            900                 905                 910

Glu Gln Asn Ile Leu Ser Arg Asp Lys Val Ile Asn Glu Leu Arg Leu
        915                 920                 925

Arg Leu Pro Ala Thr Ala Glu Arg Glu Lys Leu Ile Ala Glu Leu Gly
    930                 935                 940

Arg Lys Glu Met Glu Pro Lys Ser His His Thr Leu Lys Ile Ala His
945                 950                 955                 960

Gln Thr Ile Ala Asn Met Gln Ala Arg Leu Asn Gln Lys Glu Glu Val

```
                    965                 970                 975
Leu Lys Lys Tyr Gln Arg Leu Leu Glu Lys Ala Arg Glu Glu Gln Arg
                980                 985                 990

Glu Ile Val Lys Lys His Glu Glu Asp Leu His Ile Leu His His Arg
            995                1000               1005

Leu Glu Leu Gln Ala Asp Ser Ser Leu Asn Lys Phe Lys Gln Thr
       1010                1015               1020

Ala Trp Asp Leu Met Lys Gln Ser Pro Thr Pro Val Pro Thr Asn
       1025                1030               1035

Lys His Phe Ile Arg Leu Ala Glu Met Glu Gln Thr Val Ala Glu
       1040                1045               1050

Gln Asp Asp Ser Leu Ser Ser Leu Leu Val Lys Leu Lys Lys Val
       1055                1060               1065

Ser Gln Asp Leu Glu Arg Gln Arg Glu Ile Thr Glu Leu Lys Val
       1070                1075               1080

Lys Glu Phe Glu Asn Ile Lys Leu Gln Leu Gln Glu Asn His Glu
       1085                1090               1095

Asp Glu Val Lys Lys Val Lys Ala Glu Val Glu Asp Leu Lys Tyr
       1100                1105               1110

Leu Leu Asp
       1115

<210> SEQ ID NO 3
<211> LENGTH: 601
<212> TYPE: PRT
<213> ORGANISM: Homo sapiens

<400> SEQUENCE: 3

Thr Glu Asn Ile Ser Gln Gly Asp Arg Ile Ser Glu Arg Lys Leu Asp
1               5                  10                  15

Leu Leu Ser Leu Lys Asn Met Ser Glu Ala Gln Ser Lys Asn Glu Phe
            20                  25                  30

Leu Ser Arg Glu Leu Ile Glu Lys Glu Arg Asp Leu Glu Arg Ser Arg
        35                  40                  45

Thr Val Ile Ala Lys Phe Gln Asn Lys Leu Lys Glu Leu Val Glu Glu
    50                  55                  60

Asn Lys Gln Leu Glu Glu Gly Met Lys Glu Ile Leu Gln Ala Ile Lys
65                  70                  75                  80

Glu Met Gln Lys Asp Pro Asp Val Lys Gly Gly Glu Thr Ser Leu Ile
                85                  90                  95

Ile Pro Ser Leu Glu Arg Leu Val Asn Ala Ile Glu Ser Lys Asn Ala
            100                 105                 110

Glu Gly Ile Phe Asp Ala Ser Leu His Leu Lys Ala Gln Val Asp Gln
        115                 120                 125

Leu Thr Gly Arg Asn Glu Glu Leu Arg Gln Glu Leu Arg Glu Ser Arg
    130                 135                 140

Lys Glu Ala Ile Asn Tyr Ser Gln Gln Leu Ala Lys Ala Asn Leu Lys
145                 150                 155                 160

Ile Asp His Leu Glu Lys Glu Thr Ser Leu Leu Arg Gln Ser Glu Gly
                165                 170                 175

Ser Asn Val Val Phe Lys Gly Ile Asp Leu Pro Asp Gly Ile Ala Pro
            180                 185                 190

Ser Ser Ala Ser Ile Ile Asn Ser Gln Asn Glu Tyr Leu Ile His Leu
        195                 200                 205
```

```
Leu Gln Glu Leu Glu Asn Lys Glu Lys Lys Leu Lys Asn Leu Glu Asp
    210             215                 220
Ser Leu Glu Asp Tyr Asn Arg Lys Phe Ala Val Ile Arg His Gln Gln
225             230                 235                 240
Ser Leu Leu Tyr Lys Glu Tyr Leu Ser Glu Lys Glu Thr Trp Lys Thr
                245                 250                 255
Glu Ser Lys Thr Ile Lys Glu Lys Arg Lys Leu Glu Asp Gln Val
            260                 265                 270
Gln Gln Asp Ala Ile Lys Val Lys Glu Tyr Asn Asn Leu Leu Asn Ala
            275                 280                 285
Leu Gln Met Asp Ser Asp Glu Met Lys Lys Ile Leu Ala Glu Asn Ser
    290                 295                 300
Arg Lys Ile Thr Val Leu Gln Val Asn Glu Lys Ser Leu Ile Arg Gln
305                 310                 315                 320
Tyr Thr Thr Leu Val Glu Leu Glu Arg Gln Leu Arg Lys Glu Asn Glu
                325                 330                 335
Lys Gln Lys Asn Glu Leu Leu Ser Met Glu Ala Glu Val Cys Glu Lys
            340                 345                 350
Ile Gly Cys Leu Gln Arg Phe Lys Glu Met Ala Ile Phe Lys Ile Ala
        355                 360                 365
Ala Leu Gln Lys Val Val Asp Asn Ser Val Ser Leu Ser Glu Leu Glu
    370                 375                 380
Leu Ala Asn Lys Gln Tyr Asn Glu Leu Thr Ala Lys Tyr Arg Asp Ile
385                 390                 395                 400
Leu Gln Lys Asp Asn Met Leu Val Gln Arg Thr Ser Asn Leu Glu His
                405                 410                 415
Leu Glu Cys Glu Asn Ile Ser Leu Lys Glu Gln Val Glu Ser Ile Asn
            420                 425                 430
Lys Glu Leu Glu Ile Thr Lys Glu Lys Leu His Thr Ile Glu Gln Ala
        435                 440                 445
Trp Glu Gln Glu Thr Lys Leu Gly Asn Glu Ser Ser Met Asp Lys Ala
    450                 455                 460
Lys Lys Ser Ile Thr Asn Ser Asp Ile Val Ser Ile Ser Lys Lys Ile
465                 470                 475                 480
Thr Met Leu Glu Met Lys Glu Leu Asn Glu Arg Gln Arg Ala Glu His
                485                 490                 495
Cys Gln Lys Met Tyr Glu His Leu Arg Thr Ser Leu Lys Gln Met Glu
            500                 505                 510
Glu Arg Asn Phe Glu Leu Glu Thr Lys Phe Ala Glu Leu Thr Lys Ile
        515                 520                 525
Asn Leu Asp Ala Gln Lys Val Glu Gln Met Leu Arg Asp Glu Leu Ala
    530                 535                 540
Asp Ser Val Ser Lys Ala Val Ser Asp Ala Asp Arg Gln Arg Ile Leu
545                 550                 555                 560
Glu Leu Glu Lys Asn Glu Met Glu Leu Lys Val Glu Val Ser Lys Leu
                565                 570                 575
Arg Glu Ile Ser Asp Ile Ala Arg Arg Gln Val Glu Ile Leu Asn Ala
            580                 585                 590
Gln Gln Gln Ser Arg Asp Lys Glu Val
        595                 600

<210> SEQ ID NO 4
<211> LENGTH: 515
<212> TYPE: PRT
```

-continued

<213> ORGANISM: Homo sapiens

<400> SEQUENCE: 4

Glu Ser Leu Arg Met Gln Leu Asp Tyr Gln Ala Gln Ser Asp Glu
1               5                   10                  15

Lys Ser Leu Ile Ala Lys Leu His Gln His Asn Val Ser Leu Gln Leu
            20                  25                  30

Ser Glu Ala Thr Ala Leu Gly Lys Leu Glu Ser Ile Thr Ser Lys Leu
        35                  40                  45

Gln Lys Met Glu Ala Tyr Asn Leu Arg Leu Glu Gln Lys Leu Asp Glu
    50                  55                  60

Lys Glu Gln Ala Leu Tyr Tyr Ala Arg Leu Glu Gly Arg Asn Arg Ala
65                  70                  75                  80

Lys His Leu Arg Gln Thr Ile Gln Ser Leu Arg Arg Gln Phe Ser Gly
                85                  90                  95

Ala Leu Pro Leu Ala Gln Gln Glu Lys Phe Ser Lys Thr Met Ile Gln
            100                 105                 110

Leu Gln Asn Asp Lys Leu Lys Ile Met Gln Glu Met Lys Asn Ser Gln
        115                 120                 125

Gln Glu His Arg Asn Met Glu Asn Lys Thr Leu Glu Met Glu Leu Lys
    130                 135                 140

Leu Lys Gly Leu Glu Glu Leu Ile Ser Thr Leu Lys Asp Thr Lys Gly
145                 150                 155                 160

Ala Gln Lys Val Ile Asn Trp His Met Lys Ile Glu Glu Leu Arg Leu
                165                 170                 175

Gln Glu Leu Lys Leu Asn Arg Glu Leu Val Lys Asp Lys Glu Glu Ile
            180                 185                 190

Lys Tyr Leu Asn Asn Ile Ile Ser Glu Tyr Glu Arg Thr Ile Ser Ser
        195                 200                 205

Leu Glu Glu Glu Ile Val Gln Gln Asn Lys Phe His Glu Glu Arg Gln
    210                 215                 220

Met Ala Trp Asp Gln Arg Glu Val Asp Leu Glu Arg Gln Leu Asp Ile
225                 230                 235                 240

Phe Asp Arg Gln Gln Asn Glu Ile Leu Asn Ala Ala Gln Lys Phe Glu
                245                 250                 255

Glu Ala Thr Gly Ser Ile Pro Asp Pro Ser Leu Pro Leu Pro Asn Gln
            260                 265                 270

Leu Glu Ile Ala Leu Arg Lys Ile Lys Glu Asn Ile Arg Ile Ile Leu
        275                 280                 285

Glu Thr Arg Ala Thr Cys Lys Ser Leu Glu Glu Lys Leu Lys Glu Lys
    290                 295                 300

Glu Ser Ala Leu Arg Leu Ala Glu Gln Asn Ile Leu Ser Arg Asp Lys
305                 310                 315                 320

Val Ile Asn Glu Leu Arg Leu Arg Leu Pro Ala Thr Ala Glu Arg Glu
                325                 330                 335

Lys Leu Ile Ala Glu Leu Gly Arg Lys Glu Met Glu Pro Lys Ser His
            340                 345                 350

His Thr Leu Lys Ile Ala His Gln Thr Ile Ala Asn Met Gln Ala Arg
        355                 360                 365

Leu Asn Gln Lys Glu Glu Val Leu Lys Lys Tyr Gln Arg Leu Leu Glu
    370                 375                 380

Lys Ala Arg Glu Glu Gln Arg Glu Ile Val Lys Lys His Glu Glu Asp
385                 390                 395                 400

| | | | | | | | | | | | |
|---|---|---|---|---|---|---|---|---|---|---|---|
|Leu|His|Ile|Leu|His|His|Arg|Leu|Glu|Leu|Gln|Ala|Asp|Ser|Ser|Leu|
| | | | |405| | | |410| | | |415| | | |

Asn Lys Phe Lys Gln Thr Ala Trp Asp Leu Met Lys Gln Ser Pro Thr
            420                 425                 430

Pro Val Pro Thr Asn Lys His Phe Ile Arg Leu Ala Glu Met Glu Gln
        435                 440                 445

Thr Val Ala Glu Gln Asp Asp Ser Leu Ser Ser Leu Leu Val Lys Leu
    450                 455                 460

Lys Lys Val Ser Gln Asp Leu Glu Arg Gln Arg Glu Ile Thr Glu Leu
465                 470                 475                 480

Lys Val Lys Glu Phe Glu Asn Ile Lys Leu Gln Leu Gln Glu Asn His
                485                 490                 495

Glu Asp Glu Val Lys Lys Val Lys Ala Glu Val Glu Asp Leu Lys Tyr
            500                 505                 510

Leu Leu Asp
        515

<210> SEQ ID NO 5
<211> LENGTH: 3606
<212> TYPE: DNA
<213> ORGANISM: Homo sapiens

<400> SEQUENCE: 5

```
actgaaaaca tttctcaagg agatagaata agtgaaagaa aattggattt attgagcctc      60
aaaaatatga gtgaagcaca atcaaagaat gaatttcttt caagagaact aattgaaaaa     120
gaaagagatt tagaaaggag taggacagtg atagccaaat tcagaataaa attaaaagaa     180
ttagttgaag aaaataagca acttgaagaa ggtatgaaag aaatattgca agcaattaag     240
gaaatgcaga aagatcctga tgttaaagga ggagaaacat ctctaattat ccctagcctt     300
gaaagactag ttaatgctat agaatcaaag aatgcagaag gaatctttga tgcgagtctg     360
catttgaaag cccaagttga tcagcttacc ggaagaaatg aagaattaag acaggagctc     420
agggaatctc ggaaagaggc tataaattat tcacagcagt tggcaaaagc taatttaaag     480
atagaccatc ttgaaaaaga aactagtctt ttacgacaat cagaaggatc gaatgttgtt     540
tttaaaggaa ttgacttacc tgatgggata gcaccatcta gtgccagtat cattaattct     600
cagaatgaat atttaataca tttgttacag gaactagaaa ataagaaaaa aagttaaag     660
aatttagaag attctcttga agattacaac agaaaatttg ctgtaattcg tcatcaacaa     720
agtttgttgt ataagaaata cctaagtgaa aaggagacct ggaaaacaga atctaaaaca     780
ataaaagagg aaaagagaaa acttgaggat caagtccaac aagatgctat aaaagtaaaa     840
gaatataata atttgctcaa tgctcttcag atggattcgg atgaaatgaa aaaaatactt     900
gcagaaaata gtaggaaaat tactgttttg caagtgaatg aaaaatcact tataaggcaa     960
tatacaacct tagtagaatt ggagcgacaa cttagaaaag aaaatgagaa gcaaagaat    1020
gaattgttgt caatggaggc tgaagtttgt gaaaaaattg ggtgtttgca agatttaag    1080
gaaatggcca ttttcaagat tgcagctctc caaaaagttg tagataatag tgtttctttg    1140
tctgaactag aactggctaa taacagtac aatgaactga ctgctaagta cagggacatc    1200
ttgcaaaaag ataatatgct tgttcaaaga acaagtaact tggaacacct ggagtgtgaa    1260
aacatctcct taaagaaaca agtggagtct ataaataaag aactggagat taccaaggaa    1320
aaacttcaca ctattgaaca agcctgggaa caggaaacta attaggtaa tgaatctagc    1380
atggataagg caaagaaatc aataaccaac agtgacattg tttccatttc aaaaaaaata    1440
```

```
actatgctgg aaatgaagga attaaatgaa aggcagcggg ctgaacattg tcaaaaaatg   1500
tatgaacact tacggacttc gttaaagcaa atggaggaac gtaattttga attggaaacc   1560
aaatttgctg agcttaccaa atcaatttg gatgcacaga aggtggaaca gatgttaaga    1620
gatgaattag ctgatagtgt gagcaaggca gtaagtgatg ctgataggca acggattcta   1680
gaattagaga agaatgaaat ggaactaaaa gttgaagtgt caaaactgag agagatttct   1740
gatattgcca aagacaagt tgaaattttg aatgcacaac aacaatctag ggacaaggaa    1800
gtaactgaaa acatttctca aggagataga ataagtgaaa gaaaattgga tttattgagc   1860
ctcaaaaata tgagtgaagc acaatcaaag aatgaatttc tttcaagaga actaattgaa   1920
aaagaaagag atttagaaag gagtaggaca gtgatagcca aatttcagaa taaattaaaa   1980
gaattagttg aagaaaataa gcaacttgaa gaaggtatga agaaatatt gcaagcaatt    2040 aaggaaatgc agaaagatcc tgatgttaaa ggaggagaaa catctctaat tatccctagc   2100
cttgaaagac tagttaatgc tatagaatca agaatgcag aaggaatctt tgatgcgagt    2160
ctgcatttga aagcccaagt tgatcagctt accggaagaa atgaagaatt aagacaggag   2220
ctcagggaat ctcggaaaga ggctataaat tattcacagc agttggcaaa agctaattta   2280
aagatagacc atcttgaaaa agaaactagt ctttttacgac aatcagaagg atcgaatgtt   2340 gttttttaaag gaattgactt acctgatggg atagcaccat ctagtgccag tatcattaat   2400
tctcagaatg aatatttaat acatttgtta caggaactag aaaataaaga aaaaagtta    2460 aagaatttag aagattctct tgaagattac aacagaaaat ttgctgtaat tcgtcatcaa   2520
caaagtttgt tgtataaaga ataccataagt gaaaaggaga cctggaaaac agaatctaaa   2580
acaataaaag aggaaaagag aaaacttgag gatcaagtcc aacaagatgc tataaaagta   2640
aaagaatata ataatttgct caatgctctt cagatggatt cggatgaaat gaaaaaaata   2700
cttgcagaaa atagtaggaa aattactgtt ttgcaagtga atgaaaaatc acttataagg   2760
caatatacaa ccttagtaga attggagcga caacttagaa aagaaatga gaagcaaaag    2820 aatgaatttgt tgtcaatgga ggctgaagtt tgtgaaaaaa ttgggtgttt gcaaagattt   2880
aaggaaatgg ccatttcaa gattgcagct ctccaaaaag ttgtagataa tagtgtttct    2940
ttgtctgaac tagaactggc taataaacag tacaatgaac tgactgctaa gtacagggac   3000
atcttgcaaa aagataatat gcttgttcaa agaacaagta acttggaaca cctggagtgt   3060
gaaacatctc ccttaaaaga acaagtggag tctataaata agaactgga gattaccaag   3120 gaaaaacttc acactattga acaagcctgg aacaggaaa ctaaattagg taatgaatct    3180
agcatggata aggcaaagaa atcaataacc aacagtgaca ttgtttccat ttcaaaaaaa   3240
ataactatgc tggaaatgaa ggaattaaat gaaaggcagc gggctgaaca ttgtcaaaaa   3300
atgtatgaac acttacggac ttcgttaaag caaatggagg aacgtaattt tgaattggaa   3360
accaaatttg ctgagcttac caaatcaat ttggatgcac agaaggtgga acagatgtta    3420
agagatgaat tagctgatag tgtgagcaag gcagtaagtg atgctgatag caacggatt    3480 ctagaattag agaagaatga aatggaacta aagttgaag tgtcaaaact gagagagatt   3540
tctgatattg ccagaagaca agttgaaatt ttgaatgcac aacaacaatc tagggacaag   3600
gaagta                                                             3606
```

<210> SEQ ID NO 6
<211> LENGTH: 1803
<212> TYPE: DNA

<213> ORGANISM: Homo sapiens

<400> SEQUENCE: 6

| | | | | | |
|---|---|---|---|---|---|
| actgaaaaca | tttctcaagg | agatagaata | agtgaaagaa | aattggattt | attgagcctc | 60 |
| aaaaatatga | gtgaagcaca | atcaaagaat | gaatttcttt | caagagaact | aattgaaaaa | 120 |
| gaaagagatt | tagaaaggag | taggacagtg | atagccaaat | tcagaataa | attaaaagaa | 180 |
| ttagttgaag | aaaataagca | acttgaagaa | ggtatgaaag | aaatattgca | agcaattaag | 240 |
| gaaatgcaga | aagatcctga | tgttaaagga | ggagaaacat | ctctaattat | ccctagcctt | 300 |
| gaaagactag | ttaatgctat | agaatcaaag | aatgcagaag | gaatctttga | tgcgagtctg | 360 |
| catttgaaag | cccaagttga | tcagcttacc | ggaagaaatg | aagaattaag | acaggagctc | 420 |
| agggaatctc | ggaaagaggc | tataaattat | tcacagcagt | tggcaaaagc | taatttaaag | 480 |
| atagaccatc | ttgaaaaaga | aactagtctt | ttacgacaat | cagaaggatc | gaatgttgtt | 540 |
| tttaaaggaa | ttgacttacc | tgatgggata | gcaccatcta | gtgccagtat | cattaattct | 600 |
| cagaatgaat | atttaataca | tttgttacag | gaactagaaa | ataaagaaaa | aaagttaaag | 660 |
| aatttagaag | attctcttga | agattacaac | agaaaatttg | ctgtaattcg | tcatcaacaa | 720 |
| agtttgttgt | ataagaata | cctaagtgaa | aaggagacct | ggaaaacaga | atctaaaaca | 780 |
| ataaaagagg | aaaagagaaa | acttgaggat | caagtccaac | aagatgctat | aaaagtaaaa | 840 |
| gaatataata | atttgctcaa | tgctcttcag | atggattcgg | atgaaatgaa | aaaaatactt | 900 |
| gcagaaaata | gtaggaaaat | tactgttttg | caagtgaatg | aaaaatcact | tataaggcaa | 960 |
| tatacaacct | tagtagaatt | ggagcgacaa | cttagaaaag | aaaatgagaa | gcaaaagaat | 1020 |
| gaattgttgt | caatggaggc | tgaagtttgt | gaaaaaattg | ggtgtttgca | aagatttaag | 1080 |
| gaaatggcca | ttttcaagat | tgcagctctc | caaaaagttg | tagataatag | tgtttctttg | 1140 |
| tctgaactag | aactggctaa | taaacagtac | aatgaactga | ctgctaagta | cagggacatc | 1200 |
| ttgcaaaaag | ataatatgct | tgttcaaaga | acaagtaact | tggaacaccct | ggagtgtgaa | 1260 |
| aacatctcct | taaaagaaca | agtggagtct | ataaataaag | aactggagat | taccaaggaa | 1320 |
| aaacttcaca | ctattgaaca | agcctgggaa | caggaaacta | aattaggtaa | tgaatctagc | 1380 |
| atggataagg | caaagaaatc | aataaccaac | agtgacattg | tttccatttc | aaaaaaaata | 1440 |
| actatgctgg | aaatgaagga | attaaatgaa | aggcagcggg | ctgaacattg | tcaaaaaatg | 1500 |
| tatgaacact | tacggacttc | gttaaagcaa | atggaggaac | gtaattttga | attggaaacc | 1560 |
| aaatttgctg | agcttaccaa | aatcaatttg | gatgcacaga | aggtggaaca | gatgttaaga | 1620 |
| gatgaattag | ctgatagtgt | gagcaaggca | gtaagtgatg | ctgataggca | acggattcta | 1680 |
| gaattagaga | agaatgaaat | ggaactaaaa | gttgaagtgt | caaaactgag | agagatttct | 1740 |
| gatattgcca | gaagacaagt | tgaaattttg | aatgcacaac | aacaatctag | ggacaaggaa | 1800 |
| gta | | | | | | 1803 |

<210> SEQ ID NO 7
<211> LENGTH: 1545
<212> TYPE: DNA
<213> ORGANISM: Homo sapiens

<400> SEQUENCE: 7

| | | | | | |
|---|---|---|---|---|---|
| gagtccctca | gaatgcaact | gctagactat | caggcacagt | ctgatgaaaa | gtcgctcatt | 60 |
| gccaagttgc | accaacataa | tgtctctctt | caactgagtg | aggctactgc | tcttggtaag | 120 |
| ttggagtcaa | ttacatctaa | actgcagaag | atggaggcct | acaacttgcg | cttagagcag | 180 |

```
aaacttgatg aaaaagaaca ggctctctat tatgctcgtt tggagggaag aaacagagca      240
aaacatctgc gccaaacaat tcagtctcta cgacgacagt ttagtggagc tttacccttg      300
gcacaacagg aaaagttctc caaaacaatg attcaactac aaaatgacaa acttaagata      360
atgcaagaaa tgaaaaattc tcaacaagaa catagaaata tggagaacaa acattggag       420 atggaattaa aattaaaggg cctggaagag ttaataagca ctttaaagga taccaaagga      480
gcccaaaagg taatcaactg gcatatgaaa atagaagaac ttcgtcttca agaacttaaa      540
ctaaatcggg aattagtcaa ggataaagaa gaaataaaat atttgaataa cataatttct      600
gaatatgaac gtacaatcag cagtcttgaa gaagaaattg tgcaacagaa caagtttcat      660
gaagaaagac aaatggcctg ggatcaaaga gaagttgacc tggaacgcca actagacatt      720
tttgaccgtc agcaaaatga aatactaaat gcggcacaaa agtttgaaga agctacagga      780
tcaatccctg accctagttt gccccttcca aatcaacttg agatcgctct aaggaaaatt      840
aaggagaaca ttcgaataat tctagaaaca cgggcaactt gcaaatcact agaagagaaa      900
ctaaaagaga aagaatctgc tttaaggtta gcagaacaaa atatactgtc aagagacaaa      960
gtaatcaatg aactgaggct tcgattgcct gccactgcag aaagagaaaa gctcatagct     1020
gagctaggca gaaaagagat ggaaccaaaa tctcaccaca cattgaaaat tgctcatcaa     1080
accattgcaa acatgcaagc aaggttaaat caaaaagaag aagtattaaa gaagtatcaa     1140
cgtcttctag aaaaagccag agaggagcaa agagaaattg tgaagaaaca tgaggaagac     1200
cttcatattc ttcatcacag attagaacta caggctgata gttcactaaa taaattcaaa     1260
caaacggctt gggatttaat gaaacagtct cccactccag ttcctaccaa caagcatttt     1320
attcgtctgg ctgagatgga acagacagta gcagaacaag atgactctct ttcctcactc     1380
ttggtcaaac taagaaaagt atcacaagat ttggagagac aaagagaaat cactgaatta     1440
aaagtaaaag aatttgaaaa tatcaaatta cagcttcaag aaaaccatga agatgaagtg     1500
aaaaaagtaa aagcggaagt agaggattta aagtatcttc tggac                     1545
```

<210> SEQ ID NO 8
<211> LENGTH: 7972
<212> TYPE: DNA
<213> ORGANISM: Homo sapiens

<400> SEQUENCE: 8

```
atttgaagtc ctcgttccac gccttctcat catcctgaac accgagctct gggactccgg       60
cggagaatct aaacgtaaag catcacccac ggtcgtgaac tgtaggctct cctggcatcc      120
gggatcttat tctggccttg gcggagttgg ggatggtgtc gcctagcagc cgctgccgct      180
ttggcttgct cgggaccatt tggctggacc cagagtccgc gtgaaccgc gatagggatc        240 tgtcagggcc gcggccggg tccagcttgg tggttgcggt agtgagaggc ctccgctggt        300
tgccaggctt ggtctagagg tggagcacag tgaaagaatt caagatgcca cctaatataa      360
actgaaagaa aataatgaaa gttgacccag atgacctgcc ccgtcaagaa gaactggcag      420
ataatttatt gatttcctta tccaaggtgg aagtaaatga gctaaaaagt gaaaagcaag      480
aaaatgtgat acacctttc agaattactc agtcactaat gaagatgaaa gctcaagaag       540
tggagctggc tttggaagaa gtagaaaaag ctggagaaga acaagcaaaa tttgaaaatc      600
aattaaaaac taaagtaatg aaactggaaa atgaactgga gatggctcag cagtctgcag      660
gtggacgaga tactcggttt ttacgtaatg aaatttgcca acttgaaaaa caattagaac      720
```

```
aaaaagatag agaattggag gacatggaaa aggagttgga gaaagagaag aaagttaatg    780
agcaattggc tcttcgaaat gaggaggcag aaaatgaaaa cagcaaatta agaagagaga    840
acaaacgtct aaagaaaaag aatgaacaac tttgtcagga tattattgac taccagaaac    900
aaatagattc acagaagaa acacttttat caagaagagg ggaagacagt gactaccgat     960
cacagttgtc taaaaaaaac tatgagctta tccaatatct tgatgaaatt cagactttaa   1020
cagaagctaa tgagaaaatt gaagttcaga atcaagaaat gagaaaaaat ttagaagagt   1080
ctgtacagga aatggagaag atgactgatg aatataatag aatgaaagct attgtgcatc   1140
agacagataa tgtaatagat cagttaaaaa aagaaaacga tcattatcaa cttcaagtgc   1200
aggagcttac agatcttctg aaatcaaaaa atgaagaaga tgatccaatt atggtagctg   1260
tcaatgcaaa agtagaagaa tggaagctaa ttttgtcttc taaagatgat gaaattattg   1320
agtatcagca aatgttacat aacctaaggg agaaacttaa gaatgctcag cttgatgctg   1380
ataaaagtaa tgttatggct ctacagcagg gtatacagga acgagacagt caaattaaga   1440
tgctcaccga acaagtagaa caatatacaa aagaaatgga aagaatact tgtattattg     1500
aagatttgaa aaatgagctc caaagaaaca aaggtgcttc aacccttct caacagactc     1560
atatgaaaat tcagtcaacg ttagacattt taaaagagaa aactaaagag ctgagagaa    1620
cagctgaact ggctgaggct gatgctaggg aaaaggataa agaattagtt gaggctctga   1680
agaggttaaa agattatgaa tcgggagtat atggtttaga agatgctgtc gttgaaataa   1740
agaattgtaa aaaccaaatt aaaataagag atcgagagat tgaaatatta acaaaggaaa   1800
tcaataaact tgaattgaag atcagtgatt tccttgatga aatgaggca cttagagagc     1860
gtgtgggcct tgaaccaaag acaatgattg atttaactga atttagaaat agcaaacact   1920
taaaacagca gcagtacaga gctgaaaacc agattctttt gaaagagatt gaagtctag    1980
aggaagaacg acttgatctg aaaaaaaaaa ttcgtcaaat ggctcaagaa agaggaaaaa   2040
gaagtgcaac ttcaggatta accactgagg acctgaacct aactgaaaac atttctcaag   2100
gagatagaat aagtgaaaga aaattggatt tattgagcct caaaatatg agtgaagcac     2160
aatcaaagaa tgaatttctt tcaagagaac taattgaaaa agaaagagat ttagaaagga   2220
gtaggacagt gatagccaaa tttcagaata aattaaaaga attagttgaa gaaaataagc   2280
aacttgaaga aggtatgaaa gaaatattgc aagcaattaa ggaaatgcag aaagatcctg   2340
atgttaaagg aggagaaaca tctctaatta tccctagcct tgaaagacta gttaatgcta   2400
tagaatcaaa gaatgcagaa ggaatctttg atgcgagtct gcatttgaaa gcccaagttg   2460
atcagcttac cggaagaaat gaagaattaa gacaggagct cagggaatct cggaaagagg   2520
ctataaaatta ttcacagcag ttggcaaaag ctaatttaaa gatagaccat cttgaaaaag   2580
aaactagtct tttacgacaa tcagaaggat cgaatgttgt ttttaaagga attgacttac   2640
ctgatgggat agcaccatct agtgccagta tcattaattc tcagaatgaa tatttaatac   2700
atttgttaca ggaactagaa aataaagaaa aaagttaaa gaatttagaa gattctcttg     2760
aagattacaa cagaaaattt gctgtaattc gtcatcaaca agtttgttg tataaagaat     2820
acctaagtga aaaggagacc tggaaaacag aatctaaaac aataaaagag gaaaagagaa   2880
aacttgagga tcaagtccaa caagatgcta taaaagtaaa agaatataat aatttgctca   2940
atgctcttca gatggattcg gatgaaatga aaaaatact gcagaaaat agtaggaaaa      3000
ttactgttt gcaagtgaat gaaaaaatcac ttataaggca atatacaacc ttagtagaat   3060
tggagcgaca acttagaaaa gaaaatgaga agcaaaagaa tgaattgttg tcaatggagg   3120
```

```
ctgaagtttg tgaaaaaatt gggtgtttgc aaagatttaa ggaaatggcc attttcaaga   3180
ttgcagctct ccaaaaagtt gtagataata gtgtttcttt gtctgaacta gaactggcta   3240
ataaacagta caatgaactg actgctaagt acagggacat cttgcaaaaa gataatatgc   3300
ttgttcaaag aacaagtaac ttggaacacc tggagtgtga aaacatctcc ttaaaagaac   3360
aagtggagtc tataaataaa gaactggaga ttaccaagga aaaacttcac actattgaac   3420
aagcctggga acaggaaact aaattaggta atgaatctag catggataag gcaaagaaat   3480
caataaccaa cagtgacatt gtttccattt caaaaaaaat aactatgctg gaaatgaagg   3540
aattaaatga aaggcagcgg gctgaacatt gtcaaaaaat gtatgaacac ttacggactt   3600
cgttaaagca aatggaggaa cgtaattttg aattggaaac caaatttgct gagcttacca   3660
aaatcaattt ggatgcacag aaggtggaac agatgttaag agatgaatta gctgatagtg   3720
tgagcaaggc agtaagtgat gctgataggc aacggattct agaattagag aagaatgaaa   3780
tggaactaaa agttgaagtg tcaaaactga gagagatttc tgatattgcc agaagacaag   3840
ttgaaatttt gaatgcacaa caacaatcta gggacaagga agtagagtcc ctcagaatgc   3900
aactgctaga ctatcaggca cagtctgatg aaaagtcgct cattgccaag ttgcaccaac   3960
ataatgtctc tcttcaactg agtgaggcta ctgctcttgg taagttggag tcaattacat   4020
ctaaactgca gaagatggag gcctacaact gcgcttaga gcagaaactt gatgaaaaag   4080
aacaggctct ctattatgct cgtttggagg aagaaacag agcaaaacat ctgcgccaaa   4140
caattcagtc tctacgacga cagtttagtg gagcttacc cttggcacaa caggaaaagt   4200
tctccaaaac aatgattcaa ctacaaaatg acaaacttaa gataatgcaa gaaatgaaaa   4260
attctcaaca agaacataga aatatggaga acaaaacatt ggagatggaa ttaaaattaa   4320
agggcctgga agagttaata agcactttaa aggataccaa aggagcccaa aaggtaatca   4380
actggcatat gaaaatagaa gaacttcgtc ttcaagaact taaactaaat cgggaattag   4440
tcaaggataa agaagaaata aaatatttga ataacataat ttctgaatat gaacgtacaa   4500
tcagcagtct tgaagaagaa attgtgcaac agaacaagtt tcatgaagaa agacaaatgg   4560
cctgggatca aagagaagtt gacctggaac gccaactaga catttttgac cgtcagcaaa   4620
atgaaatact aaatgcggca caaaagtttg aagaagctac aggatcaatc cctgacccta   4680
gtttgcccct tccaaatcaa cttgagatcg ctctaaggaa aattaaggag aacattcgaa   4740
taattctaga aacacgggca acttgcaaat cactagaaga gaaactaaaa gagaaagaat   4800
ctgctttaag gttagcagaa caaaatatac tgtcaagaga caaagtaatc aatgaactga   4860
ggcttcgatt gcctgccact gcagaaagag aaaagctcat agctgagcta ggcagaaaag   4920
agatggaacc aaaaatctca cacacattga aaattgctca tcaaaccatt gcaaacatgc   4980
aagcaaggtt aaatcaaaaa gaagaagtat taagaagta tcaacgtctt ctagaaaaag   5040
ccagagagga gcaaagagaa attgtgaaga acatgagga agaccttcat attcttcatc   5100
acagattaga actacaggct gatagttcac taaataaatt caaacaaacg gcttgggatt   5160
taatgaaaca gtctcccact ccagttccta ccaacaagca ttttattcgt ctggctgaga   5220
tggaacagac agtagcagaa caagatgact ctctttcctc actcttggtc aaactaaaga   5280
aagtatcaca agatttggag agacaaagag aaatcactga attaaaagta aaagaatttg   5340
aaaatatcaa attacagctt caagaaaacc atgaagatga agtgaaaaaa gtaaagcgg   5400 aagtagagga tttaaagtat cttctggacc agtcacaaaa ggagtcacag tgtttaaaat   5460
```

```
ctgaacttca ggctcaaaaa gaagcaaatt caagagctcc aacaactaca atgagaaatc    5520
tagtagaacg gctaaagagc caattagcct tgaaggagaa acaacagaaa gcacttagtc    5580
gggcactttt agaactccgg gcagaaatga cagcagctgc tgaagaacgt attatttctg    5640
caacttctca aaaagaggcc catctcaatg ttcaacaaat cgttgatcga catactagag    5700
agctaaagac acaagttgaa gatttaaatg aaaatctttt aaaattgaaa gaagcactta    5760
aaacaagtaa aaacagagaa aactcactaa ctgataattt gaatgactta ataatgaac    5820 tgcaaaagaa acaaaaagcc tataataaaa tacttagaga gaaagaggaa attgatcaag    5880
agaatgatga actgaaaagg caaattaaaa gactaaccag tggattacag ggcaaacccc    5940
tgacagataa taaacaaagt ctaattgaag aactccaaag gaaagttaaa aaactagaga    6000
accaattaga gggaaaggtg gaggaagtag acctaaaacc tatgaaagaa aagaatgcta    6060
aagaagaatt aattaggtgg gaagaaggta aaaagtggca agccaaaata gaaggaattc    6120
gaaacaagtt aaaagagaaa gagggggaag tctttacttt aacaaagcag ttgaatactt    6180
tgaaggatct ttttgccaaa gccgataaag agaaacttac tttgcagagg aaactaaaaa    6240
caactggcat gactgttgat caggttttgg gaatacgagc tttggagtca gaaaaagaat    6300
tggaagaatt aaaaaagaga aatcttgact tagaaaatga tatattgtat atgagggccc    6360
accaagctct tcctcgagat tctgttgtag aagatttaca tttacaaaat agatacctcc    6420
aagaaaaact tcatgcttta gaaaacagtt tttcaaagga tacatattct aagccttcaa    6480
tttcaggaat agagtcagat gatcattgtc agagagaaca ggagcttcag aaggaaaact    6540
tgaagttgtc atctgaaaat attgaactga aatttcagct tgaacaagca aataaagatt    6600
tgccaagatt aaagaatcaa gtcagagatt tgaaggaaat gtgtgaattt cttaagaaag    6660
aaaaagcaga agttcagcgg aaacttggcc atgttagagg gtctggtaga agtggaagaa    6720
caatcccaga actggaaaaa accattggtt taatgaaaaa agtagttgaa aaagtccaga    6780
gagaaaatga acagttgaaa aaagcatcag gaatattgac tagtgaaaaa atggctaata    6840
ttgagcagga aaatgaaaaa ttgaaggctg aattagaaaa acttaaagct catcttgggc    6900
atcagttgag catgcactat gaatccaaga ccaaaggcac agaaaaaatt attgctgaaa    6960
atgaaaggct tcgtaaagaa cttaaaaaag aaactgatgc tgcagagaaa ttacggatag    7020
caaagaataa tttagagata ttaaatgaga agatgacagt tcaactagaa gagactggta    7080
agagattgca gtttgcagaa agcagaggtc cacagcttga aggtgctgac agtaagagct    7140
ggaaatccat tgtggttaca agaatgtatg aaaccaagtt aaaagaattg aaactgata    7200 ttgccaaaaa aaatcaaagc attactgacc ttaaacagct tgtaaaagaa gcaacagaga    7260
gagaacaaaa agttaacaaa tacaatgaag accttgaaca acagattaag attcttaaac    7320
atgttcctga aggtgctgag acagagcaag gccttaaacg ggagcttcaa gttcttagat    7380
tagctaatca tcagctggat aaagagaaag cagaattaat ccatcagata gaagctaaca    7440
aggaccaaag tggagctgaa agcaccatac ctgatgctga tcaactaaag gaaaaaataa    7500
aagatctaga gacacagctc aaaatgtcag atctagaaaa gcagcatttg aaggaggaaa    7560 taagaagct gaaaaagaa ctggaaaatt ttgatccttc attttttgaa gaaattgaag    7620
atcttaagta taattacaag gaagaagtga agaagaatat tctcttagaa gagaaggtaa    7680
aaaaactttc agaacaattg ggagttgaat taactagccc tgttgctgct tctgaagagt    7740
ttgaagatga agaagaaagt cctgttaatt tccccatttta ctaaaggtca cctataaact    7800
ttgtttcatt taactattta ttaactttat aagttaaata tacttggaaa taagcagttc    7860
```

```
tccgaactgt agtatttcct tctcactacc ttgtaccttt atacttagat tggaattctt    7920
aataaataaa attatatgaa attttcaact tattaaaaaa aaaaaaaaaa aa            7972
```

<210> SEQ ID NO 9
<211> LENGTH: 738
<212> TYPE: PRT
<213> ORGANISM: Unknown
<220> FEATURE:
<223> OTHER INFORMATION: AAV8 capsid protein

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
```

```
                340                 345                 350
Leu Pro Tyr Val Leu Gly Ser Ala His Gln Gly Cys Leu Pro Pro Phe
            355                 360                 365
Pro Ala Asp Val Phe Met Ile Pro Gln Tyr Gly Tyr Leu Thr Leu Asn
        370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Gln Phe Thr Tyr
                405                 410                 415
Thr Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Thr Thr Gly Gly Thr Ala Asn Thr Gln Thr Leu Gly
    450                 455                 460
Phe Ser Gln Gly Gly Pro Asn Thr Met Ala Asn Gln Ala Lys Asn Trp
465                 470                 475                 480
Leu Pro Gly Pro Cys Tyr Arg Gln Gln Arg Val Ser Thr Thr Thr Gly
                485                 490                 495
Gln Asn Asn Asn Ser Asn Phe Ala Trp Thr Ala Gly Thr Lys Tyr His
            500                 505                 510
Leu Asn Gly Arg Asn Ser Leu Ala Asn Pro Gly Ile Ala Met Ala Thr
        515                 520                 525
His Lys Asp Asp Glu Glu Arg Phe Phe Pro Ser Asn Gly Ile Leu Ile
    530                 535                 540
Phe Gly Lys Gln Asn Ala Ala Arg Asp Asn Ala Asp Tyr Ser Asp Val
545                 550                 555                 560
Met Leu Thr Ser Glu Glu Ile Lys Thr Thr Asn Pro Val Ala Thr
                565                 570                 575
Glu Glu Tyr Gly Ile Val Ala Asp Asn Leu Gln Gln Gln Asn Thr Ala
            580                 585                 590
Pro Gln Ile Gly Thr Val Asn Ser Gln Gly Ala Leu Pro Gly Met Val
        595                 600                 605
Trp Gln Asn Arg Asp Val Tyr Leu Gln Gly Pro Ile Trp Ala Lys Ile
    610                 615                 620
Pro His Thr Asp Gly Asn Phe His Pro Ser Pro Leu Met Gly Gly Phe
625                 630                 635                 640
Gly Leu Lys His Pro Pro Pro Gln Ile Leu Ile Lys Asn Thr Pro Val
                645                 650                 655
Pro Ala Asp Pro Pro Thr Thr Phe Asn Gln Ser Lys Leu Asn Ser Phe
            660                 665                 670
Ile Thr Gln Tyr Ser Thr Gly Gln Val Ser Val Glu Ile Glu Trp Glu
        675                 680                 685
Leu Gln Lys Glu Asn Ser Lys Arg Trp Asn Pro Glu Ile Gln Tyr Thr
    690                 695                 700
Ser Asn Tyr Tyr Lys Ser Thr Ser Val Asp Phe Ala Val Asn Thr Glu
705                 710                 715                 720
Gly Val Tyr Ser Glu Pro Arg Pro Ile Gly Thr Arg Tyr Leu Thr Arg
                725                 730                 735
Asn Leu

<210> SEQ ID NO 10
<211> LENGTH: 1299
```

```
<212> TYPE: PRT
<213> ORGANISM: Homo sapiens

<400> SEQUENCE: 10

Glu Ser Leu Arg Met Gln Leu Asp Tyr Gln Ala Gln Ser Asp Glu
1               5                   10                  15

Lys Ser Leu Ile Ala Lys Leu His Gln His Asn Val Ser Leu Gln Leu
            20                  25                  30

Ser Glu Ala Thr Ala Leu Gly Lys Leu Glu Ser Ile Thr Ser Lys Leu
        35                  40                  45

Gln Lys Met Glu Ala Tyr Asn Leu Arg Leu Glu Gln Lys Leu Asp Glu
    50                  55                  60

Lys Glu Gln Ala Leu Tyr Tyr Ala Arg Leu Glu Gly Arg Asn Arg Ala
65                  70                  75                  80

Lys His Leu Arg Gln Thr Ile Gln Ser Leu Arg Arg Gln Phe Ser Gly
                85                  90                  95

Ala Leu Pro Leu Ala Gln Gln Glu Lys Phe Ser Lys Thr Met Ile Gln
            100                 105                 110

Leu Gln Asn Asp Lys Leu Lys Ile Met Gln Glu Met Lys Asn Ser Gln
        115                 120                 125

Gln Glu His Arg Asn Met Glu Asn Lys Thr Leu Glu Met Glu Leu Lys
    130                 135                 140

Leu Lys Gly Leu Glu Glu Leu Ile Ser Thr Leu Lys Asp Thr Lys Gly
145                 150                 155                 160

Ala Gln Lys Val Ile Asn Trp His Met Lys Ile Glu Glu Leu Arg Leu
                165                 170                 175

Gln Glu Leu Lys Leu Asn Arg Glu Leu Val Lys Asp Lys Glu Glu Ile
            180                 185                 190

Lys Tyr Leu Asn Asn Ile Ile Ser Glu Tyr Glu Arg Thr Ile Ser Ser
        195                 200                 205

Leu Glu Glu Glu Ile Val Gln Gln Asn Lys Phe His Glu Glu Arg Gln
    210                 215                 220

Met Ala Trp Asp Gln Arg Glu Val Asp Leu Gly Arg Gln Leu Asp Ile
225                 230                 235                 240

Phe Asp Arg Gln Gln Asn Glu Ile Leu Asn Ala Ala Gln Lys Phe Glu
                245                 250                 255

Glu Ala Thr Gly Ser Ile Pro Asp Pro Ser Leu Pro Leu Pro Asn Gln
            260                 265                 270

Leu Glu Ile Ala Leu Arg Lys Ile Lys Glu Asn Ile Arg Ile Ile Leu
        275                 280                 285

Glu Thr Arg Ala Thr Cys Lys Ser Leu Glu Glu Lys Leu Lys Glu Lys
    290                 295                 300

Glu Ser Ala Leu Arg Leu Ala Glu Gln Asn Ile Leu Ser Arg Asp Lys
305                 310                 315                 320

Val Ile Asn Glu Leu Arg Leu Arg Leu Pro Ala Thr Ala Glu Arg Glu
                325                 330                 335

Lys Leu Ile Ala Glu Leu Gly Arg Lys Glu Met Glu Pro Lys Ser His
            340                 345                 350

His Thr Leu Lys Ile Ala His Gln Thr Ile Ala Asn Met Gln Ala Arg
        355                 360                 365

Leu Asn Gln Lys Glu Glu Val Leu Lys Lys Tyr Gln Arg Leu Leu Glu
    370                 375                 380

Lys Ala Arg Glu Glu Gln Arg Glu Ile Val Lys Lys His Glu Glu Asp
385                 390                 395                 400
```

```
Leu His Ile Leu His His Arg Leu Glu Leu Gln Ala Asp Ser Ser Leu
                405                 410                 415
Asn Lys Phe Lys Gln Thr Ala Trp Asp Leu Met Lys Gln Ser Pro Thr
            420                 425                 430
Pro Val Pro Thr Asn Lys His Phe Ile Arg Leu Ala Glu Met Glu Gln
        435                 440                 445
Thr Val Ala Glu Gln Asp Asp Ser Leu Ser Ser Leu Leu Val Lys Leu
450                 455                 460
Lys Lys Val Ser Gln Asp Leu Glu Arg Gln Arg Glu Ile Thr Glu Leu
465                 470                 475                 480
Lys Val Lys Glu Phe Glu Asn Ile Lys Leu Gln Leu Gln Glu Asn His
                485                 490                 495
Glu Asp Glu Val Lys Lys Val Lys Ala Glu Val Glu Asp Leu Lys Tyr
            500                 505                 510
Leu Leu Asp Gln Ser Gln Lys Glu Ser Gln Cys Leu Lys Ser Glu Leu
        515                 520                 525
Gln Ala Gln Lys Glu Ala Asn Ser Arg Ala Pro Thr Thr Thr Met Arg
530                 535                 540
Asn Leu Val Glu Arg Leu Lys Ser Gln Leu Ala Leu Lys Glu Lys Gln
545                 550                 555                 560
Gln Lys Ala Leu Ser Arg Ala Leu Leu Glu Leu Arg Ala Glu Met Thr
                565                 570                 575
Ala Ala Ala Glu Glu Arg Ile Ile Ser Ala Thr Ser Gln Lys Glu Ala
            580                 585                 590
His Leu Asn Val Gln Gln Ile Val Asp Arg His Thr Arg Glu Leu Lys
        595                 600                 605
Thr Gln Val Glu Asp Leu Asn Glu Asn Leu Leu Lys Leu Lys Glu Ala
610                 615                 620
Leu Lys Thr Ser Lys Asn Arg Glu Asn Ser Leu Thr Asp Asn Leu Asn
625                 630                 635                 640
Asp Leu Asn Asn Glu Leu Gln Lys Lys Gln Lys Ala Tyr Asn Lys Ile
                645                 650                 655
Leu Arg Glu Lys Glu Glu Ile Asp Gln Glu Asn Asp Glu Leu Lys Arg
            660                 665                 670
Gln Ile Lys Arg Leu Thr Ser Gly Leu Gln Gly Lys Pro Leu Thr Asp
        675                 680                 685
Asn Lys Gln Ser Leu Ile Glu Glu Leu Gln Arg Lys Val Lys Lys Leu
        690                 695                 700
Glu Asn Gln Leu Glu Gly Lys Val Glu Glu Val Asp Leu Lys Pro Met
705                 710                 715                 720
Lys Glu Lys Asn Ala Lys Glu Glu Leu Ile Arg Trp Glu Glu Gly Lys
                725                 730                 735
Lys Trp Gln Ala Lys Ile Glu Gly Ile Arg Asn Lys Leu Lys Glu Lys
            740                 745                 750
Glu Gly Glu Val Phe Thr Leu Thr Lys Gln Leu Asn Thr Leu Lys Asp
        755                 760                 765
Leu Phe Ala Lys Ala Asp Lys Glu Lys Leu Thr Leu Gln Arg Lys Leu
        770                 775                 780
Lys Thr Thr Gly Met Thr Val Asp Gln Val Leu Gly Ile Arg Ala Leu
785                 790                 795                 800
Glu Ser Glu Lys Glu Leu Glu Glu Leu Lys Lys Arg Asn Leu Asp Leu
                805                 810                 815
```

-continued

```
Glu Asn Asp Ile Leu Tyr Met Arg Ala His Gln Ala Leu Pro Arg Asp
                820                 825                 830

Ser Val Val Glu Asp Leu His Leu Gln Asn Arg Tyr Leu Gln Glu Lys
            835                 840                 845

Leu His Ala Leu Glu Lys Gln Phe Ser Lys Asp Thr Tyr Ser Lys Pro
    850                 855                 860

Ser Ile Ser Gly Ile Glu Ser Asp Asp His Cys Gln Arg Glu Gln Glu
865                 870                 875                 880

Leu Gln Lys Glu Asn Leu Lys Leu Ser Ser Glu Asn Ile Glu Leu Lys
                885                 890                 895

Phe Gln Leu Glu Gln Ala Asn Lys Asp Leu Pro Arg Leu Lys Asn Gln
            900                 905                 910

Val Arg Asp Leu Lys Glu Met Cys Glu Phe Leu Lys Lys Glu Lys Ala
    915                 920                 925

Glu Val Gln Arg Lys Leu Gly His Val Arg Gly Ser Gly Arg Ser Gly
930                 935                 940

Lys Thr Ile Pro Glu Leu Glu Lys Thr Ile Gly Leu Met Lys Lys Val
945                 950                 955                 960

Val Glu Lys Val Gln Arg Glu Asn Glu Gln Leu Lys Lys Ala Ser Gly
                965                 970                 975

Ile Leu Thr Ser Glu Lys Met Ala Asn Ile Glu Gln Glu Asn Glu Lys
            980                 985                 990

Leu Lys Ala Glu Leu Glu Lys Leu Lys Ala His Leu Gly His Gln Leu
    995                 1000                1005

Ser Met His Tyr Glu Ser Lys Thr Lys Gly Thr Glu Lys Ile Ile
    1010                1015                1020

Ala Glu Asn Glu Arg Leu Arg Lys Glu Leu Lys Lys Glu Thr Asp
    1025                1030                1035

Ala Ala Glu Lys Leu Arg Ile Ala Lys Asn Asn Leu Glu Ile Leu
    1040                1045                1050

Asn Glu Lys Met Thr Val Gln Leu Glu Glu Thr Gly Lys Arg Leu
    1055                1060                1065

Gln Phe Ala Glu Ser Arg Gly Pro Gln Leu Glu Gly Ala Asp Ser
    1070                1075                1080

Lys Ser Trp Lys Ser Ile Val Val Thr Arg Met Tyr Glu Thr Lys
    1085                1090                1095

Leu Lys Glu Leu Glu Thr Asp Ile Ala Lys Lys Asn Gln Ser Ile
    1100                1105                1110

Thr Asp Leu Lys Gln Leu Val Lys Glu Ala Thr Glu Arg Glu Gln
    1115                1120                1125

Lys Val Asn Lys Tyr Asn Glu Asp Leu Glu Gln Gln Ile Lys Ile
    1130                1135                1140

Leu Lys His Val Pro Glu Gly Ala Glu Thr Glu Gln Gly Leu Lys
    1145                1150                1155

Arg Glu Leu Gln Val Leu Arg Leu Ala Asn His Gln Leu Asp Lys
    1160                1165                1170

Glu Lys Ala Glu Leu Ile His Gln Ile Glu Ala Asn Lys Asp Gln
    1175                1180                1185

Ser Gly Ala Glu Ser Thr Ile Pro Asp Ala Asp Gln Leu Lys Glu
    1190                1195                1200

Lys Ile Lys Asp Leu Glu Thr Gln Leu Lys Met Ser Asp Leu Glu
    1205                1210                1215

Lys Gln His Leu Lys Glu Glu Ile Lys Lys Leu Lys Lys Glu Leu
```

```
                    1220                1225                1230

Glu  Asn  Phe  Asp  Pro  Ser  Phe  Phe  Glu  Glu  Ile  Glu  Asp  Leu  Lys
               1235                1240                1245

Tyr  Asn  Tyr  Lys  Glu  Glu  Val  Lys  Lys  Asn  Ile  Leu  Leu  Glu  Glu
          1250                1255                1260

Lys  Val  Lys  Lys  Leu  Ser  Glu  Gln  Leu  Gly  Val  Glu  Leu  Thr  Ser
     1265                1270                1275

Pro  Val  Ala  Ala  Ser  Glu  Glu  Phe  Glu  Asp  Glu  Glu  Ser  Pro
1280                1285                1290

Val  Asn  Phe  Pro  Ile  Tyr
     1295

<210> SEQ ID NO 11
<211> LENGTH: 400
<212> TYPE: PRT
<213> ORGANISM: Homo sapiens

<400> SEQUENCE: 11

Ile  Leu  Thr  Lys  Glu  Ile  Asn  Lys  Leu  Glu  Leu  Lys  Ile  Ser  Asp  Phe
1                   5                   10                  15

Leu  Asp  Glu  Asn  Glu  Ala  Leu  Arg  Glu  Arg  Val  Gly  Leu  Glu  Pro  Lys
               20                  25                  30

Thr  Met  Ile  Asp  Leu  Thr  Glu  Phe  Arg  Asn  Ser  Lys  His  Leu  Lys  Gln
          35                  40                  45

Gln  Gln  Tyr  Arg  Ala  Glu  Asn  Gln  Ile  Leu  Leu  Lys  Glu  Ile  Glu  Ser
     50                  55                  60

Leu  Glu  Glu  Glu  Arg  Leu  Asp  Leu  Lys  Lys  Lys  Ile  Arg  Gln  Met  Ala
65                  70                  75                  80

Gln  Glu  Arg  Gly  Lys  Arg  Ser  Ala  Thr  Ser  Gly  Leu  Thr  Thr  Glu  Asp
               85                  90                  95

Leu  Asn  Leu  Thr  Glu  Asn  Ile  Ser  Gln  Gly  Asp  Arg  Ile  Ser  Glu  Arg
          100                 105                 110

Lys  Leu  Asp  Leu  Leu  Ser  Leu  Lys  Asn  Met  Ser  Glu  Ala  Gln  Ser  Lys
     115                 120                 125

Asn  Glu  Phe  Leu  Ser  Arg  Glu  Leu  Ile  Glu  Lys  Glu  Arg  Asp  Leu  Glu
130                 135                 140

Arg  Ser  Arg  Thr  Val  Ile  Ala  Lys  Phe  Gln  Asn  Lys  Leu  Lys  Glu  Leu
145                 150                 155                 160

Val  Glu  Glu  Asn  Lys  Gln  Leu  Glu  Glu  Gly  Met  Lys  Glu  Ile  Leu  Gln
               165                 170                 175

Ala  Ile  Lys  Glu  Met  Gln  Lys  Asp  Pro  Asp  Val  Lys  Gly  Gly  Glu  Thr
          180                 185                 190

Ser  Leu  Ile  Ile  Pro  Ser  Leu  Glu  Arg  Leu  Val  Asn  Ala  Ile  Glu  Ser
     195                 200                 205

Lys  Asn  Ala  Glu  Gly  Ile  Phe  Asp  Ala  Ser  Leu  His  Leu  Lys  Ala  Gln
210                 215                 220

Val  Asp  Gln  Leu  Thr  Gly  Arg  Asn  Glu  Glu  Leu  Arg  Gln  Glu  Leu  Arg
225                 230                 235                 240

Glu  Ser  Arg  Lys  Glu  Ala  Ile  Asn  Tyr  Ser  Gln  Gln  Leu  Ala  Lys  Ala
               245                 250                 255

Asn  Leu  Lys  Ile  Asp  His  Leu  Glu  Lys  Glu  Thr  Ser  Leu  Leu  Arg  Gln
          260                 265                 270

Ser  Glu  Gly  Ser  Asn  Val  Val  Phe  Lys  Gly  Ile  Asp  Leu  Pro  Asp  Gly
     275                 280                 285
```

```
Ile Ala Pro Ser Ser Ala Ser Ile Ile Asn Ser Gln Asn Glu Tyr Leu
            290                 295                 300

Ile His Leu Leu Gln Glu Leu Glu Asn Lys Glu Lys Lys Leu Lys Asn
305                 310                 315                 320

Leu Glu Asp Ser Leu Glu Asp Tyr Asn Arg Lys Phe Ala Val Ile Arg
                325                 330                 335

His Gln Gln Ser Leu Leu Tyr Lys Glu Tyr Leu Ser Glu Lys Glu Thr
            340                 345                 350

Trp Lys Thr Glu Ser Lys Thr Ile Lys Glu Glu Lys Arg Lys Leu Glu
                355                 360                 365

Asp Gln Val Gln Gln Asp Ala Ile Lys Val Lys Glu Tyr Asn Asn Leu
370                 375                 380

Leu Asn Ala Leu Gln Met Asp Ser Asp Glu Met Lys Lys Ile Leu Ala
385                 390                 395                 400

<210> SEQ ID NO 12
<211> LENGTH: 1029
<212> TYPE: PRT
<213> ORGANISM: Homo sapiens

<400> SEQUENCE: 12

Glu Ser Leu Arg Met Gln Leu Asp Tyr Gln Ala Gln Ser Asp Glu
1               5                   10                  15

Lys Ser Leu Ile Ala Lys Leu His Gln His Asn Val Ser Leu Gln Leu
                20                  25                  30

Ser Glu Ala Thr Ala Leu Gly Lys Leu Glu Ser Ile Thr Ser Lys Leu
            35                  40                  45

Gln Lys Met Glu Ala Tyr Asn Leu Arg Leu Glu Gln Lys Leu Asp Glu
50                  55                  60

Lys Glu Gln Ala Leu Tyr Tyr Ala Arg Leu Glu Gly Arg Asn Arg Ala
65                  70                  75                  80

Lys His Leu Arg Gln Thr Ile Gln Ser Leu Arg Arg Gln Phe Ser Gly
                85                  90                  95

Ala Leu Pro Leu Ala Gln Gln Glu Lys Phe Ser Lys Thr Met Ile Gln
            100                 105                 110

Leu Gln Asn Asp Lys Leu Lys Ile Met Gln Glu Met Lys Asn Ser Gln
        115                 120                 125

Gln Glu His Arg Asn Met Glu Asn Lys Thr Leu Glu Met Glu Leu Lys
130                 135                 140

Leu Lys Gly Leu Glu Glu Leu Ile Ser Thr Leu Lys Asp Thr Lys Gly
145                 150                 155                 160

Ala Gln Lys Val Ile Asn Trp His Met Lys Ile Glu Glu Leu Arg Leu
                165                 170                 175

Gln Glu Leu Lys Leu Asn Arg Glu Leu Val Lys Asp Lys Glu Glu Ile
            180                 185                 190

Lys Tyr Leu Asn Asn Ile Ile Ser Glu Tyr Glu Arg Thr Ile Ser Ser
        195                 200                 205

Leu Glu Glu Glu Ile Val Gln Gln Asn Lys Phe His Glu Glu Arg Gln
210                 215                 220

Met Ala Trp Asp Gln Arg Glu Val Asp Leu Glu Arg Gln Leu Asp Ile
225                 230                 235                 240

Phe Asp Arg Gln Gln Asn Glu Ile Leu Asn Ala Ala Gln Lys Phe Glu
                245                 250                 255

Glu Ala Thr Gly Ser Ile Pro Asp Pro Ser Leu Pro Leu Pro Asn Gln
            260                 265                 270
```

-continued

Leu Glu Ile Ala Leu Arg Lys Ile Lys Glu Asn Ile Arg Ile Ile Leu
            275                 280                 285

Glu Thr Arg Ala Thr Cys Lys Ser Leu Glu Glu Lys Leu Lys Glu Lys
        290                 295                 300

Glu Ser Ala Leu Arg Leu Ala Glu Gln Asn Ile Leu Ser Arg Asp Lys
305                 310                 315                 320

Val Ile Asn Glu Leu Arg Leu Arg Leu Pro Ala Thr Ala Glu Arg Glu
                325                 330                 335

Lys Leu Ile Ala Glu Leu Gly Arg Lys Glu Met Glu Pro Lys Ser His
            340                 345                 350

His Thr Leu Lys Ile Ala His Gln Thr Ile Ala Asn Met Gln Ala Arg
        355                 360                 365

Leu Asn Gln Lys Glu Glu Val Leu Lys Lys Tyr Gln Arg Leu Leu Glu
    370                 375                 380

Lys Ala Arg Glu Glu Gln Arg Glu Ile Val Lys Lys His Glu Glu Asp
385                 390                 395                 400

Leu His Ile Leu His His Arg Leu Glu Leu Gln Ala Asp Ser Ser Leu
                405                 410                 415

Asn Lys Phe Lys Gln Thr Ala Trp Asp Leu Met Lys Gln Ser Pro Thr
            420                 425                 430

Pro Val Pro Thr Asn Lys His Phe Ile Arg Leu Ala Glu Met Glu Gln
        435                 440                 445

Thr Val Ala Glu Gln Asp Asp Ser Leu Ser Ser Leu Leu Val Lys Leu
    450                 455                 460

Lys Lys Val Ser Gln Asp Leu Glu Arg Gln Arg Glu Ile Thr Glu Leu
465                 470                 475                 480

Lys Val Lys Glu Phe Glu Asn Ile Lys Leu Gln Leu Gln Glu Asn His
                485                 490                 495

Glu Asp Glu Val Lys Lys Val Lys Ala Glu Val Glu Asp Leu Lys Tyr
            500                 505                 510

Leu Leu Asp Thr Thr Gly Met Thr Val Asp Gln Val Leu Gly Ile Arg
        515                 520                 525

Ala Leu Glu Ser Glu Lys Glu Leu Glu Glu Leu Lys Lys Arg Asn Leu
    530                 535                 540

Asp Leu Glu Asn Asp Ile Leu Tyr Met Arg Ala His Gln Ala Leu Pro
545                 550                 555                 560

Arg Asp Ser Val Val Glu Asp Leu His Leu Gln Asn Arg Tyr Leu Gln
                565                 570                 575

Glu Lys Leu His Ala Leu Glu Lys Gln Phe Ser Lys Asp Thr Tyr Ser
            580                 585                 590

Lys Pro Ser Ile Ser Gly Ile Glu Ser Asp Asp His Cys Gln Arg Glu
        595                 600                 605

Gln Glu Leu Gln Lys Glu Asn Leu Lys Leu Ser Ser Glu Asn Ile Glu
    610                 615                 620

Leu Lys Phe Gln Leu Glu Gln Ala Asn Lys Asp Leu Pro Arg Leu Lys
625                 630                 635                 640

Asn Gln Val Arg Asp Leu Lys Glu Met Cys Glu Phe Leu Lys Lys Glu
                645                 650                 655

Lys Ala Glu Val Gln Arg Lys Leu Gly His Val Arg Gly Ser Gly Arg
            660                 665                 670

Ser Gly Lys Thr Ile Pro Glu Leu Glu Lys Thr Ile Gly Leu Met Lys
        675                 680                 685

-continued

```
Lys Val Val Glu Lys Val Gln Arg Glu Asn Glu Gln Leu Lys Lys Ala
    690             695                 700

Ser Gly Ile Leu Thr Ser Glu Lys Met Ala Asn Ile Glu Gln Glu Asn
705                 710                 715                 720

Glu Lys Leu Lys Ala Glu Leu Glu Lys Leu Lys Ala His Leu Gly His
            725                 730                 735

Gln Leu Ser Met His Tyr Glu Ser Lys Thr Lys Gly Thr Glu Lys Ile
                740                 745                 750

Ile Ala Glu Asn Glu Arg Leu Arg Lys Glu Leu Lys Lys Glu Thr Asp
            755                 760                 765

Ala Ala Glu Lys Leu Arg Ile Ala Lys Asn Asn Leu Glu Ile Leu Asn
770                 775                 780

Glu Lys Met Thr Val Gln Leu Glu Glu Thr Gly Lys Arg Leu Gln Phe
785                 790                 795                 800

Ala Glu Ser Arg Gly Pro Gln Leu Gly Ala Asp Ser Lys Ser Trp
                805                 810                 815

Lys Ser Ile Val Val Thr Arg Met Tyr Glu Thr Lys Leu Lys Glu Leu
            820                 825                 830

Glu Thr Asp Ile Ala Lys Lys Asn Gln Ser Ile Thr Asp Leu Lys Gln
        835                 840                 845

Leu Val Lys Glu Ala Thr Glu Arg Glu Gln Lys Val Asn Lys Tyr Asn
850                 855                 860

Glu Asp Leu Glu Gln Gln Ile Lys Ile Leu Lys His Val Pro Glu Gly
865                 870                 875                 880

Ala Glu Thr Glu Gln Gly Leu Lys Arg Glu Leu Gln Val Leu Arg Leu
            885                 890                 895

Ala Asn His Gln Leu Asp Lys Glu Lys Ala Glu Leu Ile His Gln Ile
        900                 905                 910

Glu Ala Asn Lys Asp Gln Ser Gly Ala Glu Ser Thr Ile Pro Asp Ala
    915                 920                 925

Asp Gln Leu Lys Glu Lys Ile Lys Asp Leu Glu Thr Gln Leu Lys Met
930                 935                 940

Ser Asp Leu Glu Lys Gln His Leu Lys Glu Glu Ile Lys Lys Leu Lys
945                 950                 955                 960

Lys Glu Leu Glu Asn Phe Asp Pro Ser Phe Phe Glu Glu Ile Glu Asp
            965                 970                 975

Leu Lys Tyr Asn Tyr Lys Glu Val Lys Lys Asn Ile Leu Leu Glu
        980                 985                 990

Glu Lys Val Lys Lys Leu Ser Glu Gln Leu Gly Val Glu Leu Thr Ser
            995                1000                1005

Pro Val Ala Ala Ser Glu Glu Phe Glu Asp Glu Glu Glu Ser Pro
    1010                1015                1020

Val Asn Phe Pro Ile Tyr
    1025

<210> SEQ ID NO 13
<211> LENGTH: 1281
<212> TYPE: PRT
<213> ORGANISM: Homo sapiens

<400> SEQUENCE: 13

Thr Glu Asn Ile Ser Gln Gly Asp Arg Ile Ser Glu Arg Lys Leu Asp
1               5                   10                  15

Leu Leu Ser Leu Lys Asn Met Ser Glu Ala Gln Ser Lys Asn Glu Phe
            20                  25                  30
```

```
Leu Ser Arg Glu Leu Ile Glu Lys Glu Arg Asp Leu Glu Arg Ser Arg
        35                  40                  45

Thr Val Ile Ala Lys Phe Gln Asn Lys Leu Lys Glu Leu Val Glu Glu
    50                  55                  60

Asn Lys Gln Leu Glu Glu Gly Met Lys Glu Ile Leu Gln Ala Ile Lys
65                  70                  75                  80

Glu Met Gln Lys Asp Pro Asp Val Lys Gly Glu Thr Ser Leu Ile
                85                  90                  95

Ile Pro Ser Leu Glu Arg Leu Val Asn Ala Ile Glu Ser Lys Asn Ala
                100                 105                 110

Glu Gly Ile Phe Asp Ala Ser Leu His Leu Lys Ala Gln Val Asp Gln
                115                 120                 125

Leu Thr Gly Arg Asn Glu Glu Leu Arg Gln Glu Leu Arg Glu Ser Arg
    130                 135                 140

Lys Glu Ala Ile Asn Tyr Ser Gln Gln Leu Ala Lys Ala Asn Leu Lys
145                 150                 155                 160

Ile Asp His Leu Glu Lys Glu Thr Ser Leu Leu Arg Gln Ser Glu Gly
                165                 170                 175

Ser Asn Val Val Phe Lys Gly Ile Asp Leu Pro Asp Gly Ile Ala Pro
                180                 185                 190

Ser Ser Ala Ser Ile Ile Asn Ser Gln Asn Glu Tyr Leu Ile His Leu
                195                 200                 205

Leu Gln Glu Leu Glu Asn Lys Glu Lys Lys Leu Lys Asn Leu Glu Asp
    210                 215                 220

Ser Leu Glu Asp Tyr Asn Arg Lys Phe Ala Val Ile Arg His Gln Gln
225                 230                 235                 240

Ser Leu Leu Tyr Lys Glu Tyr Leu Ser Glu Lys Glu Thr Trp Lys Thr
                245                 250                 255

Glu Ser Lys Thr Ile Lys Glu Glu Lys Arg Lys Leu Glu Asp Gln Val
                260                 265                 270

Gln Gln Asp Ala Ile Lys Val Lys Glu Tyr Asn Asn Leu Leu Asn Ala
    275                 280                 285

Leu Gln Met Asp Ser Asp Glu Met Lys Lys Ile Leu Ala Glu Asn Ser
    290                 295                 300

Arg Lys Ile Thr Val Leu Gln Val Asn Glu Lys Ser Leu Ile Arg Gln
305                 310                 315                 320

Tyr Thr Thr Leu Val Glu Leu Glu Arg Gln Leu Arg Lys Glu Asn Glu
                325                 330                 335

Lys Gln Lys Asn Glu Leu Leu Ser Met Glu Ala Glu Val Cys Glu Lys
                340                 345                 350

Ile Gly Cys Leu Gln Arg Phe Lys Glu Met Ala Ile Phe Lys Ile Ala
    355                 360                 365

Ala Leu Gln Lys Val Val Asp Asn Ser Val Ser Leu Ser Glu Leu Glu
    370                 375                 380

Leu Ala Asn Lys Gln Tyr Asn Glu Leu Thr Ala Lys Tyr Arg Asp Ile
385                 390                 395                 400

Leu Gln Lys Asp Asn Met Leu Val Gln Arg Thr Ser Asn Leu Glu His
                405                 410                 415

Leu Glu Cys Glu Asn Ile Ser Leu Lys Glu Gln Val Glu Ser Ile Asn
                420                 425                 430

Lys Glu Leu Glu Ile Thr Lys Glu Lys Leu His Thr Ile Glu Gln Ala
                435                 440                 445
```

-continued

```
Trp Glu Gln Glu Thr Lys Leu Gly Asn Glu Ser Ser Met Asp Lys Ala
450                 455                 460

Lys Lys Ser Ile Thr Asn Ser Asp Ile Val Ser Ile Ser Lys Lys Ile
465                 470                 475                 480

Thr Met Leu Glu Met Lys Glu Leu Asn Glu Arg Gln Arg Ala Glu His
                485                 490                 495

Cys Gln Lys Met Tyr Glu His Leu Arg Thr Ser Leu Lys Gln Met Glu
                500                 505                 510

Glu Arg Asn Phe Glu Leu Glu Thr Lys Phe Ala Glu Leu Thr Lys Ile
                515                 520                 525

Asn Leu Asp Ala Gln Lys Val Glu Gln Met Leu Arg Asp Glu Leu Ala
530                 535                 540

Asp Ser Val Ser Lys Ala Val Ser Asp Ala Asp Arg Gln Arg Ile Leu
545                 550                 555                 560

Glu Leu Glu Lys Asn Glu Met Glu Leu Lys Val Glu Val Ser Lys Leu
                565                 570                 575

Arg Glu Ile Ser Asp Ile Ala Arg Arg Gln Val Glu Ile Leu Asn Ala
                580                 585                 590

Gln Gln Gln Ser Arg Asp Lys Glu Val Lys Leu Lys Glu Ala Leu Lys
                595                 600                 605

Thr Ser Lys Asn Arg Glu Asn Ser Leu Thr Asp Asn Leu Asn Asp Leu
                610                 615                 620

Asn Asn Glu Leu Gln Lys Gln Lys Ala Tyr Asn Lys Ile Leu Arg
625                 630                 635                 640

Glu Lys Glu Glu Ile Asp Gln Glu Asn Asp Glu Leu Lys Arg Gln Ile
                645                 650                 655

Lys Arg Leu Thr Ser Gly Leu Gln Gly Lys Pro Leu Thr Asp Asn Lys
                660                 665                 670

Gln Ser Leu Ile Glu Glu Leu Gln Arg Lys Val Lys Lys Leu Glu Asn
                675                 680                 685

Gln Leu Glu Gly Lys Val Glu Glu Val Asp Leu Lys Pro Met Lys Glu
                690                 695                 700

Lys Asn Ala Lys Glu Glu Leu Ile Arg Trp Glu Glu Gly Lys Lys Trp
705                 710                 715                 720

Gln Ala Lys Ile Glu Gly Ile Arg Asn Lys Leu Lys Glu Lys Glu Gly
                725                 730                 735

Glu Val Phe Thr Leu Thr Lys Gln Leu Asn Thr Leu Lys Asp Leu Phe
                740                 745                 750

Ala Lys Ala Asp Lys Glu Lys Leu Thr Leu Gln Arg Lys Leu Lys Thr
                755                 760                 765

Thr Gly Met Thr Val Asp Gln Val Leu Gly Ile Arg Ala Leu Glu Ser
770                 775                 780

Glu Lys Glu Leu Glu Glu Leu Lys Lys Arg Asn Leu Asp Leu Glu Asn
785                 790                 795                 800

Asp Ile Leu Tyr Met Arg Ala His Gln Ala Leu Pro Arg Asp Ser Val
                805                 810                 815

Val Glu Asp Leu His Leu Gln Asn Arg Tyr Leu Gln Glu Lys Leu His
                820                 825                 830

Ala Leu Glu Lys Gln Phe Ser Lys Asp Thr Tyr Ser Lys Pro Ser Ile
                835                 840                 845

Ser Gly Ile Glu Ser Asp Asp His Cys Gln Arg Glu Gln Glu Leu Gln
850                 855                 860

Lys Glu Asn Leu Lys Leu Ser Ser Glu Asn Ile Glu Leu Lys Phe Gln
```

-continued

```
              865                 870                 875                 880
Leu Glu Gln Ala Asn Lys Asp Leu Pro Arg Leu Lys Asn Gln Val Arg
                    885                 890                 895

Asp Leu Lys Glu Met Cys Glu Phe Leu Lys Lys Glu Lys Ala Glu Val
                    900                 905                 910

Gln Arg Lys Leu Gly His Val Arg Gly Ser Gly Arg Ser Gly Lys Thr
                    915                 920                 925

Ile Pro Glu Leu Glu Lys Thr Ile Gly Leu Met Lys Lys Val Val Glu
                    930                 935                 940

Lys Val Gln Arg Glu Asn Glu Gln Leu Lys Lys Ala Ser Gly Ile Leu
945                 950                 955                 960

Thr Ser Glu Lys Met Ala Asn Ile Glu Gln Glu Asn Glu Lys Leu Lys
                    965                 970                 975

Ala Glu Leu Glu Lys Leu Lys Ala His Leu Gly His Gln Leu Ser Met
                    980                 985                 990

His Tyr Glu Ser Lys Thr Lys Gly Thr Glu Lys Ile Ile Ala Glu Asn
                    995                 1000                1005

Glu Arg Leu Arg Lys Glu Leu Lys Lys Glu Thr Asp Ala Ala Glu
                    1010                1015                1020

Lys Leu Arg Ile Ala Lys Asn Asn Leu Glu Ile Leu Asn Glu Lys
                    1025                1030                1035

Met Thr Val Gln Leu Glu Glu Thr Gly Lys Arg Leu Gln Phe Ala
                    1040                1045                1050

Glu Ser Arg Gly Pro Gln Leu Glu Gly Ala Asp Ser Lys Ser Trp
                    1055                1060                1065

Lys Ser Ile Val Val Thr Arg Met Tyr Glu Thr Lys Leu Lys Glu
                    1070                1075                1080

Leu Glu Thr Asp Ile Ala Lys Lys Asn Gln Ser Ile Thr Asp Leu
                    1085                1090                1095

Lys Gln Leu Val Lys Glu Ala Thr Glu Arg Glu Gln Lys Val Asn
                    1100                1105                1110

Lys Tyr Asn Glu Asp Leu Glu Gln Gln Ile Lys Ile Leu Lys His
                    1115                1120                1125

Val Pro Glu Gly Ala Glu Thr Glu Gln Gly Leu Lys Arg Glu Leu
                    1130                1135                1140

Gln Val Leu Arg Leu Ala Asn His Gln Leu Asp Lys Glu Lys Ala
                    1145                1150                1155

Glu Leu Ile His Gln Ile Glu Ala Asn Lys Asp Gln Ser Gly Ala
                    1160                1165                1170

Glu Ser Thr Ile Pro Asp Ala Asp Gln Leu Lys Glu Lys Ile Lys
                    1175                1180                1185

Asp Leu Glu Thr Gln Leu Lys Met Ser Asp Leu Glu Lys Gln His
                    1190                1195                1200

Leu Lys Glu Glu Ile Lys Lys Leu Lys Lys Glu Leu Glu Asn Phe
                    1205                1210                1215

Asp Pro Ser Phe Phe Glu Glu Ile Glu Asp Leu Lys Tyr Asn Tyr
                    1220                1225                1230

Lys Glu Glu Val Lys Lys Asn Ile Leu Leu Glu Glu Lys Val Lys
                    1235                1240                1245

Lys Leu Ser Glu Gln Leu Gly Val Glu Leu Thr Ser Pro Val Ala
                    1250                1255                1260

Ala Ser Glu Glu Phe Glu Asp Glu Glu Glu Ser Pro Val Asn Phe
                    1265                1270                1275
```

Pro Ile Tyr
     1280

<210> SEQ ID NO 14
<211> LENGTH: 786
<212> TYPE: PRT
<213> ORGANISM: Homo sapiens

<400> SEQUENCE: 14

Glu Ser Leu Arg Met Gln Leu Leu Asp Tyr Gln Ala Gln Ser Asp Glu
1               5                   10                  15

Lys Ser Leu Ile Ala Lys Leu His Gln His Asn Val Ser Leu Gln Leu
            20                  25                  30

Ser Glu Ala Thr Ala Leu Gly Lys Leu Glu Ser Ile Thr Ser Lys Leu
        35                  40                  45

Gln Lys Met Glu Ala Tyr Asn Leu Arg Leu Glu Gln Lys Leu Asp Glu
    50                  55                  60

Lys Glu Gln Ala Leu Tyr Tyr Ala Arg Leu Glu Gly Arg Asn Arg Ala
65                  70                  75                  80

Lys His Leu Arg Gln Thr Ile Gln Ser Leu Arg Arg Gln Phe Ser Gly
                85                  90                  95

Ala Leu Pro Leu Ala Gln Gln Glu Lys Phe Ser Lys Thr Met Ile Gln
            100                 105                 110

Leu Gln Asn Asp Lys Leu Lys Ile Met Gln Glu Met Lys Asn Ser Gln
        115                 120                 125

Gln Glu His Arg Asn Met Glu Asn Lys Thr Leu Glu Met Glu Leu Lys
    130                 135                 140

Leu Lys Gly Leu Glu Glu Leu Ile Ser Thr Leu Lys Asp Thr Lys Gly
145                 150                 155                 160

Ala Gln Lys Val Ile Asn Trp His Met Lys Ile Glu Glu Leu Arg Leu
                165                 170                 175

Gln Glu Leu Lys Leu Asn Arg Glu Leu Val Lys Asp Lys Glu Glu Ile
            180                 185                 190

Lys Tyr Leu Asn Asn Ile Ile Ser Glu Tyr Glu Arg Thr Ile Ser Ser
        195                 200                 205

Leu Glu Glu Glu Ile Val Gln Gln Asn Lys Phe His Glu Glu Arg Gln
    210                 215                 220

Met Ala Trp Asp Gln Arg Glu Val Asp Leu Glu Arg Gln Leu Asp Ile
225                 230                 235                 240

Phe Asp Arg Gln Gln Asn Glu Ile Leu Asn Ala Ala Gln Lys Phe Glu
                245                 250                 255

Glu Ala Thr Gly Ser Ile Pro Asp Pro Ser Leu Pro Leu Pro Asn Gln
            260                 265                 270

Leu Glu Ile Ala Leu Arg Lys Ile Lys Glu Asn Ile Arg Ile Ile Leu
        275                 280                 285

Glu Thr Arg Ala Thr Cys Lys Ser Leu Glu Glu Lys Leu Lys Glu Lys
    290                 295                 300

Glu Ser Ala Leu Arg Leu Ala Glu Gln Asn Ile Leu Ser Arg Asp Lys
305                 310                 315                 320

Val Ile Asn Glu Leu Arg Leu Arg Leu Pro Ala Thr Ala Glu Arg Glu
                325                 330                 335

Lys Leu Ile Ala Glu Leu Gly Arg Lys Glu Met Glu Pro Lys Ser His
            340                 345                 350

His Thr Leu Lys Ile Ala His Gln Thr Ile Ala Asn Met Gln Ala Arg

```
                355                 360                 365
Leu Asn Gln Lys Glu Val Leu Lys Tyr Gln Arg Leu Leu Glu
    370                 375                 380
Lys Ala Arg Glu Glu Gln Arg Glu Ile Val Lys Lys His Glu Glu Asp
385                 390                 395                 400
Leu His Ile Leu His His Arg Leu Glu Leu Gln Ala Asp Ser Ser Leu
                405                 410                 415
Asn Lys Phe Lys Gln Thr Ala Trp Asp Leu Met Lys Gln Ser Pro Thr
            420                 425                 430
Pro Val Pro Thr Asn Lys His Phe Ile Arg Leu Ala Glu Met Glu Gln
        435                 440                 445
Thr Val Ala Glu Gln Asp Asp Ser Leu Ser Ser Leu Leu Val Lys Leu
    450                 455                 460
Lys Lys Val Ser Gln Asp Leu Glu Arg Gln Arg Glu Ile Thr Glu Leu
465                 470                 475                 480
Lys Val Lys Glu Phe Glu Asn Ile Lys Leu Gln Leu Gln Glu Asn His
                485                 490                 495
Glu Asp Glu Val Lys Lys Val Lys Ala Glu Val Glu Asp Leu Lys Tyr
            500                 505                 510
Leu Leu Asp Gln Ser Gln Lys Glu Ser Gln Cys Leu Lys Ser Glu Leu
        515                 520                 525
Gln Ala Gln Lys Glu Ala Asn Ser Arg Ala Pro Thr Thr Thr Met Arg
    530                 535                 540
Asn Leu Val Glu Arg Leu Lys Ser Gln Leu Ala Leu Lys Glu Lys Gln
545                 550                 555                 560
Gln Lys Ala Leu Ser Arg Ala Leu Leu Glu Leu Arg Ala Glu Met Thr
                565                 570                 575
Ala Ala Ala Glu Glu Arg Ile Ile Ser Ala Thr Ser Gln Lys Glu Ala
            580                 585                 590
His Leu Asn Val Gln Gln Ile Val Asp Arg His Thr Arg Glu Leu Lys
        595                 600                 605
Thr Gln Val Glu Asp Leu Asn Glu Asn Leu Leu Lys Leu Lys Glu Ala
    610                 615                 620
Leu Lys Thr Ser Lys Asn Arg Glu Asn Ser Leu Thr Asp Asn Leu Asn
625                 630                 635                 640
Asp Leu Asn Asn Glu Leu Gln Lys Lys Gln Lys Ala Tyr Asn Lys Ile
                645                 650                 655
Leu Arg Glu Lys Glu Glu Ile Asp Gln Glu Asn Asp Glu Leu Lys Arg
            660                 665                 670
Gln Ile Lys Arg Leu Thr Ser Gly Leu Gln Gly Lys Pro Leu Thr Asp
        675                 680                 685
Asn Lys Gln Ser Leu Ile Glu Glu Leu Gln Arg Lys Val Lys Lys Leu
    690                 695                 700
Glu Asn Gln Leu Glu Gly Lys Val Glu Val Asp Leu Lys Pro Met
705                 710                 715                 720
Lys Glu Lys Asn Ala Lys Glu Leu Ile Arg Trp Glu Glu Gly Lys
                725                 730                 735
Lys Trp Gln Ala Lys Ile Glu Gly Ile Arg Asn Lys Leu Lys Glu Lys
            740                 745                 750
Glu Gly Glu Val Phe Thr Leu Thr Lys Gln Leu Asn Thr Leu Lys Asp
        755                 760                 765
Leu Phe Ala Lys Ala Asp Lys Glu Lys Leu Thr Leu Gln Arg Lys Leu
    770                 775                 780
```

```
Lys Thr
785

<210> SEQ ID NO 15
<211> LENGTH: 914
<212> TYPE: PRT
<213> ORGANISM: Homo sapiens

<400> SEQUENCE: 15

Ile Leu Thr Lys Glu Ile Asn Lys Leu Glu Leu Lys Ile Ser Asp Phe
1               5                   10                  15

Leu Asp Glu Asn Glu Ala Leu Arg Glu Arg Val Gly Leu Glu Pro Lys
                20                  25                  30

Thr Met Ile Asp Leu Thr Glu Phe Arg Asn Ser Lys His Leu Lys Gln
            35                  40                  45

Gln Gln Tyr Arg Ala Glu Asn Gln Ile Leu Leu Lys Glu Ile Glu Ser
        50                  55                  60

Leu Glu Glu Glu Arg Leu Asp Leu Lys Lys Lys Ile Arg Gln Met Ala
65                  70                  75                  80

Gln Glu Arg Gly Lys Arg Ser Ala Thr Ser Gly Leu Thr Thr Glu Asp
                85                  90                  95

Leu Asn Leu Thr Glu Asn Ile Ser Gln Gly Asp Arg Ile Ser Glu Arg
            100                 105                 110

Lys Leu Asp Leu Leu Ser Leu Lys Asn Met Ser Glu Ala Gln Ser Lys
        115                 120                 125

Asn Glu Phe Leu Ser Arg Glu Leu Ile Glu Lys Glu Arg Asp Leu Glu
130                 135                 140

Arg Ser Arg Thr Val Ile Ala Lys Phe Gln Asn Lys Leu Lys Glu Leu
145                 150                 155                 160

Val Glu Glu Asn Lys Gln Leu Glu Glu Gly Met Lys Glu Ile Leu Gln
                165                 170                 175

Ala Ile Lys Glu Met Gln Lys Asp Pro Asp Val Lys Gly Gly Glu Thr
            180                 185                 190

Ser Leu Ile Ile Pro Ser Leu Glu Arg Leu Val Asn Ala Ile Glu Ser
        195                 200                 205

Lys Asn Ala Glu Gly Ile Phe Asp Ala Ser Leu His Leu Lys Ala Gln
210                 215                 220

Val Asp Gln Leu Thr Gly Arg Asn Glu Glu Leu Arg Gln Glu Leu Arg
225                 230                 235                 240

Glu Ser Arg Lys Glu Ala Ile Asn Tyr Ser Gln Gln Leu Ala Lys Ala
                245                 250                 255

Asn Leu Lys Ile Asp His Leu Glu Lys Glu Thr Ser Leu Leu Arg Gln
            260                 265                 270

Ser Glu Gly Ser Asn Val Val Phe Lys Gly Ile Asp Leu Pro Asp Gly
        275                 280                 285

Ile Ala Pro Ser Ser Ala Ser Ile Ile Asn Ser Gln Asn Glu Tyr Leu
290                 295                 300

Ile His Leu Leu Gln Glu Leu Glu Asn Lys Glu Lys Lys Leu Lys Asn
305                 310                 315                 320

Leu Glu Asp Ser Leu Glu Asp Tyr Asn Arg Lys Phe Ala Val Ile Arg
                325                 330                 335

His Gln Gln Ser Leu Leu Tyr Lys Glu Tyr Leu Ser Glu Lys Glu Thr
            340                 345                 350

Trp Lys Thr Glu Ser Lys Thr Ile Lys Glu Glu Lys Arg Lys Leu Glu
```

-continued

```
            355                 360                 365
Asp Gln Val Gln Gln Asp Ala Ile Lys Val Lys Glu Tyr Asn Asn Leu
    370                 375                 380
Leu Asn Ala Leu Gln Met Asp Ser Asp Glu Met Lys Lys Ile Leu Ala
385                 390                 395                 400
Thr Thr Gly Met Thr Val Asp Gln Val Leu Gly Ile Arg Ala Leu Glu
                405                 410                 415
Ser Glu Lys Glu Leu Glu Glu Leu Lys Lys Arg Asn Leu Asp Leu Glu
                420                 425                 430
Asn Asp Ile Leu Tyr Met Arg Ala His Gln Ala Leu Pro Arg Asp Ser
            435                 440                 445
Val Val Glu Asp Leu His Leu Gln Asn Arg Tyr Leu Gln Glu Lys Leu
    450                 455                 460
His Ala Leu Glu Lys Gln Phe Ser Lys Asp Thr Tyr Ser Lys Pro Ser
465                 470                 475                 480
Ile Ser Gly Ile Glu Ser Asp Asp His Cys Gln Arg Glu Gln Glu Leu
                485                 490                 495
Gln Lys Glu Asn Leu Lys Leu Ser Ser Glu Asn Ile Glu Leu Lys Phe
                500                 505                 510
Gln Leu Glu Gln Ala Asn Lys Asp Leu Pro Arg Leu Lys Asn Gln Val
            515                 520                 525
Arg Asp Leu Lys Glu Met Cys Glu Phe Leu Lys Lys Glu Lys Ala Glu
    530                 535                 540
Val Gln Arg Lys Leu Gly His Val Arg Gly Ser Gly Arg Ser Gly Lys
545                 550                 555                 560
Thr Ile Pro Glu Leu Glu Lys Thr Ile Gly Leu Met Lys Lys Val Val
                565                 570                 575
Glu Lys Val Gln Arg Glu Asn Glu Gln Leu Lys Lys Ala Ser Gly Ile
                580                 585                 590
Leu Thr Ser Glu Lys Met Ala Asn Ile Glu Gln Glu Asn Gly Lys Leu
            595                 600                 605
Lys Ala Glu Leu Glu Lys Leu Lys Ala His Leu Gly His Gln Leu Ser
    610                 615                 620
Met His Tyr Glu Ser Lys Thr Lys Gly Thr Glu Lys Ile Ile Ala Glu
625                 630                 635                 640
Asn Glu Arg Leu Arg Lys Glu Leu Lys Lys Glu Thr Asp Ala Ala Glu
                645                 650                 655
Lys Leu Arg Ile Ala Lys Asn Asn Leu Glu Ile Leu Asn Glu Lys Met
                660                 665                 670
Thr Val Gln Leu Glu Glu Thr Gly Lys Arg Leu Gln Phe Ala Glu Ser
            675                 680                 685
Arg Gly Pro Gln Leu Glu Gly Ala Asp Ser Lys Ser Trp Lys Ser Ile
    690                 695                 700
Val Val Thr Arg Met Tyr Glu Thr Lys Leu Lys Glu Leu Glu Thr Asp
705                 710                 715                 720
Ile Ala Lys Lys Asn Gln Ser Ile Thr Asp Leu Lys Gln Leu Val Lys
                725                 730                 735
Glu Ala Thr Glu Arg Glu Gln Lys Val Asn Lys Tyr Asn Glu Asp Leu
                740                 745                 750
Glu Gln Gln Ile Lys Ile Leu Lys His Val Pro Glu Gly Ala Glu Thr
            755                 760                 765
Glu Gln Gly Leu Lys Arg Glu Leu Gln Val Leu Arg Leu Ala Asn His
    770                 775                 780
```

Gln Leu Asp Lys Glu Lys Ala Glu Leu Ile His Gln Ile Glu Ala Asn
785                 790                 795                 800

Lys Asp Gln Ser Gly Ala Glu Ser Thr Ile Pro Asp Ala Asp Gln Leu
            805                 810                 815

Lys Glu Lys Ile Lys Asp Leu Glu Thr Gln Leu Lys Met Ser Asp Leu
            820                 825                 830

Glu Lys Gln His Leu Lys Glu Glu Ile Lys Lys Leu Lys Lys Glu Leu
            835                 840                 845

Glu Asn Phe Asp Pro Ser Phe Phe Glu Glu Ile Glu Asp Leu Lys Tyr
850                 855                 860

Asn Tyr Lys Glu Glu Val Lys Lys Asn Ile Leu Glu Glu Lys Val
865                 870                 875                 880

Lys Lys Leu Ser Glu Gln Leu Gly Val Glu Leu Thr Ser Pro Val Ala
            885                 890                 895

Ala Ser Glu Glu Phe Glu Asp Glu Glu Ser Pro Val Asn Phe Pro
                900                 905                 910

Ile Tyr

<210> SEQ ID NO 16
<211> LENGTH: 885
<212> TYPE: PRT
<213> ORGANISM: Homo sapiens

<400> SEQUENCE: 16

Ile Leu Thr Lys Glu Ile Asn Lys Leu Glu Leu Lys Ile Ser Asp Phe
1               5                   10                  15

Leu Asp Glu Asn Glu Ala Leu Arg Glu Arg Val Gly Leu Glu Pro Lys
                20                  25                  30

Thr Met Ile Asp Leu Thr Glu Phe Arg Asn Ser Lys His Leu Lys Gln
            35                  40                  45

Gln Gln Tyr Arg Ala Glu Asn Gln Ile Leu Leu Lys Glu Ile Glu Ser
        50                  55                  60

Leu Glu Glu Glu Arg Leu Asp Leu Lys Lys Ile Arg Gln Met Ala
65                  70                  75                  80

Gln Glu Arg Gly Lys Arg Ser Ala Thr Ser Gly Leu Thr Thr Glu Asp
                85                  90                  95

Leu Asn Leu Glu Ser Leu Arg Met Gln Leu Leu Asp Tyr Gln Ala Gln
            100                 105                 110

Ser Asp Glu Lys Ser Leu Ile Ala Lys Leu His Gln His Asn Val Ser
        115                 120                 125

Leu Gln Leu Ser Glu Ala Thr Ala Leu Gly Lys Leu Glu Ser Ile Thr
130                 135                 140

Ser Lys Leu Gln Lys Met Glu Ala Tyr Asn Arg Leu Glu Gln Lys
145                 150                 155                 160

Leu Asp Glu Lys Glu Gln Ala Leu Tyr Tyr Ala Arg Leu Glu Gly Arg
                165                 170                 175

Asn Arg Ala Lys His Leu Arg Gln Thr Ile Gln Ser Leu Arg Arg Gln
            180                 185                 190

Phe Ser Gly Ala Leu Pro Leu Ala Gln Gln Glu Lys Phe Ser Lys Thr
        195                 200                 205

Met Ile Gln Leu Gln Asn Asp Lys Leu Lys Ile Met Gln Glu Met Lys
210                 215                 220

Asn Ser Gln Gln Glu His Arg Asn Met Glu Asn Lys Thr Leu Glu Met
225                 230                 235                 240

```
Glu Leu Lys Leu Lys Gly Leu Glu Glu Leu Ile Ser Thr Leu Lys Asp
                245                 250                 255
Thr Lys Gly Ala Gln Lys Val Ile Asn Trp His Met Lys Ile Glu Glu
            260                 265                 270
Leu Arg Leu Gln Glu Leu Lys Leu Asn Arg Glu Leu Val Lys Asp Lys
        275                 280                 285
Glu Glu Ile Lys Tyr Leu Asn Asn Ile Ile Ser Glu Tyr Glu Arg Thr
    290                 295                 300
Ile Ser Ser Leu Glu Glu Ile Val Gln Gln Asn Lys Phe His Glu
305                 310                 315                 320
Glu Arg Gln Met Ala Trp Asp Gln Arg Glu Val Asp Leu Glu Arg Gln
                325                 330                 335
Leu Asp Ile Phe Asp Arg Gln Gln Asn Glu Ile Leu Asn Ala Ala Gln
            340                 345                 350
Lys Phe Glu Glu Ala Thr Gly Ser Ile Pro Asp Pro Ser Leu Pro Leu
        355                 360                 365
Pro Asn Gln Leu Glu Ile Ala Leu Arg Lys Ile Lys Glu Asn Ile Arg
    370                 375                 380
Ile Ile Leu Glu Thr Arg Ala Thr Cys Lys Ser Leu Glu Glu Lys Leu
385                 390                 395                 400
Lys Glu Lys Glu Ser Ala Leu Arg Leu Ala Glu Gln Asn Ile Leu Ser
                405                 410                 415
Arg Asp Lys Val Ile Asn Glu Leu Arg Leu Arg Leu Pro Ala Thr Ala
            420                 425                 430
Glu Arg Glu Lys Leu Ile Ala Glu Leu Gly Arg Lys Glu Met Glu Pro
        435                 440                 445
Lys Ser His His Thr Leu Lys Ile Ala His Gln Thr Ile Ala Asn Met
    450                 455                 460
Gln Ala Arg Leu Asn Gln Lys Glu Glu Val Leu Lys Lys Tyr Gln Arg
465                 470                 475                 480
Leu Leu Glu Lys Ala Arg Glu Gln Arg Glu Ile Val Lys His
                485                 490                 495
Glu Glu Asp Leu His Ile Leu His His Arg Leu Glu Leu Gln Ala Asp
            500                 505                 510
Ser Ser Leu Asn Lys Phe Lys Gln Thr Ala Trp Asp Leu Met Lys Gln
        515                 520                 525
Ser Pro Thr Pro Val Pro Thr Asn Lys His Phe Ile Arg Leu Ala Glu
    530                 535                 540
Met Glu Gln Thr Val Ala Glu Gln Asp Asp Ser Leu Ser Ser Leu Leu
545                 550                 555                 560
Val Lys Leu Lys Lys Val Ser Gln Asp Leu Glu Arg Gln Arg Glu Ile
                565                 570                 575
Thr Glu Leu Lys Val Lys Glu Phe Glu Asn Ile Lys Leu Gln Leu Gln
            580                 585                 590
Glu Asn His Glu Asp Glu Val Lys Val Lys Ala Glu Val Glu Asp
        595                 600                 605
Leu Lys Tyr Leu Leu Asp Gln Ser Gln Lys Glu Ser Gln Cys Leu Lys
    610                 615                 620
Ser Glu Leu Gln Ala Gln Lys Glu Ala Asn Ser Arg Ala Pro Thr Thr
625                 630                 635                 640
Thr Met Arg Asn Leu Val Glu Arg Leu Lys Ser Gln Leu Ala Leu Lys
                645                 650                 655
```

```
Glu Lys Gln Gln Lys Ala Leu Ser Arg Ala Leu Leu Glu Leu Arg Ala
            660                 665                 670

Glu Met Thr Ala Ala Ala Glu Glu Arg Ile Ile Ser Ala Thr Ser Gln
        675                 680                 685

Lys Glu Ala His Leu Asn Val Gln Gln Ile Val Asp Arg His Thr Arg
    690                 695                 700

Glu Leu Lys Thr Gln Val Glu Asp Leu Asn Glu Asn Leu Leu Lys Leu
705                 710                 715                 720

Lys Glu Ala Leu Lys Thr Ser Lys Asn Arg Glu Asn Ser Leu Thr Asp
                725                 730                 735

Asn Leu Asn Asp Leu Asn Asn Glu Leu Gln Lys Lys Gln Lys Ala Tyr
            740                 745                 750

Asn Lys Ile Leu Arg Glu Lys Glu Ile Asp Gln Glu Asn Asp Glu
            755                 760                 765

Leu Lys Arg Gln Ile Lys Arg Leu Thr Ser Gly Leu Gln Gly Lys Pro
        770                 775                 780

Leu Thr Asp Asn Lys Gln Ser Leu Ile Glu Glu Leu Gln Arg Lys Val
785                 790                 795                 800

Lys Lys Leu Glu Asn Gln Leu Glu Gly Lys Val Glu Glu Val Asp Leu
                805                 810                 815

Lys Pro Met Lys Glu Lys Asn Ala Lys Glu Glu Leu Ile Arg Trp Glu
            820                 825                 830

Glu Gly Lys Lys Trp Gln Ala Lys Ile Glu Gly Ile Arg Asn Lys Leu
        835                 840                 845

Lys Glu Lys Glu Gly Glu Val Phe Thr Leu Thr Lys Gln Leu Asn Thr
850                 855                 860

Leu Lys Asp Leu Phe Ala Lys Ala Asp Lys Glu Lys Leu Thr Leu Gln
865                 870                 875                 880

Arg Lys Leu Lys Thr
                885

<210> SEQ ID NO 17
<211> LENGTH: 671
<212> TYPE: PRT
<213> ORGANISM: Homo sapiens

<400> SEQUENCE: 17

Ile Leu Thr Lys Glu Ile Asn Lys Leu Glu Leu Lys Ile Ser Asp Phe
1               5                  10                   15

Leu Asp Glu Asn Glu Ala Leu Arg Glu Arg Val Gly Leu Glu Pro Lys
            20                  25                  30

Thr Met Ile Asp Leu Thr Glu Phe Arg Asn Ser Lys His Leu Lys Gln
        35                  40                  45

Gln Gln Tyr Arg Ala Glu Asn Gln Ile Leu Leu Lys Glu Ile Glu Ser
    50                  55                  60

Leu Glu Glu Glu Arg Leu Asp Leu Lys Lys Lys Ile Arg Gln Met Ala
65                  70                  75                  80

Gln Glu Arg Gly Lys Arg Ser Ala Thr Ser Gly Leu Thr Thr Glu Asp
                85                  90                  95

Leu Asn Leu Thr Glu Asn Ile Ser Gln Gly Asp Arg Ile Ser Glu Arg
            100                 105                 110

Lys Leu Asp Leu Leu Ser Leu Lys Asn Met Ser Glu Ala Gln Ser Lys
        115                 120                 125

Asn Glu Phe Leu Ser Arg Glu Leu Ile Glu Lys Glu Arg Asp Leu Glu
    130                 135                 140
```

-continued

```
Arg Ser Arg Thr Val Ile Ala Lys Phe Gln Asn Lys Leu Lys Glu Leu
145                 150                 155                 160

Val Glu Glu Asn Lys Gln Leu Glu Glu Gly Met Lys Glu Ile Leu Gln
            165                 170                 175

Ala Ile Lys Glu Met Gln Lys Asp Pro Asp Val Lys Gly Gly Glu Thr
        180                 185                 190

Ser Leu Ile Ile Pro Ser Leu Glu Arg Leu Val Asn Ala Ile Glu Ser
            195                 200                 205

Lys Asn Ala Glu Gly Ile Phe Asp Ala Ser Leu His Leu Lys Ala Gln
        210                 215                 220

Val Asp Gln Leu Thr Gly Arg Asn Glu Glu Leu Arg Gln Glu Leu Arg
225                 230                 235                 240

Glu Ser Arg Lys Glu Ala Ile Asn Tyr Ser Gln Gln Leu Ala Lys Ala
                245                 250                 255

Asn Leu Lys Ile Asp His Leu Glu Lys Glu Thr Ser Leu Leu Arg Gln
            260                 265                 270

Ser Glu Gly Ser Asn Val Val Phe Lys Gly Ile Asp Leu Pro Asp Gly
        275                 280                 285

Ile Ala Pro Ser Ser Ala Ser Ile Ile Asn Ser Gln Asn Glu Tyr Leu
290                 295                 300

Ile His Leu Leu Gln Glu Leu Glu Asn Lys Glu Lys Lys Leu Lys Asn
305                 310                 315                 320

Leu Glu Asp Ser Leu Glu Asp Tyr Asn Arg Lys Phe Ala Val Ile Arg
                325                 330                 335

His Gln Gln Ser Leu Leu Tyr Lys Glu Tyr Leu Ser Glu Lys Glu Thr
            340                 345                 350

Trp Lys Thr Glu Ser Lys Thr Ile Lys Glu Glu Lys Arg Lys Leu Glu
        355                 360                 365

Asp Gln Val Gln Gln Asp Ala Ile Lys Val Lys Glu Tyr Asn Asn Leu
    370                 375                 380

Leu Asn Ala Leu Gln Met Asp Ser Asp Glu Met Lys Lys Ile Leu Ala
385                 390                 395                 400

Gln Ser Gln Lys Glu Ser Gln Cys Leu Lys Ser Glu Leu Gln Ala Gln
                405                 410                 415

Lys Glu Ala Asn Ser Arg Ala Pro Thr Thr Met Arg Asn Leu Val
            420                 425                 430

Glu Arg Leu Lys Ser Gln Leu Ala Leu Lys Glu Lys Gln Gln Lys Ala
        435                 440                 445

Leu Ser Arg Ala Leu Leu Glu Leu Arg Ala Glu Met Thr Ala Ala Ala
    450                 455                 460

Glu Glu Arg Ile Ile Ser Ala Thr Ser Gln Lys Glu Ala His Leu Asn
465                 470                 475                 480

Val Gln Gln Ile Val Asp Arg His Thr Arg Glu Leu Lys Thr Gln Val
                485                 490                 495

Glu Asp Leu Asn Glu Asn Leu Leu Leu Lys Glu Ala Leu Lys Thr
            500                 505                 510

Ser Lys Asn Arg Glu Asn Ser Leu Thr Asp Asn Leu Asn Asp Leu Asn
        515                 520                 525

Asn Glu Leu Gln Lys Lys Gln Lys Ala Tyr Asn Lys Ile Leu Arg Glu
    530                 535                 540

Lys Glu Glu Ile Asp Gln Glu Asn Asp Glu Leu Lys Arg Gln Ile Lys
545                 550                 555                 560
```

Arg Leu Thr Ser Gly Leu Gln Gly Lys Pro Leu Thr Asp Asn Lys Gln
                565                 570                 575

Ser Leu Ile Glu Glu Leu Gln Arg Lys Val Lys Lys Leu Glu Asn Gln
            580                 585                 590

Leu Glu Gly Lys Val Glu Val Asp Leu Lys Pro Met Lys Glu Lys
        595                 600                 605

Asn Ala Lys Glu Glu Leu Ile Arg Trp Glu Gly Lys Lys Trp Gln
    610                 615                 620

Ala Lys Ile Glu Gly Ile Arg Asn Lys Leu Lys Glu Lys Gly Glu
625                 630                 635                 640

Val Phe Thr Leu Thr Lys Gln Leu Asn Thr Leu Lys Asp Leu Phe Ala
                645                 650                 655

Lys Ala Asp Lys Glu Lys Leu Thr Leu Gln Arg Lys Leu Lys Thr
            660                 665                 670

<210> SEQ ID NO 18
<211> LENGTH: 572
<212> TYPE: PRT
<213> ORGANISM: Homo sapiens

<400> SEQUENCE: 18

Thr Glu Asn Ile Ser Gln Gly Asp Arg Ile Ser Glu Arg Lys Leu Asp
1               5                   10                  15

Leu Leu Ser Leu Lys Asn Met Ser Glu Ala Gln Ser Lys Asn Glu Phe
            20                  25                  30

Leu Ser Arg Glu Leu Ile Glu Lys Glu Arg Asp Leu Glu Arg Ser Arg
        35                  40                  45

Thr Val Ile Ala Lys Phe Gln Asn Lys Leu Lys Glu Leu Val Glu Glu
    50                  55                  60

Asn Lys Gln Leu Glu Glu Gly Met Lys Glu Ile Leu Gln Ala Ile Lys
65                  70                  75                  80

Glu Met Gln Lys Asp Pro Asp Val Lys Gly Gly Glu Thr Ser Leu Ile
                85                  90                  95

Ile Pro Ser Leu Glu Arg Leu Val Asn Ala Ile Glu Ser Lys Asn Ala
            100                 105                 110

Glu Gly Ile Phe Asp Ala Ser Leu His Leu Lys Ala Gln Val Asp Gln
        115                 120                 125

Leu Thr Gly Arg Asn Glu Glu Leu Arg Gln Glu Leu Arg Glu Ser Arg
    130                 135                 140

Lys Glu Ala Ile Asn Tyr Ser Gln Gln Leu Ala Lys Ala Asn Leu Lys
145                 150                 155                 160

Ile Asp His Leu Glu Lys Glu Thr Ser Leu Leu Arg Gln Ser Glu Gly
                165                 170                 175

Ser Asn Val Val Phe Lys Gly Ile Asp Leu Pro Asp Gly Ile Ala Pro
            180                 185                 190

Ser Ser Ala Ser Ile Ile Asn Ser Gln Asn Glu Tyr Leu Ile His Leu
        195                 200                 205

Leu Gln Glu Leu Glu Asn Lys Glu Lys Leu Lys Asn Leu Glu Asp
    210                 215                 220

Ser Leu Glu Asp Tyr Asn Arg Lys Phe Ala Val Ile Arg His Gln Gln
225                 230                 235                 240

Ser Leu Leu Tyr Lys Glu Tyr Leu Ser Glu Lys Glu Thr Trp Lys Thr
                245                 250                 255

Glu Ser Lys Thr Ile Lys Glu Glu Lys Arg Lys Leu Glu Asp Gln Val
            260                 265                 270

Gln Gln Asp Ala Ile Lys Val Lys Glu Tyr Asn Asn Leu Leu Asn Ala
            275                 280                 285

Leu Gln Met Asp Ser Asp Glu Met Lys Lys Ile Leu Ala Gln Ser Gln
        290                 295                 300

Lys Glu Ser Gln Cys Leu Lys Ser Glu Leu Gln Ala Gln Lys Glu Ala
305                 310                 315                 320

Asn Ser Arg Ala Pro Thr Thr Thr Met Arg Asn Leu Val Glu Arg Leu
                325                 330                 335

Lys Ser Gln Leu Ala Leu Lys Glu Lys Gln Gln Lys Ala Leu Ser Arg
            340                 345                 350

Ala Leu Leu Glu Leu Arg Ala Glu Met Thr Ala Ala Glu Glu Arg
        355                 360                 365

Ile Ile Ser Ala Thr Ser Gln Lys Glu Ala His Leu Asn Val Gln Gln
    370                 375                 380

Ile Val Asp Arg His Thr Arg Glu Leu Lys Thr Gln Val Glu Asp Leu
385                 390                 395                 400

Asn Glu Asn Leu Leu Lys Leu Lys Glu Ala Leu Lys Thr Ser Lys Asn
                405                 410                 415

Arg Glu Asn Ser Leu Thr Asp Asn Leu Asn Asp Leu Asn Asn Glu Leu
            420                 425                 430

Gln Lys Lys Gln Lys Ala Tyr Asn Lys Ile Leu Arg Glu Lys Glu Glu
        435                 440                 445

Ile Asp Gln Glu Asn Asp Glu Leu Lys Arg Gln Ile Lys Arg Leu Thr
    450                 455                 460

Ser Gly Leu Gln Gly Lys Pro Leu Thr Asp Asn Lys Gln Ser Leu Ile
465                 470                 475                 480

Glu Glu Leu Gln Arg Lys Val Lys Lys Leu Glu Asn Gln Leu Glu Gly
                485                 490                 495

Lys Val Glu Glu Val Asp Leu Lys Pro Met Lys Glu Lys Asn Ala Lys
            500                 505                 510

Glu Glu Leu Ile Arg Trp Glu Glu Gly Lys Lys Trp Gln Ala Lys Ile
        515                 520                 525

Glu Gly Ile Arg Asn Lys Leu Lys Glu Lys Gly Glu Val Phe Thr
    530                 535                 540

Leu Thr Lys Gln Leu Asn Thr Leu Lys Asp Leu Phe Ala Lys Ala Asp
545                 550                 555                 560

Lys Glu Lys Leu Thr Leu Gln Arg Lys Leu Lys Thr
                565                 570

<210> SEQ ID NO 19
<211> LENGTH: 801
<212> TYPE: PRT
<213> ORGANISM: Homo sapiens

<400> SEQUENCE: 19

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln

```
                65                  70                  75                  80
Ala Lys Phe Glu Asn Gln Leu Lys Thr Lys Val Met Lys Leu Glu Asn
                    85                  90                  95
Glu Leu Glu Met Ala Gln Gln Ser Ala Gly Gly Arg Asp Thr Arg Phe
                    100                 105                 110
Leu Arg Asn Glu Ile Cys Gln Leu Glu Lys Gln Leu Glu Gln Lys Asp
                    115                 120                 125
Arg Glu Leu Glu Asp Met Glu Lys Glu Leu Glu Lys Glu Lys Lys Val
            130                 135                 140
Asn Glu Gln Leu Ala Leu Arg Asn Glu Glu Ala Glu Asn Glu Asn Ser
145                 150                 155                 160
Lys Leu Arg Arg Glu Asn Lys Arg Leu Lys Lys Asn Glu Gln Leu
                165                 170                 175
Cys Gln Asp Ile Ile Asp Tyr Gln Lys Gln Ile Asp Ser Gln Lys Glu
                180                 185                 190
Thr Leu Leu Ser Arg Arg Gly Glu Thr Glu Asn Ile Ser Gln Gly Asp
            195                 200                 205
Arg Ile Ser Glu Arg Lys Leu Asp Leu Leu Ser Leu Lys Asn Met Ser
210                 215                 220
Glu Ala Gln Ser Lys Asn Glu Phe Leu Ser Arg Glu Leu Ile Glu Lys
225                 230                 235                 240
Glu Arg Asp Leu Glu Arg Ser Arg Thr Val Ile Ala Lys Phe Gln Asn
                245                 250                 255
Lys Leu Lys Glu Leu Val Glu Glu Asn Lys Gln Leu Glu Glu Gly Met
                260                 265                 270
Lys Glu Ile Leu Gln Ala Ile Lys Glu Met Gln Lys Asp Pro Asp Val
            275                 280                 285
Lys Gly Gly Glu Thr Ser Leu Ile Ile Pro Ser Leu Glu Arg Leu Val
            290                 295                 300
Asn Ala Ile Glu Ser Lys Asn Ala Glu Gly Ile Phe Asp Ala Ser Leu
305                 310                 315                 320
His Leu Lys Ala Gln Val Asp Gln Leu Thr Gly Arg Asn Glu Glu Leu
                325                 330                 335
Arg Gln Glu Leu Arg Glu Ser Arg Lys Glu Ala Ile Asn Tyr Ser Gln
                340                 345                 350
Gln Leu Ala Lys Ala Asn Leu Lys Ile Asp His Leu Glu Lys Glu Thr
            355                 360                 365
Ser Leu Leu Arg Gln Ser Glu Gly Ser Asn Val Val Phe Lys Gly Ile
            370                 375                 380
Asp Leu Pro Asp Gly Ile Ala Pro Ser Ser Ala Ser Ile Ile Asn Ser
385                 390                 395                 400
Gln Asn Glu Tyr Leu Ile His Leu Leu Gln Glu Leu Glu Asn Lys Glu
                405                 410                 415
Lys Lys Leu Lys Asn Leu Glu Asp Ser Leu Glu Asp Tyr Asn Arg Lys
                420                 425                 430
Phe Ala Val Ile Arg His Gln Gln Ser Leu Leu Tyr Lys Glu Tyr Leu
            435                 440                 445
Ser Glu Lys Glu Thr Trp Lys Thr Glu Ser Lys Thr Ile Lys Glu Glu
            450                 455                 460
Lys Arg Lys Leu Glu Asp Gln Val Gln Gln Asp Ala Ile Lys Val Lys
465                 470                 475                 480
Glu Tyr Asn Asn Leu Leu Asn Ala Leu Gln Met Asp Ser Asp Glu Met
                485                 490                 495
```

Lys Lys Ile Leu Ala Glu Asn Ser Arg Lys Ile Thr Val Leu Gln Val
            500                 505                 510

Asn Glu Lys Ser Leu Ile Arg Gln Tyr Thr Thr Leu Val Glu Leu Glu
            515                 520                 525

Arg Gln Leu Arg Lys Glu Asn Glu Lys Gln Lys Asn Glu Leu Leu Ser
            530                 535                 540

Met Glu Ala Glu Val Cys Glu Lys Ile Gly Cys Leu Gln Arg Phe Lys
545                 550                 555                 560

Glu Met Ala Ile Phe Lys Ile Ala Ala Leu Gln Lys Val Val Asp Asn
                565                 570                 575

Ser Val Ser Leu Ser Glu Leu Glu Leu Ala Asn Lys Tyr Asn Glu
            580                 585                 590

Leu Thr Ala Lys Tyr Arg Asp Ile Leu Gln Lys Asp Asn Met Leu Val
            595                 600                 605

Gln Arg Thr Ser Asn Leu Glu His Leu Glu Cys Glu Asn Ile Ser Leu
            610                 615                 620

Lys Glu Gln Val Glu Ser Ile Asn Lys Glu Leu Glu Ile Thr Lys Glu
625                 630                 635                 640

Lys Leu His Thr Ile Glu Gln Ala Trp Glu Gln Glu Thr Lys Leu Gly
                645                 650                 655

Asn Glu Ser Ser Met Asp Lys Ala Lys Lys Ser Ile Thr Asn Ser Asp
            660                 665                 670

Ile Val Ser Ile Ser Lys Lys Ile Thr Met Leu Glu Met Lys Glu Leu
            675                 680                 685

Asn Glu Arg Gln Arg Ala Glu His Cys Gln Lys Met Tyr Glu His Leu
            690                 695                 700

Arg Thr Ser Leu Lys Gln Met Glu Glu Arg Asn Phe Glu Leu Glu Thr
705                 710                 715                 720

Lys Phe Ala Glu Leu Thr Lys Ile Asn Leu Asp Ala Gln Lys Val Glu
                725                 730                 735

Gln Met Leu Arg Asp Glu Leu Ala Asp Ser Val Ser Lys Ala Val Ser
            740                 745                 750

Asp Ala Asp Arg Gln Arg Ile Leu Glu Leu Glu Lys Asn Glu Met Glu
            755                 760                 765

Leu Lys Val Glu Val Ser Lys Leu Arg Glu Ile Ser Asp Ile Ala Arg
            770                 775                 780

Arg Gln Val Glu Ile Leu Asn Ala Gln Gln Ser Arg Asp Lys Glu
785                 790                 795                 800

Val

<210> SEQ ID NO 20
<211> LENGTH: 3900
<212> TYPE: DNA
<213> ORGANISM: Homo sapiens

<400> SEQUENCE: 20
gagtccctca gaatgcaact gctagactat caggcacagt ctgatgaaaa gtcgctcatt        60
gccaagttgc accaacataa tgtctctctt caactgagtg aggctactgc tcttggtaag       120
ttggagtcaa ttacatctaa actgcagaag atggaggcct acaacttgcg cttagagcag       180
aaacttgatg aaaagaaca ggctctctat tatgctcgtt tggagggaag aaacagagca       240
aaacatctgc gccaaacaat tcagtctcta cgacgacagt ttagtggagc tttacccttg       300
gcacaacagg aaaagttctc caaaacaatg attcaactac aaaatgacaa acttaagata       360

```
atgcaagaaa tgaaaaattc tcaacaagaa catagaaata tggagaacaa aacattggag      420
atggaattaa aattaaaggg cctggaagag ttaataagca ctttaaagga taccaaagga      480
gcccaaaagg taatcaactg gcatatgaaa atagaagaac ttcgtcttca agaacttaaa      540
ctaaatcggg aattagtcaa ggataaagaa gaaataaaat atttgaataa cataatttct      600
gaatatgaac gtacaatcag cagtcttgaa gaagaaattg tgcaacagaa caagtttcat      660
gaagaaagac aaatggcctg ggatcaaaga gaagttgacc tggaacgcca actagacatt      720
tttgaccgtc agcaaaatga atactaaat gcggcacaaa agtttgaaga agctacagga      780
tcaatccctg accctagttt gccccttcca aatcaacttg agatcgctct aaggaaaatt      840
aaggagaaca ttcgaataat tctagaaaca cgggcaactt gcaaatcact agaagagaaa      900
ctaaaagaga agaatctgc tttaaggtta gcagaacaaa atatactgtc aagagacaaa      960
gtaatcaatg aactgaggct tcgattgcct gccactgcag aaagagaaaa gctcatagct     1020
gagctaggca gaaagagat ggaaccaaaa tctcaccaca cattgaaaat tgctcatcaa     1080
accattgcaa acatgcaagc aaggttaaat caaaagaag aagtattaaa gaagtatcaa     1140
cgtcttctag aaaagccag agaggagcaa agagaaattg tgaagaaaca tgaggaagac     1200
cttcatattc ttcatcacag attagaacta caggctgata gttcactaaa taaattcaaa     1260
caaacggctt gggatttaat gaaacagtct cccactccag ttcctaccaa caagcatttt     1320
attcgtctgg ctgagatgga acagacagta gcagaacaag atgactctct ttcctcactc     1380
ttggtcaaac taagaaagt atcacaagat ttggagagac aaagagaaat cactgaatta     1440
aaagtaaaag aatttgaaaa tatcaaatta cagcttcaag aaaaccatga agatgaagtg     1500 aaaaagtaa aagcggaagt agaggattta agtatcttc tggaccagtc acaaaaggag     1560
tcacagtgtt taaatctga acttcaggct caaaaagaag caaattcaag agctccaaca     1620
actacaatga gaaatctagt agaacggcta aagagccaat tagccttgaa ggagaaacaa     1680
cagaaagcac ttagtcgggc acttttagaa ctccgggcag aaatgacagc agctgctgaa     1740
gaacgtatta tttctgcaac ttctcaaaaa gaggcccatc tcaatgttca acaaatcgtt     1800
gatcgacata ctagagagct aaagacacaa gttgaagatt taaatgaaaa tcttttaaaa     1860
ttgaaagaag cacttaaaac aagtaaaaac agagaaaact cactaactga taatttgaat     1920
gacttaaata atgaactgca aaagaaacaa aaagcctata ataaatact agagagaaa     1980 gaggaaattg atcaagagaa tgatgaactg aaaaggcaaa ttaaaagact aaccagtgga     2040
ttacagggca acccctgac agataataaa caaagtctaa ttgaagaact ccaaaggaaa     2100
gttaaaaaac tagagaacca attagaggga aggtggagg agtagacct aaaacctatg     2160 aaagaaaaga atgctaaaga agaattaatt aggtgggaag aaggtaaaaa gtggcaagcc     2220
aaaatagaag gaattcgaaa caagttaaaa gagaaagagg gggaagtctt tactttaaca     2280
aagcagttga atactttgaa ggatcttttt gccaaagccg ataaagagaa acttactttg     2340
cagaggaaac taaaaacaac tggcatgact gttgatcagg ttttgggaat acgagctttg     2400
gagtcagaaa aagaattgga agaattaaaa agagaaatc ttgacttaga aaatgatata     2460
ttgtatatga gggcccacca agctcttcct cgagattctg ttgtagaaga tttacattta     2520
caaaatagat acctccaaga aaaacttcat gctttagaaa aacagttttc aaaggataca     2580
tattctaagc cttcaatttc aggaatagag tcagatgatc attgtcagag agaacaggag     2640
cttcagaagg aaaacttgaa gttgtcatct gaaaatattg aactgaaatt tcagcttgaa     2700
```

| | |
|---|---:|
| caagcaaata aagatttgcc aagattaaag aatcaagtca gagatttgaa ggaaatgtgt | 2760 |
| gaatttctta agaaagaaaa agcagaagtt cagcggaaac ttggccatgt tagagggtct | 2820 |
| ggtagaagtg gaaagacaat cccagaactg gaaaaaacca ttggtttaat gaaaaaagta | 2880 |
| gttgaaaaag tccagagaga aaatgaacag ttgaaaaaag catcaggaat attgactagt | 2940 |
| gaaaaaatgg ctaatattga gcaggaaaat gaaaaattga aggctgaatt agaaaaactt | 3000 |
| aaagctcatc ttgggcatca gttgagcatg cactatgaat ccaagaccaa aggcacagaa | 3060 |
| aaaattattg ctgaaaatga aaggcttcgt aaagaactta aaaagaaac tgatgctgca | 3120 |
| gagaaattac ggatagcaaa gaataattta gagatattaa atgagaagat gacagttcaa | 3180 |
| ctagaagaga ctggtaagag attgcagttt gcagaaagca gaggtccaca gcttgaaggt | 3240 |
| gctgacagta agagctggaa atccattgtg gttacaagaa tgtatgaaac caagttaaaa | 3300 |
| gaattggaaa ctgatattgc caaaaaaaat caaagcatta ctgaccttaa acagcttgta | 3360 |
| aaagaagcaa cagagagaga acaaaaagtt aacaaataca atgaagacct tgaacaacag | 3420 |
| attaagattc ttaaacatgt tcctgaaggt gctgagacag agcaaggcct taaacgggag | 3480 |
| cttcaagttc ttagattagc taatcatcag ctggataaag agaaagcaga attaatccat | 3540 |
| cagatagaag ctaacaagga ccaaagtgga gctgaaagca ccatacctga tgctgatcaa | 3600 |
| ctaaaggaaa aaataaaaga tctagagaca cagctcaaaa tgtcagatct agaaaagcag | 3660 |
| catttgaagg aggaaataaa gaagctgaaa aaagaactgg aaaattttga tccttcattt | 3720 |
| tttgaagaaa ttgaagatct taagtataat tacaaggaag aagtgaagaa gaatattctc | 3780 |
| ttagaagaga aggtaaaaaa actttcagaa caattgggag ttgaattaac tagccctgtt | 3840 |
| gctgcttctg aagagtttga agatgaagaa gaaagtcctg ttaatttccc catttactaa | 3900 |

<210> SEQ ID NO 21
<211> LENGTH: 1200
<212> TYPE: DNA
<213> ORGANISM: Homo sapiens

<400> SEQUENCE: 21

| | |
|---|---:|
| atattaacaa aggaaatcaa taaacttgaa ttgaagatca gtgatttcct tgatgaaaat | 60 |
| gaggcactta gagagcgtgt gggccttgaa ccaaagacaa tgattgattt aactgaattt | 120 |
| agaaatagca acacttaaa acagcagcag tacagagctg aaaaccagat tcttttgaaa | 180 |
| gagattgaaa gtctagagga agaacgactt gatctgaaaa aaaaaattcg tcaaatggct | 240 |
| caagaaagag gaaaagaag tgcaacttca ggattaacca ctgaggacct gaacctaact | 300 |
| gaaaacattt ctcaaggaga tagaataagt gaaagaaaat tggatttatt gagcctcaaa | 360 |
| aatatgagtg aagcacaatc aaagaatgaa tttctttcaa gagaactaat tgaaaaagaa | 420 |
| agagatttag aaaggagtag gacagtgata gccaaatttc agaataaatt aaaagaatta | 480 |
| gttgaagaaa ataagcaact tgaagaaggt atgaaagaaa tattgcaagc aattaaggaa | 540 |
| atgcagaaag atcctgatgt taaggaggaa gaaacatctc taattatccc tagccttgaa | 600 |
| agactagtta atgctataga atcaaagaat gcagaaggaa tctttgatgc gagtctgcat | 660 |
| ttgaaagccc aagttgatca gcttaccgga agaaatgaag aattaagaca ggagctcagg | 720 |
| gaatctcgga agagggctat aaattattca cagcagttgg caaaagctaa tttaaagata | 780 |
| gaccatcttg aaaaagaaac tagtcttta cgacaatcag aaggatcgaa tgttgttttt | 840 |
| aaaggaattg acttacctga tgggatagca ccatctagtg ccagtatcat taattctcag | 900 |
| aatgaatatt taatacattt gttacaggaa ctagaaaata agaaaaaaa gttaaagaat | 960 |

```
ttagaagatt ctcttgaaga ttacaacaga aaatttgctg taattcgtca tcaacaaagt   1020
ttgttgtata aagaatacct aagtgaaaag gagacctgga aaacagaatc taaaacaata   1080
aaagaggaaa agagaaaact tgaggatcaa gtccaacaag atgctataaa agtaaaagaa   1140
tataataatt tgctcaatgc tcttcagatg gattcggatg aaatgaaaaa aatacttgca   1200

<210> SEQ ID NO 22
<211> LENGTH: 3090
<212> TYPE: DNA
<213> ORGANISM: Homo sapiens

<400> SEQUENCE: 22
gagtccctca gaatgcaact gctagactat caggcacagt ctgatgaaaa gtcgctcatt     60
gccaagttgc accaacataa tgtctctctt caactgagtg aggctactgc tcttggtaag    120
ttggagtcaa ttacatctaa actgcagaag atggaggcct acaacttgcg cttagagcag    180
aaacttgatg aaaagaaaca ggctctctat tatgctcgtt tggagggaag aaacagagca    240
aaacatctgc gccaaacaat tcagtctcta cgacgacagt ttagtggagc tttacccttg    300
gcacaacagg aaaagttctc caaaacaatg attcaactac aaaatgacaa acttaagata    360
atgcaagaaa tgaaaaattc tcaacaagaa catagaaata tggagaacaa acattggag    420 atggaattaa aattaaaggg cctggaagag ttaataagca cttttaaagga taccaaagga    480 gcccaaaagg taatcaactg gcatatgaaa atagaagaac ttcgtcttca agaacttaaa    540
ctaaatcggg aattagtcaa ggataaagaa gaaataaaat atttgaataa cataatttct    600
gaatatgaac gtacaatcag cagtcttgaa gaagaaattg tgcaacagaa caagtttcat    660
gaagaaagac aaatggcctg ggatcaaaga gaagttgacc tggaacgcca actagacatt    720
tttgaccgtc agcaaaatga aatactaaat gcggcacaaa agtttgaaga agctacagga    780
tcaatccctg accctagttt gccccttcca aatcaacttg agatcgctct aaggaaaatt    840
aaggagaaca ttcgaataat tctagaaaca cgggcaactt gcaaatcact agaagagaaa    900
ctaaaagaga aagaatctgc tttaaggtta gcagaacaaa atatactgtc aagagacaaa    960
gtaatcaatg aactgaggct tcgattgcct gccactgcag aaagagaaaa gctcatagct   1020
gagctaggca gaaagagat ggaaccaaaa tctcaccaca cattgaaaat tgctcatcaa   1080
accattgcaa acatgcaagc aaggttaaat caaaagaag aagtattaaa gaagtatcaa   1140
cgtcttctag aaaagccag agaggagcaa agagaaattg tgaagaaaca tgaggaagac   1200
cttcatattc ttcatcacag attagaacta caggctgata gttcactaaa taaattcaaa   1260
caaacggctt gggatttaat gaaacagtct cccactccag ttcctaccaa caagcattt   1320 attcgtctgg ctgagatgga acagacagta gcagaacaag atgactctct ttcctcactc   1380
ttggtcaaac taagaaagt atcacaagat ttggagagac aaagagaaat cactgaatta   1440
aaagtaaaag aatttgaaaa tatcaaatta cagcttcaag aaaaccatga agatgaagtg   1500
aaaaaagtaa aagcggaagt agaggattta agtatcttc tggacacaac tggcatgact   1560
gttgatcagg ttttgggaat cgagctttg gagtcagaaa aagaattgga agaattaaaa   1620
aagagaaatc ttgacttaga aaatgatata ttgtatatga gggcccacca agctcttcct   1680
cgagattctg ttgtagaaga tttacattta caaaatagat acctccaaga aaaacttcat   1740
gctttagaaa aacagttttc aaaggataca tattctaagc cttcaatttc aggaatagag   1800
tcagatgatc attgtcagag agaacaggag cttcagaagg aaaacttgaa gttgtcatct   1860
```

-continued

```
gaaaatattg aactgaaatt tcagcttgaa caagcaaata agatttgcc aagattaaag   1920 aatcaagtca gagatttgaa ggaaatgtgt gaatttctta agaaagaaaa agcagaagtt   1980
cagcggaaac ttggccatgt tagagggtct ggtagaagtg aaagacaat cccagaactg    2040 gaaaaaacca ttggtttaat gaaaaaagta gttgaaaaag tccagagaga aaatgaacag   2100
ttgaaaaaag catcaggaat attgactagt gaaaaaatgg ctaatattga gcaggaaaat   2160
gaaaaattga aggctgaatt agaaaaactt aaagctcatc ttgggcatca gttgagcatg   2220
cactatgaat ccaagaccaa aggcacagaa aaaattattg ctgaaaatga aggcttcgt    2280 aaagaactta aaaagaaac tgatgctgca gagaaattac ggatagcaaa gaataattta    2340
gagatattaa atgagaagat gacagttcaa ctagaagaga ctggtaagag attgcagttt   2400
gcagaaagca gaggtccaca gcttgaaggt gctgacagta agagctggaa atccattgtg   2460
gttacaagaa tgtatgaaac caagttaaaa gaattggaaa ctgatattgc caaaaaaaat   2520
caaagcatta ctgaccttaa acagcttgta aagaagcaa cagagagaga acaaaaagtt    2580
aacaaataca atgaagacct tgaacaacag attaagattc ttaaacatgt tcctgaaggt   2640
gctgagacag agcaaggcct taacgggag cttcaagttc ttagattagc taatcatcag    2700
ctggataaag agaaagcaga attaatccat cagatagaag ctaacaagga ccaaagtgga   2760
gctgaaagca ccatacctga tgctgatcaa ctaaaggaaa aaataaaaga tctagagaca   2820
cagctcaaaa tgtcagatct agaaaagcag catttgaagg aggaaataaa gaagctgaaa   2880
aaagaactgg aaaattttga tccttcattt tttgaagaaa ttgaagatct taagtataat   2940
tacaaggaag aagtgaagaa gaatattctc ttagaagaga aggtaaaaaa actttcagaa   3000
caattgggag ttgaattaac tagccctgtt gctgcttctg aagagtttga agatgaagaa   3060
gaaagtcctg ttaatttccc catttactaa                                    3090
```

<210> SEQ ID NO 23
<211> LENGTH: 3846
<212> TYPE: DNA
<213> ORGANISM: Homo sapiens

<400> SEQUENCE: 23

```
actgaaaaca tttctcaagg agatagaata agtgaaagaa aattggattt attgagcctc     60
aaaaatatga gtgaagcaca atcaaagaat gaatttcttt caagagaact aattgaaaaa    120
gaaagagatt tagaaaggag taggacagtg atagccaaat ttcagaataa attaaaagaa    180
ttagttgaag aaaataagca acttgaagaa ggtatgaaag aaatattgca agcaattaag    240
gaaatgcaga agatcctga tgttaaagga ggagaaacat ctctaattat ccctagcctt      300
gaaagactag ttaatgctat agaatcaaag aatgcagaag gaatctttga tgcgagtctg    360
catttgaaag cccaagttga tcagcttacc ggaagaaatg aagaattaag acaggagctc    420
agggaatctc ggaagagggc tataaattat tcacagcagt tggcaaaagc taatttaaag    480
atagaccatc ttgaaaaaga aactagtctt ttacgacaat cagaaggatc gaatgttgtt    540
tttaaaggaa ttgacttacc tgatgggata gcaccatcta gtgccagtat cattaattct   600
cagaatgaat atttaataca tttgttacag gaactgaaaa ataaagaaaa aaagttaaag   660
aatttagaag attctcttga agattacaac agaaaatttg ctgtaattcg tcatcaacaa   720
agtttgttgt ataagaaata cctaagtgaa aaggagacct ggaaaacaga atctaaaaca   780 ataaagagg aaaagagaaa acttgaggat caagtccaac aagatgctat aaaagtaaaa   840
gaatataata atttgctcaa tgctcttcag atggattcgg atgaaatgaa aaaaatactt   900
```

```
gcagaaaata gtaggaaaat tactgttttg caagtgaatg aaaaatcact tataaggcaa    960
tatacaacct tagtagaatt ggagcgacaa cttagaaaag aaaatgagaa gcaaaagaat   1020
gaattgttgt caatggaggc tgaagtttgt gaaaaaattg ggtgtttgca aagatttaag   1080
gaaatggcca ttttcaagat tgcagctctc caaaaagttg tagataatag tgtttctttg   1140
tctgaactag aactggctaa taaacagtac aatgaactga ctgctaagta cagggacatc   1200
ttgcaaaaag ataatatgct tgttcaaaga acaagtaact tggaacacct ggagtgtgaa   1260
aacatctcct taaaagaaca agtggagtct ataaataaag aactggagat taccaaggaa   1320
aaacttcaca ctattgaaca agcctgggaa caggaaacta aattaggtaa tgaatctagc   1380
atggataagg caaagaaatc aataaccaac agtgacattg tttccatttc aaaaaaaata   1440
actatgctgg aaatgaagga attaaatgaa aggcagcggg ctgaacattg tcaaaaaatg   1500
tatgaacact tacggacttc gttaaagcaa atggaggaac gtaattttga attggaaacc   1560
aaatttgctg agcttaccaa aatcaatttg gatgcacaga aggtggaaca gatgttaaga   1620
gatgaattag ctgatagtgt gagcaaggca gtaagtgatg ctgataggca acggattcta   1680
gaattagaga agaatgaaat ggaactaaaa gttgaagtgt caaaactgag agagatttct   1740
gatattgcca gaagacaagt tgaaattttg aatgcacaac aacaatctag ggacaaggaa   1800
gtaaaattga agaagcact taaaacaagt aaaaacagag aaaactcact aactgataat   1860
ttgaatgact taaataatga actgcaaaag aaacaaaaag cctataataa aatacttaga   1920
gagaaagagg aaattgatca agagaatgat gaactgaaaa ggcaaattaa aagactaacc   1980
agtggattac agggcaaacc cctgacagat aataaacaaa gtctaattga agaactccaa   2040
aggaaagtta aaaaactaga gaaccaatta gagggaaagg tggaggaagt agacctaaaa   2100
cctatgaaag aaaagaatgc taagaagaa ttaattaggt gggaagaagg taaaaagtgg   2160
caagccaaaa tagaaggaat tcgaaacaag ttaaaagaga aagagggga agtctttact   2220 ttaacaaagc agttgaatac tttgaaggat cttttttgcca aagccgataa agagaaactt   2280
actttgcaga ggaaactaaa aacaactggc atgactgttg atcaggtttt gggaatacga   2340
gctttggagt cagaaaaaga attggaagaa ttaaaaaaga gaaatcttga cttagaaaat   2400
gatatattgt atatgagggc ccaccaagct cttcctcgag attctgttgt agaagattta   2460
catttacaaa atagataccct ccaagaaaaa cttcatgctt tagaaaaaca gttttcaaag   2520
gatacatatt ctaagccttc aatttcagga atagagtcag atgatcattg tcagagagaa   2580
caggagcttc agaaggaaaa cttgaagttg tcatctgaaa atattgaact gaaatttcag   2640
cttgaacaag caaataaaga tttgccaaga ttaaagaatc aagtcagaga tttgaaggaa   2700
atgtgtgaat tcttaagaa agaaaaagca gaagttcagc ggaaacttgg ccatgttaga   2760
gggtctggta gaagtggaaa gacaatccca gaactggaaa aaaccattgg tttaatgaaa   2820
aaagtagttg aaaagtcca gagagaaaat gaacagttga aaaagcatc aggaatattg   2880 actagtgaaa aatggctaa tattgagcag gaaaatgaaa aattgaaggc tgaattagaa   2940
aaacttaaag ctcatcttgg gcatcagttg agcatgcact atgaatccaa gaccaaaggc   3000
acagaaaaaa ttattgctga aaatgaaagg cttcgtaaag aacttaaaaa agaaactgat   3060
gctgcagaga aattacggat agcaaagaat aatttagaga tattaaatga gaagatgaca   3120
gttcaactag aagagactgg taagagattg cagtttgcag aaagcagagg tccacagctt   3180
gaaggtgctg acagtaagag ctggaaatcc attgtggtta caagaatgta tgaaaccaag   3240
```

```
ttaaaagaat tggaaactga tattgccaaa aaaaatcaaa gcattactga ccttaaacag    3300
cttgtaaaag aagcaacaga gagagaacaa aaagttaaca aatacaatga agaccttgaa    3360
caacagatta agattcttaa acatgttcct gaaggtgctg agacagagca aggccttaaa    3420
cgggagcttc aagttcttag attagctaat catcagctgg ataaagagaa agcagaatta    3480
atccatcaga tagaagctaa caaggaccaa agtggagctg aaagcaccat acctgatgct    3540
gatcaactaa aggaaaaaat aaaagatcta gagacacagc tcaaaatgtc agatctagaa    3600
aagcagcatt tgaaggagga aataaagaag ctgaaaaaag aactggaaaa ttttgatcct    3660 tcatttttg aagaaattga agatcttaag tataattaca aggaagaagt gaagaagaat     3720
attctcttag aagagaaggt aaaaaaactt tcagaacaat gggagttga attaactagc     3780 cctgttgctg cttctgaaga gtttgaagat gaagaagaaa gtcctgttaa tttccccatt    3840
tactaa                                                              3846

<210> SEQ ID NO 24
<211> LENGTH: 2358
<212> TYPE: DNA
<213> ORGANISM: Homo sapiens

<400> SEQUENCE: 24
gagtccctca gaatgcaact gctagactat caggcacagt ctgatgaaaa gtcgctcatt      60
gccaagttgc accaacataa tgtctctctt caactgagtg aggctactgc tcttggtaag     120
ttggagtcaa ttacatctaa actgcagaag atggaggcct acaacttgcg cttagagcag     180
aaacttgatg aaaagaaca ggctctctat tatgctcgtt tggagggaag aaacagagca     240
aaacatctgc gccaaacaat tcagtctcta cgacgacagt ttagtggagc tttacccttg     300
gcacaacagg aaaagttctc caaaacaatg attcaactac aaaatgacaa acttaagata     360
atgcaagaaa tgaaaaattc tcaacaagaa catagaaata tggagaacaa acattggag     420 atggaattaa aattaaaggg cctggaagag ttaataagca cttaaaagga taccaaagga     480
gcccaaaagg taatcaactg gcatatgaaa atagaagaac ttcgtcttca agaacttaaa     540
ctaaatcggg aattagtcaa ggataaagaa gaaataaaat atttgaataa cataatttct     600
gaatatgaac gtacaatcag cagtcttgaa gaagaaattg tgcaacagaa caagtttcat     660
gaagaaagac aaatggcctg ggatcaaaga gaagttgacc tggaacgcca actagacatt     720
tttgaccgtc agcaaaatga aatactaaat gcggcacaaa agtttgaaga agctacagga     780
tcaatccctg accctagttt gccccttcca aatcaacttg agatcgctct aaggaaaatt     840
aaggagaaca ttcgaataat tctagaaaca cgggcaactt gcaaatcact agaagagaaa     900
ctaaaagaga aagaatctgc tttaaggtta gcagaacaaa atatactgtc aagagacaaa     960
gtaatcaatg aactgaggct tcgattgcct gccactgcag aaagagaaaa gctcatagct    1020
gagctaggca gaaagagat ggaaccaaaa tctcaccaca cattgaaaat tgctcatcaa     1080
accattgcaa acatgcaagc aaggttaaat caaaagaag agtattaaa gaagtatcaa     1140 cgtcttctag aaaaagccag agaggagcaa agagaaattg tgaagaaaca tgaggaagac    1200
cttcatattc ttcatcacag attagaacta caggctgata gttcactaaa taaattcaaa    1260
caaacggctt gggatttaat gaaacagtct cccactccag ttcctaccaa caagcatttt    1320
attcgtctgg ctgagatgga acagacagta gcagaacaag atgactctct ttcctcactc    1380
ttggtcaaac taagaaagt atcacaagat ttggagagac aaagagaaat cactgaatta    1440
aaagtaaaag aatttgaaaa tatcaaatta cagcttcaag aaaaccatga agatgaagtg    1500
```

-continued

```
aaaaaagtaa aagcggaagt agaggattta agtatcttc tggaccagtc acaaaaggag      1560
tcacagtgtt taaatctga acttcaggct caaaaagaag caaattcaag agctccaaca      1620
actacaatga gaaatctagt agaacggcta aagagccaat tagccttgaa ggagaaacaa     1680
cagaaagcac ttagtcgggc acttttagaa ctccgggcag aaatgacagc agctgctgaa    1740
gaacgtatta tttctgcaac ttctcaaaaa gaggcccatc tcaatgttca acaaatcgtt    1800
gatcgacata ctagagagct aaagacacaa gttgaagatt taaatgaaaa tcttttaaaa    1860
ttgaaagaag cacttaaaac aagtaaaaac agagaaaact cactaactga taatttgaat    1920
gacttaaata atgaactgca aaagaaacaa aaagcctata ataaaatact tagagagaaa    1980
gaggaaattg atcaagagaa tgatgaactg aaaaggcaaa ttaaaagact aaccagtgga    2040
ttacagggca accccctgac agataataaa caaagtctaa ttgaagaact ccaaaggaaa    2100
gttaaaaaac tagagaacca attagaggga aaggtggagg aagtagacct aaaacctatg    2160
aaagaaaaga atgctaaaga agaattaatt aggtgggaag aaggtaaaaa gtggcaagcc    2220
aaaatagaag gaattcgaaa caagttaaaa gagaaagagg gggaagtctt tactttaaca    2280
aagcagttga atactttgaa ggatcttttt gccaaagccg ataaagagaa acttactttg    2340
cagaggaaac taaaaaca                                                  2358
```

<210> SEQ ID NO 25
<211> LENGTH: 2745
<212> TYPE: DNA
<213> ORGANISM: Homo sapiens

<400> SEQUENCE: 25

```
atattaacaa aggaaatcaa taaacttgaa ttgaagatca gtgatttcct tgatgaaaat      60
gaggcactta gagagcgtgt gggccttgaa ccaaagacaa tgattgattt aactgaattt     120
agaaatagca acacttaaa acagcagcag tacagagctg aaaaccagat tcttttgaaa     180
gagattgaaa gtctagagga agaacgactt gatctgaaaa aaaaaattcg tcaaatggct    240
caagaaagag gaaaagaag tgcaacttca ggattaacca ctgaggacct gaacctaact    300
gaaaacattt ctcaaggaga tagaataagt gaaagaaaat tggatttatt gagcctcaaa    360
aatatgagtg aagcacaatc aaagaatgaa tttctttcaa gagaactaat tgaaaaagaa    420
agagatttag aaaggagtag gacagtgata gccaaatttc agaataaatt aaaagaatta    480
gttgaagaaa ataagcaact tgaagaaggt atgaagaaa tattgcaagc aattaaggaa     540
atgcagaaag atcctgatgt taaaggagga gaaacatctc taattatccc tagccttgaa    600
agactagtta atgctataga atcaaagaat gcagaaggaa tctttgatgc gagtctgcat    660
ttgaaagccc aagttgatca gcttaccgga agaaatgaag aattaagaca ggagctcagg    720
gaatctcgga agaggctat aaattattca cagcagttgg caaaagctaa tttaaagata    780
gaccatcttg aaaagaaac tagtctttta cgacaatcag aaggatcgaa tgttgttttt    840
aaaggaattg acttacctga tgggatagca ccatctagtg ccagtatcat taattctcag    900
aatgaatatt taatacattt gttacaggaa ctagaaaata agaaaaaaa gttaaagaat    960
ttagaagatt ctcttgaaga ttacaacaga aaatttgctg taattcgtca tcaacaaagt   1020
ttgttgtata agaataccct aagtgaaaag gagacctgga aaacagaatc taaaacaata   1080
aaagaggaaa agagaaaact tgaggatcaa gtccaacaag atgctataaa agtaaaagaa   1140
tataataatt tgctcaatgc tcttcagatg gattcggatg aaatgaaaaa aatacttgca   1200
```

| | |
|---|---:|
| acaactggca tgactgttga tcaggttttg ggaatacgag ctttggagtc agaaaaagaa | 1260 |
| ttggaagaat taaaaagag aaatcttgac ttagaaaatg atatattgta tatgagggcc | 1320 |
| caccaagctc ttcctcgaga ttctgttgta gaagatttac atttacaaaa tagatacctc | 1380 |
| caagaaaaac ttcatgcttt agaaaaacag ttttcaaagg atacatattc taagccttca | 1440 |
| atttcaggaa tagagtcaga tgatcattgt cagagagaac aggagcttca gaaggaaaac | 1500 |
| ttgaagttgt catctgaaaa tattgaactg aaatttcagc ttgaacaagc aaataaagat | 1560 |
| ttgccaagat taaagaatca agtcagagat ttgaaggaaa tgtgtgaatt tcttaagaaa | 1620 |
| gaaaaagcag aagttcagcg gaaacttggc catgttagag ggtctggtag aagtggaaag | 1680 |
| acaatcccag aactggaaaa aaccattggt ttaatgaaaa aagtagttga aaagtccag | 1740 |
| agagaaaatg aacagttgaa aaaagcatca ggaatattga ctagtgaaaa aatggctaat | 1800 |
| attgagcagg aaaatgaaaa attgaaggct gaattagaaa aacttaaagc tcatcttggg | 1860 |
| catcagttga gcatgcacta tgaatccaag accaaaggca cagaaaaaat tattgctgaa | 1920 |
| aatgaaaggc ttcgtaaaga acttaaaaaa gaaactgatg ctgcagagaa attacggata | 1980 |
| gcaaagaata atttagagat attaaatgag aagatgacag ttcaactaga agagactggt | 2040 |
| aagagattgc agtttgcaga aagcagaggt ccacagcttg aaggtgctga cagtaagagc | 2100 |
| tggaaatcca ttgtggttac aagaatgtat gaaccaagt taaaagaatt ggaaactgat | 2160 |
| attgccaaaa aaatcaaag cattactgac cttaaacagc ttgtaaaaga agcaacagag | 2220 |
| agagaacaaa aagttaacaa atacaatgaa gaccttgaac aacagattaa gattcttaaa | 2280 |
| catgttcctg aaggtgctga gacagagcaa ggccttaaac gggagcttca agttcttaga | 2340 |
| ttagctaatc atcagctgga taaagagaaa gcagaattaa tccatcagat agaagctaac | 2400 |
| aaggaccaaa gtggagctga aagcaccata cctgatgctg atcaactaaa ggaaaaaata | 2460 |
| aaagatctag agacacagct caaaatgtca gatctagaaa agcagcattt gaaggaggaa | 2520 |
| ataaagaagc tgaaaaaaga actggaaaat tttgatcctt cattttttga agaaattgaa | 2580 |
| gatcttaagt ataattacaa ggaagaagtg aagaagaata ttctcttaga agagaaggta | 2640 |
| aaaaaacttt cagaacaatt gggagttgaa ttaactagcc ctgttgctgc ttctgaagag | 2700 |
| tttgaagatg aagaagaaag tcctgttaat ttccccattt actaa | 2745 |

```
<210> SEQ ID NO 26
<211> LENGTH: 2655
<212> TYPE: DNA
<213> ORGANISM: Homo sapiens

<400> SEQUENCE: 26
```

| | |
|---|---:|
| atattaacaa aggaaatcaa taaacttgaa ttgaagatca gtgatttcct tgatgaaaat | 60 |
| gaggcactta gagagcgtgt gggccttgaa ccaaagacaa tgattgattt aactgaattt | 120 |
| agaaatagca acacttaaa acagcagcag tacagagctg aaaaccagat tcttttgaaa | 180 |
| gagattgaaa gtctagagga agaacgactt gatctgaaaa aaaaaattcg tcaaatggct | 240 |
| caagaaagag gaaaagaag tgcaacttca ggattaacca ctgaggacct gaacctagag | 300 |
| tccctcagaa tgcaactgct agactatcag gcacagtctg atgaaaagtc gctcattgcc | 360 |
| aagttgcacc aacataatgt ctctcttcaa ctgagtgagg ctactgctct tggtaagttg | 420 |
| gagtcaatta catctaaact gcagaagatg gaggcctaca acttgcgctt agagcagaaa | 480 |
| cttgatgaaa aagaacaggc tctctattat gctcgtttgg agggaagaaa cagagcaaaa | 540 |
| catctgcgcc aaacaattca gtctctacga cgacagtttta gtggagcttt accccttggca | 600 |

```
caacaggaaa agttctccaa aacaatgatt caactacaaa atgacaaact taagataatg      660
caagaaatga aaaattctca acaagaacat agaaatatgg agaacaaaac attggagatg      720
gaattaaaat taagggcct ggaagagtta ataagcactt taaaggatac caaaggagcc       780
caaaaggtaa tcaactggca tatgaaaata gaagaacttc gtcttcaaga acttaaacta      840
aatcgggaat tagtcaagga taaagaagaa ataaaatatt tgaataacat aatttctgaa      900
tatgaacgta caatcagcag tcttgaagaa gaaattgtgc aacagaacaa gtttcatgaa      960
gaaagacaaa tggcctggga tcaaagagaa gttgacctgg aacgccaact agacattttt     1020
gaccgtcagc aaaatgaaat actaaatgcg gcacaaaagt ttgaagaagc tacaggatca     1080
atccctgacc ctagtttgcc ccttccaaat caacttgaga tcgctctaag gaaaattaag     1140
gagaacattc gaataattct agaaacacgg gcaacttgca aatcactaga agagaaacta     1200
aaagagaaag aatctgcttt aaggttagca gaacaaaata tactgtcaag agacaaagta     1260
atcaatgaac tgaggcttcg attgcctgcc actgcagaaa gagaaaagct catagctgag     1320
ctaggcagaa aagagatgga accaaaatct caccacacat tgaaaattgc tcatcaaacc     1380
attgcaaaca tgcaagcaag gttaaatcaa aagaagaag tattaaagaa gtatcaacgt      1440
cttctagaaa aagccagaga ggagcaaaga gaaattgtga agaaacatga ggaagacctt     1500
catattcttc atcacagatt agaactacag gctgatagtt cactaaataa attcaaacaa     1560
acggcttggg atttaatgaa acagtctccc actccagttc ctaccaacaa gcattttatt     1620
cgtctggctg agatggaaca gacagtagca gaacaagatg actctctttc ctcactcttg     1680
gtcaaactaa agaaagtatc acaagatttg gagagacaaa gagaaatcac tgaattaaaa     1740 gtaaagaat ttgaaaatat caattacag cttcaagaaa accatgaaga tgaagtgaaa       1800
aaagtaaaag cggaagtaga ggatttaaag tatcttctgg accagtcaca aaaggagtca     1860
cagtgtttaa aatctgaact tcaggctcaa aaagaagcaa attcaagagc tccaacaact     1920
acaatgagaa atctagtaga acggctaaag agccaattag ccttgaagga gaaacaacag     1980
aaagcactta gtcgggcact tttagaactc cgggcagaaa tgacagcagc tgctgaagaa     2040
cgtattattt ctgcaacttc tcaaaaagag gcccatctca atgttcaaca aatcgttgat     2100
cgacatacta gagagctaaa gacacaagtt gaagatttaa atgaaaatct tttaaaattg     2160
aaagaagcac ttaaaacaag taaaaacaga gaaaactcac taactgataa tttgaatgac     2220
ttaaataatg aactgcaaaa gaaacaaaaa gcctataata aaatacttag agagaaagag     2280
gaaattgatc aagagaatga tgaactgaaa aggcaaatta aagactaac cagtggatta     2340 cagggcaaac ccctgacaga taataaacaa agtctaattg aagaactcca aggaaagtt     2400 aaaaaactag agaaccaatt agagggaaag gtggaggaag tagacctaaa acctatgaaa     2460
gaaaagaatg ctaaagaaga attaattagg tgggaagaag gtaaaaagtg gcaagccaaa     2520
atagaaggaa ttcgaaacaa gttaaaagag aagaggggg aagtctttac tttaacaaag     2580
cagttgaata ctttgaagga tcttttttgcc aaagccgata agagaaact tactttgcag     2640 aggaaactaa aaaca                                                      2655
```

<210> SEQ ID NO 27
<211> LENGTH: 2013
<212> TYPE: DNA
<213> ORGANISM: Homo sapiens

<400> SEQUENCE: 27

| | |
|---|---|
| atattaacaa aggaaatcaa taaacttgaa ttgaagatca gtgatttcct tgatgaaaat | 60 |
| gaggcactta gagagcgtgt gggccttgaa ccaaagacaa tgattgattt aactgaattt | 120 |
| agaaatagca aacacttaaa acagcagcag tacagagctg aaaaccagat tcttttgaaa | 180 |
| gagattgaaa gtctagagga agaacgactt gatctgaaaa aaaaaattcg tcaaatggct | 240 |
| caagaaagag gaaaagaag tgcaacttca ggattaacca ctgaggacct gaacctaact | 300 |
| gaaaacattt ctcaaggaga tagaataagt gaaagaaaat tggatttatt gagcctcaaa | 360 |
| aatatgagtg aagcacaatc aaagaatgaa tttctttcaa gagaactaat tgaaaagaa | 420 |
| agagatttag aaaggagtag gacagtgata gccaaatttc agaataaatt aaagaatta | 480 |
| gttgaagaaa ataagcaact tgaagaaggt atgaaagaaa tattgcaagc aattaaggaa | 540 |
| atgcagaaag atcctgatgt taaaggagga gaaacatctc taattatccc tagccttgaa | 600 |
| agactagtta atgctataga atcaaagaat gcagaaggaa tctttgatgc gagtctgcat | 660 |
| ttgaaagccc aagttgatca gcttaccgga agaaatgaag aattaagaca ggagctcagg | 720 |
| gaatctcgga aagaggctat aaattattca cagcagttgg caaaagctaa tttaaagata | 780 |
| gaccatcttg aaaagaaac tagtctttta cgacaatcag aaggatcgaa tgttgttttt | 840 |
| aaggaattg acttacctga tgggatagca ccatctagtg ccagtatcat taattctcag | 900 |
| aatgaatatt taatacattt gttacaggaa ctagaaaata agaaaaaaa gttaaagaat | 960 |
| ttagaagatt ctcttgaaga ttacaacaga aaatttgctg taattcgtca tcaacaaagt | 1020 |
| ttgttgtata aagaataccc taagtgaaaag gagacctgga aaacagaatc taaaacaata | 1080 |
| aaagaggaaa agagaaaact tgaggatcaa gtccaacaag atgctataaa agtaaaagaa | 1140 |
| tataataatt tgctcaatgc tcttcagatg gattcggatg aaatgaaaaa aatacttgca | 1200 |
| cagtcacaaa aggagtcaca gtgtttaaaa tctgaacttc aggctcaaaa agaagcaaat | 1260 |
| tcaagagctc caacaactac aatgagaaat ctagtagaac ggctaaagag ccaattagcc | 1320 |
| ttgaaggaga acaacagaa agcacttagt cgggcacttt tagaactccg ggcagaaatg | 1380 |
| acagcagctg ctgaagaacg tattatttct gcaacttctc aaaaagaggc ccatctcaat | 1440 |
| gttcaacaaa tcgttgatcg acatactaga gagctaaaga cacaagttga agatttaaat | 1500 |
| gaaaatcttt taaattgaa agaagcactt aaaacaagta aaacagaga aaactcacta | 1560 |
| actgataatt tgaatgactt aaataatgaa ctgcaaaaga acaaaaagc ctataataaa | 1620 |
| atacttagag agaaagagga aattgatcaa gagaatgatg aactgaaag gcaaattaaa | 1680 |
| agactaacca gtggattaca gggcaaaccc ctgacagata taaacaaag tctaattgaa | 1740 |
| gaactccaaa ggaaagttaa aaaactagag aaccaattag agggaaggt ggaggaagta | 1800 |
| gacctaaaac ctatgaaaga aaagaatgct aagaagaat taattaggtg ggaagaaggt | 1860 |
| aaaaagtggc aagccaaaat agaaggaatt cgaaacaagt taaagagaa agaggggaa | 1920 |
| gtctttactt taacaaagca gttgaatact ttgaaggatc tttttgccaa agccgataaa | 1980 |
| gagaaactta ctttgcagag gaaactaaaa aca | 2013 |

<210> SEQ ID NO 28
<211> LENGTH: 1716
<212> TYPE: DNA
<213> ORGANISM: Homo sapiens

<400> SEQUENCE: 28

| | |
|---|---|
| actgaaaaca tttctcaagg agatagaata agtgaaagaa aattggatt attgagcctc | 60 |
| aaaaatatga gtgaagcaca atcaaagaat gaatttcttt caagagaact aattgaaaaa | 120 |

```
gaaagagatt tagaaaggag taggacagtg atagccaaat ttcagaataa attaaaagaa    180
ttagttgaag aaaataagca acttgaagaa ggtatgaaag aaatattgca agcaattaag    240
gaaatgcaga aagatcctga tgttaaagga ggagaaacat ctctaattat ccctagcctt    300
gaaagactag ttaatgctat agaatcaaag aatgcagaag gaatctttga tgcgagtctg    360
catttgaaag cccaagttga tcagcttacc ggaagaaatg aagaattaag acaggagctc    420
agggaatctc ggaaagaggc tataaattat tcacagcagt tggcaaaagc taatttaaag    480
atagaccatc ttgaaaaaga aactagtctt ttacgacaat cagaaggatc gaatgttgtt    540
tttaaaggaa ttgacttacc tgatgggata gcaccatcta gtgccagtat cattaattct    600
cagaatgaat atttaataca tttgttacag gaactagaaa ataaagaaaa aagttaaag    660 aatttagaag attctcttga agattacaac agaaaatttg ctgtaattcg tcatcaacaa    720
agtttgttgt ataaagaata cctaagtgaa aaggagacct ggaaaacaga atctaaaaca    780
ataaaagagg aaaagagaaa acttgaggat caagtccaac aagatgctat aaaagtaaaa    840
gaatataata atttgctcaa tgctcttcag atggattcgg atgaaatgaa aaaaatactt    900
gcacagtcac aaaaggagtc acagtgttta aaatctgaac ttcaggctca aaagaagca    960 aattcaagag ctccaacaac tacaatgaga aatctagtag aacggctaaa gagccaatta   1020
gccttgaagg agaaacaaca gaaagcactt agtcgggcac ttttagaact ccgggcagaa   1080
atgacagcag ctgctgaaga acgtattatt tctgcaactt ctcaaaaaga ggcccatctc   1140
aatgttcaac aaatcgttga tcgacatact agagagctaa agacacaagt tgaagattta   1200
aatgaaaatc tttttaaaatt gaaagaagca cttaaaacaa gtaaaaacag agaaaactca   1260
ctaactgata atttgaatga cttaaataat gaactgcaaa agaaacaaaa agcctataat   1320
aaaatactta gagagaaaga ggaaattgat caagagaatg atgaactgaa aaggcaaatt   1380
aaaagactaa ccagtggatt acagggcaaa cccctgacag ataataaaca aagtctaatt   1440
gaagaactcc aaaggaaagt taaaaaacta gagaaccaat tagagggaaa ggtggaggaa   1500
gtagacctaa aacctatgaa agaaaagaat gctaaagaag aattaattag gtgggaagaa   1560
ggtaaaaagt ggcaagccaa aatagaagga attcgaaaca gttaaaaga gaaagagggg   1620 gaagtctttta ctttaacaaa gcagttgaat actttgaagg atctttttgc caaagccgat   1680
aaagagaaac ttactttgca gaggaaacta aaaaca                             1716
```

<210> SEQ ID NO 29
<211> LENGTH: 2406
<212> TYPE: DNA
<213> ORGANISM: Homo sapiens

<400> SEQUENCE: 29

```
atgccaccta atataaactg aaagaaaata atgaaagttg acccagatga cctgccccgt     60
caagaagaac tggcagataa tttattgatt tccttatcca aggtggaagt aaatgagcta    120
aaaagtgaaa agcaagaaaa tgtgatacac cttttcagaa ttactcagtc actaatgaag    180
atgaaagctc aagaagtgga gctggctttg gaagaagtag aaaaagctgg agaagaacaa    240
gcaaaatttg aaaatcaatt aaaaactaaa gtaatgaaac tggaaaatga actggagatg    300
gctcagcagt ctgcaggtgg acgagatact cggttttac gtaatgaaat ttgccaactt    360
gaaaaacaat agaacaaaa agatagaaa ttggaggaca tggaaaagga gttggagaaa    420
gagaagaaag ttaatgagca attggctctt cgaaatgagg aggcagaaaa tgaaaacagc    480
```

```
aaattaagaa gagagaacaa acgtctaaag aaaaagaatg aacaactttg tcaggatatt    540
attgactacc agaaacaaat agattcacag aagaaacac  tttatcaag  aagaggggaa    600 actgaaaaca tttctcaagg agatagaata agtgaaagaa aattggattt attgagcctc    660
aaaaatatga gtgaagcaca atcaaagaat gaatttcttt caagagaact aattgaaaaa    720
gaaagagatt tagaaaggag taggacagtg atagccaaat tcagaataa  attaaaagaa    780 ttagttgaag aaaataagca acttgaagaa ggtatgaaag aaatattgca agcaattaag    840
gaaatgcaga aagatcctga tgttaaagga ggagaaacat ctctaattat ccctagcctt    900
gaaagactag ttaatgctat agaatcaaag aatgcagaag gaatctttga tgcgagtctg    960
catttgaaag cccaagttga tcagcttacc ggaagaaatg aagaattaag acaggagctc   1020
agggaatctc ggaaagaggc tataaattat tcacagcagt tggcaaaagc taatttaaag   1080
atagaccatc ttgaaaaaga aactagtctt ttacgacaat cagaaggatc gaatgttgtt   1140
tttaaaggaa ttgacttacc tgatgggata gcaccatcta gtgccagtat cattaattct   1200
cagaatgaat atttaataca tttgttacag gaactagaaa ataaagaaaa aaagttaaag   1260
aatttagaag attctcttga agattacaac agaaaatttg ctgtaattcg tcatcaacaa   1320
agtttgttgt ataagaata  cctaagtgaa aaggagacct ggaaaacaga atctaaaaca   1380
ataaaagagg aaaagagaaa acttgaggat caagtccaac aagatgctat aaaagtaaaa   1440
gaatataata atttgctcaa tgctcttcag atggattcgg atgaaatgaa aaaaatactt   1500
gcagaaaata gtaggaaaat tactgttttg caagtgaatg aaaaatcact tataaggcaa   1560
tatacaacct tagtagaatt ggagcgacaa cttagaaaag aaaatgagaa gcaaaagaat   1620
gaattgttgt caatggaggc tgaagtttgt gaaaaaattg ggtgtttgca agatttaag    1680 gaaatggcca ttttcaagat tgcagctctc caaaaagttg tagataatag tgtttctttg   1740
tctgaactag aactggctaa taaacagtac aatgaactga ctgctaagta cagggacatc   1800
ttgcaaaaag ataatatgct tgttcaaaga acaagtaact tggaacaccct ggagtgtgaa   1860 aacatctcct taaaagaaca agtggagtct ataaataaag aactggagat taccaaggaa   1920
aaacttcaca ctattgaaca agcctgggaa caggaaacta aattaggtaa tgaatctagc   1980
atggataagg caaagaaatc aataaccaac agtgacattg tttccatttc aaaaaaaata   2040
actatgctgg aaatgaagga attaaatgaa aggcagcggg ctgaacattg tcaaaaaatg   2100
tatgaacact tacggacttc gttaaagcaa atggaggaac gtaattttga attggaaacc   2160
aaatttgctg agcttaccaa aatcaatttg gatgcacaga aggtggaaca gatgttaaga   2220
gatgaattag ctgatagtgt gagcaaggca gtaagtgatg ctgataggca acggattcta   2280
gaattagaga agaatgaaat ggaactaaaa gttgaagtgt caaaactgag agagatttct   2340
gatattgcca gaagacaagt tgaaattttg aatgcacaac aacaatctag ggacaaggaa   2400
gtataa                                                              2406
```

<210> SEQ ID NO 30  
<211> LENGTH: 1316  
<212> TYPE: PRT  
<213> ORGANISM: Homo sapiens

<400> SEQUENCE: 30

Lys Asn Thr Cys Ile Ile Glu Asp Leu Lys Asn Glu Leu Gln Arg Asn
1               5                   10                  15

Lys Gly Ala Ser Thr Leu Ser Gln Gln Thr His Met Lys Ile Gln Ser
            20                  25                  30

Thr Leu Asp Ile Leu Lys Glu Lys Thr Lys Glu Ala Glu Arg Thr Ala
                35                  40                  45
Glu Leu Ala Glu Ala Asp Ala Arg Glu Lys Asp Lys Glu Leu Val Glu
 50                  55                  60
Ala Leu Lys Arg Leu Lys Asp Tyr Glu Ser Gly Val Tyr Gly Leu Glu
 65                  70                  75                  80
Asp Ala Val Val Glu Ile Lys Asn Cys Lys Asn Gln Ile Lys Ile Arg
                    85                  90                  95
Asp Arg Glu Ile Glu Ile Leu Thr Lys Glu Ile Asn Lys Leu Glu Leu
                100                 105                 110
Lys Ile Ser Asp Phe Leu Asp Glu Asn Glu Ala Leu Arg Glu Arg Val
                115                 120                 125
Gly Leu Glu Pro Lys Thr Met Ile Asp Leu Thr Glu Phe Arg Asn Ser
130                 135                 140
Lys His Leu Lys Gln Gln Gln Tyr Arg Ala Glu Asn Gln Ile Leu Leu
145                 150                 155                 160
Lys Glu Ile Glu Ser Leu Glu Glu Arg Leu Asp Leu Lys Lys Lys
                    165                 170                 175
Ile Arg Gln Met Ala Gln Glu Arg Gly Lys Arg Ser Ala Thr Ser Gly
                180                 185                 190
Leu Thr Thr Glu Asp Leu Asn Leu Thr Glu Asn Ile Ser Gln Gly Asp
                195                 200                 205
Arg Ile Ser Glu Arg Lys Leu Asp Leu Leu Ser Leu Lys Asn Met Ser
                210                 215                 220
Glu Ala Gln Ser Lys Asn Glu Phe Leu Ser Arg Glu Leu Ile Glu Lys
225                 230                 235                 240
Glu Arg Asp Leu Glu Arg Ser Arg Thr Val Ile Ala Lys Phe Gln Asn
                245                 250                 255
Lys Leu Lys Glu Leu Val Glu Glu Asn Lys Gln Leu Glu Glu Gly Met
                260                 265                 270
Lys Glu Ile Leu Gln Ala Ile Lys Glu Met Gln Lys Asp Pro Asp Val
                275                 280                 285
Lys Gly Gly Glu Thr Ser Leu Ile Ile Pro Ser Leu Glu Arg Leu Val
                290                 295                 300
Asn Ala Ile Glu Ser Lys Asn Ala Glu Gly Ile Phe Asp Ala Ser Leu
305                 310                 315                 320
His Leu Lys Ala Gln Val Asp Gln Leu Thr Gly Arg Asn Glu Glu Leu
                325                 330                 335
Arg Gln Glu Leu Arg Glu Ser Arg Lys Glu Ala Ile Asn Tyr Ser Gln
                340                 345                 350
Gln Leu Ala Lys Ala Asn Leu Lys Ile Asp His Leu Glu Lys Glu Thr
                355                 360                 365
Ser Leu Leu Arg Gln Ser Glu Gly Ser Asn Val Val Phe Lys Gly Ile
370                 375                 380
Asp Leu Pro Asp Gly Ile Ala Pro Ser Ser Ala Ser Ile Ile Asn Ser
385                 390                 395                 400
Gln Asn Glu Tyr Leu Ile His Leu Leu Gln Glu Leu Glu Asn Lys Glu
                405                 410                 415
Lys Lys Leu Lys Asn Leu Glu Asp Ser Leu Glu Asp Tyr Asn Arg Lys
                420                 425                 430
Phe Ala Val Ile Arg His Gln Gln Ser Leu Leu Tyr Lys Glu Tyr Leu
                435                 440                 445

-continued

```
Ser Glu Lys Glu Thr Trp Lys Thr Glu Ser Lys Thr Ile Lys Glu Glu
    450                 455                 460

Lys Arg Lys Leu Glu Asp Gln Val Gln Gln Asp Ala Ile Lys Val Lys
465                 470                 475                 480

Glu Tyr Asn Asn Leu Leu Asn Ala Leu Gln Met Asp Ser Asp Glu Met
                485                 490                 495

Lys Lys Ile Leu Ala Glu Asn Ser Arg Lys Ile Thr Val Leu Gln Val
            500                 505                 510

Asn Glu Lys Ser Leu Ile Arg Gln Tyr Thr Thr Leu Val Glu Leu Glu
            515                 520                 525

Arg Gln Leu Arg Lys Glu Asn Glu Lys Gln Lys Asn Glu Leu Leu Ser
530                 535                 540

Met Glu Ala Glu Val Cys Glu Lys Ile Gly Cys Leu Gln Arg Phe Lys
545                 550                 555                 560

Glu Met Ala Ile Phe Lys Ile Ala Ala Leu Gln Lys Val Val Asp Asn
                565                 570                 575

Ser Val Ser Leu Ser Glu Leu Glu Leu Ala Asn Lys Gln Tyr Asn Glu
            580                 585                 590

Leu Thr Ala Lys Tyr Arg Asp Ile Leu Gln Lys Asp Asn Met Leu Val
            595                 600                 605

Gln Arg Thr Ser Asn Leu Glu His Leu Glu Cys Glu Asn Ile Ser Leu
610                 615                 620

Lys Glu Gln Val Glu Ser Ile Asn Lys Glu Leu Glu Ile Thr Lys Glu
625                 630                 635                 640

Lys Leu His Thr Ile Glu Gln Ala Trp Glu Gln Glu Thr Lys Leu Gly
                645                 650                 655

Asn Glu Ser Ser Met Asp Lys Ala Lys Lys Ser Ile Thr Asn Ser Asp
            660                 665                 670

Ile Val Ser Ile Ser Lys Lys Ile Thr Met Leu Glu Met Lys Glu Leu
            675                 680                 685

Asn Glu Arg Gln Arg Ala Glu His Cys Gln Lys Met Tyr Glu His Leu
690                 695                 700

Arg Thr Ser Leu Lys Gln Met Glu Glu Arg Asn Phe Glu Leu Glu Thr
705                 710                 715                 720

Lys Phe Ala Glu Leu Thr Lys Ile Asn Leu Asp Ala Gln Lys Val Glu
                725                 730                 735

Gln Met Leu Arg Asp Glu Leu Ala Asp Ser Val Ser Lys Ala Val Ser
            740                 745                 750

Asp Ala Asp Arg Gln Arg Ile Leu Glu Leu Lys Asn Glu Met Glu
            755                 760                 765

Leu Lys Val Glu Val Ser Lys Leu Arg Glu Ile Ser Asp Ile Ala Arg
770                 775                 780

Arg Gln Val Glu Ile Leu Asn Ala Gln Gln Ser Arg Asp Lys Glu
785                 790                 795                 800

Val Glu Ser Leu Arg Met Gln Leu Leu Asp Tyr Gln Ala Gln Ser Asp
                805                 810                 815

Glu Lys Ser Leu Ile Ala Lys Leu His Gln His Asn Val Ser Leu Gln
            820                 825                 830

Leu Ser Glu Ala Thr Ala Leu Gly Lys Leu Glu Ser Ile Thr Ser Lys
            835                 840                 845

Leu Gln Lys Met Glu Ala Tyr Asn Leu Arg Leu Glu Gln Lys Leu Asp
850                 855                 860

Glu Lys Glu Gln Ala Leu Tyr Tyr Ala Arg Leu Glu Gly Arg Asn Arg
```

-continued

```
                865                 870                 875                 880
Ala Lys His Leu Arg Gln Thr Ile Gln Ser Leu Arg Arg Gln Phe Ser
                    885                 890                 895
Gly Ala Leu Pro Leu Ala Gln Gln Glu Lys Phe Ser Lys Thr Met Ile
                    900                 905                 910
Gln Leu Gln Asn Asp Lys Leu Lys Ile Met Gln Glu Met Lys Asn Ser
                    915                 920                 925
Gln Gln Glu His Arg Asn Met Glu Asn Lys Thr Leu Glu Met Glu Leu
                    930                 935                 940
Lys Leu Lys Gly Leu Glu Glu Leu Ile Ser Thr Leu Lys Asp Thr Lys
945                 950                 955                 960
Gly Ala Gln Lys Val Ile Asn Trp His Met Lys Ile Glu Glu Leu Arg
                    965                 970                 975
Leu Gln Glu Leu Lys Leu Asn Arg Glu Leu Val Lys Asp Lys Glu Glu
                    980                 985                 990
Ile Lys Tyr Leu Asn Asn Ile Ile Ser Glu Tyr Glu Arg Thr Ile Ser
                    995                 1000                1005
Ser Leu Glu Glu Glu Ile Val Gln Gln Asn Lys Phe His Glu Glu
    1010                1015                1020
Arg Gln Met Ala Trp Asp Gln Arg Glu Val Asp Leu Glu Arg Gln
    1025                1030                1035
Leu Asp Ile Phe Asp Arg Gln Gln Asn Glu Ile Leu Asn Ala Ala
    1040                1045                1050
Gln Lys Phe Glu Glu Ala Thr Gly Ser Ile Pro Asp Pro Ser Leu
    1055                1060                1065
Pro Leu Pro Asn Gln Leu Glu Ile Ala Leu Arg Lys Ile Lys Glu
    1070                1075                1080
Asn Ile Arg Ile Ile Leu Glu Thr Arg Ala Thr Cys Lys Ser Leu
    1085                1090                1095
Glu Glu Lys Leu Lys Glu Lys Glu Ser Ala Leu Arg Leu Ala Glu
    1100                1105                1110
Gln Asn Ile Leu Ser Arg Asp Lys Val Ile Asn Glu Leu Arg Leu
    1115                1120                1125
Arg Leu Pro Ala Thr Ala Glu Arg Glu Lys Leu Ile Ala Glu Leu
    1130                1135                1140
Gly Arg Lys Glu Met Glu Pro Lys Ser His His Thr Leu Lys Ile
    1145                1150                1155
Ala His Gln Thr Ile Ala Asn Met Gln Ala Arg Leu Asn Gln Lys
    1160                1165                1170
Glu Glu Val Leu Lys Lys Tyr Gln Arg Leu Leu Glu Lys Ala Arg
    1175                1180                1185
Glu Glu Gln Arg Glu Ile Val Lys Lys His Glu Glu Asp Leu His
    1190                1195                1200
Ile Leu His His Arg Leu Glu Leu Gln Ala Asp Ser Ser Leu Asn
    1205                1210                1215
Lys Phe Lys Gln Thr Ala Trp Asp Leu Met Lys Gln Ser Pro Thr
    1220                1225                1230
Pro Val Pro Thr Asn Lys His Phe Ile Arg Leu Ala Glu Met Glu
    1235                1240                1245
Gln Thr Val Ala Glu Gln Asp Asp Ser Leu Ser Ser Leu Leu Val
    1250                1255                1260
Lys Leu Lys Lys Val Ser Gln Asp Leu Glu Arg Gln Arg Glu Ile
    1265                1270                1275
```

Thr Glu Leu Lys Val Lys Glu Phe Glu Asn Ile Lys Leu Gln Leu
    1280                1285                1290

Gln Glu Asn His Glu Asp Glu Val Lys Lys Val Lys Ala Glu Val
1295                1300                1305

Glu Asp Leu Lys Tyr Leu Leu Asp
1310                1315

<210> SEQ ID NO 31
<211> LENGTH: 514
<212> TYPE: PRT
<213> ORGANISM: Homo sapiens

<400> SEQUENCE: 31

Thr Thr Gly Met Thr Val Asp Gln Val Leu Gly Ile Arg Ala Leu Glu
1               5                   10                  15

Ser Glu Lys Glu Leu Glu Glu Leu Lys Lys Arg Asn Leu Asp Leu Glu
            20                  25                  30

Asn Asp Ile Leu Tyr Met Arg Ala His Gln Ala Leu Pro Arg Asp Ser
        35                  40                  45

Val Val Glu Asp Leu His Leu Gln Asn Arg Tyr Leu Gln Glu Lys Leu
    50                  55                  60

His Ala Leu Glu Lys Gln Phe Ser Lys Asp Thr Tyr Ser Lys Pro Ser
65                  70                  75                  80

Ile Ser Gly Ile Glu Ser Asp Asp His Cys Gln Arg Glu Gln Glu Leu
                85                  90                  95

Gln Lys Glu Asn Leu Lys Leu Ser Ser Glu Asn Ile Glu Leu Lys Phe
            100                 105                 110

Gln Leu Glu Gln Ala Asn Lys Asp Leu Pro Arg Leu Lys Asn Gln Val
        115                 120                 125

Arg Asp Leu Lys Glu Met Cys Glu Phe Leu Lys Lys Glu Lys Ala Glu
    130                 135                 140

Val Gln Arg Lys Leu Gly His Val Arg Gly Ser Gly Arg Ser Gly Lys
145                 150                 155                 160

Thr Ile Pro Glu Leu Glu Lys Thr Ile Gly Leu Met Lys Lys Val Val
                165                 170                 175

Glu Lys Val Gln Arg Glu Asn Glu Gln Leu Lys Lys Ala Ser Gly Ile
            180                 185                 190

Leu Thr Ser Glu Lys Met Ala Asn Ile Glu Gln Glu Asn Glu Lys Leu
        195                 200                 205

Lys Ala Glu Leu Glu Lys Leu Lys Ala His Leu Gly His Gln Leu Ser
    210                 215                 220

Met His Tyr Glu Ser Lys Thr Lys Gly Thr Glu Lys Ile Ile Ala Glu
225                 230                 235                 240

Asn Glu Arg Leu Arg Lys Glu Leu Lys Lys Glu Thr Asp Ala Ala Glu
                245                 250                 255

Lys Leu Arg Ile Ala Lys Asn Asn Leu Glu Ile Leu Asn Glu Lys Met
            260                 265                 270

Thr Val Gln Leu Glu Glu Thr Gly Lys Arg Leu Gln Phe Ala Glu Ser
        275                 280                 285

Arg Gly Pro Gln Leu Glu Gly Ala Asp Ser Lys Ser Trp Lys Ser Ile
    290                 295                 300

Val Val Thr Arg Met Tyr Glu Thr Lys Leu Lys Glu Leu Glu Thr Asp
305                 310                 315                 320

Ile Ala Lys Lys Asn Gln Ser Ile Thr Asp Leu Lys Gln Leu Val Lys

```
                    325                 330                 335
Glu Ala Thr Glu Arg Glu Gln Lys Val Asn Lys Tyr Asn Glu Asp Leu
            340                 345                 350
Glu Gln Gln Ile Lys Ile Leu Lys His Val Pro Glu Gly Ala Glu Thr
        355                 360                 365
Glu Gln Gly Leu Lys Arg Glu Leu Gln Val Leu Arg Leu Ala Asn His
    370                 375                 380
Gln Leu Asp Lys Glu Lys Ala Glu Leu Ile His Gln Ile Glu Ala Asn
385                 390                 395                 400
Lys Asp Gln Ser Gly Ala Glu Ser Thr Ile Pro Asp Ala Asp Gln Leu
                405                 410                 415
Lys Glu Lys Ile Lys Asp Leu Glu Thr Gln Leu Lys Met Ser Asp Leu
            420                 425                 430
Glu Lys Gln His Leu Lys Glu Glu Ile Lys Lys Leu Lys Lys Glu Leu
        435                 440                 445
Glu Asn Phe Asp Pro Ser Phe Phe Glu Glu Ile Glu Asp Leu Lys Tyr
    450                 455                 460
Asn Tyr Lys Glu Glu Val Lys Lys Asn Ile Leu Leu Glu Glu Lys Val
465                 470                 475                 480
Lys Lys Leu Ser Glu Gln Leu Gly Val Glu Leu Thr Ser Pro Val Ala
                485                 490                 495
Ala Ser Glu Glu Phe Glu Asp Glu Glu Glu Ser Pro Val Asn Phe Pro
            500                 505                 510
Ile Tyr

<210> SEQ ID NO 32
<211> LENGTH: 1545
<212> TYPE: DNA
<213> ORGANISM: Homo sapiens

<400> SEQUENCE: 32
acaactggca tgactgttga tcaggttttg ggaatacgag ctttggagtc agaaaaagaa     60
ttggaagaat taaaaagag aaatcttgac ttagaaaatg atatattgta tatgagggcc    120
caccaagctc ttcctcgaga ttctgttgta gaagatttac atttacaaaa tagatacctc    180
caagaaaaac ttcatgcttt agaaaaacag ttttcaaagg atacatattc taagccttca    240
atttcaggaa tagagtcaga tgatcattgt cagagagaac aggagcttca gaaggaaaac    300
ttgaagttgt catctgaaaa tattgaactg aaatttcagc ttgaacaagc aaataaagat    360
ttgccaagat taaagaatca agtcagagat ttgaaggaaa tgtgtgaatt tcttaagaaa    420 gaaaagcag aagttcagcg gaaacttggc catgttagag ggtctggtag aagtggaaag    480
acaatcccag aactggaaaa aaccattggt ttaatgaaaa aagtagttga aaagtccag    540 agagaaaatg aacagttgaa aaaagcatca ggaatattga ctagtgaaaa aatggctaat    600
attgagcagg aaaatgaaaa attgaaggct gaattagaaa aacttaaagc tcatcttggg    660
catcagttga gcatgcacta tgaatccaag accaaaggca cagaaaaaat tattgctgaa    720
aatgaaaggc ttcgtaaaga acttaaaaaa gaaactgatg ctgcagagaa attacggata    780
gcaaagaata tttagagat attaaatgag aagatgacag ttcaactaga agagactggt    840
aagagattgc agtttgcaga aagcagaggt ccacagcttg aaggtgctga cagtaagagc    900
tggaaatcca ttgtggttac aagaatgtat gaaaccaagt taaagaatt ggaaactgat    960 attgccaaaa aaatcaaag cattactgac cttaaacagc ttgtaaaaga agcaacagag   1020
```

| | |
|---|---|
| agagaacaaa aagttaacaa atacaatgaa gaccttgaac aacagattaa gattcttaaa | 1080 |
| catgttcctg aaggtgctga gacagagcaa ggccttaaac gggagcttca agttcttaga | 1140 |
| ttagctaatc atcagctgga taaagagaaa gcagaattaa tccatcagat agaagctaac | 1200 |
| aaggaccaaa gtggagctga aagcaccata cctgatgctg atcaactaaa ggaaaaaata | 1260 |
| aaagatctag agacacagct caaaatgtca gatctagaaa agcagcattt gaaggaggaa | 1320 |
| ataaagaagc tgaaaaaaga actggaaaat tttgatcctt catttttga agaaattgaa | 1380 |
| gatcttaagt ataattacaa ggaagaagtg aagaagaata ttctcttaga agagaaggta | 1440 |
| aaaaaacttt cagaacaatt gggagttgaa ttaactagcc ctgttgctgc ttctgaagag | 1500 |
| tttgaagatg aagaagaaag tcctgttaat ttccccattt actaa | 1545 |

<210> SEQ ID NO 33
<211> LENGTH: 3948
<212> TYPE: DNA
<213> ORGANISM: Homo sapiens

<400> SEQUENCE: 33

| | |
|---|---|
| aagaatactt gtattattga agatttgaaa aatgagctcc aaagaaacaa aggtgcttca | 60 |
| acccttctc aacagactca tatgaaaatt cagtcaacgt tagacatttt aaaagagaaa | 120 |
| actaaagagg ctgagagaac agctgaactg gctgaggctg atgctaggga aaaggataaa | 180 |
| gaattagttg aggctctgaa gaggttaaaa gattatgaat cgggagtata tggtttagaa | 240 |
| gatgctgtcg ttgaaataaa gaattgtaaa aaccaaatta aaataagaga tcgagagatt | 300 |
| gaaatattaa caaaggaaat caataaactt gaattgaaga tcagtgattt ccttgatgaa | 360 |
| aatgaggcac ttagagagcg tgtgggcctt gaaccaaaga caatgattga tttaactgaa | 420 |
| tttagaaata gcaaacactt aaaacagcag cagtacagag ctgaaaaacca gattcttttg | 480 |
| aaagagattg aaagtctaga ggaagaacga cttgatctga aaaaaaaaat tcgtcaaatg | 540 |
| gctcaagaaa gaggaaaaag aagtgcaact tcaggattaa ccactgagga cctgaaccta | 600 |
| actgaaaaca tttctcaagg agatagaata agtgaaagaa aattggattt attgagcctc | 660 |
| aaaaatatga gtgaagcaca atcaaagaat gaatttcttt caagagaact aattgaaaaa | 720 |
| gaaagagatt tagaaaggag taggacagtg atagccaaat tcagaataa attaaaagaa | 780 |
| ttagttgaag aaaataagca acttgaagaa ggtatgaaag aaatattgca agcaattaag | 840 |
| gaaatgcaga aagatcctga tgttaaagga ggagaaacat ctctaattat ccctagcctt | 900 |
| gaaagactag ttaatgctat agaatcaaag aatgcagaag gaatctttga tgcgagtctg | 960 |
| catttgaaag cccaagttga tcagcttacc ggaagaaatg aagaattaag acaggagctc | 1020 |
| agggaatctc ggaagagggc tataaattat tcacagcagt tggcaaaagc taatttaaag | 1080 |
| atagaccatc ttgaaaaaga aactagtctt ttacgacaat cagaaggatc gaatgttgtt | 1140 |
| tttaaaggaa ttgacttacc tgatgggata gcaccatcta gtgccagtat cattaattct | 1200 |
| cagaatgaat atttaataca tttgttacag gaactagaaa ataagaaaa aaagttaaag | 1260 |
| aatttagaag attctcttga agattacaac agaaaatttg ctgtaattcg tcatcaacaa | 1320 |
| agtttgttgt ataagaata cctaagtgaa aaggagacct ggaaaacaga atctaaaaca | 1380 |
| ataaagagg aaaagagaaa acttgaggat caagtccaac aagatgctat aaaagtaaaa | 1440 |
| gaatataata atttgctcaa tgctcttcag atggattcgg atgaaatgaa aaaaatactt | 1500 |
| gcagaaaata gtaggaaaat tactgttttg caagtgaatg aaaaatcact tataaggcaa | 1560 |
| tatacaaccct tagtagaatt ggagcgacaa cttagaaaag aaaatgagaa gcaaaagaat | 1620 |

```
gaattgttgt caatggaggc tgaagtttgt gaaaaaattg ggtgtttgca aagatttaag    1680
gaaatggcca ttttcaagat tgcagctctc caaaaagttg tagataatag tgtttctttg    1740
tctgaactag aactggctaa taaacagtac aatgaactga ctgctaagta cagggacatc    1800
ttgcaaaaag ataatatgct tgttcaaaga acaagtaact tggaacacct ggagtgtgaa    1860
aacatctcct taaaagaaca agtggagtct ataaataaag aactggagat taccaaggaa    1920
aaacttcaca ctattgaaca agcctgggaa caggaaacta aattaggtaa tgaatctagc    1980
atggataagg caaagaaatc aataaccaac agtgacattg tttccatttc aaaaaaaata    2040
actatgctgg aaatgaagga attaaatgaa aggcagcggg ctgaacattg tcaaaaaatg    2100
tatgaacact tacggacttc gttaaagcaa atggaggaac gtaattttga attggaaacc    2160
aaatttgctg agcttaccaa aatcaatttg gatgcacaga aggtggaaca gatgttaaga    2220
gatgaattag ctgatagtgt gagcaaggca gtaagtgatg ctgataggca acggattcta    2280
gaattagaga agaatgaaat ggaactaaaa gttgaagtgt caaaactgag agagatttct    2340
gatattgcca gaagacaagt tgaaattttg aatgcacaac aacaatctag ggacaaggaa    2400
gtagagtccc tcagaatgca actgctagac tatcaggcac agtctgatga aaagtcgctc    2460
attgccaagt tgcaccaaca taatgtctct cttcaactga gtgaggctac tgctcttggt    2520
aagttggagt caattacatc taaactgcag aagatggagg cctacaactt gcgcttagag    2580
cagaaacttg atgaaaaaga acaggctctc tattatgctc gtttggaggg aagaaacaga    2640
gcaaaacatc tgcgccaaac aattcagtct ctacgacgac agtttagtgg agctttaccc    2700
ttggcacaac aggaaaagtt ctccaaaaca atgattcaac tacaaaatga caaacttaag    2760
ataatgcaag aaatgaaaaa ttctcaacaa gaacatagaa atatggagaa caaaacattg    2820
gagatggaat taaaattaaa gggcctggaa gagttaataa gcactttaaa ggataccaaa    2880
ggagcccaaa aggtaatcaa ctggcatatg aaaatagaag aacttcgtct tcaagaactt    2940
aaactaaatc gggaattagt caaggataaa gaagaaataa aatatttgaa taacataatt    3000
tctgaatatg aacgtacaat cagcagtctt gaagaagaaa ttgtgcaaca gaacaagttt    3060
catgaagaaa gacaaatggc ctgggatcaa agagaagttg acctggaacg ccaactagac    3120
atttttgacc gtcagcaaaa tgaaatacta aatgcggcac aaaagtttga agaagctaca    3180
ggatcaatcc ctgaccctag tttgcccctt ccaaatcaac ttgagatcgc tctaaggaaa    3240
attaaggaga acattcgaat aattctagaa acacgggcaa cttgcaaatc actagaagag    3300
aaactaaaag agaaagaatc tgctttaagg ttagcagaac aaaatatact gtcaagagac    3360
aaagtaatca atgaactgag gcttcgattg cctgccactg cagaaagaga aaagctcata    3420
gctgagctag gcagaaaaga gatggaacca aaatctcacc acacattgaa aattgctcat    3480
caaaccattg caaacatgca agcaaggtta aatcaaaaag aagaagtatt aagaagtat    3540 caacgtcttc tagaaaaagc cagagaggag caaagagaaa ttgtgaagaa acatgaggaa    3600
gaccttcata ttcttcatca cagattagaa ctacaggctg atagttcact aaataaattc    3660
aaacaaacgg cttgggattt aatgaaacag tctcccactc cagttcctac caacaagcat    3720
tttattcgtc tggctgagat ggaacagaca gtagcagaac aagatgactc tctttcctca    3780
ctcttggtca aactaaagaa agtatcacaa gatttggaga gacaaagaga aatcactgaa    3840
ttaaaagtaa aagaatttga aaatatcaaa ttacagcttc aagaaaacca tgaagatgaa    3900
gtgaaaaaag taaaagcgga agtagaggat ttaaagtatc ttctggac           3948
```

<210> SEQ ID NO 34
<211> LENGTH: 2406
<212> TYPE: DNA
<213> ORGANISM: Homo sapiens

<400> SEQUENCE: 34

| | | | | | |
|---|---|---|---|---|---|
| atgccaccta | atataaactg | gaaagaaata | atgaaagttg | acccagatga | cctgccccgt | 60 |
| caagaagaac | tggcagataa | tttattgatt | tccttatcca | aggtggaagt | aaatgagcta | 120 |
| aaaagtgaaa | agcaagaaaa | tgtgatacac | cttttcagaa | ttactcagtc | actaatgaag | 180 |
| atgaaagctc | aagaagtgga | gctggctttg | gaagaagtag | aaaaagctgg | agaagaacaa | 240 |
| gcaaaatttg | aaaatcaatt | aaaaactaaa | gtaatgaaac | tggaaaatga | actggagatg | 300 |
| gctcagcagt | ctgcaggtgg | acgagatact | cggttttttac | gtaatgaaat | ttgccaactt | 360 |
| gaaaaacaat | tagaacaaaa | agatagagaa | ttggaggaca | tggaaaagga | gttggagaaa | 420 |
| gagaagaaag | ttaatgagca | attggctctt | cgaaatgagg | aggcagaaaa | tgaaaacagc | 480 |
| aaattaagaa | gagagaacaa | acgtctaaag | aaaagaatg | aacaactttg | tcaggatatt | 540 |
| attgactacc | agaaacaaat | agattcacag | aaagaaacac | ttttatcaag | aagaggggaa | 600 |
| actgaaaaca | tttctcaagg | agatagaata | agtgaaagaa | aattggattt | attgagcctc | 660 |
| aaaaatatga | gtgaagcaca | atcaaagaat | gaatttcttt | caagagaact | aattgaaaaa | 720 |
| gaaagagatt | tagaaaggag | taggacagtg | atagccaaat | tcagaataa | attaaaagaa | 780 |
| ttagttgaag | aaaataagca | acttgaagaa | ggtatgaaag | aatattgca | agcaattaag | 840 |
| gaaatgcaga | agatcctga | tgttaaagga | ggagaaacat | ctctaattat | ccctagcctt | 900 |
| gaaagactag | ttaatgctat | agaatcaaag | aatgcagaag | gaatctttga | tgcgagtctg | 960 |
| catttgaaag | cccaagttga | tcagcttacc | ggaagaaatg | aagaattaag | acaggagctc | 1020 |
| agggaatctc | ggaaagaggc | tataaattat | tcacagcagt | tggcaaaagc | taatttaaag | 1080 |
| atagaccatc | ttgaaaaaga | aactagtctt | ttacgacaat | cagaaggatc | gaatgttgtt | 1140 |
| tttaaaggaa | ttgacttacc | tgatgggata | gcaccatcta | gtgccagtat | cattaattct | 1200 |
| cagaatgaat | atttaataca | tttgttacag | gaactagaaa | ataagaaaaa | aaagttaaag | 1260 |
| aatttagaag | attctcttga | agattacaac | agaaaatttg | ctgtaattcg | tcatcaacaa | 1320 |
| agtttgttgt | ataagaata | cctaagtgaa | aaggagacct | ggaaaacaga | atctaaaaca | 1380 |
| ataaaagagg | aaaagagaaa | acttgaggat | caagtccaac | aagatgctat | aaaagtaaaa | 1440 |
| gaatataata | atttgctcaa | tgctcttcag | atggattcgg | atgaaatgaa | aaaaatactt | 1500 |
| gcagaaaata | gtaggaaaat | tactgttttg | caagtgaatg | aaaaatcact | tataaggcaa | 1560 |
| tatacaacct | agtagaatt | ggagcgacaa | cttagaaaag | aaaatgagaa | gcaaaagaat | 1620 |
| gaattgttgt | caatggaggc | tgaagtttgt | gaaaaaattg | ggtgtttgca | aagatttaag | 1680 |
| gaaatggcca | ttttcaagat | tgcagctctc | caaaaagttg | tagataatag | tgtttctttg | 1740 |
| tctgaactag | aactggctaa | taacagtac | aatgaactga | ctgctaagta | cagggacatc | 1800 |
| ttgcaaaaag | ataatatgct | tgttcaaaga | acaagtaact | tggaacaccct | ggagtgtgaa | 1860 |
| aacatctcct | taaagaaaca | agtggagtct | ataaataaag | aactggagat | taccaaggaa | 1920 |
| aaacttcaca | ctattgaaca | agcctgggaa | caggaaacta | aattaggtaa | tgaatctagc | 1980 |
| atggataagg | caaagaaatc | aataaccaac | agtgacattg | tttccatttc | aaaaaaaata | 2040 |
| actatgctgg | aaatgaagga | attaaatgaa | aggcagcggg | ctgaacattg | tcaaaaaatg | 2100 |
| tatgaacact | tacggacttc | gttaaagcaa | atggaggaac | gtaattttga | attggaaacc | 2160 |

| | |
|---|---|
| aaatttgctg agcttaccaa aatcaatttg gatgcacaga aggtggaaca gatgttaaga | 2220 |
| gatgaattag ctgatagtgt gagcaaggca gtaagtgatg ctgataggca acggattcta | 2280 |
| gaattagaga agaatgaaat ggaactaaaa gttgaagtgt caaaactgag agagatttct | 2340 |
| gatattgcca gaagacaagt tgaaattttg aatgcacaac aacaatctag ggacaaggaa | 2400 |
| gtataa | 2406 |

<210> SEQ ID NO 35
<211> LENGTH: 2946
<212> TYPE: DNA
<213> ORGANISM: Homo sapiens

<400> SEQUENCE: 35

| | |
|---|---|
| atgcccccaa acatcaactg gaaagagatt atgaaagtgg accctgacga cctgcctaga | 60 |
| caggaagaac tggctgacaa cctgctgatc agcctgtcca aggtggaagt gaatgagctg | 120 |
| aagtctgaga agcaggagaa cgtgatccac ctgttcagaa tcacccagag cctgatgaag | 180 |
| atgaaggcac aggaggtgga gctggccctg gaggaggtgg agaaggcagg agaggagcag | 240 |
| gccaagttcg agaatcagct gaagaccaaa gtgatgaagc tggagaacga gctggagatg | 300 |
| gcacagcagt ccgccggagg cagggataca cgctttctgc ggaacgagat ctgccagctg | 360 |
| gagaagcagc tggagcagaa ggacagggag ctggaggata tggagaagga gctggagaag | 420 |
| gagaagaagg tgaacgagca gctggccctg cgcaatgagg aggccgagaa tgagaatagc | 480 |
| aagctgcgga gagagaacaa gcggctgaag aagaagaacg agcagctgtg ccaggacatc | 540 |
| atcgattacc agaagcagat cgactcccag aaggagacac tgctgagcag gaggggagag | 600 |
| gactccgatt atcgcagcca gctgtccaag aagaattacg agctgatcca gtatctggat | 660 |
| gagatccaga ccctgacaga ggccaacgag aagatcgagg tgcagaacca ggagatgaga | 720 |
| aagaatctgg aggagtccgt gcaggagatg gagaagatga ccgacgagta caacaggatg | 780 |
| aaggccatcg tgcaccagac agacaatgtg atcgatcagc tgaagaagga gaacgaccac | 840 |
| tatcagctgc aggtgcagga gctgaccgat ctgctgaagt ccaagaatga ggaggacgat | 900 |
| cccatcatgg tggccgtgaa cgccaaggtg gaggagtgga gctgatcct gagctccaag | 960 |
| gacgatgaga tcatcgagta ccagcagatg ctgcacaacc tgcgcgagaa gctgaagaat | 1020 |
| gcccagctgg acgccgataa gagcaatgtg atggcactgc agcagggaat ccaggagagg | 1080 |
| gactcccaga tcaagatgct gaccgagcag gtggagcagt ataccaagga gatggagaag | 1140 |
| acagagaaca tctctcaggg cgacagaatc agcgagagga gctggatct gctgtccctg | 1200 |
| aagaacatgt ccgaggccca gtctaagaat gagttcctgt cccgcgagct gatcgagaag | 1260 |
| gagcgggacc tggagcggag ccggacagtg atcgccaagt tcagaataa gctgaaggag | 1320 |
| ctggtggagg agaacaagca gctggaggag ggcatgaagg agatcctgca ggccatcaag | 1380 |
| gagatgcaga aggacccaga tgtgaagggc ggcgagacaa gcctgatcat ccctctctg | 1440 |
| gagcgcctgg tgaacgccat cgagagcaag aatgccgagg gcatctttga cgcctccctg | 1500 |
| cacctgaagg cccaggtgga tcagctgaca ggccgcaatg aggagctgcg gcaggagctg | 1560 |
| agagagtcta ggaaggaggc catcaattac agccagcagc tggccaaggc caacctgaag | 1620 |
| atcgaccacc tggagaagga gacaagcctg ctgcggcagt ctgagggcag caacgtggtg | 1680 |
| ttcaagggaa tcgacctgcc agatggaatc gcaccttcta gcgccagcat catcaactcc | 1740 |
| cagaatgagt acctgatcca cctgctgcag gagctggaga acaaggagaa gaagctgaag | 1800 |

```
aatctggagg actctctgga ggattataat agaaagtttg ccgtgatcag gcaccagcag   1860
tccctgctgt acaaggagta tctgtctgag aaggagacat ggaagacaga gagcaagacc   1920
atcaaggagg agaagaggaa gctggaggac caggtgcagc aggatgccat caaggtgaag   1980
gagtacaaca atctgctgaa cgccctgcag atggactctg atgagatgaa gaagatcctg   2040
gccgagaata gcagaaagat cacagtgctg caggtgaacg agaagtccct gatcaggcag   2100
tataccacac tggtggagct ggagcgccag ctgcggaagg agaacgagaa gcagaagaat   2160
gagctgctgt ctatggaggc cgaggtgtgc gagaagatcg gctgtctgca gagattcaag   2220
gagatggcca tctttaagat cgccgccctg cagaaggtgg tggacaattc tgtgagcctg   2280
tccgagctgg agctggccaa caagcagtac aatgagctga ccgccaagta tcgcgacatc   2340
ctgcagaagg ataacatgct ggtgcagcgg acaagcaatc tggagcacct ggagtgcgag   2400
aacatcagcc tgaaggagca ggtggagtcc atcaacaagg agctggagat caccaaggag   2460
aagctgcaca aatcgagca ggcctgggag caggagacaa agctgggcaa tgagtcctct   2520
atggacaagg ccaagaagtc tatcaccaac agcgatatcg tgtctatcag caagaagatc   2580
acaatgctgg agatgaagga gctgaatgag aggcagcgcg ccgagcactg tcagaagatg   2640
tacgagcacc tgagaacatc cctgaagcag atggaggaga ggaatttcga gctggagaca   2700
aagtttgccg agctgacaaa gatcaacctg gacgcccaga aggtggagca gatgctgaga   2760
gacgagctgg ccgattccgt gtctaaggcc gtgagcgacg ccgatcggca gagaatcctg   2820
gagctggaga gaacgagat ggagctgaag gtggaggtgt ccaagctgag ggagatctct   2880
gatatcgctc ggcggcaggt ggagattctg aacgcacagc agcagtcacg ggacaaggaa   2940
gtctga                                                             2946

<210> SEQ ID NO 36
<211> LENGTH: 981
<212> TYPE: PRT
<213> ORGANISM: Homo sapiens

<400> SEQUENCE: 36

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
```

```
              165                 170                 175
Cys Gln Asp Ile Ile Asp Tyr Gln Lys Gln Ile Asp Ser Gln Lys Glu
              180                 185                 190

Thr Leu Leu Ser Arg Arg Gly Glu Asp Ser Asp Tyr Arg Ser Gln Leu
              195                 200                 205

Ser Lys Lys Asn Tyr Glu Leu Ile Gln Tyr Leu Asp Glu Ile Gln Thr
              210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
              245                 250                 255

Tyr Asn Arg Met Lys Ala Ile Val His Gln Thr Asp Asn Val Ile Asp
              260                 265                 270

Gln Leu Lys Lys Glu Asn Asp His Tyr Gln Leu Gln Val Gln Glu Leu
              275                 280                 285

Thr Asp Leu Leu Lys Ser Lys Asn Glu Glu Asp Asp Pro Ile Met Val
              290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
              325                 330                 335

Lys Leu Lys Asn Ala Gln Leu Asp Ala Asp Lys Ser Asn Val Met Ala
              340                 345                 350

Leu Gln Gln Gly Ile Gln Glu Arg Asp Ser Gln Ile Lys Met Leu Thr
              355                 360                 365

Glu Gln Val Glu Gln Tyr Thr Lys Glu Met Glu Lys Thr Glu Asn Ile
              370                 375                 380

Ser Gln Gly Asp Arg Ile Ser Glu Arg Lys Leu Asp Leu Leu Ser Leu
385                 390                 395                 400

Lys Asn Met Ser Glu Ala Gln Ser Lys Asn Glu Phe Leu Ser Arg Glu
              405                 410                 415

Leu Ile Glu Lys Glu Arg Asp Leu Glu Arg Ser Arg Thr Val Ile Ala
              420                 425                 430

Lys Phe Gln Asn Lys Leu Lys Glu Leu Val Glu Glu Asn Lys Gln Leu
              435                 440                 445

Glu Glu Gly Met Lys Glu Ile Leu Gln Ala Ile Lys Glu Met Gln Lys
              450                 455                 460

Asp Pro Asp Val Lys Gly Gly Glu Thr Ser Leu Ile Ile Pro Ser Leu
465                 470                 475                 480

Glu Arg Leu Val Asn Ala Ile Glu Ser Lys Asn Ala Glu Gly Ile Phe
              485                 490                 495

Asp Ala Ser Leu His Leu Lys Ala Gln Val Asp Gln Leu Thr Gly Arg
              500                 505                 510

Asn Glu Glu Leu Arg Gln Glu Leu Arg Glu Ser Arg Lys Glu Ala Ile
              515                 520                 525

Asn Tyr Ser Gln Gln Leu Ala Lys Ala Asn Leu Lys Ile Asp His Leu
              530                 535                 540

Glu Lys Glu Thr Ser Leu Leu Arg Gln Ser Glu Gly Ser Asn Val Val
545                 550                 555                 560

Phe Lys Gly Ile Asp Leu Pro Asp Gly Ile Ala Pro Ser Ser Ala Ser
              565                 570                 575

Ile Ile Asn Ser Gln Asn Glu Tyr Leu Ile His Leu Leu Gln Glu Leu
              580                 585                 590
```

```
Glu Asn Lys Glu Lys Lys Leu Lys Asn Leu Glu Asp Ser Leu Glu Asp
            595                 600                 605

Tyr Asn Arg Lys Phe Ala Val Ile Arg His Gln Gln Ser Leu Leu Tyr
    610                 615                 620

Lys Glu Tyr Leu Ser Glu Lys Glu Thr Trp Lys Thr Glu Ser Lys Thr
625                 630                 635                 640

Ile Lys Glu Glu Lys Arg Lys Leu Glu Asp Gln Val Gln Gln Asp Ala
                645                 650                 655

Ile Lys Val Lys Glu Tyr Asn Asn Leu Leu Asn Ala Leu Gln Met Asp
            660                 665                 670

Ser Asp Glu Met Lys Lys Ile Leu Ala Glu Asn Ser Arg Lys Ile Thr
        675                 680                 685

Val Leu Gln Val Asn Glu Lys Ser Leu Ile Arg Gln Tyr Thr Thr Leu
    690                 695                 700

Val Glu Leu Glu Arg Gln Leu Arg Lys Glu Asn Glu Lys Gln Lys Asn
705                 710                 715                 720

Glu Leu Leu Ser Met Glu Ala Glu Val Cys Glu Lys Ile Gly Cys Leu
                725                 730                 735

Gln Arg Phe Lys Glu Met Ala Ile Phe Lys Ile Ala Ala Leu Gln Lys
            740                 745                 750

Val Val Asp Asn Ser Val Ser Leu Ser Glu Leu Glu Leu Ala Asn Lys
        755                 760                 765

Gln Tyr Asn Glu Leu Thr Ala Lys Tyr Arg Asp Ile Leu Gln Lys Asp
    770                 775                 780

Asn Met Leu Val Gln Arg Thr Ser Asn Leu Glu His Leu Glu Cys Glu
785                 790                 795                 800

Asn Ile Ser Leu Lys Glu Gln Val Glu Ser Ile Asn Lys Glu Leu Glu
                805                 810                 815

Ile Thr Lys Glu Lys Leu His Thr Ile Glu Gln Ala Trp Glu Gln Glu
            820                 825                 830

Thr Lys Leu Gly Asn Glu Ser Ser Met Asp Lys Ala Lys Lys Ser Ile
        835                 840                 845

Thr Asn Ser Asp Ile Val Ser Ile Ser Lys Lys Ile Thr Met Leu Glu
    850                 855                 860

Met Lys Glu Leu Asn Glu Arg Gln Arg Ala Glu His Cys Gln Lys Met
865                 870                 875                 880

Tyr Glu His Leu Arg Thr Ser Leu Lys Gln Met Glu Glu Arg Asn Phe
                885                 890                 895

Glu Leu Glu Thr Lys Phe Ala Glu Leu Thr Lys Ile Asn Leu Asp Ala
            900                 905                 910

Gln Lys Val Glu Gln Met Leu Arg Asp Glu Leu Ala Asp Ser Val Ser
        915                 920                 925

Lys Ala Val Ser Asp Ala Asp Arg Gln Arg Ile Leu Glu Leu Glu Lys
    930                 935                 940

Asn Glu Met Glu Leu Lys Val Glu Val Ser Lys Leu Arg Glu Ile Ser
945                 950                 955                 960

Asp Ile Ala Arg Arg Gln Val Glu Ile Leu Asn Ala Gln Gln Gln Ser
                965                 970                 975

Arg Asp Lys Glu Val
            980

<210> SEQ ID NO 37
<211> LENGTH: 973
```

```
<212> TYPE: DNA
<213> ORGANISM: Gallus domesticus

<400> SEQUENCE: 37
gtgagcgggc gggacggccc ttctcctccg ggctgtaatt agcgcttggt ttaatgacgg      60
cttgtttctt ttctgtggct gcgtgaaagc cttgaggggc tccggagggg ccctttgtgc     120
gggggagcg gctcggggg tgcgtgcgtg tgtgtgcg tggggagcgc cgcgtgcggc        180
tccgcgctgc ccggcggctg tgagcgctgc gggcgcggcg cggggctttg tgcgctccgc     240
agtgtgcgcg aggggagcgc ggccgggggc ggtgccccgc ggtgcggggg gggctgcgag    300
gggaacaaag gctgcgtgcg gggtgtgtgc gtgggggggt gagcagggg tgtgggcgcg      360
tcggtcgggc tgcaaccccc cctgcacccc cctccccgag ttgctgagca cggcccggct     420
tcgggtgcgg ggctccgtac ggggcgtggc gcggggctcg ccgtgccggg cggggggtgg     480
cggcaggtgg gggtgccggg cggggcgggg ccgcctcggg ccggggaggg ctcgggggag     540
gggcgcggcg gcccccggag cgccggcggc tgtcgaggcg cggcgagccg cagccattgc     600
cttttatggt aatcgtgcga gagggcgcag ggacttcctt tgtcccaaat ctgtgcggag     660
ccgaaatctg ggaggcgccg ccgcaccccc tctagcgggc gcggggcgaa gcggtgcggc    720
gccggcagga aggaaatggg cggggagggc cttcgtgcgt cgccgcgccg ccgtcccctt     780
ctccctctcc agcctcgggg ctgtccgcgg ggggacggct gccttcgggg gggacggggc    840
agggcggggt tcggcttctg gcgtgtgacc ggcggctcta gagcctctgc taaccatgtt     900
catgccttct tcttttcct acagctcctg ggcaacgtgc tggttattgt gctgtctcat      960
cattttggca aag                                                         973

<210> SEQ ID NO 38
<211> LENGTH: 172
<212> TYPE: DNA
<213> ORGANISM: Artificial Sequence
<220> FEATURE:
<223> OTHER INFORMATION: Synthetic Polynucleotide

<400> SEQUENCE: 38
gaactgaaaa accagaaagt taactggtaa gtttagtctt tttgtctttt atttcaggtc      60
ccggatccgg tggtggtgca aatcaaagaa ctgctcctca gtggatgttg cctttacttc    120
taggcctgta cggaagtgtt acttctgctc taaaagctgc ggaattgtac cc             172

<210> SEQ ID NO 39
<211> LENGTH: 384
<212> TYPE: DNA
<213> ORGANISM: Unknown
<220> FEATURE:
<223> OTHER INFORMATION: MBL intron

<400> SEQUENCE: 39
tcagatcgcc tggagacgcc atccacgctg ttttgacctc catagaagac accgggaccg      60
atccagcctc cgcggccggg aacggtgcat tggaacgcgg attcccgtg ccaagagtga     120
cgtaagtacc gcctatagag tctataggcc cacccccttg gcttcttatg catgctatac     180
tgttttggc ttggggtcta tacaccccg cttcctcatg tttgctgccc gtgaccagca      240
cgtcaacgat tttgtgggca cgggcgacac cgcagtgtag tctgagcagt actcgttgct     300
gccgcgcgcg ccaccagaca taatagctga cagactaaca gactgttcct ttccatgggt    360
cttttctgca gtcaccgtcg ccgc                                             384
```